United States Patent
Or et al.

(10) Patent No.: US 8,846,638 B2
(45) Date of Patent: Sep. 30, 2014

(54) MACROCYCLIC NUCLEOSIDE PHOSPHORAMIDATE DERIVATIVES

(71) Applicant: Enanta Pharmaceuticals, Inc., Watertown, MA (US)

(72) Inventors: Yat Sun Or, Watertown, MA (US); Jun Ma, Belmont, MA (US); Guoqiang Wang, Belmont, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 13/897,023

(22) Filed: May 17, 2013

(65) Prior Publication Data
US 2013/0315864 A1   Nov. 28, 2013

Related U.S. Application Data

(60) Provisional application No. 61/648,172, filed on May 17, 2012.

(51) Int. Cl.

| | |
|---|---|
| C07H 19/00 | (2006.01) |
| A61K 31/70 | (2006.01) |
| C07H 19/14 | (2006.01) |
| C07H 19/23 | (2006.01) |
| A61K 45/06 | (2006.01) |
| A61K 31/7076 | (2006.01) |
| C07H 19/10 | (2006.01) |
| C07H 19/20 | (2006.01) |
| C07H 19/207 | (2006.01) |
| A61K 31/7064 | (2006.01) |

(52) U.S. Cl.
CPC .............. *C07H 19/207* (2013.01); *C07H 19/14* (2013.01); *C07H 19/23* (2013.01); *A61K 45/06* (2013.01); *A61K 31/7076* (2013.01); *C07H 19/10* (2013.01); *C07H 19/20* (2013.01); *A61K 31/7064* (2013.01)
USPC .......... 514/48; 514/51; 536/26.11; 536/26.12

(58) Field of Classification Search
None
See application file for complete search history.

(56) References Cited

U.S. PATENT DOCUMENTS

| 5,750,806 | A | 5/1998 | Brocker et al. |
|---|---|---|---|
| 7,247,621 | B2 | 7/2007 | Hong et al. |
| 7,438,920 | B1 | 10/2008 | Kim et al. |
| 7,589,077 | B2 | 9/2009 | Kumar et al. |
| 8,163,707 | B2 | 4/2012 | Qiu et al. |
| 2010/0074889 | A1 | 3/2010 | Qiu et al. |
| 2010/0074890 | A1 | 3/2010 | Hagel et al. |
| 2011/0257122 | A1 | 10/2011 | Sofia et al. |
| 2012/0237480 | A1 | 9/2012 | Or et al. |
| 2013/0078217 | A1 | 3/2013 | Wang et al. |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Li, et al. Synthesis of 2'-C-Branched Nucleosides, Organic Preparations and Procedures International, 42:191-283 (2010).
Hayashi, et al., "Adenallene and cytallene: Acyclic nucleoside analogues that inhibit replication and cytopathic effect of human immunodeficiency virus in vitro," Proceedings of the National Academy of Science, 85:6127-6131,1988.
International Search Report for PCT/US12/29381, dated Jun. 28, 2012.

* cited by examiner

*Primary Examiner* — Traviss C McIntosh, III
(74) *Attorney, Agent, or Firm* — Edgar W. Harlan; Carolyn S. Elmore, Esq.; Elmore Patent Law Group, P.C.

(57) ABSTRACT

The present invention provides nucleoside phosphoramidate compounds of Formula I,

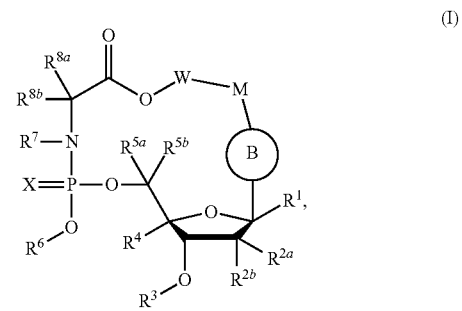

(I)

where $R^1$, $R^{2a}$, $R^{2b}$, $R^3$, $R^4$, $R^{5a}$, $R^{5b}$, $R^6$, $R^7$, $R^{8a}$, $R^{8b}$, M and W are as defined herein. The invention further includes pharmaceutical compositions comprising a compound of Formula I, methods of use of these compounds for treating a viral infection, and methods of producing these compounds.

22 Claims, No Drawings

MACROCYCLIC NUCLEOSIDE PHOSPHORAMIDATE DERIVATIVES

RELATED APPLICATION(S)

This application claims the benefit of U.S. Provisional Application No. 61/648,172, filed on May 17, 2012. The entire teachings of the above application are incorporated herein by reference.

TECHNICAL FIELD

The present invention relates generally to compounds and pharmaceutical compositions useful as antiviral and antiproliferative agents. Specifically, the present invention relates to macrocyclic nucleoside phosphoramidate derivatives and methods for their preparation and use.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver diseases and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al.) 'An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology $2^{nd}$ Edition, p 931-960; Raven Press, N.Y.). There are three structural proteins, C, E1 and E2. The P7 protein is of unknown function and is comprised of a highly variable sequence. There are several non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyperphosphorylated (58 kDa) forms. While its function has not fully been elucidated, NS5A is believed to be important in viral replication. The NS5B protein (591 amino acids, 65 kDa) of HCV (Behrens, S. E. et al (1996) EMBO J. 151 2-22), encodes an RNA-dependent RNA polymerase (RdRp) activity and contains canonical motifs present in other RNA viral polymerases. The NS5B protein is fairly well conserved both intra-typically (~95-98% amino acid (aa) identity across 1b isolates) and inter-typically (~85% aa identity between genotype 1a and 1b isolates). The essentiality of the HCV NS5B RdRp activity for the generation of infectious progeny virions has been formally proven in chimpanzees (A. A. Kolykhalov et al. (2000) Journal of Virology, 74(4): 2046-2051). Thus, inhibition of NS5B RdRp activity (inhibition of RNA replication) is predicted to be useful to treat HCV infection.

Current standard of care (SOD) therapy is the combination of peg-interferon-a and ribavirin. However, this therapy is limited in its clinical effectiveness and only ~50% of genotype 1a patients respond to the therapy. Recent approved NS3 protease inhibitors, Boceprevir and Telaprevir, used in combination with SOC slightly improved effectiveness, but suffered significant side effects, such as rash. Therefore, there is still significant unmet medical need for more effective agents.

Inhibitors of HCV NS5B as potential therapies for HCV infection have been review: S. Tan, A. Pause, Y. Shi, N. Sonenberg, Hepatitis C Therapeutics: Current Status and Emerging Strategies, Nature Rev. Drug Discov. 1, 867-881 (2002). The potential for the emergence of resistant HCV strains and the need to identify compounds with Pan-genotypic coverage supports the continuing efforts to identify novel and more effective nucleosides or nucleotides as HCV NS5B polymerase inhibitors.

SUMMARY OF THE INVENTION

In one aspect, the invention provides compounds represented by Formula I, and pharmaceutically acceptable salts, esters, stereoisomers, tautomers, solvates, and combination thereof:

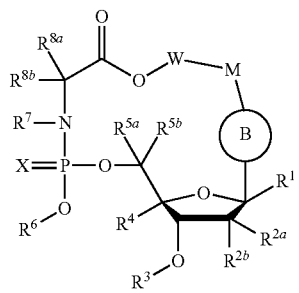
(I)

wherein:

$R^1$ and $R^4$ are each independently selected from the group consisting of:
 1) hydrogen;
 2) —CN;
 3) halogen;
 4) —$N_3$;
 5) Substituted or unsubstituted —$C_1$-$C_8$ alkyl;
 6) Substituted or unsubstituted —$C_2$-$C_8$ alkenyl; and
 7) Substituted or unsubstituted —$C_2$-$C_8$ alkynyl;

$R^{2a}$ at each occurrence is selected from the group consisting of:
 1) hydrogen;
 2) halogen;
 3) Substituted or unsubstituted —$C_1$-$C_8$ alkyl;
 4) Substituted or unsubstituted —$C_2$-$C_8$ alkenyl; and
 5) Substituted or unsubstituted —$C_2$-$C_8$ alkynyl;

$R^{2b}$ at each occurrence is selected from the group consisting of:
 1) hydrogen;
 2) halogen;
 3) —CN;
 4) —$N_3$; and
 5) $OR^9$;

$R^3$ and $R^9$ are each independently selected from the group consisting of: hydrogen, hydroxy protecting group, $R^{10}$, —C(O)$R^{10}$, —C(O)O$R^{10}$, and —C(O)N$R^{11a}R^{11b}$; wherein $R^{10}$ at each occurrence is independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic;

$R^{11a}$ and $R^{11b}$ at each occurrence are each independently selected from the group consisting of: hydrogen and $R^{10}$; or alternatively $R^{11a}$ and $R^{11b}$ taken together with the nitrogen atom to which they are attached form a heterocyclic ring;

is an optionally substituted heterocyclic base. In some embodiments,

is selected from the following structures:

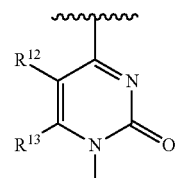
(B1)

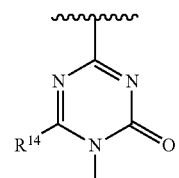
(B2)

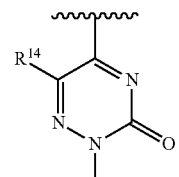
(B3)

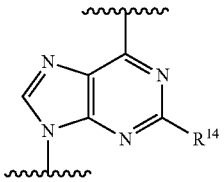
(B4)

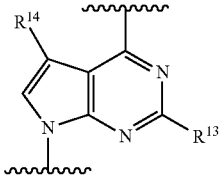
(B5)

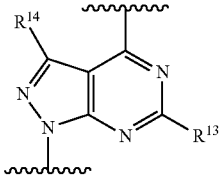
(B6)

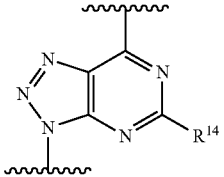
(B7)

-continued

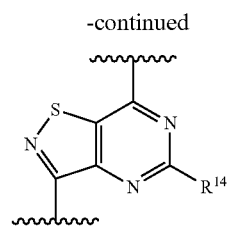

(B8)

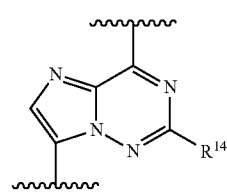

(B9)

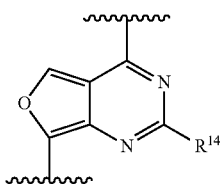

(B10)

$R^{12}$, $R^{13}$ and $R^{14}$ are each independently selected from the group consisting of: hydrogen, halogen, —CN, $N_3$, —C(O)$NR^{11a}R^{11b}$, —$NO_2$, —$OR^9$, —$SR^9$, —$NR^{11a}R^{11b}$, —NHC(O)$R^{10}$, —NHC(O)O$R^{10}$ and —NHC(O)$NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl;

$R^{5a}$ and $R^{5b}$ are independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;
or $R^{5a}$ and $R^{5b}$ are taken together with the carbon atom to which they are attached to form a group selected from —$C_3$-$C_8$ cycloalkyl, —$C_3$-$C_8$ cycloalkenyl, or —$C_3$-$C_8$ cycloalkynyl.

$R^6$ at each occurrence is each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; such as, but not limited to, phenyl or naphthyl; and
5) Substituted or unsubstituted heteroaryl;

X is O or S;

$R^7$ at each occurrence is each independently selected from the group consisting of:
1) hydrogen; and
2) Substituted or unsubstituted —$C_1$-$C_8$ alkyl; or $R^7$ and $R^{8a}$ or $R^{8b}$ together are —$(CH_2)_n$— so as to form a cyclic ring which includes the adjoining N and C; wherein n is 2 to 6.

$R^{8a}$ and $R^{8b}$ are independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl; or $R^{8a}$ and $R^{8b}$ combined together form —$(CH_2)_m$—, so as to form a spiro ring with the carbon they are attached to; wherein, m is 2 to 5.

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—.

W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_8$ alkynylene each containing 0, 1, 2, or 3 heteroatoms selected from O, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_3$-$C_{12}$ cycloalkenylene each containing 0, 1, 2, or 3 heteroatoms selected from O, S or N;

In another embodiment, the present invention provides a pharmaceutical composition comprising a therapeutically effective amount of a compound or combination of compounds of the present invention, or a pharmaceutically acceptable salt form, stereoisomer, tautomer, solvate, or combination thereof, in combination with a pharmaceutically acceptable carrier or excipient.

In yet another embodiment, the present invention provides a method of inhibiting the replication of an RNA or DNA containing virus comprising contacting said virus with a therapeutically effective amount of a compound or a combination of compounds of the present invention, or a pharmaceutically acceptable salt, stereoisomer, tautomer, solvate, or combination thereof. Particularly, this invention is directed to methods of inhibiting the replication of HCV, HBV and HIV.

In still another embodiment, the present invention provides a method of treating or preventing infection caused by an RNA or DNA-containing virus comprising administering to a patient in need of such treatment a therapeutically effective amount of a compound or combination of compounds of the present invention, or a pharmaceutically acceptable salt form, stereoisomer, or tautomer, solvate, or combination thereof. Particularly, this invention is directed to methods of treating or preventing infection caused by HCV, HBV and HIV.

Yet another embodiment of the present invention provides the use of a compound or combination of compounds of the present invention, or a therapeutically acceptable salt form, stereoisomer or tautomer, solvate, or combination thereof, as defined hereinafter, in the preparation of a medicament for the treatment or prevention of infection caused by RNA or DNA-containing virus, specifically HCV, HBV and HIV.

DETAILED DESCRIPTION OF THE INVENTION

A first embodiment of the invention is a compound represented by Formula I as described above, or a pharmaceutically acceptable salt, ester or prodrug thereof.

A second embodiment of the invention is a compound represented by Formula II or a pharmaceutically acceptable salt, ester or prodrug thereof.

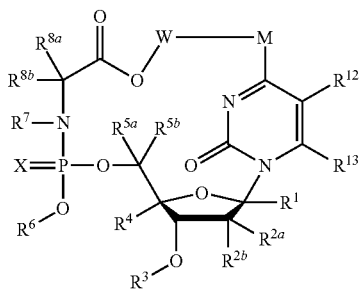

(II)

wherein:
$R^1$ and $R^4$ are each independently selected from the group consisting of:
1) hydrogen;
2) —CN;
3) halogen;
4) —N$_3$; and
5) Substituted or unsubstituted —C$_1$-C$_8$ alkyl;
6) Substituted or unsubstituted —C$_2$-C$_8$ alkenyl; and
7) Substituted or unsubstituted —C$_2$-C$_8$ alkynyl;

$R^{2a}$ is selected from the group consisting of:
1) hydrogen;
2) halogen;
3) Substituted or unsubstituted —C$_1$-C$_8$ alkyl;
4) Substituted or unsubstituted —C$_2$-C$_8$ alkenyl; and
5) Substituted or unsubstituted —C$_2$-C$_8$ alkynyl;

$R^{2b}$ is selected from the group consisting of:
1) hydrogen;
2) halogen;
3) —CN;
4) —N$_3$; and
5) OR$^9$;

$R^3$ and $R_9$ are each independently selected from the group consisting of: hydrogen, hydroxy protecting group, $R^{10}$, —C(O)R$^{10}$, —C(O)OR$^{10}$, and —C(O)NR$^{11a}$R$^{11b}$;
wherein $R^{10}$ at each occurrence is each independently selected from the group consisting of: substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted aryl, substituted or unsubstituted heteroaryl, and substituted or unsubstituted heterocyclic;

$R^{11a}$; and R$^{11b}$ at each occurrence is each independently selected from the group consisting of: hydrogen and R$^{10}$; or alternatively R$^{11a}$ and R$^{11b}$ taken together with the nitrogen atom to which they are attached form a heterocyclic ring;

$R^{5a}$ and R$^{5b}$ are independently selected from the group consisting of:
1) hydrogen;
2) substituted or unsubstituted —C$_1$-C$_8$ alkyl;
3) substituted or unsubstituted —C$_2$-C$_8$ alkenyl; and
4) substituted or unsubstituted —C$_2$-C$_8$ alkynyl;
or R$^{5a}$ and R$^{5b}$ are taken together with the carbon atom to which they are attached to form a group selected from —C$_3$-C$_8$ cycloalkyl, —C$_3$-C$_8$ cycloalkenyl, or —C$_3$-C$_8$ cycloalkynyl.

$R^6$ at each occurrence is each independently selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —C$_1$-C$_8$ alkyl;
or R$^7$ together with R$^{8a}$ or R$^{8b}$ form —(CH$_2$)$_n$— so as to form a cyclic ring which includes the adjoining N and C; wherein n is 2 to 6.

$R^{8a}$ and R$^{8b}$ are each independently selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; and
5) Substituted or unsubstituted heteroaryl;
Or R$^{8a}$ and R$^{8b}$ are taken together to form —(CH$_2$)$_m$—, so as to form a spiro ring with the carbon they are attached to; wherein, m is 2 to 5.

$R^{12}$ and R$^{13}$ are each independently selected from the group consisting of: hydrogen, halogen, —CN, N$_3$, —C(O)NR$^{11a}$R$^{11b}$, —NO$_2$, —OR$^9$, —SR$^9$, —NR$^{11a}$R$^{11b}$, —NHC(O)R$^{10}$, —NHC(O)OR$^{10}$ and —NHC(O)NR$^{11a}$R$^{11b}$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, and substituted or unsubstituted —C$_2$-C$_8$ alkynyl; preferably, R$^{12}$ and R$^{13}$ are both hydrogen;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—.

W is selected from —C$_4$-C$_{12}$ alkylene, —C$_4$-C$_{12}$ alkenylene, or —C$_4$-C$_{12}$ alkynylene each containing 0, 1, 2, or 3 heteroatoms selected from O, S, or N; substituted —C$_4$-C$_{12}$ alkylene, substituted —C$_4$-C$_{12}$ alkenylene, or substituted —C$_4$-C$_8$ alkynylene each containing 0, 1, 2, or 3 heteroatoms selected from O, S or N; —C$_4$-C$_{12}$ cycloalkylene, or substituted —C$_4$-C$_{12}$ cycloalkylene each containing 0, 1, 2, or 3 heteroatoms selected from O, S or N; and —C$_4$-C$_{12}$ cycloalkenylene or substituted —C$_3$-C$_{12}$ cycloalkenylene each containing 0, 1, 2, or 3 heteroatoms selected from O, S or N;

A third embodiment of the invention is a compound represented by Formula III or a pharmaceutically acceptable salt, ester or prodrug thereof.

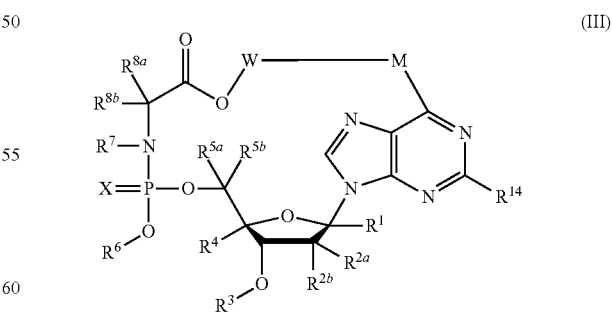

(III)

wherein:
$R^1$ and $R^4$ are each independently selected from the group consisting of:
1) hydrogen;
2) —CN;

3) halogen;
4) —N$_3$; and
5) Substituted or unsubstituted —C$_1$-C$_8$ alkyl;
6) Substituted or unsubstituted —C$_2$-C$_8$ alkenyl; and
7) Substituted or unsubstituted —C$_2$-C$_8$ alkynyl;

R$^{2a}$ at each occurrence is selected from the group consisting of:
1) hydrogen;
2) halogen;
3) Substituted or unsubstituted —C$_1$-C$_8$ alkyl;
4) Substituted or unsubstituted —C$_2$-C$_8$ alkenyl; and
5) Substituted or unsubstituted —C$_2$-C$_8$ alkynyl;

R$^{2b}$ at each occurrence is selected from the group consisting of:
1) hydrogen;
2) halogen;
3) —CN;
4) —N$_3$; and
5) OR$^9$;

R$^3$ and R$^9$ are each independently selected from the group consisting of: hydrogen, hydroxy protecting group, R$^{10}$, —C(O)R$^{10}$, —C(O)OR$^{10}$, and —C(O)NR$^{11a}$R$^{11b}$; wherein R$^{10}$ at each occurrence is each independently selected from the group consisting of: substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted aryl, substituted or unsubstituted heteroaryl, and substituted or unsubstituted heterocyclic; R$^{11a}$; and R$^{11b}$ at each occurrence is each independently selected from the group consisting of: hydrogen and R$^{10}$; or alternatively R$^{11a}$ and R$^{11b}$ taken together with the nitrogen atom to which they are attached form a heterocyclic ring;

R$^{5a}$ and R$^{5b}$ are independently selected from the group consisting of:
1) hydrogen;
2) substituted or unsubstituted —C$_1$-C$_8$ alkyl;
3) substituted or unsubstituted —C$_2$-C$_8$ alkenyl; and
4) substituted or unsubstituted —C$_2$-C$_8$ alkynyl;
or R$^{5a}$ and R$^{5b}$ are taken together with the carbon atom to which they are attached to form a group selected from —C$_3$-C$_8$ cycloalkyl, —C$_3$-C$_8$ cycloalkenyl, or —C$_3$-C$_8$ cycloalkynyl.

R$^6$ at each occurrence is selected from a group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; such as, but not limited to, phenyl or naphthyl; and
5) Substituted or unsubstituted heteroaryl;

X is O or S;

R$^7$ at each occurrence is each independently selected from a group consisting of:
1) hydrogen; and
2) Substituted or unsubstituted —C$_1$-C$_8$ alkyl;
or R$^7$ and R$^{8a}$ or R$^{8b}$ together form —(CH$_2$)$_n$— so as to form a cyclic ring which includes the adjoining N and C; wherein n is 2 to 6.

R$^{8a}$ and R$^{8b}$ are independently selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; and
5) Substituted or unsubstituted heteroaryl;

or R$^{8a}$ and R$^{8b}$ taken together form —(CH$_2$)$_m$—, so as to form a spiro ring with the carbon to which they are attached; wherein, m is 2 to 5.

R$^{14}$ is selected from the group consisting of: hydrogen, halogen, —CN, N$_3$, —C(O)NR$^{11a}$R$^{11b}$, —NO$_2$, —OR$^9$, —SR$^9$, —NR$^{11a}$R$^{11b}$, —NHC(O)R$^{10}$, —NHC(O)OR$^{10}$ and —NHC(O)NR$^{11a}$R$^{11b}$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, and substituted or unsubstituted —C$_2$-C$_8$ alkynyl; preferably R$^{14}$ is —NH$_2$;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, or —NHC(O)NH—.

W is selected from —C$_4$-C$_{12}$ alkylene, —C$_4$-C$_{12}$ alkenylene, or —C$_4$-C$_{12}$ alkynylene each containing 0, 1, 2, or 3 heteroatoms selected from O, S, or N; substituted —C$_4$-C$_{12}$ alkylene, substituted —C$_4$-C$_{12}$ alkenylene, or substituted —C$_4$-C$_8$ alkynylene each containing 0, 1, 2, or 3 heteroatoms selected from O, S or N; —C$_4$-C$_{12}$ cycloalkylene, or substituted —C$_4$-C$_{12}$ cycloalkylene each containing 0, 1, 2, or 3 heteroatoms selected from O, S or N; and —C$_4$-C$_{12}$ cycloalkenylene or substituted —C$_3$-C$_{12}$ cycloalkenylene each containing 0, 1, 2, or 3 heteroatoms selected from O, S or N;

A fourth embodiment of the invention is a compound represented by Formula IV or a pharmaceutically acceptable salt, ester or prodrug thereof, alone or in combination with a pharmaceutically acceptable carrier or excipient.

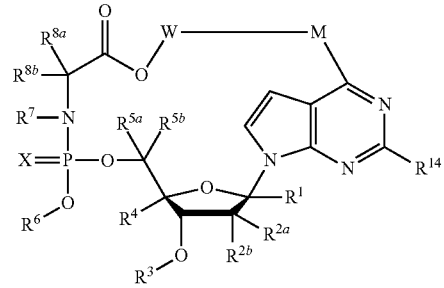

(IV)

wherein:
R$^1$ and R$^4$ are each independently selected from the group consisting of:
1) hydrogen;
2) —CN;
3) halogen;
4) —N$_3$;
5) Substituted or unsubstituted —C$_1$-C$_8$ alkyl;
6) Substituted or unsubstituted —C$_2$-C$_8$ alkenyl; and
7) Substituted or unsubstituted —C$_2$-C$_8$ alkynyl;

R$^{2a}$ is selected from the group consisting of:
1) hydrogen;
2) halogen;
3) Substituted or unsubstituted —C$_1$-C$_8$ alkyl;
4) Substituted or unsubstituted —C$_2$-C$_8$ alkenyl; and
5) Substituted or unsubstituted —C$_2$-C$_8$ alkynyl;

R$^{2b}$ at each occurrence is selected from the group consisting of:
1) hydrogen;
2) halogen;
3) —CN;
4) —N$_3$; and

5) OR$^9$;

R$^3$ and R$^9$ are each independently selected from the group consisting of: hydrogen, hydroxy protecting group, R$^{10}$, —C(O)R$^{10}$, —C(O)OR$^{10}$, and —C(O)NR$^{11a}$R$^{11b}$; wherein R$^{10}$ at each occurrence is each independently selected from the group consisting of: substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted aryl, substituted or unsubstituted heteroaryl, and substituted or unsubstituted heterocyclic;

R$^{11a}$; and R$^{11b}$ at each occurrence is each independently selected from the group consisting of: hydrogen and R$^{10}$; or alternatively R$^{11a}$ and R$^{11b}$ taken together with the nitrogen atom to which they are attached form a heterocyclic ring;

R$^{5a}$ and R$^{5b}$ are independently selected from the group consisting of:
1) hydrogen;
2) substituted or unsubstituted —C$_1$-C$_8$ alkyl;
3) substituted or unsubstituted —C$_2$-C$_8$ alkenyl;
4) substituted or unsubstituted —C$_2$-C$_8$ alkynyl;
or R$^{5a}$ and R$^{5b}$ are taken together with the carbon atom to which they are attached to form a group selected from —C$_3$-C$_8$ cycloalkyl, —C$_3$-C$_8$ cycloalkenyl, and —C$_3$-C$_8$ cycloalkynyl.

R$^6$ is selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; such as, but not limited to, phenyl or naphthyl; and
5) Substituted or unsubstituted heteroaryl;

X is O or S;

R$^7$ is selected from the group consisting of:
1) hydrogen; and
2) Substituted or unsubstituted —C$_1$-C$_8$ alkyl;
or R$^7$ and R$^{8a}$ or R$^{8b}$ together are —(CH$_2$)$_n$— so as to form a cyclic ring which includes the adjoining N and C; wherein n is 2 to 6.

R$^{8a}$ and R$^{8b}$ are independently selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; and
5) Substituted or unsubstituted heteroaryl;
or R$^{8a}$ and R$^{8b}$ combined together form —(CH$_2$)$_m$—, so as to form a spiro ring with the carbon they are attached to; wherein, m is 2 to 5.

R$^{14}$ is selected from the group consisting of: hydrogen, halogen, —CN, N$_3$, —C(O)NR$^{11a}$R$^{11b}$, —NO$_2$, —OR$^9$, —SR$^9$, —NR$^{11a}$R$^{11b}$, —NHC(O)R$^{10}$, —NHC(O)OR$^{10}$ and —NHC(O)NR$^{11a}$R$^{11b}$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, and substituted or unsubstituted —C$_2$-C$_8$ alkynyl; preferably R$^{14}$ is hydrogen;

M is selected from a group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—.

W is selected from —C$_4$-C$_{12}$ alkylene, —C$_4$-C$_{12}$ alkenylene, or —C$_4$-C$_{12}$ alkynylene each containing 0, 1, 2, or 3 heteroatoms selected from O, S, or N; substituted —C$_4$-C$_{12}$ alkylene, substituted —C$_4$-C$_{12}$ alkenylene, or substituted —C$_4$-C$_8$ alkynylene each containing 0, 1, 2, or 3 heteroatoms selected from O, S or N; —C$_4$-C$_{12}$ cycloalkylene, or substituted —C$_4$-C$_{12}$ cycloalkylene each containing 0, 1, 2, or 3 heteroatoms selected from O, S or N; and —C$_4$-C$_{12}$ cycloalkenylene or substituted —C$_3$-C$_{12}$ cycloalkenylene each containing 0, 1, 2, or 3 heteroatoms selected from O, S or N;

A fifth embodiment of the invention is a compound represented by Formula V or a pharmaceutically acceptable salt, ester or prodrug thereof.

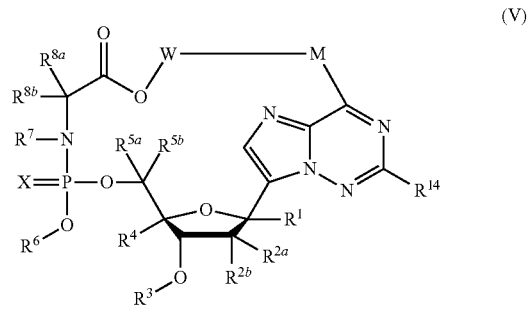

(V)

wherein:

R$^1$ and R$^4$ are each independently selected from the group consisting of:
1) hydrogen;
2) —CN;
3) halogen;
4) —N$_3$; and
5) Substituted or unsubstituted —C$_1$-C$_8$ alkyl;
6) Substituted or unsubstituted —C$_2$-C$_8$ alkenyl; and
7) Substituted or unsubstituted —C$_2$-C$_8$ alkynyl;

R$^{2a}$ is selected from the group consisting of:
1) hydrogen;
2) halogen;
3) Substituted or unsubstituted —C$_1$-C$_8$ alkyl;
4) Substituted or unsubstituted —C$_2$-C$_8$ alkenyl; and
5) Substituted or unsubstituted —C$_2$-C$_8$ alkynyl;

R$^{2b}$ at each occurrence is selected from the group consisting of:
1) hydrogen;
2) halogen;
3) —CN;
4) —N$_3$; and
5) OR$^9$;

R$^3$ and R$^9$ are each independently selected from the group consisting of: hydrogen, hydroxy protecting group, R$^{10}$, —C(O)R$^{10}$, —C(O)OR$^{10}$, and —C(O)NR$^{11a}$R$^{11b}$; wherein R$^{10}$ at each occurrence is each independently selected from the group consisting of: substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted aryl, substituted or unsubstituted heteroaryl, and substituted or unsubstituted heterocyclic;

R$^{11a}$; and R$^{11b}$ at each occurrence is each independently selected from the group consisting of: hydrogen and R$^{10}$; or alternatively R$^{11a}$ and R$^{11b}$ taken together with the nitrogen atom to which they are attached form a heterocyclic ring;

$R^{5a}$ and $R^{5b}$ are each independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;
or $R^{5a}$ and $R^{5b}$ are taken together with the carbon atom to which they are attached to form a group selected from —$C_3$-$C_8$ cycloalkyl, —$C_3$-$C_8$ cycloalkenyl, and —$C_3$-$C_8$ cycloalkynyl.

$R^6$ is selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;
or $R^7$ and $R^{8a}$ or $R^{8b}$ together are —$(CH_2)_n$— so as to form a cyclic ring which includes the adjoining N and C; wherein n is 2 to 6.

$R^{8a}$ and $R^{8b}$ are each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;
or $R^{8a}$ and $R^{8b}$ taken together form —$(CH_2)_m$—, so as to form a spiro ring with the carbon to which they are attached; wherein, m is 2 to 5.

$R^{14}$ is selected from the group consisting of: hydrogen, halogen, —CN, $N_3$, —$C(O)NR^{11a}R^{11b}$, —$NO_2$, —$OR^9$, —$SR^9$, —$NR^{11a}R^{11b}$, —$NHC(O)R^{10}$, —$NHC(O)OR^{10}$ and —$NHC(O)NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl; preferably $R^{14}$ is hydrogen;

M is selected from a group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—.

W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_8$ alkynylene each containing 0, 1, 2, or 3 heteroatoms selected from O, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_3$-$C_{12}$ cycloalkenylene each containing 0, 1, 2, or 3 heteroatoms selected from O, S or N.

A sixth embodiment of the invention is a compound represented by Formula VI or a pharmaceutically acceptable salt, ester or prodrug thereof.

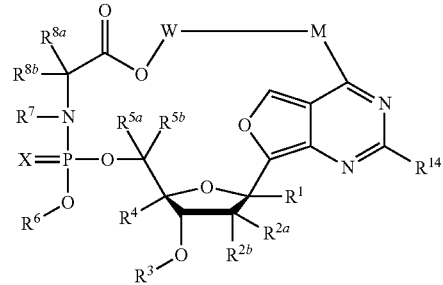

(VI)

wherein:
$R^1$ and $R^4$ are each independently selected from the group consisting of:
1) hydrogen;
2) —CN;
3) halogen;
4) —$N_3$; and
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R^{2a}$ is selected from the group consisting of:
1) hydrogen;
2) halogen;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;

$R^{2b}$ at each occurrence is selected from the group consisting of:
1) hydrogen;
2) halogen;
3) —CN;
4) —$N_3$; and
5) $OR^9$;

$R^3$ and $R^9$ are each independently selected from the group consisting of: hydrogen, hydroxy protecting group, $R^{10}$, —$C(O)R^{10}$, —$C(O)OR^{10}$, and —$C(O)NR^{11a}R^{11b}$; wherein $R^{10}$ at each occurrence is each independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic;

$R^{11a}$ and $R^{11b}$ at each occurrence are each independently selected from the group consisting of: hydrogen and $R^{10}$; or alternatively $R^{11a}$ and $R^{11b}$ taken together with the nitrogen atom to which they are attached form a heterocyclic ring;

$R^{5a}$ and $R^{5b}$ are independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;
or $R^{5a}$ and $R^{5b}$ together with the carbon atom to which they are attached form a group selected from —$C_3$-$C_8$ cycloalkyl, —$C_3$-$C_8$ cycloalkenyl, and —$C_3$-$C_8$ cycloalkynyl.

$R^6$ is selected from the group consisting of:
1) hydrogen;
2) Substituted or unsubstituted —$C_1$-$C_8$ alkyl;
3) Substituted or unsubstituted —$C_3$-$C_8$ cycloalkyl;

4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;
Or $R^7$ and $R^{8a}$ or $R^{8b}$ together form —$(CH_2)_n$— so as to form a cyclic ring which includes the adjoining N and C; wherein n is 2 to 6.

$R^{8a}$ and $R^{8b}$ are independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;
Or $R^{8a}$ and $R^{8b}$ are taken together to form —$(CH_2)_m$—, so as to form a spiro ring with the carbon to which they are attached; wherein, m is 2 to 5.

$R^{14}$ is selected from the group consisting of: hydrogen, halogen, —CN, $N_3$, —C(O)$NR^{11a}R^{11b}$, —$NO_2$, —$OR^9$, —$SR^9$, —$NR^{11a}R^{11b}$, —NHC(O)$R^{10}$, —NHC(O)$OR^{10}$ and —NHC(O)$NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, substituted or unsubstituted —$C_2$-$C_8$ alkynyl; preferably $R^{14}$ is hydrogen;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)—, —NHC(O)O—, and —NHC(O)NH—.

W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_2$ alkynylene each containing 0, 1, 2, or 3 heteroatoms selected from O, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_4$-$C_{12}$ cycloalkenylene each containing 0, 1, 2, or 3 heteroatoms selected from O, S or N;

In another embodiment, the invention provides compounds of Formula VII,

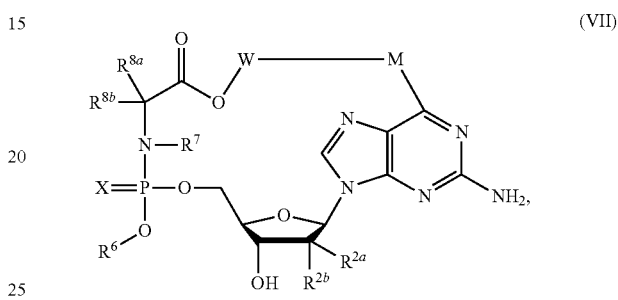

(VII)

where M, W, $R^{2a}$, $R^{2b}$, $R^6$, $R^7$, $R^{8a}$ and $R^{8b}$ are as previously defined.

Representative compounds of the invention include, but are not limited to, the following compounds (example 1 to example 200 in Table 1) according to Formula VII, wherein, $R^{2a}$, $R^{2b}$, $R^6$, $R^7$, $R^{8a}$, $R^{8b}$ and —W-M- are delineated for each example in Table 1.

TABLE 1

| Example # | $R^{2a}$ | $R^{2b}$ | $R^6$ | | —W—M— |
|---|---|---|---|---|---|
| 1 | Me | OH | phenyl | N-acyl (alanine-like) | —$(CH_2)_4$—O— |
| 2 | Me | OH | phenyl | N-acyl (alanine-like) | —$(CH_2)_5$—O— |
| 3 | Me | OH | phenyl | N-acyl (alanine-like) | —$(CH_2)_6$—O— |
| 4 | Me | OH | phenyl | N-acyl (alanine-like) | —$(CH_2)_7$—O— |

TABLE 1-continued
| Example # | $R^{2a}$ | $R^{2b}$ | $R^6$ | 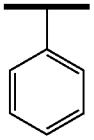 | —W—M— |
|---|---|---|---|---|---|
| 5 | Me | OH | 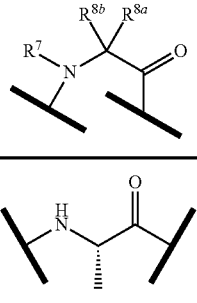 | 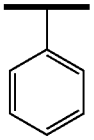 | —(CH$_2$)$_8$—O— |
| 6 | Me | OH | 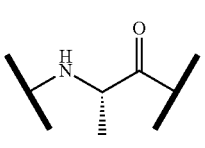 | 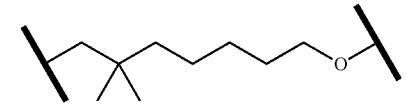 | 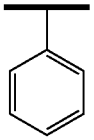 |
| 7 | Me | OH | 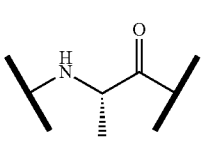 | 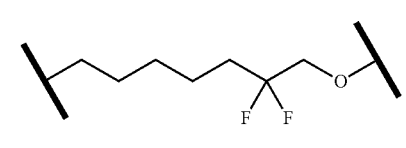 | 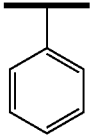 |
| 8 | Me | OH | 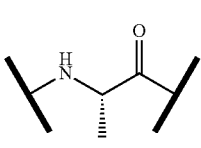 | 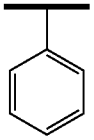 | —(CH$_2$)$_3$—O—(CH$_2$)$_5$—O— |
| 9 | Me | OH | 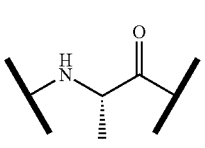 | 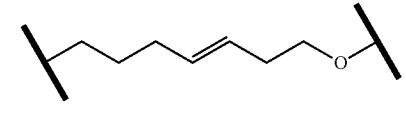 | 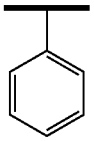 |
| 10 | Me | OH | 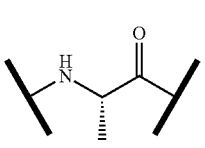 | 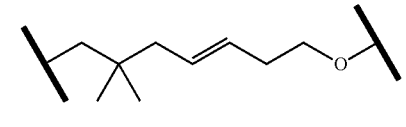 | 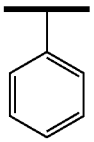 |
| 11 | Me | OH | 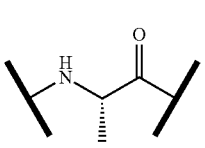 | 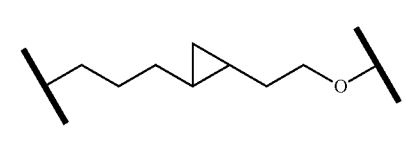 | 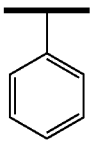 |
| 12 | Me | OH | 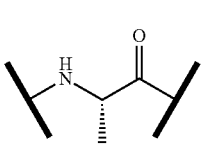 | 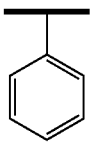 | —(CH$_2$)$_5$—NH— |
| 13 | Me | OH | 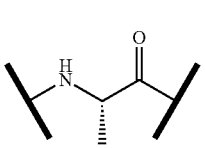 | | —(CH$_2$)$_6$—NH— |

TABLE 1-continued
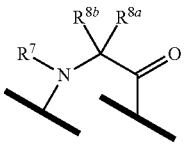
| Example # | $R^{2a}$ | $R^{2b}$ | $R^6$ | | —W—M— |
|---|---|---|---|---|---|
| 14 | Me | OH | 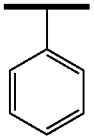 | 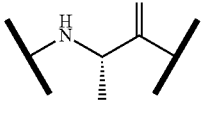 | —(CH$_2$)$_7$—NH— |
| 15 | Me | OH | 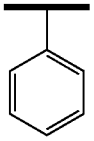 | 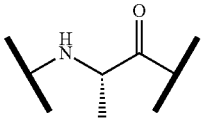 | —(CH$_2$)$_5$—C(O)NH— |
| 16 | Me | OH | 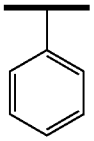 | 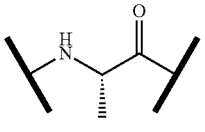 | —(CH$_2$)$_6$—C(O)NH— |
| 17 | Me | OH | 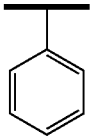 | 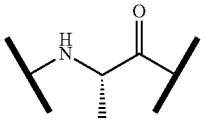 | —(CH$_2$)$_7$—C(O)NH— |
| 18 | Me | OH | 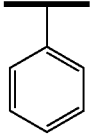 | 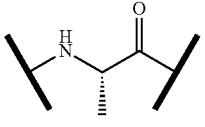 | 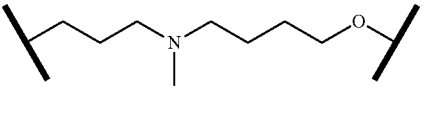 |
| 19 | Me | OH | 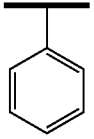 | 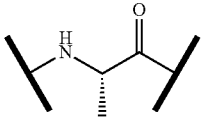 | 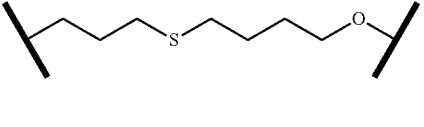 |
| 20 | Me | OH | 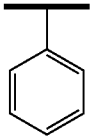 | 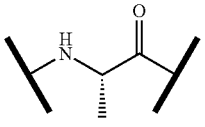 | —(CH$_2$)$_6$—OC(O)NH— |
| 21 | Me | OH | 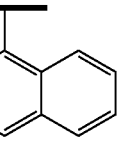 | 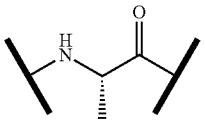 | —(CH$_2$)$_4$—O— |
| 22 | Me | OH | 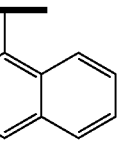 | 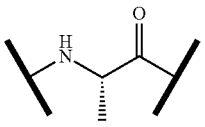 | —(CH$_2$)$_5$—O— |

TABLE 1-continued

| Example # | $R^{2a}$ | $R^{2b}$ | $R^6$ | $R^7\text{—N}(R^{8b})(R^{8a})\text{—C(=O)}$ | —W—M— |
|---|---|---|---|---|---|
| 23 | Me | OH | 1-naphthyl | N-H, α-Me, C=O (L-Ala) | —(CH$_2$)$_6$—O— |
| 24 | Me | OH | 1-naphthyl | N-H, α-Me, C=O (L-Ala) | —(CH$_2$)$_7$—O— |
| 25 | Me | OH | 1-naphthyl | N-H, α-Me, C=O (L-Ala) | —(CH$_2$)$_8$—O— |
| 26 | Me | OH | 1-naphthyl | N-H, α-Me, C=O (L-Ala) | —C(CH$_3$)$_2$(CH$_2$)$_4$—O— |
| 27 | Me | OH | 1-naphthyl | N-H, α-Me, C=O (L-Ala) | —(CH$_2$)$_5$CF$_2$CH$_2$—O— |
| 28 | Me | OH | 1-naphthyl | N-H, α-Me, C=O (L-Ala) | —(CH$_2$)$_3$—O—(CH$_2$)$_5$—O— |
| 29 | Me | OH | 1-naphthyl | N-H, α-Me, C=O (L-Ala) | —(CH$_2$)$_3$CH=CH(CH$_2$)$_2$—O— (trans) |
| 30 | Me | OH | 1-naphthyl | N-H, α-Me, C=O (L-Ala) | —C(CH$_3$)$_2$CH=CH(CH$_2$)$_2$—O— (trans) |
| 31 | Me | OH | 1-naphthyl | N-H, α-Me, C=O (L-Ala) | —(CH$_2$)$_3$-cyclopropyl-(CH$_2$)$_2$—O— |

TABLE 1-continued
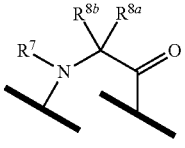
| Example # | $R^{2a}$ | $R^{2b}$ | $R^6$ | | —W—M— |
|---|---|---|---|---|---|
| 32 | Me | OH | 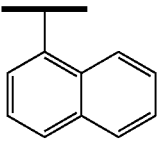 | 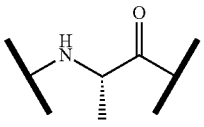 | —(CH$_2$)$_5$—NH— |
| 33 | Me | OH | 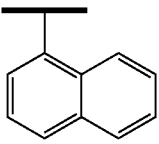 | 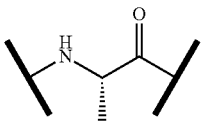 | —(CH$_2$)$_6$—NH— |
| 34 | Me | OH | 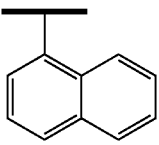 | 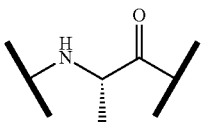 | —(CH$_2$)$_7$—NH— |
| 35 | Me | OH | 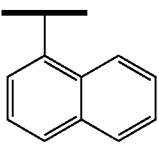 | 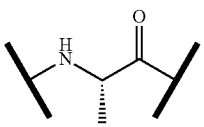 | —(CH$_2$)$_5$—C(O)NH— |
| 36 | Me | OH | 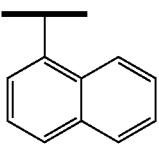 | 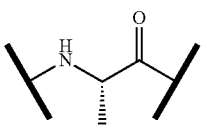 | —(CH$_2$)$_6$—C(O)NH— |
| 37 | Me | OH | 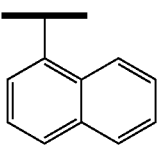 | 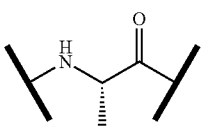 | —(CH$_2$)$_7$—C(O)NH— |
| 38 | Me | OH | 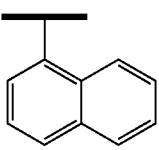 | 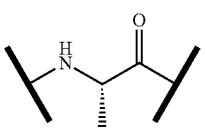 | 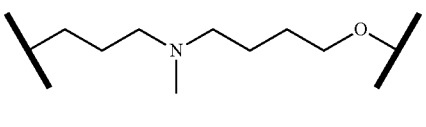 |
| 39 | Me | OH | 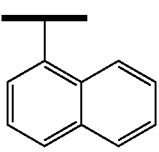 | 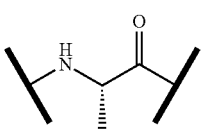 | 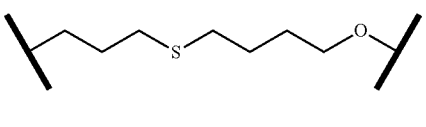 |
| 40 | Me | OH | 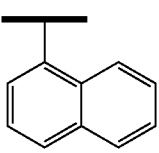 | 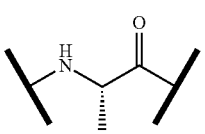 | —(CH$_2$)$_6$—OC(O)NH— |

TABLE 1-continued
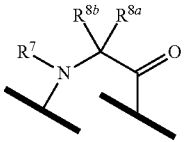
| Example # | $R^{2a}$ | $R^{2b}$ | $R^6$ | | —W—M— |
|---|---|---|---|---|---|
| 41 | Me | F | 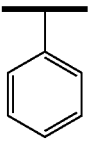 | 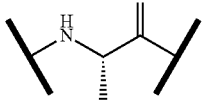 | —(CH$_2$)$_4$—O— |
| 42 | Me | F | 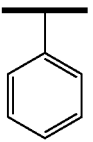 | 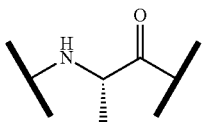 | —(CH$_2$)$_5$—O— |
| 43 | Me | F | 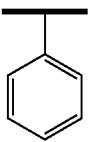 | 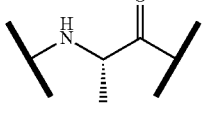 | —(CH$_2$)$_6$—O— |
| 44 | Me | F | 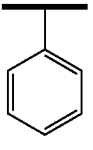 | 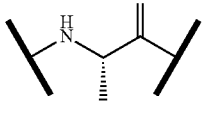 | —(CH$_2$)$_7$—O— |
| 45 | Me | F | 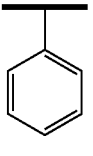 | 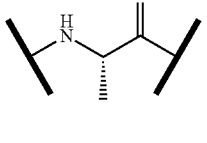 | —(CH$_2$)$_8$—O— |
| 46 | Me | F | 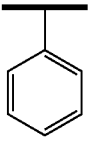 | 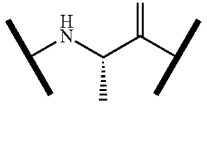 | 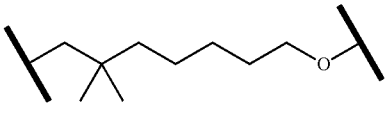 |
| 47 | Me | F | 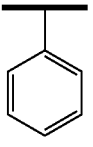 | 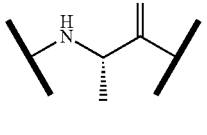 | 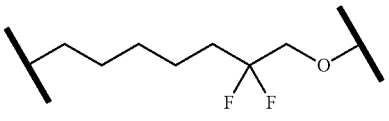 |
| 48 | Me | F | 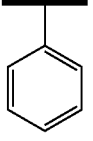 | 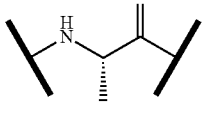 | —(CH$_2$)$_3$—O—(CH$_2$)$_5$—O— |
| 49 | Me | F | 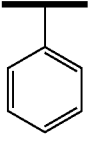 | 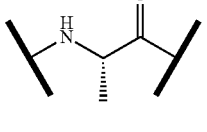 | 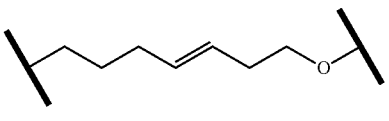 |

TABLE 1-continued

| Example # | $R^{2a}$ | $R^{2b}$ | $R^6$ | (R⁷,R⁸ᵃ,R⁸ᵇ group) | —W—M— |
|---|---|---|---|---|---|
| 50 | Me | F | phenyl | NH-CH(Me)-C(O) | gem-dimethyl-CH₂-CH=CH-CH₂-CH₂-O |
| 51 | Me | F | phenyl | NH-CH(Me)-C(O) | -(CH₂)₃-cyclopropyl-CH₂-CH₂-O- |
| 52 | Me | F | phenyl | NH-CH(Me)-C(O) | —(CH₂)₅—NH— |
| 53 | Me | F | phenyl | NH-CH(Me)-C(O) | —(CH₂)₆—NH— |
| 54 | Me | F | phenyl | NH-CH(Me)-C(O) | —(CH₂)₇—NH— |
| 55 | Me | F | phenyl | NH-CH(Me)-C(O) | —(CH₂)₅—C(O)NH— |
| 56 | Me | F | phenyl | NH-CH(Me)-C(O) | —(CH₂)₆—C(O)NH— |
| 57 | Me | F | phenyl | NH-CH(Me)-C(O) | —(CH₂)₇—C(O)NH— |
| 58 | Me | F | phenyl | NH-CH(Me)-C(O) | -(CH₂)₃-N(Me)-(CH₂)₄-O- |

TABLE 1-continued
| Example # | $R^{2a}$ | $R^{2b}$ | $R^6$ | | —W—M— |
|---|---|---|---|---|---|
| 59 | Me | F | 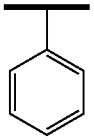 |  |  |
| 60 | Me | F |  |  | —(CH$_2$)$_6$—OC(O)NH— |
| 61 | Me | F |  |  | —(CH$_2$)$_4$—O— |
| 62 | Me | F |  |  | —(CH$_2$)$_5$—O— |
| 63 | Me | F |  |  | —(CH$_2$)$_6$—O— |
| 64 | Me | F |  |  | —(CH$_2$)$_7$—O— |
| 65 | Me | F |  |  | —(CH$_2$)$_8$—O— |
| 66 | Me | F |  |  |  |
| 67 | Me | F |  |  | |

TABLE 1-continued

| Example # | R²ᵃ | R²ᵇ | R⁶ | [central group] | —W—M— |
|---|---|---|---|---|---|
| 68 | Me | F | 1-naphthyl | NH-CH(Me)-C(O) | —(CH₂)₃—O—(CH₂)₅—O— |
| 69 | Me | F | 1-naphthyl | NH-CH(Me)-C(O) | —(CH₂)₄—CH=CH—CH₂—O— |
| 70 | Me | F | 1-naphthyl | NH-CH(Me)-C(O) | —C(Me)₂—CH₂—CH=CH—CH₂—O— |
| 71 | Me | F | 1-naphthyl | NH-CH(Me)-C(O) | —(CH₂)₃—(cyclopropyl)—CH₂—O— |
| 72 | Me | F | 1-naphthyl | NH-CH(Me)-C(O) | —(CH₂)₅—NH— |
| 73 | Me | F | 1-naphthyl | NH-CH(Me)-C(O) | —(CH₂)₆—NH— |
| 74 | Me | F | 1-naphthyl | NH-CH(Me)-C(O) | —(CH₂)₇—NH— |
| 75 | Me | F | 1-naphthyl | NH-CH(Me)-C(O) | —(CH₂)₅—C(O)NH— |
| 76 | Me | F | 1-naphthyl | NH-CH(Me)-C(O) | —(CH₂)₆—C(O)NH— |

TABLE 1-continued

| Example # | $R^{2a}$ | $R^{2b}$ | $R^6$ | (R⁷,R⁸ᵇ,R⁸ᵃ fragment) | —W—M— |
|---|---|---|---|---|---|
| 77 | Me | F | 1-naphthyl | NH-Ala | —(CH$_2$)$_7$—C(O)NH— |
| 78 | Me | F | 1-naphthyl | NH-Ala | —(CH$_2$)$_3$—N(CH$_3$)—(CH$_2$)$_4$—O— |
| 79 | Me | F | 1-naphthyl | NH-Ala | —(CH$_2$)$_3$—S—(CH$_2$)$_4$—O— |
| 80 | Me | F | 1-naphthyl | NH-Ala | —(CH$_2$)$_6$—OC(O)NH— |
| 81 | CHF$_2$ | OH | benzyl | NH-Ala | —(CH$_2$)$_4$—O— |
| 82 | CHF$_2$ | OH | benzyl | NH-Ala | —(CH$_2$)$_5$—O— |
| 83 | CHF$_2$ | OH | benzyl | NH-Ala | —(CH$_2$)$_6$—O— |
| 84 | CHF$_2$ | OH | benzyl | NH-Ala | —(CH$_2$)$_7$—O— |
| 85 | CHF$_2$ | OH | benzyl | NH-Ala | —(CH$_2$)$_8$—O— |

TABLE 1-continued

| Example # | $R^{2a}$ | $R^{2b}$ | $R^6$ | [R7/R8a/R8b group] | —W—M— |
|---|---|---|---|---|---|
| 86 | $CHF_2$ | OH | phenyl | —NH—CH(CH$_3$)—C(O)— | gem-dimethyl alkyl–O– chain |
| 87 | $CHF_2$ | OH | phenyl | —NH—CH(CH$_3$)—C(O)— | alkyl-CF$_2$-CH$_2$–O– chain |
| 88 | $CHF_2$ | OH | phenyl | —NH—CH(CH$_3$)—C(O)— | —(CH$_2$)$_3$—O—(CH$_2$)$_5$—O— |
| 89 | $CHF_2$ | OH | phenyl | —NH—CH(CH$_3$)—C(O)— | alkenyl–CH$_2$–O– chain |
| 90 | $CHF_2$ | OH | phenyl | —NH—CH(CH$_3$)—C(O)— | gem-dimethyl alkenyl–O– chain |
| 91 | $CHF_2$ | OH | phenyl | —NH—CH(CH$_3$)—C(O)— | alkyl–cyclopropyl–CH$_2$–O– chain |
| 92 | $CHF_2$ | OH | phenyl | —NH—CH(CH$_3$)—C(O)— | —(CH$_2$)$_5$—NH— |
| 93 | $CHF_2$ | OH | phenyl | —NH—CH(CH$_3$)—C(O)— | —(CH$_2$)$_6$—NH— |
| 94 | $CHF_2$ | OH | phenyl | —NH—CH(CH$_3$)—C(O)— | —(CH$_2$)$_7$—NH— |

TABLE 1-continued
| Example # | $R^{2a}$ | $R^{2b}$ | $R^6$ | 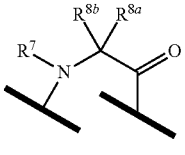 | —W—M— |
|---|---|---|---|---|---|
| 95 | $CHF_2$ | OH | 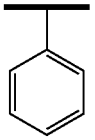 | 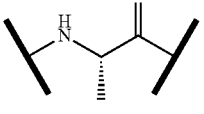 | —$(CH_2)_5$—C(O)NH— |
| 96 | $CHF_2$ | OH | 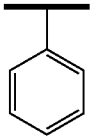 | 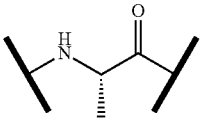 | —$(CH_2)_6$—C(O)NH— |
| 97 | $CHF_2$ | OH | 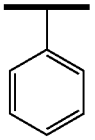 | 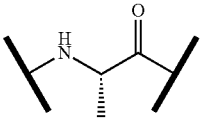 | —$(CH_2)_7$—C(O)NH— |
| 98 | $CHF_2$ | OH | 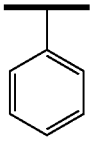 | 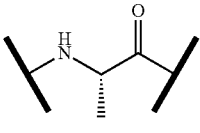 | 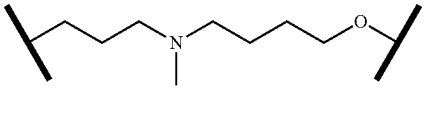 |
| 99 | $CHF_2$ | OH | 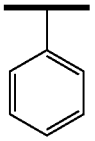 | 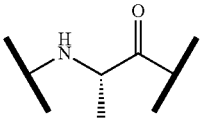 | 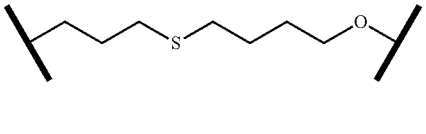 |
| 100 | $CHF_2$ | OH | 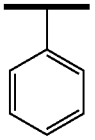 | 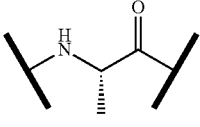 | —$(CH_2)_6$—OC(O)NH— |
| 101 | $CHF_2$ | OH | 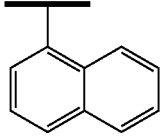 | 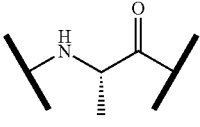 | —$(CH_2)_4$—O— |
| 102 | $CHF_2$ | OH | 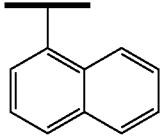 | 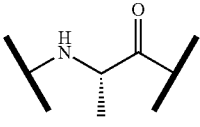 | —$(CH_2)_5$—O— |
| 103 | $CHF_2$ | OH | 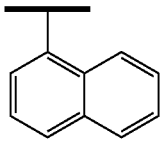 | 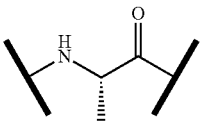 | —$(CH_2)_6$—O— |

TABLE 1-continued

| Example # | $R^{2a}$ | $R^{2b}$ | $R^6$ | [R7/R8a/R8b group] | —W—M— |
|---|---|---|---|---|---|
| 104 | $CHF_2$ | OH | naphthyl | alanine-NH | $-(CH_2)_7-O-$ |
| 105 | $CHF_2$ | OH | naphthyl | alanine-NH | $-(CH_2)_8-O-$ |
| 106 | $CHF_2$ | OH | naphthyl | alanine-NH | gem-dimethyl alkyl-O- |
| 107 | $CHF_2$ | OH | naphthyl | alanine-NH | gem-difluoro alkyl-O- |
| 108 | $CHF_2$ | OH | naphthyl | alanine-NH | $-(CH_2)_3-O-(CH_2)_5-O-$ |
| 109 | $CHF_2$ | OH | naphthyl | alanine-NH | alkenyl-O- |
| 110 | $CHF_2$ | OH | naphthyl | alanine-NH | gem-dimethyl alkenyl-O- |
| 111 | $CHF_2$ | OH | naphthyl | alanine-NH | cyclopropyl-containing alkyl-O- |
| 112 | $CHF_2$ | OH | naphthyl | alanine-NH | $-(CH_2)_5-NH-$ |

TABLE 1-continued
| Example # | R$^{2a}$ | R$^{2b}$ | R$^6$ | | —W—M— |
|---|---|---|---|---|---|
| 113 | CHF$_2$ | OH | 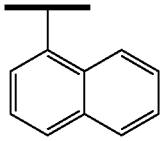 | 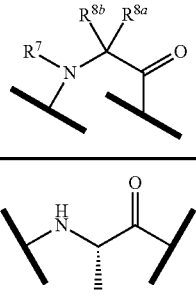 | —(CH$_2$)$_6$—NH— |
| 114 | CHF$_2$ | OH | 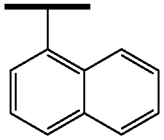 | 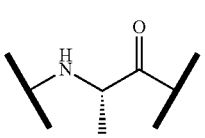 | —(CH$_2$)$_7$—NH— |
| 115 | CHF$_2$ | OH | 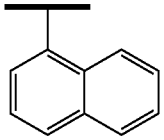 | 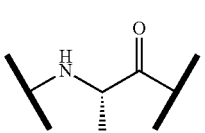 | —(CH$_2$)$_5$—C(O)NH— |
| 116 | CHF$_2$ | OH | 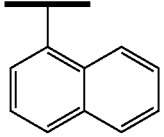 | 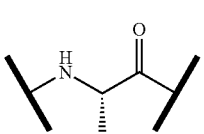 | —(CH$_2$)$_6$—C(O)NH— |
| 117 | CHF$_2$ | OH | 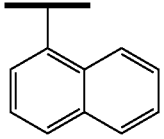 | 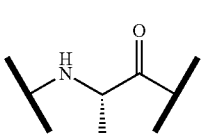 | —(CH$_2$)$_7$—C(O)NH— |
| 118 | CHF$_2$ | OH | 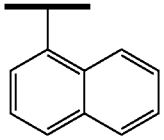 | 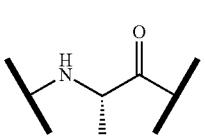 | 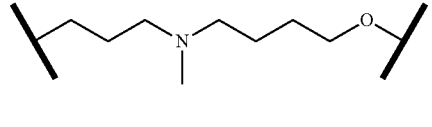 |
| 119 | CHF$_2$ | OH | 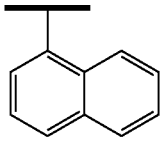 | 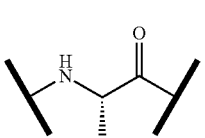 | 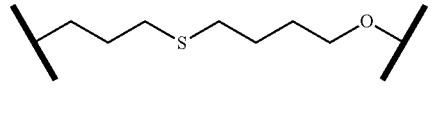 |
| 120 | CHF$_2$ | OH | 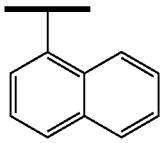 | 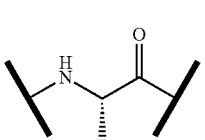 | —(CH$_2$)$_6$—OC(O)NH— |
| 121 | CHF$_2$ | F | 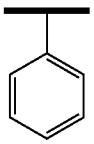 | 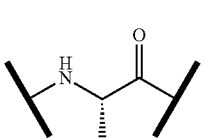 | —(CH$_2$)$_4$—O— |

TABLE 1-continued
| Example # | R²ᵃ | R²ᵇ | R⁶ | 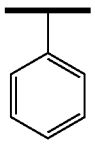 | —W—M— |
|---|---|---|---|---|---|
| 122 | CHF₂ | F | 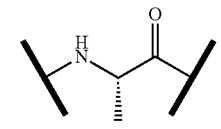 |  | —(CH₂)₅—O— |
| 123 | CHF₂ | F | 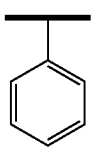 | 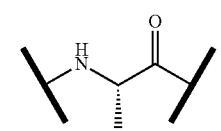 | —(CH₂)₆—O— |
| 124 | CHF₂ | F |  | 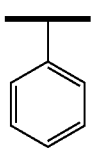 | —(CH₂)₇—O— |
| 125 | CHF₂ | F | 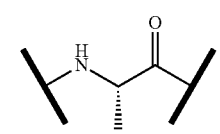 |  | —(CH₂)₈—O— |
| 126 | CHF₂ | F | 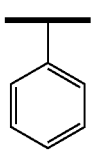 | 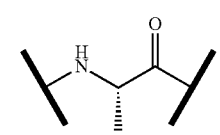 |  |
| 127 | CHF₂ | F | 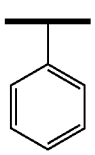 | 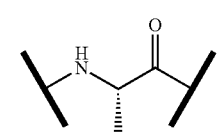 | 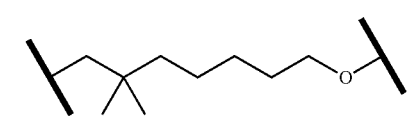 |
| 128 | CHF₂ | F | 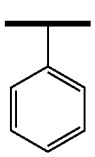 | 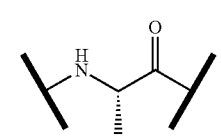 | —(CH₂)₃—O—(CH₂)₅—O— |
| 129 | CHF₂ | F | 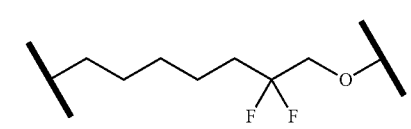 | 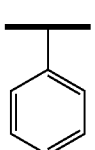 | 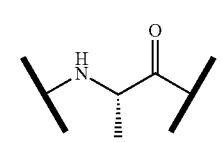 |
| 130 | CHF₂ | F | 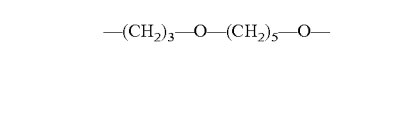 | 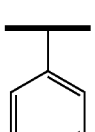 | 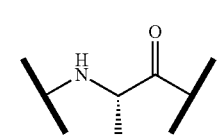 |

TABLE 1-continued

| Example # | $R^{2a}$ | $R^{2b}$ | $R^6$ | (R⁷N(R⁸ᵇ)(R⁸ᵃ)C=O group) | —W—M— |
|---|---|---|---|---|---|
| 131 | $CHF_2$ | F | phenyl | NH-CH(CH₃)-C(O) | —(CH₂)—cyclopropyl—(CH₂)₂—O— |
| 132 | $CHF_2$ | F | phenyl | NH-CH(CH₃)-C(O) | —(CH₂)₅—NH— |
| 133 | $CHF_2$ | F | phenyl | NH-CH(CH₃)-C(O) | —(CH₂)₆—NH— |
| 134 | $CHF_2$ | F | phenyl | NH-CH(CH₃)-C(O) | —(CH₂)₇—NH— |
| 135 | $CHF_2$ | F | phenyl | NH-CH(CH₃)-C(O) | —(CH₂)₅—C(O)NH— |
| 136 | $CHF_2$ | F | phenyl | NH-CH(CH₃)-C(O) | —(CH₂)₆—C(O)NH— |
| 137 | $CHF_2$ | F | phenyl | NH-CH(CH₃)-C(O) | —(CH₂)₇—C(O)NH— |
| 138 | $CHF_2$ | F | phenyl | NH-CH(CH₃)-C(O) | —(CH₂)₃—N(CH₃)—(CH₂)₄—O— |
| 139 | $CHF_2$ | F | phenyl | NH-CH(CH₃)-C(O) | —(CH₂)₃—S—(CH₂)₃—O— |

TABLE 1-continued
| Example # | $R^{2a}$ | $R^{2b}$ | $R^6$ | $R^7$, $R^{8a}$, $R^{8b}$ | —W—M— |
|---|---|---|---|---|---|
| 140 | $CHF_2$ | F | 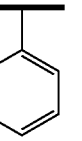 | 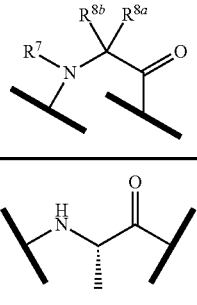 | —$(CH_2)_6$—OC(O)NH— |
| 141 | $CHF_2$ | F | 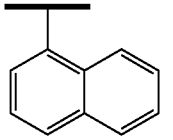 | 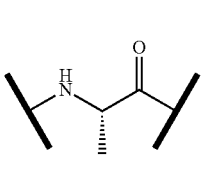 | —$(CH_2)_4$—O— |
| 142 | $CHF_2$ | F | 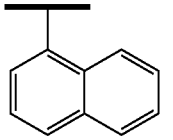 | 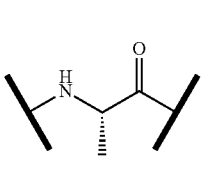 | —$(CH_2)_5$—O— |
| 143 | $CHF_2$ | F | 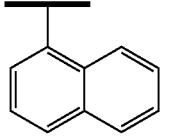 | 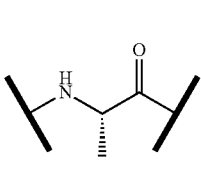 | —$(CH_2)_6$—O— |
| 144 | $CHF_2$ | F | 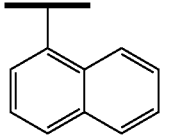 | 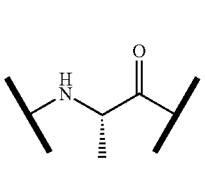 | —$(CH_2)_7$—O— |
| 145 | $CHF_2$ | F | 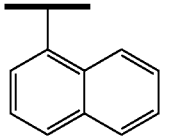 | 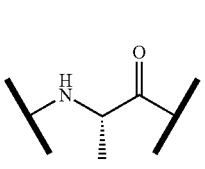 | —$(CH_2)_8$—O— |
| 146 | $CHF_2$ | F | 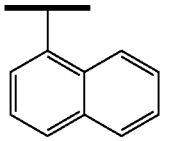 | 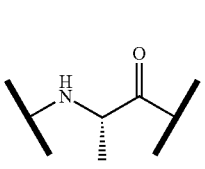 | 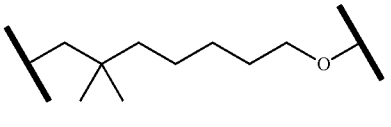 |
| 147 | $CHF_2$ | F | 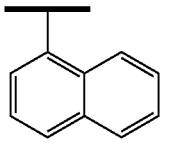 | 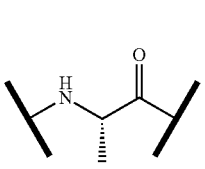 | 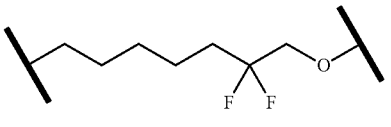 |
| 148 | $CHF_2$ | F | 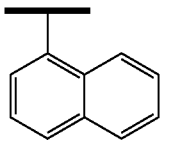 | 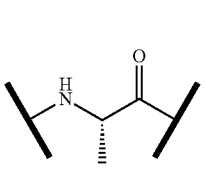 | —$(CH_2)_3$—O—$(CH_2)_5$—O— |

TABLE 1-continued

| Example # | $R^{2a}$ | $R^{2b}$ | $R^6$ | [R⁷R⁸ᵇR⁸ᵃ group] | —W—M— |
|---|---|---|---|---|---|
| 149 | $CHF_2$ | F | 1-naphthyl | NH-CH(CH₃)-C(O) | -CH₂CH₂CH₂-CH=CH-CH₂CH₂-O- |
| 150 | $CHF_2$ | F | 1-naphthyl | NH-CH(CH₃)-C(O) | -CH₂-C(CH₃)₂-CH₂-CH=CH-CH₂CH₂-O- |
| 151 | $CHF_2$ | F | 1-naphthyl | NH-CH(CH₃)-C(O) | -CH₂CH₂CH₂-(cyclopropyl)-CH₂CH₂-O- |
| 152 | $CHF_2$ | F | 1-naphthyl | NH-CH(CH₃)-C(O) | $-(CH_2)_5-NH-$ |
| 153 | $CHF_2$ | F | 1-naphthyl | NH-CH(CH₃)-C(O) | $-(CH_2)_6-NH-$ |
| 154 | $CHF_2$ | F | 1-naphthyl | NH-CH(CH₃)-C(O) | $-(CH_2)_7-NH-$ |
| 155 | $CHF_2$ | F | 1-naphthyl | NH-CH(CH₃)-C(O) | $-(CH_2)_5-C(O)NH-$ |
| 156 | $CHF_2$ | F | 1-naphthyl | NH-CH(CH₃)-C(O) | $-(CH_2)_6-C(O)NH-$ |
| 157 | $CHF_2$ | F | 1-naphthyl | NH-CH(CH₃)-C(O) | $-(CH_2)_7-C(O)NH-$ |

TABLE 1-continued

| Example # | $R^{2a}$ | $R^{2b}$ | $R^6$ | (R⁷R⁸ᵇR⁸ᵃ fragment) | —W—M— |
|---|---|---|---|---|---|
| 158 | $CHF_2$ | F | 1-naphthyl | NH-CH(CH₃)-C(O) (S) | —(CH₂)₃—N(CH₃)—(CH₂)₄—O— |
| 159 | $CHF_2$ | F | 1-naphthyl | NH-CH(CH₃)-C(O) (S) | —(CH₂)₃—S—(CH₂)₄—O— |
| 160 | $CHF_2$ | F | 1-naphthyl | NH-CH(CH₃)-C(O) (S) | —(CH₂)₆—OC(O)NH— |
| 161 | Me | OH | benzyl | NH-CH(CH₂CH(CH₃)₂)-C(O) | —(CH₂)₄—O— |
| 162 | Me | OH | benzyl | NH-CH(CH₂CH(CH₃)₂)-C(O) | —(CH₂)₅—O— |
| 163 | Me | OH | benzyl | NH-CH(CH₂CH(CH₃)₂)-C(O) | —(CH₂)₆—O— |
| 164 | Me | OH | benzyl | NH-CH(CH₂CH(CH₃)₂)-C(O) | —(CH₂)₇—O— |
| 165 | Me | OH | benzyl | NH-CH(CH₂CH(CH₃)₂)-C(O) | —(CH₂)₈—O— |

TABLE 1-continued
| Example # | $R^{2a}$ | $R^{2b}$ | $R^6$ | | —W—M— |
|---|---|---|---|---|---|
| 166 | Me | OH | 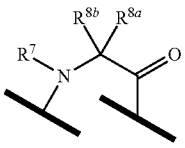 | 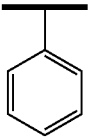 | 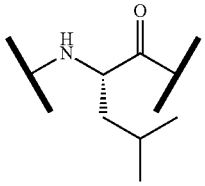 |
| 167 | Me | OH | 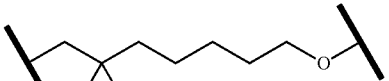 | 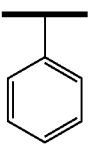 | 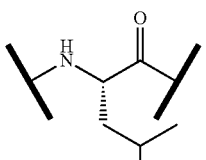 |
| 168 | Me | OH | 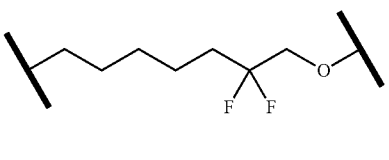 | 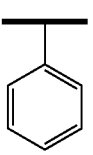 | —(CH$_2$)$_3$—O—(CH$_2$)$_5$—O— |
| 169 | Me | OH | 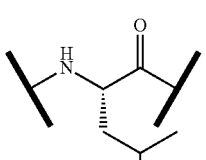 | 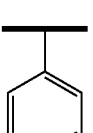 | 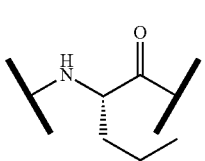 |
| 170 | Me | OH | 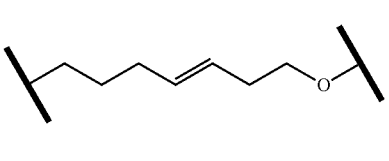 | 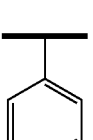 | 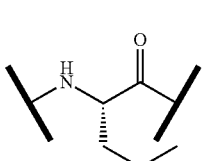 |
| 171 | Me | OH | 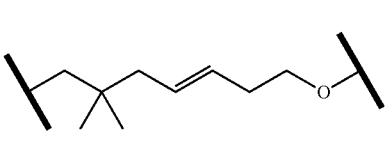 | 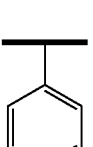 | 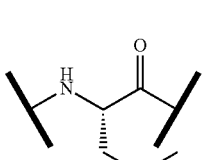 |
| 172 | Me | OH | 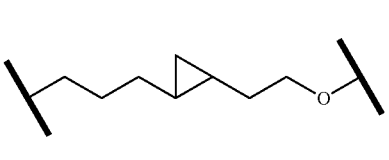 | 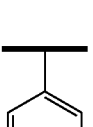 | —(CH$_2$)$_5$—NH— |

TABLE 1-continued

| Example # | R²ᵃ | R²ᵇ | R⁶ | | —W—M— |
|---|---|---|---|---|---|
| 173 | Me | OH | phenyl | leucinamide | —(CH$_2$)$_6$—NH— |
| 174 | Me | OH | phenyl | leucinamide | —(CH$_2$)$_7$—NH— |
| 175 | Me | OH | phenyl | leucinamide | —(CH$_2$)$_5$—C(O)NH— |
| 176 | Me | OH | phenyl | leucinamide | —(CH$_2$)$_6$—C(O)NH— |
| 177 | Me | OH | phenyl | leucinamide | —(CH$_2$)$_7$—C(O)NH— |
| 178 | Me | OH | phenyl | leucinamide | (CH$_2$)$_n$N(Me)(CH$_2$)$_m$O linker |
| 179 | Me | OH | phenyl | leucinamide | (CH$_2$)$_n$S(CH$_2$)$_m$O linker |

TABLE 1-continued
| Example # | $R^{2a}$ | $R^{2b}$ | $R^6$ | | —W—M— |
|---|---|---|---|---|---|
| 180 | Me | OH | 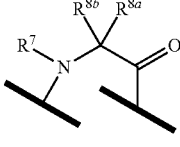 | 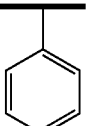 | —(CH$_2$)$_6$—OC(O)NH— |
| 181 | Me | F | 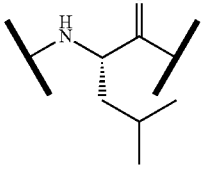 | 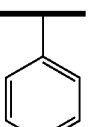 | —(CH$_2$)$_4$—O— |
| 182 | Me | F | 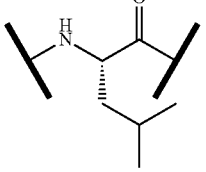 | 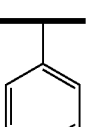 | —(CH$_2$)$_5$—O— |
| 183 | Me | F | 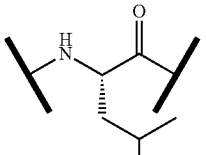 | 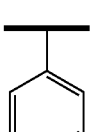 | —(CH$_2$)$_6$—O— |
| 184 | Me | F | 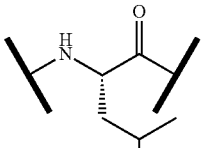 | 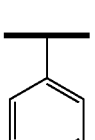 | —(CH$_2$)$_7$—O— |
| 185 | Me | F | 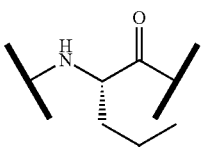 | 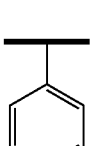 | —(CH$_2$)$_8$—O— |
| 186 | Me | F | 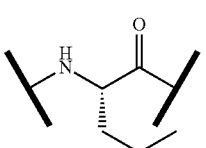 | 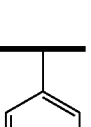 | 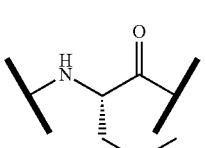 |

TABLE 1-continued
| Example # | $R^{2a}$ | $R^{2b}$ | $R^6$ | 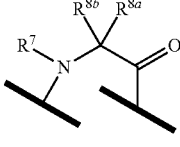 | —W—M— |
|---|---|---|---|---|---|
| 187 | Me | F | 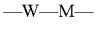 | 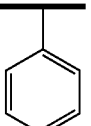 | 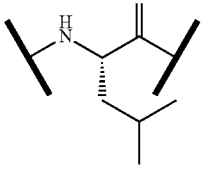 |
| 188 | Me | F | 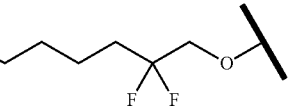 | 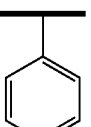 | —(CH$_2$)$_3$—O—(CH$_2$)$_5$—O— |
| 189 | Me | F | 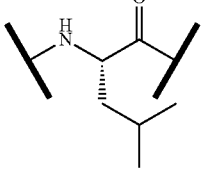 | 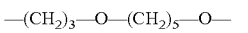 | 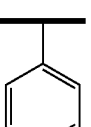 |
| 190 | Me | F | 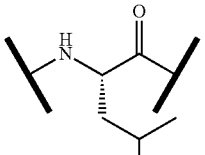 | 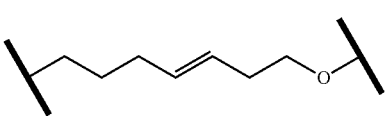 | 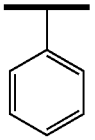 |
| 191 | Me | F |  | 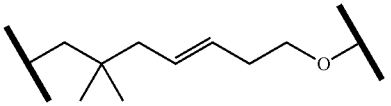 | 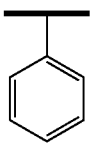 |
| 192 | Me | F | 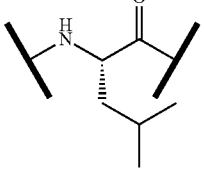 | 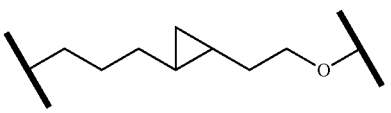 | —(CH$_2$)$_5$—NH— |
| 193 | Me | F | 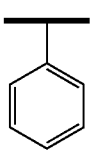 | 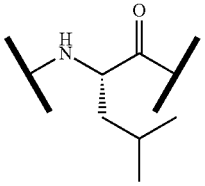 | —(CH$_2$)$_6$—NH— |

TABLE 1-continued
| Example # | $R^{2a}$ | $R^{2b}$ | $R^6$ | | —W—M— |
|---|---|---|---|---|---|
| 194 | Me | F | 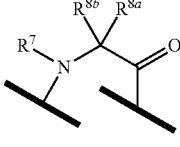 |  | —(CH$_2$)$_7$—NH— |
| 195 | Me | F | 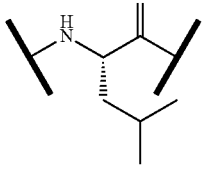 | 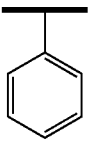 | —(CH$_2$)$_5$—C(O)NH— |
| 196 | Me | F |  | 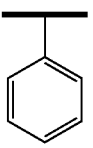 | —(CH$_2$)$_6$—C(O)NH— |
| 197 | Me | F | 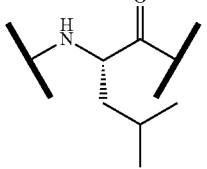 |  | —(CH$_2$)$_7$—C(O)NH— |
| 198 | Me | F | 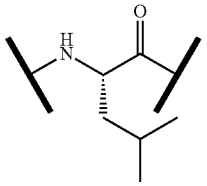 | 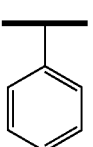 |  |
| 199 | Me | F | 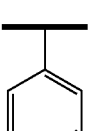 | 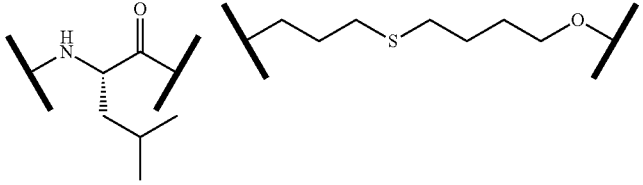 |  |
| 200 | Me | F | 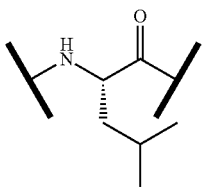 | | —(CH$_2$)$_6$—OC(O)NH— |

In another embodiment, the invention provides compounds of Formula VIII,

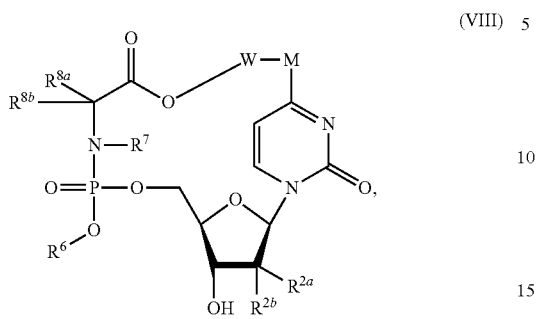

(VIII)

where M, W, $R^{2a}$, $R^{2b}$, $R^6$, $R^7$, $R^{8a}$ and $R^{8b}$ are as previously defined.

Representative compounds of the invention include, but are not limited to, the following compounds (example 201 to example 400 in Table 2) according to Formula VIII, wherein, $R^{2a}$, $R^{2b}$, $R^6$, $R^7$, $R^{8a}$, $R^{8b}$ and —W-M- are delineated for each example in Table 2.

TABLE 2

| Example# | $R^{2a}$ | $R^{2b}$ | $R^6$ | ![R8b R8a / R7-N] | —W—M— |
|---|---|---|---|---|---|
| 201 | Me | OH | Ph | NH-CH(Me)-C(=O) | —(CH$_2$)$_4$—O— |
| 202 | Me | OH | Ph | NH-CH(Me)-C(=O) | —(CH$_2$)$_5$—O— |
| 203 | Me | OH | Ph | NH-CH(Me)-C(=O) | —(CH$_2$)$_6$—O— |
| 204 | Me | OH | Ph | NH-CH(Me)-C(=O) | —(CH$_2$)$_7$—O— |
| 205 | Me | OH | Ph | NH-CH(Me)-C(=O) | —(CH$_2$)$_8$—O— |

TABLE 2-continued

| Example# | R<sup>2a</sup> | R<sup>2b</sup> | R<sup>6</sup> | R<sup>7</sup>N(R<sup>8b</sup>)(R<sup>8a</sup>)C(O) | —W—M— |
|---|---|---|---|---|---|
| 206 | Me | OH | phenyl | NH-CH(CH₃)-C(O) | gem-dimethyl alkyl-O- chain |
| 207 | Me | OH | phenyl | NH-CH(CH₃)-C(O) | alkyl-CF₂-CH₂-O- chain |
| 208 | Me | OH | phenyl | NH-CH(CH₃)-C(O) | —(CH₂)₃—O—(CH₂)₅—O— |
| 209 | Me | OH | phenyl | NH-CH(CH₃)-C(O) | alkenyl-CH₂-O- chain |
| 210 | Me | OH | phenyl | NH-CH(CH₃)-C(O) | gem-dimethyl alkenyl-CH₂-O- chain |
| 211 | Me | OH | phenyl | NH-CH(CH₃)-C(O) | cyclopropyl-containing alkyl-O- chain |
| 212 | Me | OH | phenyl | NH-CH(CH₃)-C(O) | —(CH₂)₅—NH— |
| 213 | Me | OH | phenyl | NH-CH(CH₃)-C(O) | —(CH₂)₆—NH— |
| 214 | Me | OH | phenyl | NH-CH(CH₃)-C(O) | —(CH₂)₇—NH— |

TABLE 2-continued

| Example# | R²ᵃ | R²ᵇ | R⁶ | R⁷\N(R⁸ᵇ)(R⁸ᵃ)C(O) | —W—M— |
|---|---|---|---|---|---|
| 215 | Me | OH | benzyl | NH-CH(Me)-C(O) | —(CH₂)₅—C(O)NH— |
| 216 | Me | OH | benzyl | NH-CH(Me)-C(O) | —(CH₂)₆—C(O)NH— |
| 217 | Me | OH | benzyl | NH-CH(Me)-C(O) | —(CH₂)₇—C(O)NH— |
| 218 | Me | OH | benzyl | NH-CH(Me)-C(O) | —(CH₂)₃—N(Me)—(CH₂)₄—O— |
| 219 | Me | OH | benzyl | NH-CH(Me)-C(O) | —(CH₂)₃—S—(CH₂)₄—O— |
| 220 | Me | OH | benzyl | NH-CH(Me)-C(O) | —(CH₂)₆—OC(O)NH— |
| 221 | Me | OH | 1-naphthylmethyl | NH-CH(Me)-C(O) | —(CH₂)₄—O— |
| 222 | Me | OH | 1-naphthylmethyl | NH-CH(Me)-C(O) | —(CH₂)₅—O— |
| 223 | Me | OH | 1-naphthylmethyl | NH-CH(Me)-C(O) | —(CH₂)₆—O— |

TABLE 2-continued

| Example# | R$^{2a}$ | R$^{2b}$ | R$^6$ | [R$^7$N(R$^{8b}$)(R$^{8a}$)C(O)] | —W—M— |
|---|---|---|---|---|---|
| 224 | Me | OH | 1-naphthyl-CH$_2$ | NH-CH(Me)-C(O) | —(CH$_2$)$_7$—O— |
| 225 | Me | OH | 1-naphthyl-CH$_2$ | NH-CH(Me)-C(O) | —(CH$_2$)$_8$—O— |
| 226 | Me | OH | 1-naphthyl-CH$_2$ | NH-CH(Me)-C(O) | —C(Me)$_2$(CH$_2$)$_4$—O— |
| 227 | Me | OH | 1-naphthyl-CH$_2$ | NH-CH(Me)-C(O) | —(CH$_2$)$_5$CF$_2$CH$_2$—O— |
| 228 | Me | OH | 1-naphthyl-CH$_2$ | NH-CH(Me)-C(O) | —(CH$_2$)$_3$—O—(CH$_2$)$_5$—O— |
| 229 | Me | OH | 1-naphthyl-CH$_2$ | NH-CH(Me)-C(O) | —(CH$_2$)$_4$CH=CHCH$_2$—O— |
| 230 | Me | OH | 1-naphthyl-CH$_2$ | NH-CH(Me)-C(O) | —C(Me)$_2$CH$_2$CH=CHCH$_2$—O— |
| 231 | Me | OH | 1-naphthyl-CH$_2$ | NH-CH(Me)-C(O) | —(CH$_2$)$_3$-cyclopropyl-(CH$_2$)$_2$—O— |
| 232 | Me | OH | 1-naphthyl-CH$_2$ | NH-CH(Me)-C(O) | —(CH$_2$)$_5$—NH— |

TABLE 2-continued

| Example# | R²ᵃ | R²ᵇ | R⁶ | R⁷,R⁸ᵃ,R⁸ᵇ group | —W—M— |
|---|---|---|---|---|---|
| 233 | Me | OH | 1-naphthyl | NH-CH(Me)-C(O) | —(CH$_2$)$_6$—NH— |
| 234 | Me | OH | 1-naphthyl | NH-CH(Me)-C(O) | —(CH$_2$)$_7$—NH— |
| 235 | Me | OH | 1-naphthyl | NH-CH(Me)-C(O) | —(CH$_2$)$_5$—C(O)NH— |
| 236 | Me | OH | 1-naphthyl | NH-CH(Me)-C(O) | —(CH$_2$)$_6$—C(O)NH— |
| 237 | Me | OH | 1-naphthyl | NH-CH(Me)-C(O) | —(CH$_2$)$_7$—C(O)NH— |
| 238 | Me | OH | 1-naphthyl | NH-CH(Me)-C(O) | —(CH$_2$)$_3$—N(Me)—(CH$_2$)$_4$—O— |
| 239 | Me | OH | 1-naphthyl | NH-CH(Me)-C(O) | —(CH$_2$)$_3$—S—(CH$_2$)$_4$—O— |
| 240 | Me | OH | 1-naphthyl | NH-CH(Me)-C(O) | —(CH$_2$)$_6$—OC(O)NH— |
| 241 | Me | F | phenyl | NH-CH(Me)-C(O) | —(CH$_2$)$_4$—O— |

TABLE 2-continued

| Example# | R$^{2a}$ | R$^{2b}$ | R$^6$ | R$^7$-N(R$^{8b}$)(R$^{8a}$)-C(O)- | —W—M— |
|---|---|---|---|---|---|
| 242 | Me | F | phenyl | NH-CH(CH$_3$)-C(O) | —(CH$_2$)$_5$—O— |
| 243 | Me | F | phenyl | NH-CH(CH$_3$)-C(O) | —(CH$_2$)$_6$—O— |
| 244 | Me | F | phenyl | NH-CH(CH$_3$)-C(O) | —(CH$_2$)$_7$—O— |
| 245 | Me | F | phenyl | NH-CH(CH$_3$)-C(O) | —(CH$_2$)$_8$—O— |
| 246 | Me | F | phenyl | NH-CH(CH$_3$)-C(O) | —C(CH$_3$)$_2$(CH$_2$)$_4$—O— |
| 247 | Me | F | phenyl | NH-CH(CH$_3$)-C(O) | —(CH$_2$)$_5$CF$_2$—O— |
| 248 | Me | F | phenyl | NH-CH(CH$_3$)-C(O) | —(CH$_2$)$_3$—O—(CH$_2$)$_5$—O— |
| 249 | Me | F | phenyl | NH-CH(CH$_3$)-C(O) | —CH$_2$CH$_2$CH=CHCH$_2$—O— |
| 250 | Me | F | phenyl | NH-CH(CH$_3$)-C(O) | —C(CH$_3$)$_2$CH$_2$CH=CHCH$_2$—O— |

TABLE 2-continued
| Example# | R²ᵃ | R²ᵇ | R⁶ | 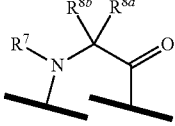 | —W—M— |
|---|---|---|---|---|---|
| 251 | Me | F | 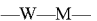 | 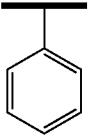 | 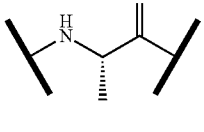 |
| 252 | Me | F | 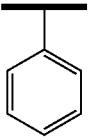 | 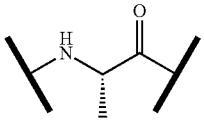 | —(CH₂)₅—NH— |
| 253 | Me | F | 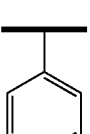 | 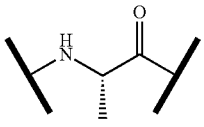 | —(CH₂)₆—NH— |
| 254 | Me | F | 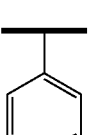 | 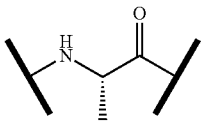 | —(CH₂)₇—NH— |
| 255 | Me | F | 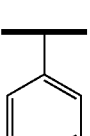 | 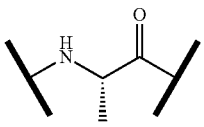 | —(CH₂)₅—C(O)NH— |
| 256 | Me | F | 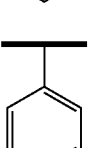 | 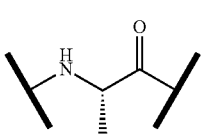 | —(CH₂)₆—C(O)NH— |
| 257 | Me | F | 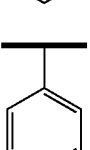 | 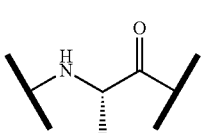 | —(CH₂)₇—C(O)NH— |
| 258 | Me | F | 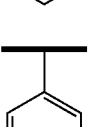 | 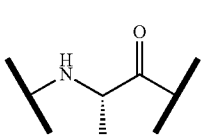 | 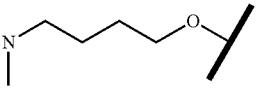 |
| 259 | Me | F | 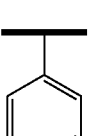 | 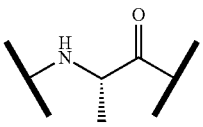 | 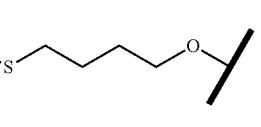 |

TABLE 2-continued

| Example# | $R^{2a}$ | $R^{2b}$ | $R^6$ | (R7/R8a/R8b group) | —W—M— |
|---|---|---|---|---|---|
| 260 | Me | F | benzyl | N-H alanyl | —(CH$_2$)$_6$—OC(O)NH— |
| 261 | Me | F | 1-naphthylmethyl | N-H alanyl | —(CH$_2$)$_4$—O— |
| 262 | Me | F | 1-naphthylmethyl | N-H alanyl | —(CH$_2$)$_5$—O— |
| 263 | Me | F | 1-naphthylmethyl | N-H alanyl | —(CH$_2$)$_6$—O— |
| 264 | Me | F | 1-naphthylmethyl | N-H alanyl | —(CH$_2$)$_7$—O— |
| 265 | Me | F | 1-naphthylmethyl | N-H alanyl | —(CH$_2$)$_8$—O— |
| 266 | Me | F | 1-naphthylmethyl | N-H alanyl | gem-dimethyl alkyl-O— |
| 267 | Me | F | 1-naphthylmethyl | N-H alanyl | gem-difluoro alkyl-O— |
| 268 | Me | F | 1-naphthylmethyl | N-H alanyl | —(CH$_2$)$_3$—O—(CH$_2$)$_5$—O— |

TABLE 2-continued

| Example# | R²ᵃ | R²ᵇ | R⁶ | $\overset{R^{8b}\ R^{8a}}{\underset{N}{R^7}}\overset{O}{\diagdown}$ | —W—M— |
|---|---|---|---|---|---|
| 269 | Me | F | 1-naphthyl | N-H alanyl | —CH₂CH₂CH=CHCH₂CH₂—O— |
| 270 | Me | F | 1-naphthyl | N-H alanyl | —C(CH₃)₂CH₂CH=CHCH₂—O— |
| 271 | Me | F | 1-naphthyl | N-H alanyl | —CH₂CH₂CH₂-cyclopropyl-CH₂CH₂—O— |
| 272 | Me | F | 1-naphthyl | N-H alanyl | —(CH₂)₅—NH— |
| 273 | Me | F | 1-naphthyl | N-H alanyl | —(CH₂)₆—NH— |
| 274 | Me | F | 1-naphthyl | N-H alanyl | —(CH₂)₇—NH— |
| 275 | Me | F | 1-naphthyl | N-H alanyl | —(CH₂)₅—C(O)NH— |
| 276 | Me | F | 1-naphthyl | N-H alanyl | —(CH₂)₆—C(O)NH— |
| 277 | Me | F | 1-naphthyl | N-H alanyl | —(CH₂)₇—C(O)NH— |

TABLE 2-continued
| Example# | R$^{2a}$ | R$^{2b}$ | R$^6$ | 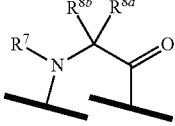 | —W—M— |
|---|---|---|---|---|---|
| 278 | Me | F | 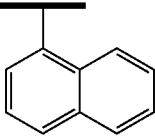 | 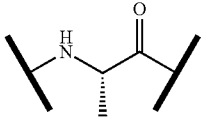 | 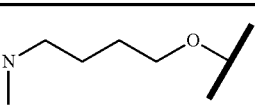 |
| 279 | Me | F | 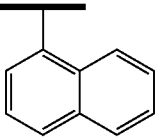 | 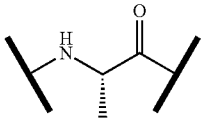 | 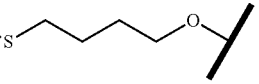 |
| 280 | Me | F | 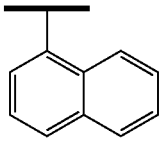 | 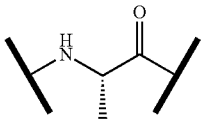 | —(CH$_2$)$_6$—OC(O)NH— |
| 281 | CHF$_2$ | OH | 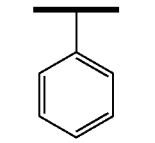 | 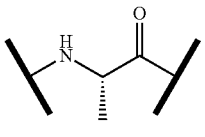 | —(CH$_2$)$_4$—O— |
| 282 | CHF$_2$ | OH | 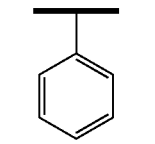 | 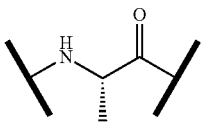 | —(CH$_2$)$_5$—O— |
| 283 | CHF$_2$ | OH | 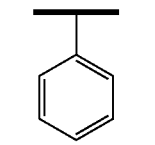 | 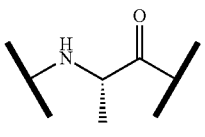 | —(CH$_2$)$_6$—O— |
| 284 | CHF$_2$ | OH | 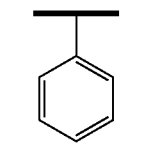 | 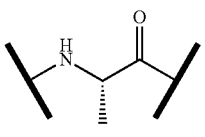 | —(CH$_2$)$_7$—O— |
| 285 | CHF$_2$ | OH | 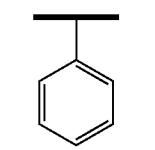 | 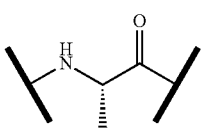 | —(CH$_2$)$_8$—O— |
| 286 | CHF$_2$ | OH | 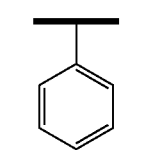 | 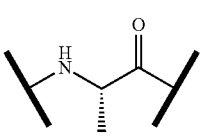 | 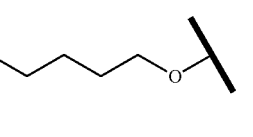 |

TABLE 2-continued
| Example # | $R^{2a}$ | $R^{2b}$ | $R^6$ | $R^7\text{-}N(R^{8b})(R^{8a})\text{-C(=O)}$ | —W—M— |
|---|---|---|---|---|---|
| 287 | $CHF_2$ | OH | 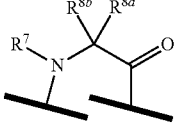 | 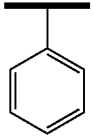 | 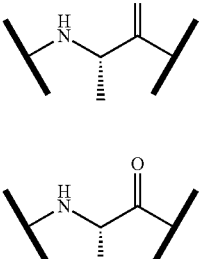 |
| 288 | $CHF_2$ | OH | 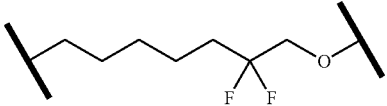 | 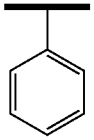 | $-(CH_2)_3-O-(CH_2)_5-O-$ |
| 289 | $CHF_2$ | OH | 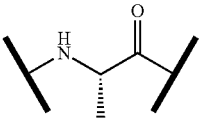 | 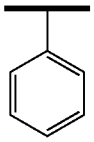 | 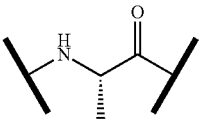 |
| 290 | $CHF_2$ | OH | 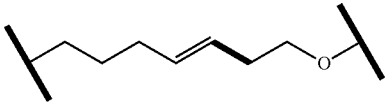 | 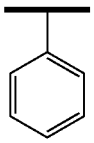 | 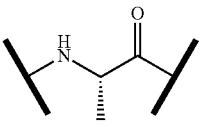 |
| 291 | $CHF_2$ | OH | 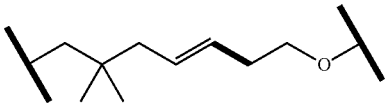 | 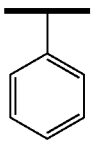 | 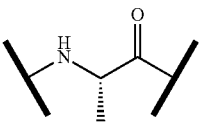 |
| 292 | $CHF_2$ | OH | 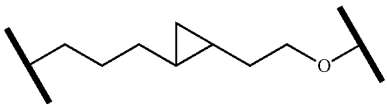 | 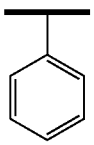 | $-(CH_2)_5-NH-$ |
| 293 | $CHF_2$ | OH | 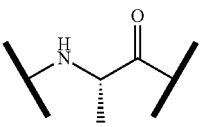 | 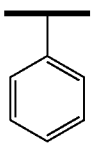 | $-(CH_2)_6-NH-$ |
| 294 | $CHF_2$ | OH | 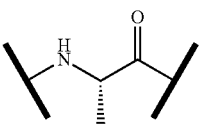 | 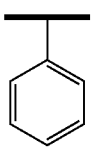 | $-(CH_2)_7-NH-$ |
| 295 | $CHF_2$ | OH | 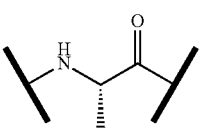 | 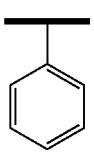 | $-(CH_2)_5-C(O)NH-$ |

TABLE 2-continued

| Example# | R2a | R2b | R6 | (R7)(R8a)(R8b)N-CH-C(O) group | —W—M— |
|---|---|---|---|---|---|
| 296 | CHF2 | OH | phenyl | NH-CH(CH3)-C(O) | —(CH2)6—C(O)NH— |
| 297 | CHF2 | OH | phenyl | NH-CH(CH3)-C(O) | —(CH2)7—C(O)NH— |
| 298 | CHF2 | OH | phenyl | NH-CH(CH3)-C(O) | —(CH2)3—N(CH3)—(CH2)4—O— |
| 299 | CHF2 | OH | phenyl | NH-CH(CH3)-C(O) | —(CH2)3—S—(CH2)4—O— |
| 300 | CHF2 | OH | phenyl | NH-CH(CH3)-C(O) | —(CH2)6—OC(O)NH— |
| 301 | CHF2 | OH | 1-naphthyl | NH-CH(CH3)-C(O) | —(CH2)4—O— |
| 302 | CHF2 | OH | 1-naphthyl | NH-CH(CH3)-C(O) | —(CH2)5—O— |
| 303 | CHF2 | OH | 1-naphthyl | NH-CH(CH3)-C(O) | —(CH2)6—O— |
| 304 | CHF2 | OH | 1-naphthyl | NH-CH(CH3)-C(O) | —(CH2)7—O— |

TABLE 2-continued

| Example# | $R^{2a}$ | $R^{2b}$ | $R^6$ | $R^7\text{-N}(R^{8b})(R^{8a})\text{-C(=O)-}$ | —W—M— |
|---|---|---|---|---|---|
| 305 | $CHF_2$ | OH | 1-naphthylmethyl | NH-CH(CH₃)-C(=O) | —(CH₂)₈—O— |
| 306 | $CHF_2$ | OH | 1-naphthylmethyl | NH-CH(CH₃)-C(=O) | —C(CH₃)₂(CH₂)₄CH₂—O— |
| 307 | $CHF_2$ | OH | 1-naphthylmethyl | NH-CH(CH₃)-C(=O) | —(CH₂)₅CF₂CH₂—O— |
| 308 | $CHF_2$ | OH | 1-naphthylmethyl | NH-CH(CH₃)-C(=O) | —(CH₂)₃—O—(CH₂)₅—O— |
| 309 | $CHF_2$ | OH | 1-naphthylmethyl | NH-CH(CH₃)-C(=O) | —(CH₂)₃CH=CHCH₂—O— |
| 310 | $CHF_2$ | OH | 1-naphthylmethyl | NH-CH(CH₃)-C(=O) | —C(CH₃)₂CH₂CH=CHCH₂—O— |
| 311 | $CHF_2$ | OH | 1-naphthylmethyl | NH-CH(CH₃)-C(=O) | —(CH₂)₃-cyclopropyl-(CH₂)₂—O— |
| 312 | $CHF_2$ | OH | 1-naphthylmethyl | NH-CH(CH₃)-C(=O) | —(CH₂)₅—NH— |
| 313 | $CHF_2$ | OH | 1-naphthylmethyl | NH-CH(CH₃)-C(=O) | —(CH₂)₆—NH— |

TABLE 2-continued
| Example# | $R^{2a}$ | $R^{2b}$ | $R^6$ | | —W—M— |
|---|---|---|---|---|---|
| 314 | $CHF_2$ | OH | 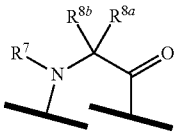 | 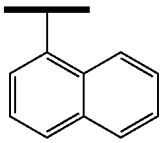 | —$(CH_2)_7$—NH— |
| 315 | $CHF_2$ | OH | 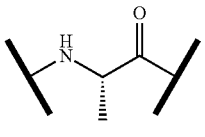 | 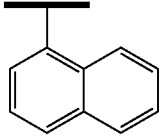 | —$(CH_2)_5$—C(O)NH— |
| 316 | $CHF_2$ | OH | 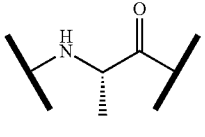 | 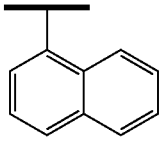 | —$(CH_2)_6$—C(O)NH— |
| 317 | $CHF_2$ | OH | 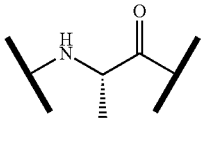 | 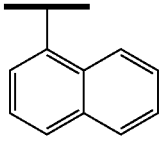 | —$(CH_2)_7$—C(O)NH— |
| 318 | $CHF_2$ | OH | 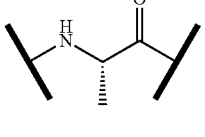 | 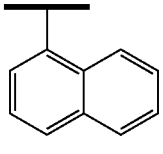 | 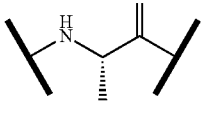 |
| 319 | $CHF_2$ | OH | 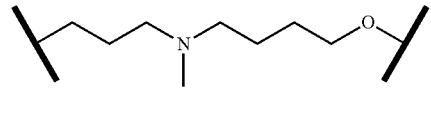 | 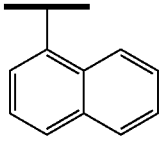 | 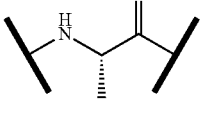 |
| 320 | $CHF_2$ | OH | 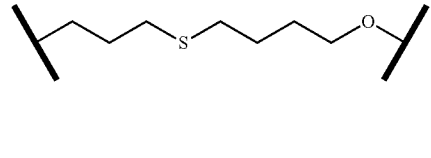 | 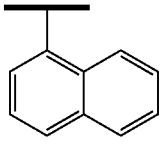 | —$(CH_2)_6$—OC(O)NH— |
| 321 | $CHF_2$ | F | 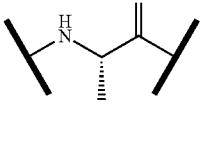 | 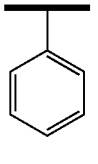 | —$(CH_2)_4$—O— |
| 322 | $CHF_2$ | F | 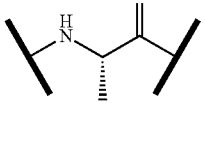 |  | —$(CH_2)_5$—O— |

TABLE 2-continued

| Example# | $R^{2a}$ | $R^{2b}$ | $R^6$ | $R^7\text{-N}(R^{8b})(R^{8a})\text{-C(=O)}$ | —W—M— |
|---|---|---|---|---|---|
| 323 | $CHF_2$ | F | phenyl | N-H alanyl | $-(CH_2)_6-O-$ |
| 324 | $CHF_2$ | F | phenyl | N-H alanyl | $-(CH_2)_7-O-$ |
| 325 | $CHF_2$ | F | phenyl | N-H alanyl | $-(CH_2)_8-O-$ |
| 326 | $CHF_2$ | F | phenyl | N-H alanyl | gem-dimethyl alkyl-O- |
| 327 | $CHF_2$ | F | phenyl | N-H alanyl | gem-difluoro alkyl-O- |
| 328 | $CHF_2$ | F | phenyl | N-H alanyl | $-(CH_2)_3-O-(CH_2)_5-O-$ |
| 329 | $CHF_2$ | F | phenyl | N-H alanyl | alkenyl-O- |
| 330 | $CHF_2$ | F | phenyl | N-H alanyl | gem-dimethyl alkenyl-O- |
| 331 | $CHF_2$ | F | phenyl | N-H alanyl | cyclopropyl-containing alkyl-O- |

TABLE 2-continued
| Example# | $R^{2a}$ | $R^{2b}$ | $R^6$ | 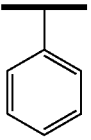 | —W—M— |
|---|---|---|---|---|---|
| 332 | $CHF_2$ | F | 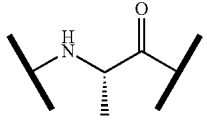 | 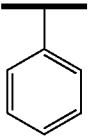 | —$(CH_2)_5$—NH— |
| 333 | $CHF_2$ | F | 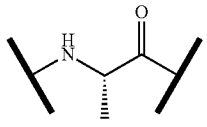 | 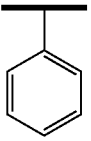 | —$(CH_2)_6$—NH— |
| 334 | $CHF_2$ | F | 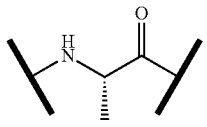 | 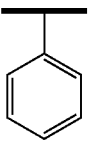 | —$(CH_2)_7$—NH— |
| 335 | $CHF_2$ | F | 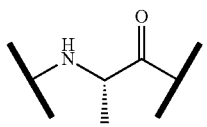 | 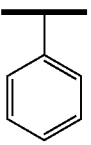 | —$(CH_2)_5$—C(O)NH— |
| 336 | $CHF_2$ | F | 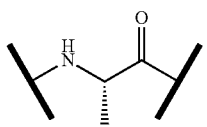 | 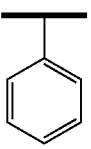 | —$(CH_2)_6$—C(O)NH— |
| 337 | $CHF_2$ | F | 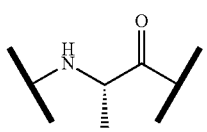 | 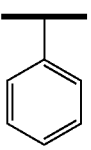 | —$(CH_2)_7$—C(O)NH— |
| 338 | $CHF_2$ | F | 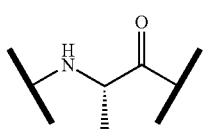 | 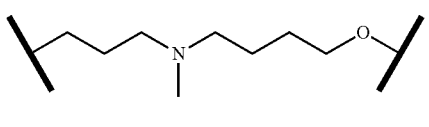 | 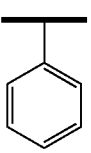 |
| 339 | $CHF_2$ | F | 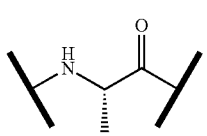 | 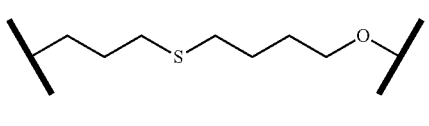 | 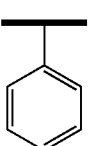 |
| 340 | $CHF_2$ | F | 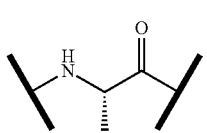 | | —$(CH_2)_6$—OC(O)NH— |

TABLE 2-continued
| Example# | R²ᵃ | R²ᵇ | R⁶ | R⁷R⁸ᵇR⁸ᵃ group | —W—M— |
|---|---|---|---|---|---|
| 341 | CHF₂ | F | 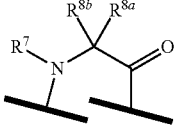 | 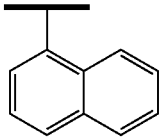 | —(CH₂)₄—O— |
| 342 | CHF₂ | F | 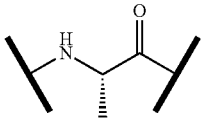 | 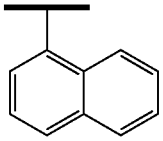 | —(CH₂)₅—O— |
| 343 | CHF₂ | F | 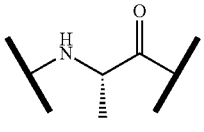 | 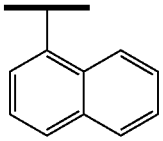 | —(CH₂)₆—O— |
| 344 | CHF₂ | F | 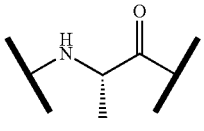 | 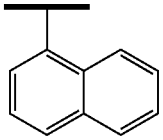 | —(CH₂)₇—O— |
| 345 | CHF₂ | F | 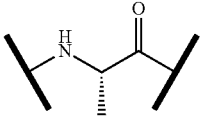 | 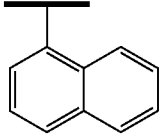 | —(CH₂)₈—O— |
| 346 | CHF₂ | F | 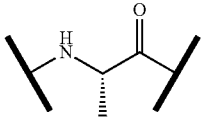 | 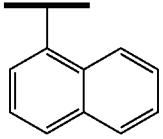 | 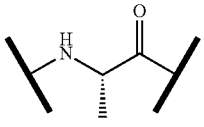 |
| 347 | CHF₂ | F | 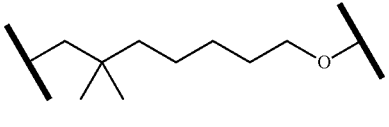 | 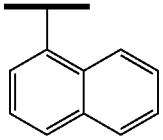 | 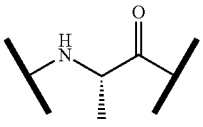 |
| 348 | CHF₂ | F | 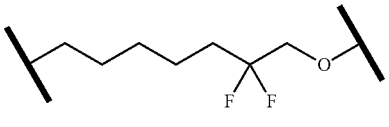 | 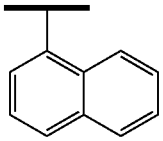 | —(CH₂)₃—O—(CH₂)₅—O— |
| 349 | CHF₂ | F | 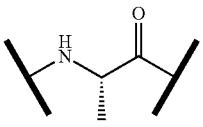 | 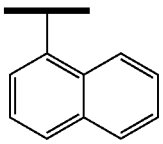 | 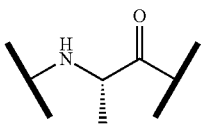 |

TABLE 2-continued

| Example# | R$^{2a}$ | R$^{2b}$ | R$^6$ | R$^7$, R$^{8a}$, R$^{8b}$ group | —W—M— |
|---|---|---|---|---|---|
| 350 | CHF$_2$ | F | 1-naphthyl | —NH—CH(CH$_3$)—C(O)— | gem-dimethyl allyl ether linker |
| 351 | CHF$_2$ | F | 1-naphthyl | —NH—CH(CH$_3$)—C(O)— | cyclopropyl-containing alkyl ether linker |
| 352 | CHF$_2$ | F | 1-naphthyl | —NH—CH(CH$_3$)—C(O)— | —(CH$_2$)$_5$—NH— |
| 353 | CHF$_2$ | F | 1-naphthyl | —NH—CH(CH$_3$)—C(O)— | —(CH$_2$)$_6$—NH— |
| 354 | CHF$_2$ | F | 1-naphthyl | —NH—CH(CH$_3$)—C(O)— | —(CH$_2$)$_7$—NH— |
| 355 | CHF$_2$ | F | 1-naphthyl | —NH—CH(CH$_3$)—C(O)— | —(CH$_2$)$_5$—C(O)NH— |
| 356 | CHF$_2$ | F | 1-naphthyl | —NH—CH(CH$_3$)—C(O)— | —(CH$_2$)$_6$—C(O)NH— |
| 357 | CHF$_2$ | F | 1-naphthyl | —NH—CH(CH$_3$)—C(O)— | —(CH$_2$)$_7$—C(O)NH— |
| 358 | CHF$_2$ | F | 1-naphthyl | —NH—CH(CH$_3$)—C(O)— | —(CH$_2$)$_3$—N(CH$_3$)—(CH$_2$)$_4$—O— |

TABLE 2-continued

| Example# | R²ᵃ | R²ᵇ | R⁶ | R⁷\N(R⁸ᵇ)(R⁸ᵃ)–C(O)– | —W—M— |
|---|---|---|---|---|---|
| 359 | CHF₂ | F | 1-naphthyl-CH₂– | –NH–CH(CH₃)–C(O)– | –(CH₂)₃–S–(CH₂)₄–O– |
| 360 | CHF₂ | F | 1-naphthyl-CH₂– | –NH–CH(CH₃)–C(O)– | —(CH₂)₆—OC(O)NH— |
| 361 | Me | OH | Ph-CH₂– | –NH–CH(CH₂CH(CH₃)₂)–C(O)– | —(CH₂)₄—O— |
| 362 | Me | OH | Ph-CH₂– | –NH–CH(CH₂CH(CH₃)₂)–C(O)– | —(CH₂)₅—O— |
| 363 | Me | OH | Ph-CH₂– | –NH–CH(CH₂CH(CH₃)₂)–C(O)– | —(CH₂)₆—O— |
| 364 | Me | OH | Ph-CH₂– | –NH–CH(CH₂CH(CH₃)₂)–C(O)– | —(CH₂)₇—O— |
| 365 | Me | OH | Ph-CH₂– | –NH–CH(CH₂CH(CH₃)₂)–C(O)– | —(CH₂)₈—O— |
| 366 | Me | OH | Ph-CH₂– | –NH–CH(CH₂CH(CH₃)₂)–C(O)– | –C(CH₃)₂–(CH₂)₅–O– |

TABLE 2-continued

| Example# | R²ᵃ | R²ᵇ | R⁶ | R⁷\N(R⁸ᵇ)(R⁸ᵃ)—C(=O)— | —W—M— |
|---|---|---|---|---|---|
| 367 | Me | OH | phenyl | Leu | —CH₂(CH₂)₅C(F)₂CH₂O— |
| 368 | Me | OH | phenyl | Leu | —(CH₂)₃—O—(CH₂)₅—O— |
| 369 | Me | OH | phenyl | Leu | —CH₂(CH₂)₃CH=CHCH₂O— |
| 370 | Me | OH | phenyl | Leu | —C(CH₃)₂CH₂CH₂CH=CHCH₂O— |
| 371 | Me | OH | phenyl | Leu | —(CH₂)₄-cyclopropyl-CH₂CH₂O— |
| 372 | Me | OH | phenyl | Leu | —(CH₂)₅—NH— |
| 373 | Me | OH | phenyl | Leu | —(CH₂)₆—NH— |

TABLE 2-continued
| Example# | R²ᵃ | R²ᵇ | R⁶ | R⁷R⁸ᵇR⁸ᵃ group | —W—M— |
|---|---|---|---|---|---|
| 374 | Me | OH | 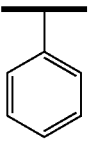 | 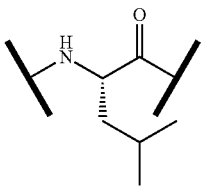 | —(CH₂)₇—NH— |
| 375 | Me | OH | 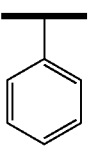 | 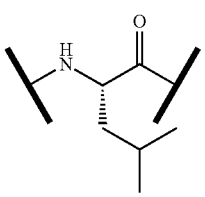 | —(CH₂)₅—C(O)NH— |
| 376 | Me | OH | 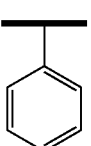 | 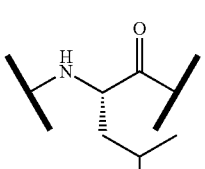 | —(CH₂)₆—C(O)NH— |
| 377 | Me | OH | 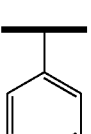 | 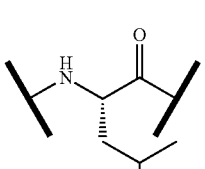 | —(CH₂)₇—C(O)NH— |
| 378 | Me | OH | 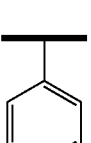 | 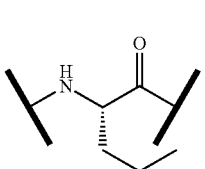 | 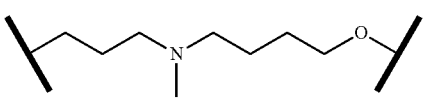 |
| 379 | Me | OH | 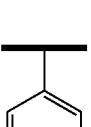 | 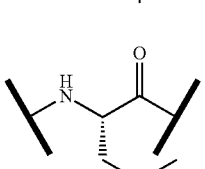 | 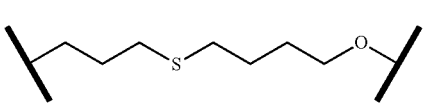 |
| 380 | Me | OH | 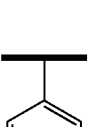 | 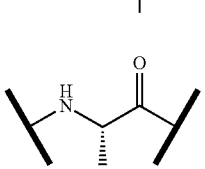 | —(CH₂)₆—OC(O)NH— |

TABLE 2-continued
| Example# | R$^{2a}$ | R$^{2b}$ | R$^6$ | 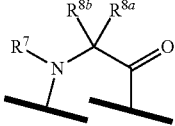 | —W—M— |
|---|---|---|---|---|---|
| 381 | Me | F | 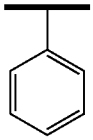 | 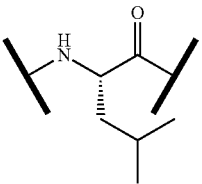 | —(CH$_2$)$_4$—O— |
| 382 | Me | F | 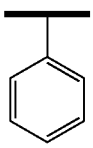 | 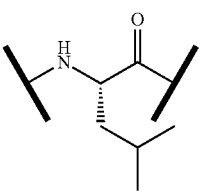 | —(CH$_2$)$_5$—O— |
| 383 | Me | F | 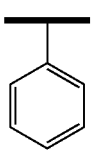 | 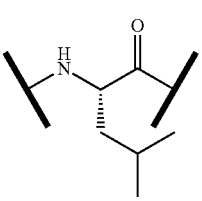 | —(CH$_2$)$_6$—O— |
| 384 | Me | F | 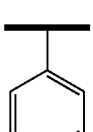 | 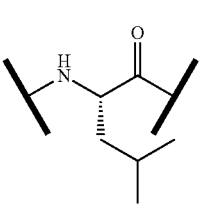 | —(CH$_2$)$_7$—O— |
| 385 | Me | F | 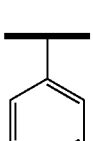 | 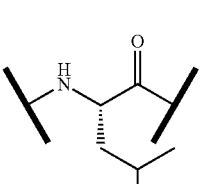 | —(CH$_2$)$_8$—O— |
| 386 | Me | F | 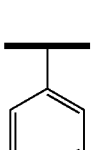 | 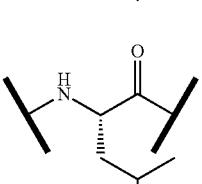 | 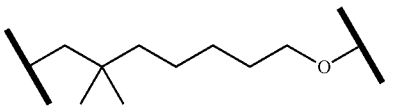 |
| 387 | Me | F | 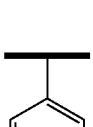 | 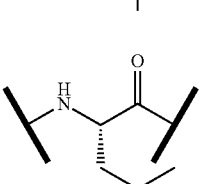 | 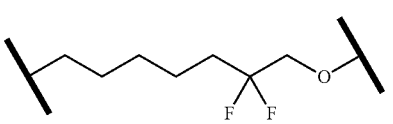 |

TABLE 2-continued
| Example# | R$^{2a}$ | R$^{2b}$ | R$^6$ | 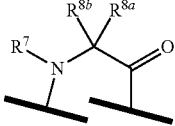 | —W—M— |
|---|---|---|---|---|---|
| 388 | Me | F | 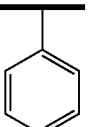 | 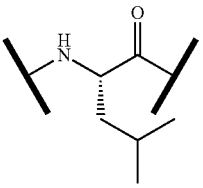 | —(CH$_2$)$_3$—O—(CH$_2$)$_5$—O— |
| 389 | Me | F | 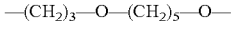 | 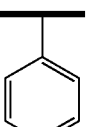 | 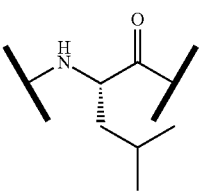 |
| 390 | Me | F | 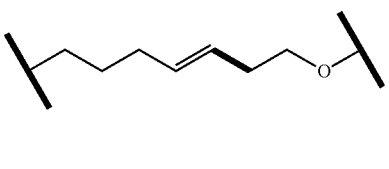 | 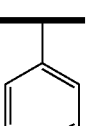 | 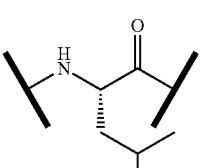 |
| 391 | Me | F | 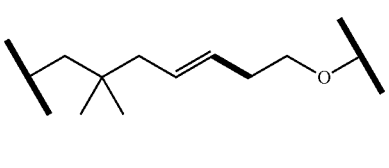 | 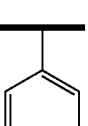 | 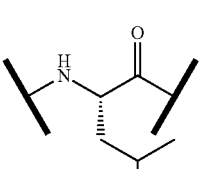 |
| 392 | Me | F |  | 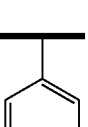 | —(CH$_2$)$_5$—NH— |
| 393 | Me | F | 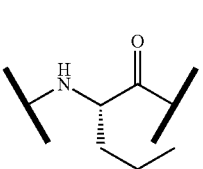 | 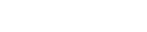 | —(CH$_2$)$_6$—NH— |
| 394 | Me | F | 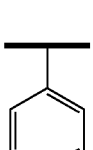 | 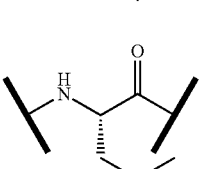 | —(CH$_2$)$_7$—NH— |

TABLE 2-continued

| Example# | R²ᵃ | R²ᵇ | R⁶ | $\begin{array}{c}R^{8b}\quad R^{8a}\\R^7\diagdown N\diagup\diagdown\diagup\diagdown\\\phantom{R^7}\diagdown\quad O\end{array}$ | —W—M— |
|---|---|---|---|---|---|
| 395 | Me | F | phenyl | N-H leucinyl ketone | —(CH₂)₅—C(O)NH— |
| 396 | Me | F | phenyl | N-H leucinyl ketone | —(CH₂)₆—C(O)NH— |
| 397 | Me | F | phenyl | N-H leucinyl ketone | —(CH₂)₇—C(O)NH— |
| 398 | Me | F | phenyl | N-H leucinyl ketone | —(CH₂)₃—N(CH₃)—(CH₂)₄—O— |
| 399 | Me | F | phenyl | N-H leucinyl ketone | —(CH₂)₃—S—(CH₂)₄—O— |
| 400 | Me | F | phenyl | N-H leucinyl ketone | —(CH₂)₆—OC(O)NH— |

In another embodiment, the invention provides compounds of Formula IX,

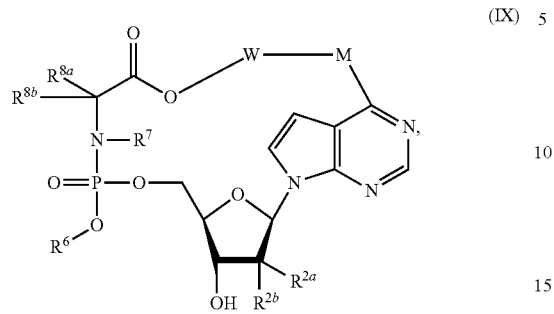

(IX)

where M, W, $R^{2a}$, $R^{2b}$, $R^6$, $R^7$, $R^{8a}$ and $R^{8b}$ are as previously defined.

Representative compounds of the invention include, but are not limited to, the following compounds (example 401 to example 600 in Table 3) according to Formula XI, wherein, $R^{2a}$, $R^{2b}$, $R^6$, $R^7$, $R^{8a}$, $R^{8b}$ and —W-M- are delineated for each example in Table 3.

TABLE 3

| Example# | $R^{2a}$ | $R^{2b}$ | $R^6$ | $R^{8b}\,R^{8a}$ on $R^7\!\!-\!\!N$ fragment | —W—M— |
|---|---|---|---|---|---|
| 401 | Me | OH | phenyl | NH-CH(Me)-C(=O) (S) | —(CH$_2$)$_4$—O— |
| 402 | Me | OH | phenyl | NH-CH(Me)-C(=O) (S) | —(CH$_2$)$_5$—O— |
| 403 | Me | OH | phenyl | NH-CH(Me)-C(=O) (S) | —(CH$_2$)$_6$—O— |
| 404 | Me | OH | phenyl | NH-CH(Me)-C(=O) (S) | —(CH$_2$)$_7$—O— |
| 405 | Me | OH | phenyl | NH-CH(Me)-C(=O) (S) | —(CH$_2$)$_8$—O— |

TABLE 3-continued

| Example# | R²ᵃ | R²ᵇ | R⁶ | R⁷N(R⁸ᵇ)(R⁸ᵃ)C=O | —W—M— |
|---|---|---|---|---|---|
| 406 | Me | OH | phenyl | NH-CH(Me)-C(=O) | -C(Me)₂-(CH₂)₄-CH₂-O- |
| 407 | Me | OH | phenyl | NH-CH(Me)-C(=O) | -(CH₂)₅-CF₂-CH₂-O- |
| 408 | Me | OH | phenyl | NH-CH(Me)-C(=O) | —(CH₂)₃—O—(CH₂)₅—O— |
| 409 | Me | OH | phenyl | NH-CH(Me)-C(=O) | -(CH₂)₃-CH=CH-CH₂-O- |
| 410 | Me | OH | phenyl | NH-CH(Me)-C(=O) | -C(Me)₂-CH₂-CH=CH-CH₂-O- |
| 411 | Me | OH | phenyl | NH-CH(Me)-C(=O) | -(CH₂)₃-cyclopropyl-CH₂-O- |
| 412 | Me | OH | phenyl | NH-CH(Me)-C(=O) | —(CH₂)₅—NH— |
| 413 | Me | OH | phenyl | NH-CH(Me)-C(=O) | —(CH₂)₆—NH— |
| 414 | Me | OH | phenyl | NH-CH(Me)-C(=O) | —(CH₂)₇—NH— |

TABLE 3-continued
| Example# | R²ᵃ | R²ᵇ | R⁶ | R⁷\N(R⁸ᵇ)(R⁸ᵃ)C(O) | —W—M— |
|---|---|---|---|---|---|
| 415 | Me | OH | 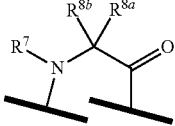 | 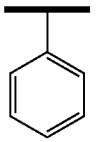 | —(CH₂)₅—C(O)NH— |
| 416 | Me | OH | 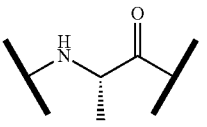 | 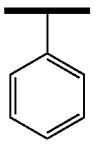 | —(CH₂)₆—C(O)NH— |
| 417 | Me | OH | 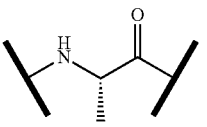 | 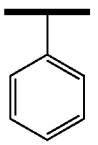 | —(CH₂)₇—C(O)NH— |
| 418 | Me | OH | 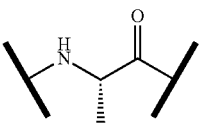 | 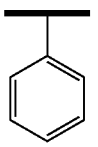 | 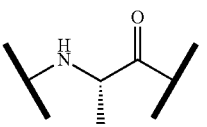 |
| 419 | Me | OH | 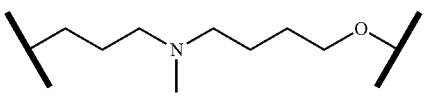 | 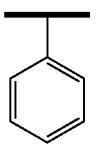 | 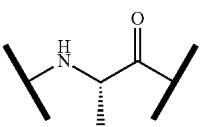 |
| 420 | Me | OH | 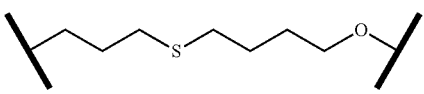 | 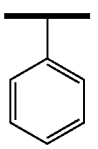 | —(CH₂)₆—OC(O)NH— |
| 421 | Me | OH | 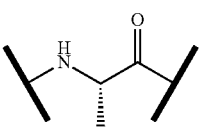 | 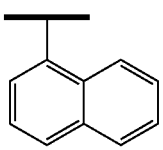 | —(CH₂)₄—O— |
| 422 | Me | OH | 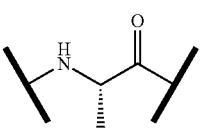 | 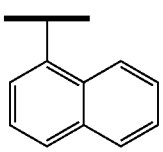 | —(CH₂)₅—O— |
| 423 | Me | OH | 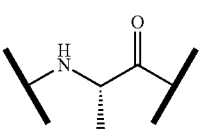 | 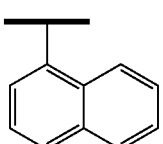 | —(CH₂)₆—O— |

TABLE 3-continued

| Example# | R² ͣ | R²ᵇ | R⁶ | R⁷-N(R⁸ᵇ)(R⁸ ͣ)-C(=O)- | —W—M— |
|---|---|---|---|---|---|
| 424 | Me | OH | 1-naphthyl | NH-CH(Me)-C(=O) | —(CH₂)₇—O— |
| 425 | Me | OH | 1-naphthyl | NH-CH(Me)-C(=O) | —(CH₂)₈—O— |
| 426 | Me | OH | 1-naphthyl | NH-CH(Me)-C(=O) | —C(Me)₂(CH₂)₄CH₂—O— |
| 427 | Me | OH | 1-naphthyl | NH-CH(Me)-C(=O) | —(CH₂)₅CF₂CH₂—O— |
| 428 | Me | OH | 1-naphthyl | NH-CH(Me)-C(=O) | —(CH₂)₃—O—(CH₂)₅—O— |
| 429 | Me | OH | 1-naphthyl | NH-CH(Me)-C(=O) | —(CH₂)₃CH=CHCH₂—O— |
| 430 | Me | OH | 1-naphthyl | NH-CH(Me)-C(=O) | —C(Me)₂CH₂CH=CHCH₂—O— |
| 431 | Me | OH | 1-naphthyl | NH-CH(Me)-C(=O) | —(CH₂)₃-cyclopropyl-CH₂CH₂—O— |
| 432 | Me | OH | 1-naphthyl | NH-CH(Me)-C(=O) | —(CH₂)₅—NH— |

TABLE 3-continued

| Example# | R²ᵃ | R²ᵇ | R⁶ | R⁷R⁸ᵇR⁸ᵃ group | —W—M— |
|---|---|---|---|---|---|
| 433 | Me | OH | naphthyl | NH-CH(Me)-C(O) | —(CH₂)₆—NH— |
| 434 | Me | OH | naphthyl | NH-CH(Me)-C(O) | —(CH₂)₇—NH— |
| 435 | Me | OH | naphthyl | NH-CH(Me)-C(O) | —(CH₂)₅—C(O)NH— |
| 436 | Me | OH | naphthyl | NH-CH(Me)-C(O) | —(CH₂)₆—C(O)NH— |
| 437 | Me | OH | naphthyl | NH-CH(Me)-C(O) | —(CH₂)₇—C(O)NH— |
| 438 | Me | OH | naphthyl | NH-CH(Me)-C(O) | —(CH₂)₃—N(Me)—(CH₂)₄—O— |
| 439 | Me | OH | naphthyl | NH-CH(Me)-C(O) | —(CH₂)₃—S—(CH₂)₄—O— |
| 440 | Me | OH | naphthyl | NH-CH(Me)-C(O) | —(CH₂)₆—OC(O)NH— |
| 441 | Me | F | benzyl | NH-CH(Me)-C(O) | —(CH₂)₄—O— |

TABLE 3-continued

| Example# | $R^{2a}$ | $R^{2b}$ | $R^6$ | $R^7R^{8b}R^{8a}$ fragment | —W—M— |
|---|---|---|---|---|---|
| 442 | Me | F | phenyl | NH-CH(CH3)-C(O) | —(CH$_2$)$_5$—O— |
| 443 | Me | F | phenyl | NH-CH(CH3)-C(O) | —(CH$_2$)$_6$—O— |
| 444 | Me | F | phenyl | NH-CH(CH3)-C(O) | —(CH$_2$)$_7$—O— |
| 445 | Me | F | phenyl | NH-CH(CH3)-C(O) | —(CH$_2$)$_8$—O— |
| 446 | Me | F | phenyl | NH-CH(CH3)-C(O) | —C(CH$_3$)$_2$(CH$_2$)$_4$CH$_2$—O— |
| 447 | Me | F | phenyl | NH-CH(CH3)-C(O) | —(CH$_2$)$_5$CF$_2$CH$_2$—O— |
| 448 | Me | F | phenyl | NH-CH(CH3)-C(O) | —(CH$_2$)$_3$—O—(CH$_2$)$_5$—O— |
| 449 | Me | F | phenyl | NH-CH(CH3)-C(O) | —CH$_2$CH$_2$CH=CHCH$_2$—O— |
| 450 | Me | F | phenyl | NH-CH(CH3)-C(O) | —C(CH$_3$)$_2$CH$_2$CH=CHCH$_2$—O— |

TABLE 3-continued
| Example# | R2a | R2b | R6 | R7R8bNR8aC(=O) group | —W—M— |
|---|---|---|---|---|---|
| 451 | Me | F | 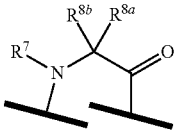 | 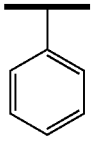 | 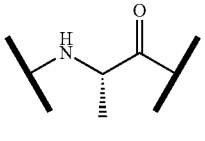 |
| 452 | Me | F | 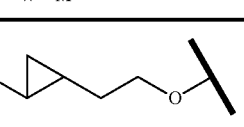 | 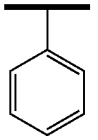 | —(CH$_2$)$_5$—NH— |
| 453 | Me | F | 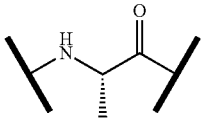 | 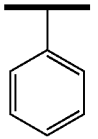 | —(CH$_2$)$_6$—NH— |
| 454 | Me | F | 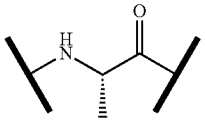 | 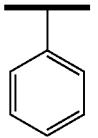 | —(CH$_2$)$_7$—NH— |
| 455 | Me | F | 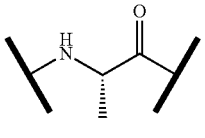 | 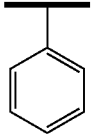 | —(CH$_2$)$_5$—C(O)NH— |
| 456 | Me | F | 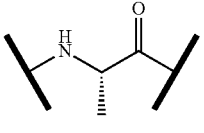 | 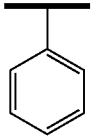 | —(CH$_2$)$_6$—C(O)NH— |
| 457 | Me | F | 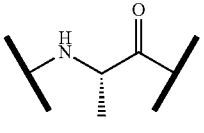 | 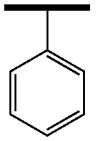 | —(CH$_2$)$_7$—C(O)NH— |
| 458 | Me | F | 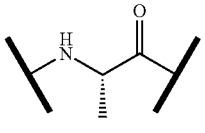 | 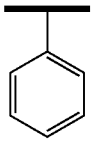 | 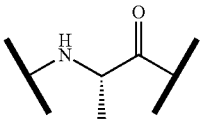 |
| 459 | Me | F | 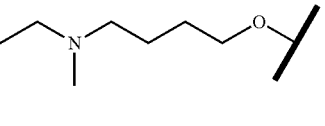 | 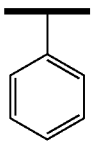 | 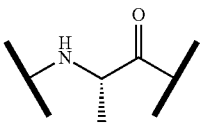 |

TABLE 3-continued
| Example# | R²ᵃ | R²ᵇ | R⁶ | 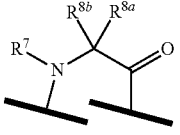 | —W—M— |
|---|---|---|---|---|---|
| 460 | Me | F | 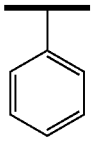 | 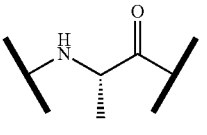 | —(CH₂)₆—OC(O)NH— |
| 461 | Me | F | 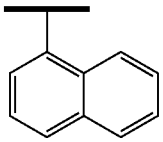 | 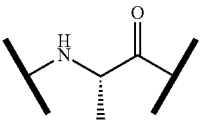 | —(CH₂)₄—O— |
| 462 | Me | F | 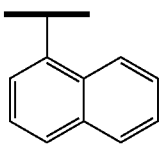 | 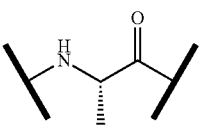 | —(CH₂)₅—O— |
| 463 | Me | F | 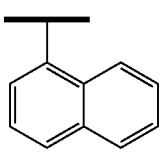 | 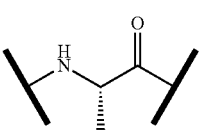 | —(CH₂)₆—O— |
| 464 | Me | F | 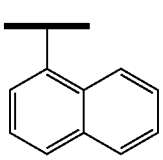 | 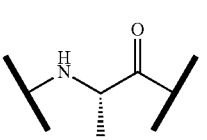 | —(CH₂)₇—O— |
| 465 | Me | F | 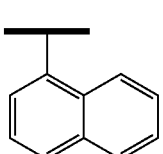 | 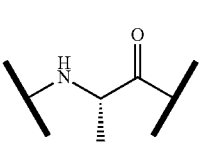 | —(CH₂)₈—O— |
| 466 | Me | F | 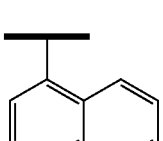 | 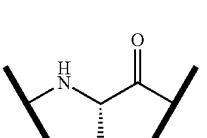 | 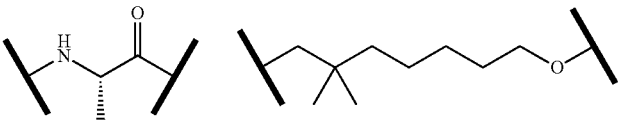 |
| 467 | Me | F | 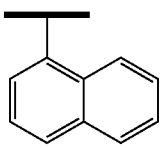 | 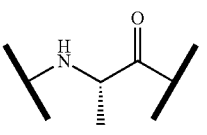 | 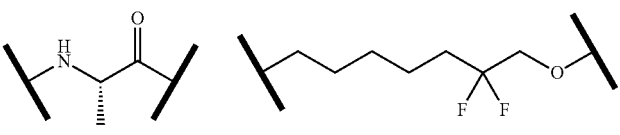 |
| 468 | Me | F | 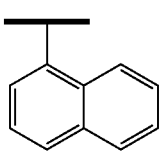 | 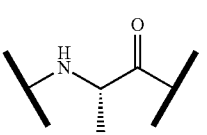 | —(CH₂)₃—O—(CH₂)₅—O— |

TABLE 3-continued
| Example# | R$^{2a}$ | R$^{2b}$ | R$^6$ | (R$^7$N(R$^{8b}$)(R$^{8a}$)C=O group) | —W—M— |
|---|---|---|---|---|---|
| 469 | Me | F | naphthyl | NH-CH(Me)-C(O) | 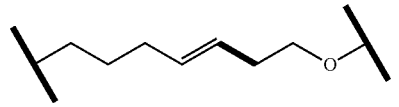 |
| 470 | Me | F | naphthyl | NH-CH(Me)-C(O) | 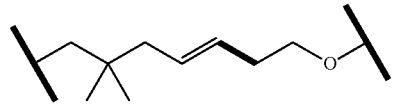 |
| 471 | Me | F | naphthyl | NH-CH(Me)-C(O) |  |
| 472 | Me | F | naphthyl | NH-CH(Me)-C(O) | —(CH$_2$)$_5$—NH— |
| 473 | Me | F | naphthyl | NH-CH(Me)-C(O) | —(CH$_2$)$_6$—NH— |
| 474 | Me | F | naphthyl | NH-CH(Me)-C(O) | —(CH$_2$)$_7$—NH— |
| 475 | Me | F | naphthyl | NH-CH(Me)-C(O) | —(CH$_2$)$_5$—C(O)NH— |
| 476 | Me | F | naphthyl | NH-CH(Me)-C(O) | —(CH$_2$)$_6$—C(O)NH— |
| 477 | Me | F | naphthyl | NH-CH(Me)-C(O) | —(CH$_2$)$_7$—C(O)NH— |

TABLE 3-continued

| Example# | R$^{2a}$ | R$^{2b}$ | R$^6$ | R$^7$,R$^{8a}$,R$^{8b}$ group | —W—M— |
|---|---|---|---|---|---|
| 478 | Me | F | naphthalen-1-yl | NH-CH(CH$_3$)-C(O) | —(CH$_2$)$_3$—N(CH$_3$)—(CH$_2$)$_4$—O— |
| 479 | Me | F | naphthalen-1-yl | NH-CH(CH$_3$)-C(O) | —(CH$_2$)$_3$—S—(CH$_2$)$_4$—O— |
| 480 | Me | F | naphthalen-1-yl | NH-CH(CH$_3$)-C(O) | —(CH$_2$)$_6$—OC(O)NH— |
| 481 | CHF$_2$ | OH | phenyl | NH-CH(CH$_3$)-C(O) | —(CH$_2$)$_4$—O— |
| 482 | CHF$_2$ | OH | phenyl | NH-CH(CH$_3$)-C(O) | —(CH$_2$)$_5$—O— |
| 483 | CHF$_2$ | OH | phenyl | NH-CH(CH$_3$)-C(O) | —(CH$_2$)$_6$—O— |
| 484 | CHF$_2$ | OH | phenyl | NH-CH(CH$_3$)-C(O) | —(CH$_2$)$_7$—O— |
| 485 | CHF$_2$ | OH | phenyl | NH-CH(CH$_3$)-C(O) | —(CH$_2$)$_8$—O— |
| 486 | CHF$_2$ | OH | phenyl | NH-CH(CH$_3$)-C(O) | —C(CH$_3$)$_2$—(CH$_2$)$_4$—O— |

TABLE 3-continued

| Example# | R²ᵃ | R²ᵇ | R⁶ | R⁷R⁸ᵇR⁸ᵃ group | —W—M— |
|---|---|---|---|---|---|
| 487 | CHF₂ | OH | phenyl | NH-CH(CH₃)-C(O) | -CH₂-(CH₂)₅-CF₂-CH₂-O- |
| 488 | CHF₂ | OH | phenyl | NH-CH(CH₃)-C(O) | —(CH₂)₃—O—(CH₂)₅—O— |
| 489 | CHF₂ | OH | phenyl | NH-CH(CH₃)-C(O) | -CH₂-CH₂-CH=CH-CH₂-CH₂-O- |
| 490 | CHF₂ | OH | phenyl | NH-CH(CH₃)-C(O) | -CH₂-C(CH₃)₂-CH₂-CH=CH-CH₂-O- |
| 491 | CHF₂ | OH | phenyl | NH-CH(CH₃)-C(O) | -CH₂-CH₂-CH₂-(cyclopropyl)-CH₂-CH₂-O- |
| 492 | CHF₂ | OH | phenyl | NH-CH(CH₃)-C(O) | —(CH₂)₅—NH— |
| 493 | CHF₂ | OH | phenyl | NH-CH(CH₃)-C(O) | —(CH₂)₆—NH— |
| 494 | CHF₂ | OH | phenyl | NH-CH(CH₃)-C(O) | —(CH₂)₇—NH— |
| 495 | CHF₂ | OH | phenyl | NH-CH(CH₃)-C(O) | —(CH₂)₅—C(O)NH— |

TABLE 3-continued

| Example# | $R^{2a}$ | $R^{2b}$ | $R^6$ | $R^7, R^{8a}, R^{8b}$ group | —W—M— |
|---|---|---|---|---|---|
| 496 | $CHF_2$ | OH | phenyl | N-H alanyl | $-(CH_2)_6-C(O)NH-$ |
| 497 | $CHF_2$ | OH | phenyl | N-H alanyl | $-(CH_2)_7-C(O)NH-$ |
| 498 | $CHF_2$ | OH | phenyl | N-H alanyl | $-(CH_2)_3-N(CH_3)-(CH_2)_3-O-$ |
| 499 | $CHF_2$ | OH | phenyl | N-H alanyl | $-(CH_2)_3-S-(CH_2)_3-O-$ |
| 500 | $CHF_2$ | OH | phenyl | N-H alanyl | $-(CH_2)_6-OC(O)NH-$ |
| 501 | $CHF_2$ | OH | 1-naphthyl | N-H alanyl | $-(CH_2)_4-O-$ |
| 502 | $CHF_2$ | OH | 1-naphthyl | N-H alanyl | $-(CH_2)_5-O-$ |
| 503 | $CHF_2$ | OH | 1-naphthyl | N-H alanyl | $-(CH_2)_6-O-$ |
| 504 | $CHF_2$ | OH | 1-naphthyl | N-H alanyl | $-(CH_2)_7-O-$ |

TABLE 3-continued
| Example# | R²ᵃ | R²ᵇ | R⁶ | R⁷\N(R⁸ᵇR⁸ᵃ)C(O) | —W—M— |
|---|---|---|---|---|---|
| 505 | CHF₂ | OH | 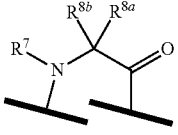 | 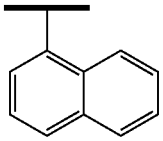 | —(CH₂)₈—O— |
| 506 | CHF₂ | OH | 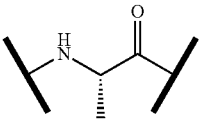 | 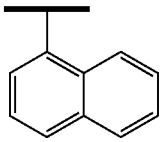 | 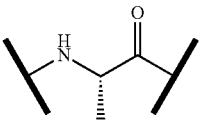 |
| 507 | CHF₂ | OH | 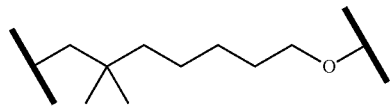 | 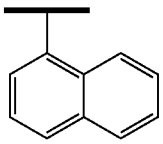 | 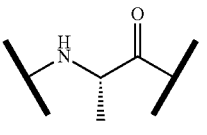 |
| 508 | CHF₂ | OH | 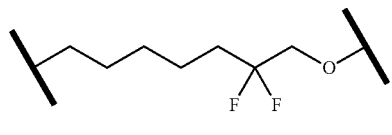 | 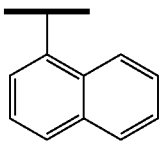 | —(CH₂)₃—O—(CH₂)₅—O— |
| 509 | CHF₂ | OH | 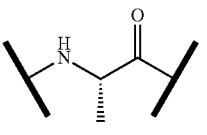 | 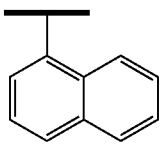 | 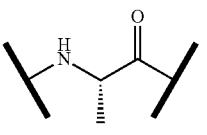 |
| 510 | CHF₂ | OH | 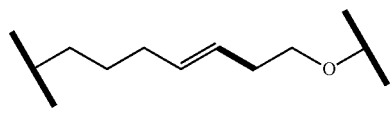 | 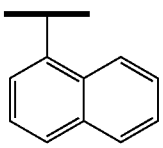 | 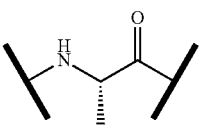 |
| 511 | CHF₂ | OH | 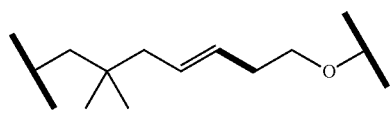 | 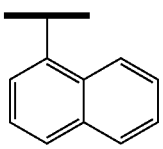 | 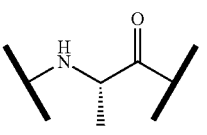 |
| 512 | CHF₂ | OH | 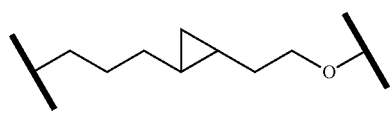 | 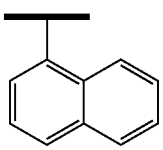 | —(CH₂)₅—NH— |
| 513 | CHF₂ | OH | 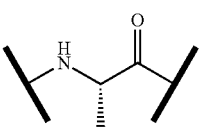 | 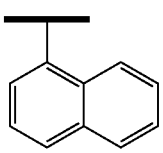 | —(CH₂)₆—NH— |

TABLE 3-continued

| Example# | $R^{2a}$ | $R^{2b}$ | $R^6$ | $R^7\text{N}(R^{8b})(R^{8a})\text{C(O)}$ | —W—M— |
|---|---|---|---|---|---|
| 514 | $CHF_2$ | OH | 1-naphthyl | NH-CH(CH₃)-C(O) | —(CH$_2$)$_7$—NH— |
| 515 | $CHF_2$ | OH | 1-naphthyl | NH-CH(CH₃)-C(O) | —(CH$_2$)$_5$—C(O)NH— |
| 516 | $CHF_2$ | OH | 1-naphthyl | NH-CH(CH₃)-C(O) | —(CH$_2$)$_6$—C(O)NH— |
| 517 | $CHF_2$ | OH | 1-naphthyl | NH-CH(CH₃)-C(O) | —(CH$_2$)$_7$—C(O)NH— |
| 518 | $CHF_2$ | OH | 1-naphthyl | NH-CH(CH₃)-C(O) | —(CH$_2$)$_3$N(CH$_3$)(CH$_2$)$_4$O— |
| 519 | $CHF_2$ | OH | 1-naphthyl | NH-CH(CH₃)-C(O) | —(CH$_2$)$_3$S(CH$_2$)$_4$O— |
| 520 | $CHF_2$ | OH | 1-naphthyl | NH-CH(CH₃)-C(O) | —(CH$_2$)$_6$—OC(O)NH— |
| 521 | $CHF_2$ | F | phenyl | NH-CH(CH₃)-C(O) | —(CH$_2$)$_4$—O— |
| 522 | $CHF_2$ | F | phenyl | NH-CH(CH₃)-C(O) | —(CH$_2$)$_5$—O— |

TABLE 3-continued
| Example# | $R^{2a}$ | $R^{2b}$ | $R^6$ | $R^7\text{N}(R^{8b})(R^{8a})\text{C(=O)}$ | —W—M— |
|---|---|---|---|---|---|
| 523 | $CHF_2$ | F | 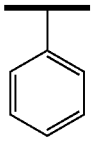 | 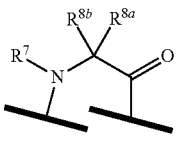 | —$(CH_2)_6$—O— |
| 524 | $CHF_2$ | F | 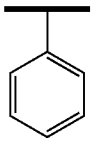 | 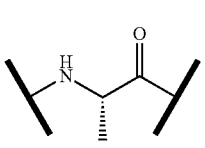 | —$(CH_2)_7$—O— |
| 525 | $CHF_2$ | F | 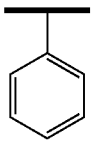 | 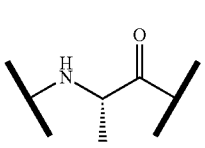 | —$(CH_2)_8$—O— |
| 526 | $CHF_2$ | F | 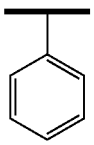 | 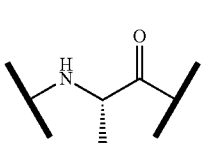 | 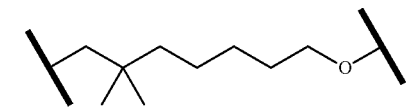 |
| 527 | $CHF_2$ | F | 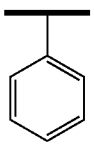 | 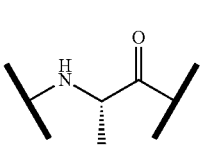 | 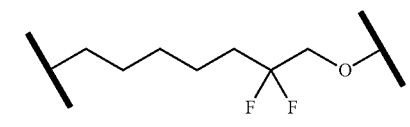 |
| 528 | $CHF_2$ | F | 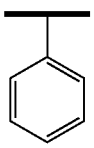 | 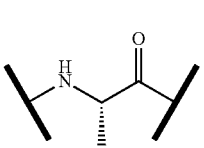 | —$(CH_2)_3$—O—$(CH_2)_5$—O— |
| 529 | $CHF_2$ | F | 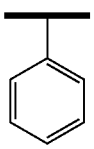 | 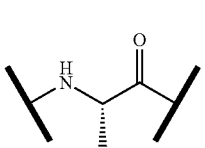 | 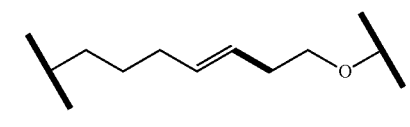 |
| 530 | $CHF_2$ | F | 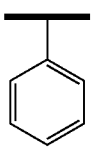 | 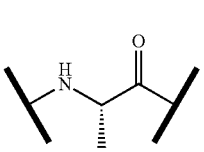 | 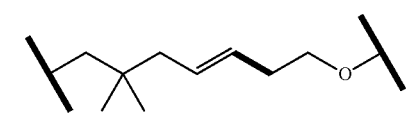 |
| 531 | $CHF_2$ | F | 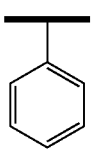 | 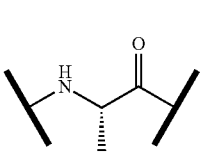 | 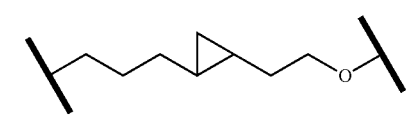 |

TABLE 3-continued
| Example# | $R^{2a}$ | $R^{2b}$ | $R^6$ | $R^7N(R^{8b})(R^{8a})C(O)$ | —W—M— |
|---|---|---|---|---|---|
| 532 | $CHF_2$ | F | 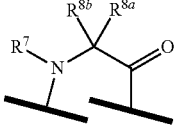 | 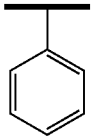 | —$(CH_2)_5$—NH— |
| 533 | $CHF_2$ | F | 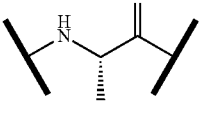 | 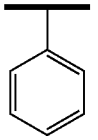 | —$(CH_2)_6$—NH— |
| 534 | $CHF_2$ | F | 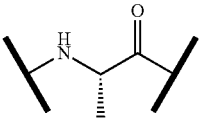 | 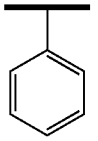 | —$(CH_2)_7$—NH— |
| 535 | $CHF_2$ | F | 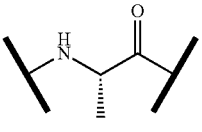 | 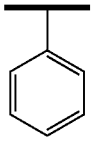 | —$(CH_2)_5$—C(O)NH— |
| 536 | $CHF_2$ | F | 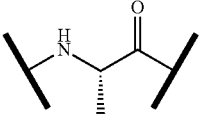 | 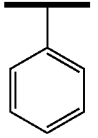 | —$(CH_2)_6$—C(O)NH— |
| 537 | $CHF_2$ | F | 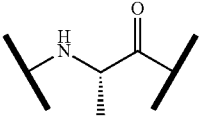 | 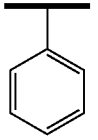 | —$(CH_2)_7$—C(O)NH— |
| 538 | $CHF_2$ | F | 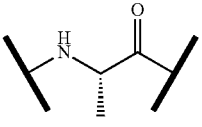 | 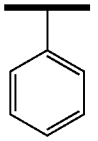 | 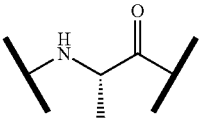 |
| 539 | $CHF_2$ | F | 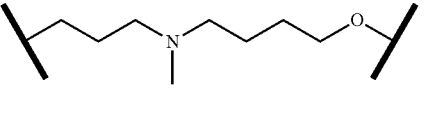 | 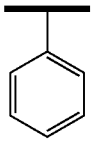 | 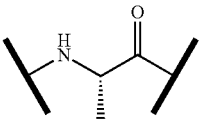 |
| 540 | $CHF_2$ | F | 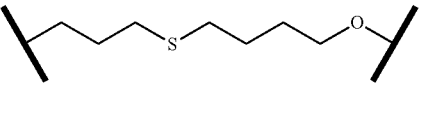 | 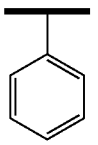 | —$(CH_2)_6$—OC(O)NH— |

TABLE 3-continued

| Example# | R$^{2a}$ | R$^{2b}$ | R$^6$ | R$^7$R$^{8b}$R$^{8a}$ group | —W—M— |
|---|---|---|---|---|---|
| 541 | CHF$_2$ | F | 1-naphthyl | NH-CH(CH$_3$)-C(O) | —(CH$_2$)$_4$—O— |
| 542 | CHF$_2$ | F | 1-naphthyl | NH-CH(CH$_3$)-C(O) | —(CH$_2$)$_5$—O— |
| 543 | CHF$_2$ | F | 1-naphthyl | NH-CH(CH$_3$)-C(O) | —(CH$_2$)$_6$—O— |
| 544 | CHF$_2$ | F | 1-naphthyl | NH-CH(CH$_3$)-C(O) | —(CH$_2$)$_7$—O— |
| 545 | CHF$_2$ | F | 1-naphthyl | NH-CH(CH$_3$)-C(O) | —(CH$_2$)$_8$—O— |
| 546 | CHF$_2$ | F | 1-naphthyl | NH-CH(CH$_3$)-C(O) | —C(CH$_3$)$_2$(CH$_2$)$_5$—O— |
| 547 | CHF$_2$ | F | 1-naphthyl | NH-CH(CH$_3$)-C(O) | —(CH$_2$)$_5$CF$_2$CH$_2$—O— |
| 548 | CHF$_2$ | F | 1-naphthyl | NH-CH(CH$_3$)-C(O) | —(CH$_2$)$_3$—O—(CH$_2$)$_5$—O— |
| 549 | CHF$_2$ | F | 1-naphthyl | NH-CH(CH$_3$)-C(O) | —CH$_2$CH$_2$CH=CHCH$_2$—O— |

TABLE 3-continued

| Example# | R²ᵃ | R²ᵇ | R⁶ | R⁷R⁸ᵇR⁸ᵃ fragment | —W—M— |
|---|---|---|---|---|---|
| 550 | CHF₂ | F | 1-naphthyl | NH-CH(CH₃)-C(O) | CH₂C(CH₃)₂CH=CHCH₂O |
| 551 | CHF₂ | F | 1-naphthyl | NH-CH(CH₃)-C(O) | (CH₂)₂-cyclopropyl-CH₂O |
| 552 | CHF₂ | F | 1-naphthyl | NH-CH(CH₃)-C(O) | —(CH₂)₅—NH— |
| 553 | CHF₂ | F | 1-naphthyl | NH-CH(CH₃)-C(O) | —(CH₂)₆—NH— |
| 554 | CHF₂ | F | 1-naphthyl | NH-CH(CH₃)-C(O) | —(CH₂)₇—NH— |
| 555 | CHF₂ | F | 1-naphthyl | NH-CH(CH₃)-C(O) | —(CH₂)₅—C(O)NH— |
| 556 | CHF₂ | F | 1-naphthyl | NH-CH(CH₃)-C(O) | —(CH₂)₆—C(O)NH— |
| 557 | CHF₂ | F | 1-naphthyl | NH-CH(CH₃)-C(O) | —(CH₂)₇—C(O)NH— |
| 558 | CHF₂ | F | 1-naphthyl | NH-CH(CH₃)-C(O) | —(CH₂)₃N(CH₃)(CH₂)₄O— |

TABLE 3-continued
| Example# | R²ᵃ | R²ᵇ | R⁶ | 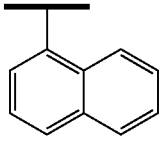 | —W—M— |
|---|---|---|---|---|---|
| 559 | CHF₂ | F | 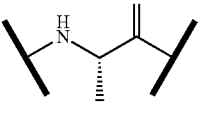 |  | 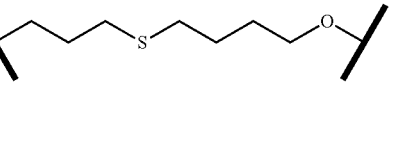 |
| 560 | CHF₂ | F | 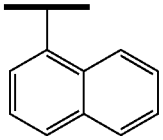 | 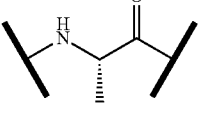 | —(CH₂)₆—OC(O)NH— |
| 561 | Me | OH | 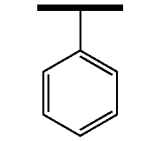 | 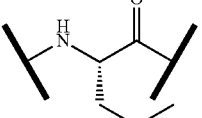 | —(CH₂)₄—O— |
| 562 | Me | OH | 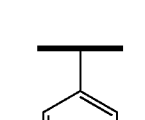 | 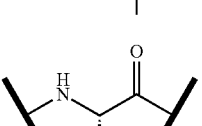 | —(CH₂)₅—O— |
| 563 | Me | OH | 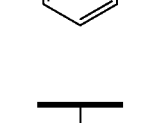 | 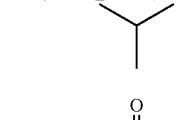 | —(CH₂)₆—O— |
| 564 | Me | OH | 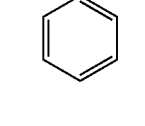 | 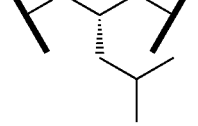 | —(CH₂)₇—O— |
| 565 | Me | OH | 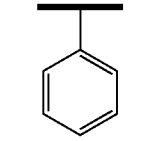 | 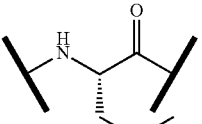 | —(CH₂)₈—O— |
| 566 | Me | OH | 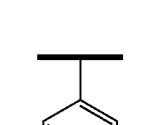 | 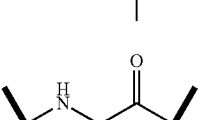 |  |

US 8,846,638 B2
TABLE 3-continued
| Example# | R²ᵃ | R²ᵇ | R⁶ | R⁷\N(R⁸ᵇR⁸ᵃ)C(O) | —W—M— |
|---|---|---|---|---|---|
| 567 | Me | OH | 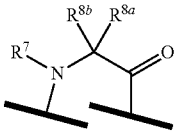 | 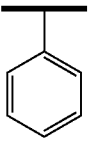 | 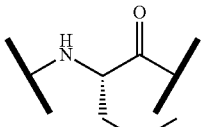 |
| 568 | Me | OH | 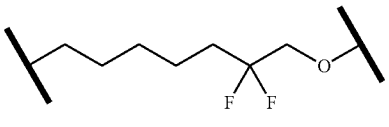 | 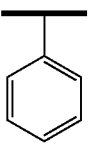 | —(CH₂)₃—O—(CH₂)₅—O— |
| 569 | Me | OH | 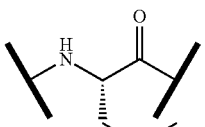 | 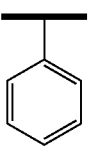 | 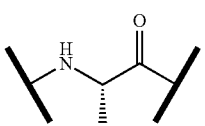 |
| 570 | Me | OH | 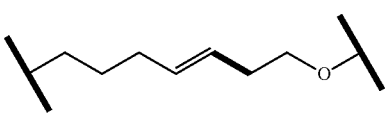 | 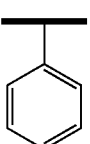 | 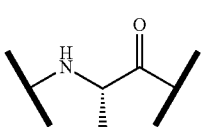 |
| 571 | Me | OH | 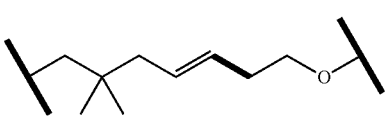 | 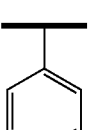 | 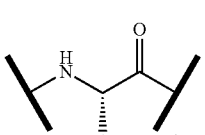 |
| 572 | Me | OH | 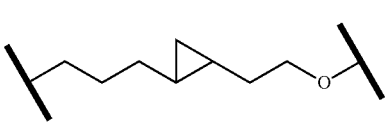 | 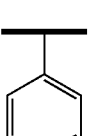 | —(CH₂)₅—NH— |
| 573 | Me | OH | 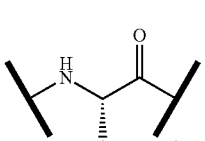 | 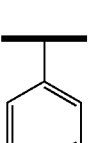 | —(CH₂)₆—NH— |

TABLE 3-continued

| Example# | R2a | R2b | R6 | (R7,R8a,R8b group) | —W—M— |
|---|---|---|---|---|---|
| 574 | Me | OH | Ph | Leu-derived | —(CH₂)₇—NH— |
| 575 | Me | OH | Ph | Leu-derived | —(CH₂)₅—C(O)NH— |
| 576 | Me | OH | Ph | Leu-derived | —(CH₂)₆—C(O)NH— |
| 577 | Me | OH | Ph | Leu-derived | —(CH₂)₇—C(O)NH— |
| 578 | Me | OH | Ph | Leu-derived | —(CH₂)₃N(CH₃)(CH₂)₄O— |
| 579 | Me | OH | Ph | Leu-derived | —(CH₂)₃S(CH₂)₄O— |
| 580 | Me | OH | Ph | Leu-derived | —(CH₂)₆—OC(O)NH— |

TABLE 3-continued
| Example# | R2a | R2b | R6 | 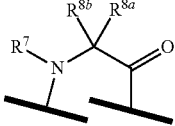 | —W—M— |
|---|---|---|---|---|---|
| 581 | Me | F | 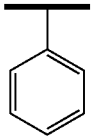 | 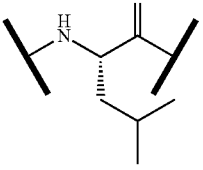 | —(CH2)4—O— |
| 582 | Me | F | 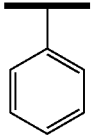 | 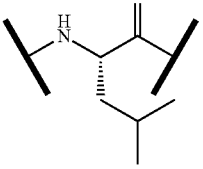 | —(CH2)5—O— |
| 583 | Me | F | 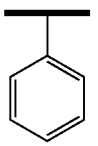 | 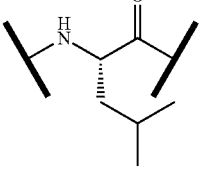 | —(CH2)6—O— |
| 584 | Me | F | 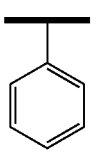 | 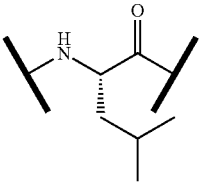 | —(CH2)7—O— |
| 585 | Me | F | 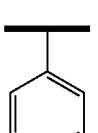 | 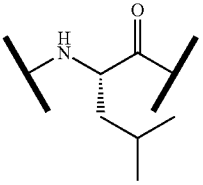 | —(CH2)8—O— |
| 586 | Me | F | 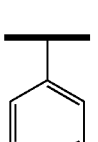 | 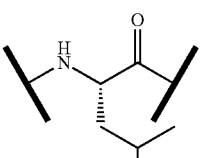 | 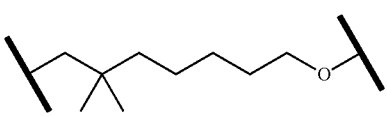 |
| 587 | Me | F | 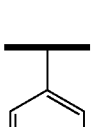 | 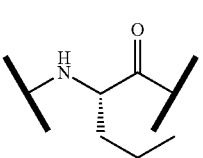 | 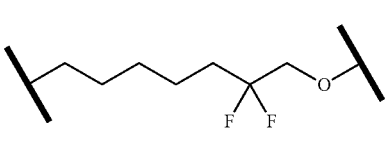 |

TABLE 3-continued
| Example# | R2a | R2b | R6 | 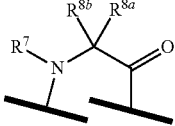 | —W—M— |
|---|---|---|---|---|---|
| 588 | Me | F | 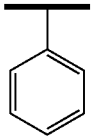 | 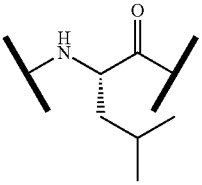 | —(CH₂)₃—O—(CH₂)₅—O— |
| 589 | Me | F | 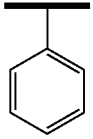 | 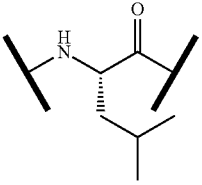 | 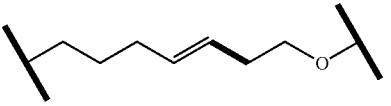 |
| 590 | Me | F | 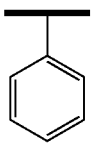 | 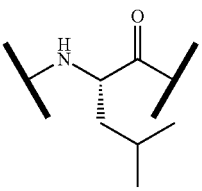 | 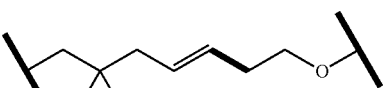 |
| 591 | Me | F | 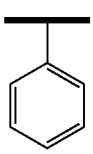 | 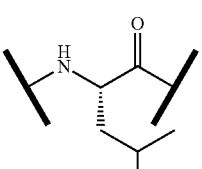 |  |
| 592 | Me | F | 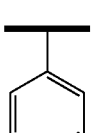 | 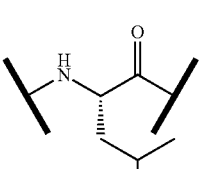 | —(CH₂)₅—NH— |
| 593 | Me | F | 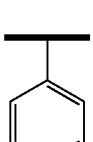 | 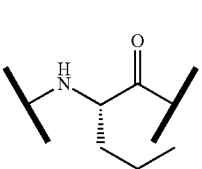 | —(CH₂)₆—NH— |
| 594 | Me | F |  | 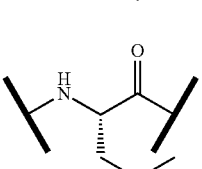 | —(CH₂)₇—NH— |

TABLE 3-continued
| Example# | $R^{2a}$ | $R^{2b}$ | $R^6$ | 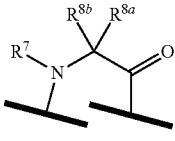 | —W—M— |
|---|---|---|---|---|---|
| 595 | Me | F | 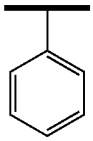 | 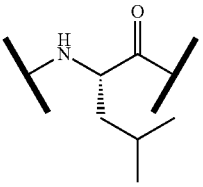 | —(CH$_2$)$_5$—C(O)NH— |
| 596 | Me | F |  | 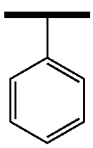 | —(CH$_2$)$_6$—C(O)NH— |
| 597 | Me | F | 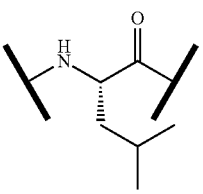 |  | —(CH$_2$)$_7$—C(O)NH— |
| 598 | Me | F | 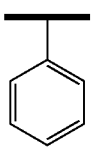 | 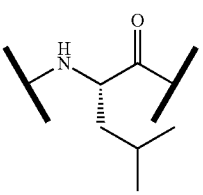 | 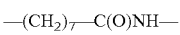 |
| 599 | Me | F | 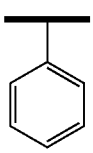 | 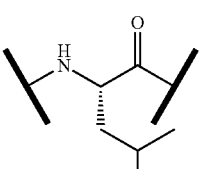 | 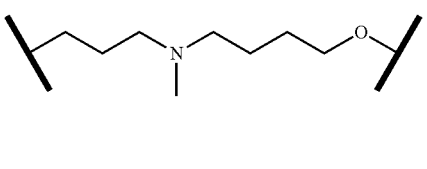 |
| 600 | Me | F | 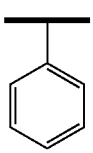 | 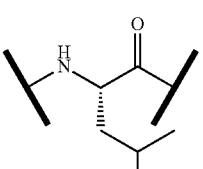 | —(CH$_2$)$_6$—OC(O)NH— |

In another embodiment, the invention provides compounds of Formula X,

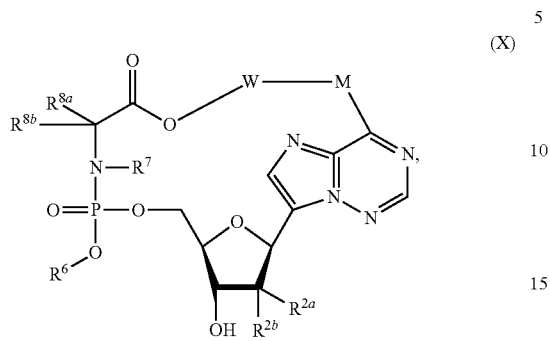

(X)

where W, M, $R^{2a}$, $R^{2b}$, $R^6$, $R^7$, $R^{8a}$ and $R^{8b}$ are as previously defined. Representative compounds of the invention include, but are not limited to, the following compounds (example 601 to example 800 in Table 4) according to Formula X, wherein, $R^{2a}$, $R^{2b}$, $R^6$, $R^7$, $R^{8a}$, $R^{8b}$ and —W-M- are delineated for each example in Table 4.

TABLE 4

| Example# | $R^{2a}$ | $R^{2b}$ | $R^6$ | | —W—M— |
|---|---|---|---|---|---|
| 601 | Me | OH | Ph | L-Ala | —(CH$_2$)$_4$—O— |
| 602 | Me | OH | Ph | L-Ala | —(CH$_2$)$_5$—O— |
| 603 | Me | OH | Ph | L-Ala | —(CH$_2$)$_6$—O— |
| 604 | Me | OH | Ph | L-Ala | —(CH$_2$)$_7$—O— |
| 605 | Me | OH | Ph | L-Ala | —(CH$_2$)$_8$—O— |

TABLE 4-continued
| Example# | R$^{2a}$ | R$^{2b}$ | R$^6$ | 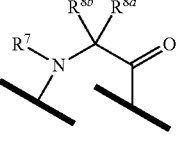 | —W—M— |
|---|---|---|---|---|---|
| 606 | Me | OH | 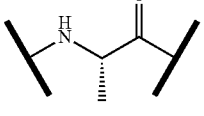 | 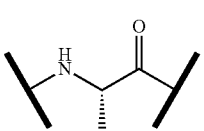 |  |
| 607 | Me | OH |  | 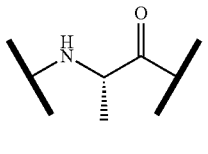 |  |
| 608 | Me | OH |  | 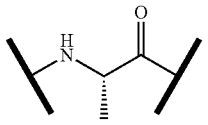 | —(CH$_2$)$_3$—O—(CH$_2$)$_5$—O— |
| 609 | Me | OH | | | |
| 610 | Me | OH | | | |
| 611 | Me | OH | | | |
| 612 | Me | OH | | | —(CH$_2$)$_5$—NH— |
| 613 | Me | OH | | | —(CH$_2$)$_6$—NH— |
| 614 | Me | OH | | | —(CH$_2$)$_7$—NH— |

TABLE 4-continued

| Example# | $R^{2a}$ | $R^{2b}$ | $R^6$ | | —W—M— |
|---|---|---|---|---|---|
| 615 | Me | OH | phenyl | Ala | —(CH$_2$)$_5$—C(O)NH— |
| 616 | Me | OH | phenyl | Ala | —(CH$_2$)$_6$—C(O)NH— |
| 617 | Me | OH | phenyl | Ala | —(CH$_2$)$_7$—C(O)NH— |
| 618 | Me | OH | phenyl | Ala | —(CH$_2$)$_3$N(CH$_3$)(CH$_2$)$_4$O— |
| 619 | Me | OH | phenyl | Ala | —(CH$_2$)$_3$S(CH$_2$)$_4$O— |
| 620 | Me | OH | phenyl | Ala | —(CH$_2$)$_6$—OC(O)NH— |
| 621 | Me | OH | 1-naphthyl | Ala | —(CH$_2$)$_4$—O— |
| 622 | Me | OH | 1-naphthyl | Ala | —(CH$_2$)$_5$—O— |
| 623 | Me | OH | 1-naphthyl | Ala | —(CH$_2$)$_6$—O— |

TABLE 4-continued
| Example# | R²ᵃ | R²ᵇ | R⁶ | 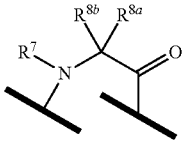 | —W—M— |
|---|---|---|---|---|---|
| 624 | Me | OH | 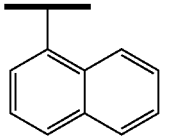 | 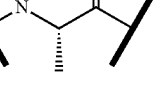 | —(CH$_2$)$_7$—O— |
| 625 | Me | OH | 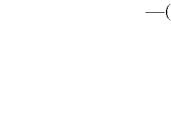 | 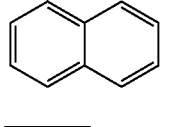 | —(CH$_2$)$_8$—O— |
| 626 | Me | OH |  |  | 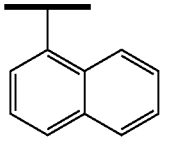 |
| 627 | Me | OH |  |  | 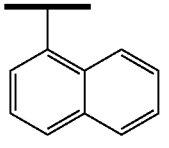 |
| 628 | Me | OH |  |  | —(CH$_2$)$_3$—O—(CH$_2$)$_5$—O— |
| 629 | Me | OH | 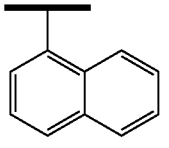 | 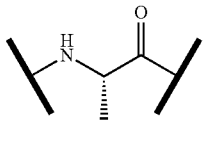 |  |
| 630 | Me | OH |  | 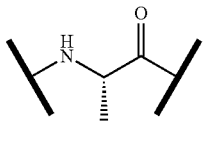 |  |
| 631 | Me | OH |  | 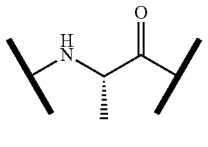 |  |
| 632 | Me | OH | 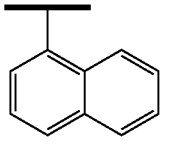 | 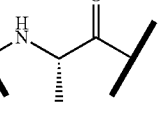 | —(CH$_2$)$_5$—NH— |

TABLE 4-continued

| Example# | $R^{2a}$ | $R^{2b}$ | $R^6$ | (R⁷R⁸ᵇR⁸ᵃN-CHC(O)) group | —W—M— |
|---|---|---|---|---|---|
| 633 | Me | OH | 1-naphthyl | NH-CH(CH₃)-C(O), (S) | —(CH₂)₆—NH— |
| 634 | Me | OH | 1-naphthyl | NH-CH(CH₃)-C(O), (S) | —(CH₂)₇—NH— |
| 635 | Me | OH | 1-naphthyl | NH-CH(CH₃)-C(O), (S) | —(CH₂)₅—C(O)NH— |
| 636 | Me | OH | 1-naphthyl | NH-CH(CH₃)-C(O), (S) | —(CH₂)₆—C(O)NH— |
| 637 | Me | OH | 1-naphthyl | NH-CH(CH₃)-C(O), (S) | —(CH₂)₇—C(O)NH— |
| 638 | Me | OH | 1-naphthyl | NH-CH(CH₃)-C(O), (S) | —(CH₂)₃N(CH₃)(CH₂)₄O— |
| 639 | Me | OH | 1-naphthyl | NH-CH(CH₃)-C(O), (S) | —(CH₂)₃S(CH₂)₄O— |
| 640 | Me | OH | 1-naphthyl | NH-CH(CH₃)-C(O), (S) | —(CH₂)₆—OC(O)NH— |
| 641 | Me | F | phenyl | NH-CH(CH₃)-C(O), (S) | —(CH₂)₄—O— |

TABLE 4-continued

| Example# | R$^{2a}$ | R$^{2b}$ | R$^6$ | [R$^7$R$^{8b}$R$^{8a}$ group] | —W—M— |
|---|---|---|---|---|---|
| 642 | Me | F | phenyl | NH-CH(CH₃)-C(O) | —(CH$_2$)$_5$—O— |
| 643 | Me | F | phenyl | NH-CH(CH₃)-C(O) | —(CH$_2$)$_6$—O— |
| 644 | Me | F | phenyl | NH-CH(CH₃)-C(O) | —(CH$_2$)$_7$—O— |
| 645 | Me | F | phenyl | NH-CH(CH₃)-C(O) | —(CH$_2$)$_8$—O— |
| 646 | Me | F | phenyl | NH-CH(CH₃)-C(O) | —C(CH$_3$)$_2$(CH$_2$)$_4$—O— |
| 647 | Me | F | phenyl | NH-CH(CH₃)-C(O) | —(CH$_2$)$_5$CF$_2$CH$_2$—O— |
| 648 | Me | F | phenyl | NH-CH(CH₃)-C(O) | —(CH$_2$)$_3$—O—(CH$_2$)$_5$—O— |
| 649 | Me | F | phenyl | NH-CH(CH₃)-C(O) | —(CH$_2$)$_3$CH=CHCH$_2$—O— |
| 650 | Me | F | phenyl | NH-CH(CH₃)-C(O) | —C(CH$_3$)$_2$(CH$_2$)$_2$CH=CHCH$_2$—O— |

TABLE 4-continued

| Example# | R$^{2a}$ | R$^{2b}$ | R$^6$ | R$^7$R$^{8b}$R$^{8a}$ group | —W—M— |
|---|---|---|---|---|---|
| 651 | Me | F | phenyl | NH-CH(CH$_3$)-C(O) | -(CH$_2$)$_3$-cyclopropyl-CH$_2$CH$_2$-O- |
| 652 | Me | F | phenyl | NH-CH(CH$_3$)-C(O) | —(CH$_2$)$_5$—NH— |
| 653 | Me | F | phenyl | NH-CH(CH$_3$)-C(O) | —(CH$_2$)$_6$—NH— |
| 654 | Me | F | phenyl | NH-CH(CH$_3$)-C(O) | —(CH$_2$)$_7$—NH— |
| 655 | Me | F | phenyl | NH-CH(CH$_3$)-C(O) | —(CH$_2$)$_5$—C(O)NH— |
| 656 | Me | F | phenyl | NH-CH(CH$_3$)-C(O) | —(CH$_2$)$_6$—C(O)NH— |
| 657 | Me | F | phenyl | NH-CH(CH$_3$)-C(O) | —(CH$_2$)$_7$—C(O)NH— |
| 658 | Me | F | phenyl | NH-CH(CH$_3$)-C(O) | -(CH$_2$)$_3$-N(CH$_3$)-(CH$_2$)$_4$-O- |
| 659 | Me | F | phenyl | NH-CH(CH$_3$)-C(O) | -(CH$_2$)$_3$-S-(CH$_2$)$_3$-O- |

TABLE 4-continued

| Example# | $R^{2a}$ | $R^{2b}$ | $R^6$ | $R^7$, $R^{8a}$, $R^{8b}$ group | —W—M— |
|---|---|---|---|---|---|
| 660 | Me | F | phenyl | NH-CH(CH₃)-C(O) (Ala) | —(CH$_2$)$_6$—OC(O)NH— |
| 661 | Me | F | 1-naphthyl | NH-CH(CH₃)-C(O) (Ala) | —(CH$_2$)$_4$—O— |
| 662 | Me | F | 1-naphthyl | NH-CH(CH₃)-C(O) (Ala) | —(CH$_2$)$_5$—O— |
| 663 | Me | F | 1-naphthyl | NH-CH(CH₃)-C(O) (Ala) | —(CH$_2$)$_6$—O— |
| 664 | Me | F | 1-naphthyl | NH-CH(CH₃)-C(O) (Ala) | —(CH$_2$)$_7$—O— |
| 665 | Me | F | 1-naphthyl | NH-CH(CH₃)-C(O) (Ala) | —(CH$_2$)$_8$—O— |
| 666 | Me | F | 1-naphthyl | NH-CH(CH₃)-C(O) (Ala) | —C(CH$_3$)$_2$(CH$_2$)$_5$—O— |
| 667 | Me | F | 1-naphthyl | NH-CH(CH₃)-C(O) (Ala) | —(CH$_2$)$_5$CF$_2$CH$_2$—O— |
| 668 | Me | F | 1-naphthyl | NH-CH(CH₃)-C(O) (Ala) | —(CH$_2$)$_3$—O—(CH$_2$)$_5$—O— |

US 8,846,638 B2
175
176
TABLE 4-continued
| Example# | $R^{2a}$ | $R^{2b}$ | $R^6$ | | —W—M— |
|---|---|---|---|---|---|
| 669 | Me | F | 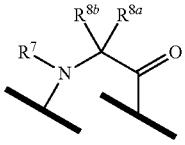 | 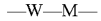 | 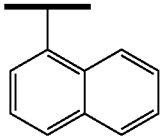 |
| 670 | Me | F | 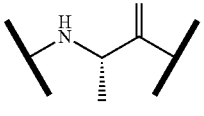 | 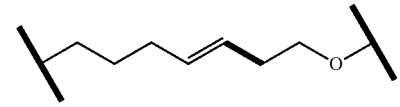 | 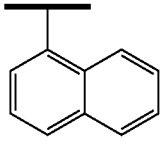 |
| 671 | Me | F | 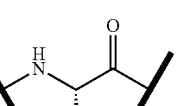 | 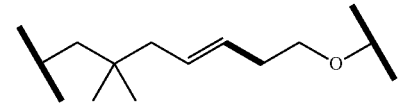 | 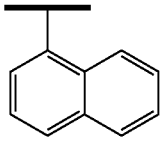 |
| 672 | Me | F | 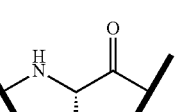 | 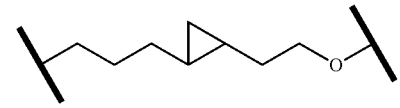 | —(CH$_2$)$_5$—NH— |
| 673 | Me | F | 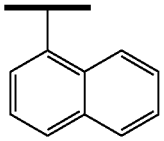 | 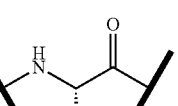 | —(CH$_2$)$_6$—NH— |
| 674 | Me | F | 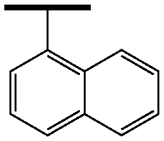 | 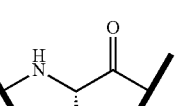 | —(CH$_2$)$_7$—NH— |
| 675 | Me | F | 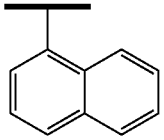 | 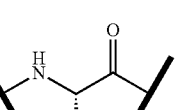 | —(CH$_2$)$_5$—C(O)NH— |
| 676 | Me | F | 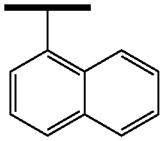 | 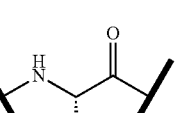 | —(CH$_2$)$_6$—C(O)NH— |
| 677 | Me | F | 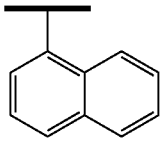 | 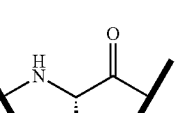 | —(CH$_2$)$_7$—C(O)NH— |

TABLE 4-continued

| Example# | $R^{2a}$ | $R^{2b}$ | $R^6$ | | —W—M— |
|---|---|---|---|---|---|
| 678 | Me | F | 1-naphthyl-CH | NH-CH(CH₃)-C(O) | -(CH₂)₃-N(CH₃)-(CH₂)₄-O- |
| 679 | Me | F | 1-naphthyl-CH | NH-CH(CH₃)-C(O) | -(CH₂)₃-S-(CH₂)₄-O- |
| 680 | Me | F | 1-naphthyl-CH | NH-CH(CH₃)-C(O) | —(CH₂)₆—OC(O)NH— |
| 681 | CHF₂ | OH | Ph-CH | NH-CH(CH₃)-C(O) | —(CH₂)₄—O— |
| 682 | CHF₂ | OH | Ph-CH | NH-CH(CH₃)-C(O) | —(CH₂)₅—O— |
| 683 | CHF₂ | OH | Ph-CH | NH-CH(CH₃)-C(O) | —(CH₂)₆—O— |
| 684 | CHF₂ | OH | Ph-CH | NH-CH(CH₃)-C(O) | —(CH₂)₇—O— |
| 685 | CHF₂ | OH | Ph-CH | NH-CH(CH₃)-C(O) | —(CH₂)₈—O— |
| 686 | CHF₂ | OH | Ph-CH | NH-CH(CH₃)-C(O) | -C(CH₃)₂-(CH₂)₄-O- |

TABLE 4-continued

| Example# | $R^{2a}$ | $R^{2b}$ | $R^6$ | [R7-N-C(R8a)(R8b)-C(O)] | —W—M— |
|---|---|---|---|---|---|
| 687 | $CHF_2$ | OH | phenyl | NH-CH(CH3)-C(O) | —CH2CH2CH2CH2CH2CH2—C(F)(F)—CH2—O— |
| 688 | $CHF_2$ | OH | phenyl | NH-CH(CH3)-C(O) | —(CH2)3—O—(CH2)5—O— |
| 689 | $CHF_2$ | OH | phenyl | NH-CH(CH3)-C(O) | —(CH2)4—CH=CH—CH2—O— |
| 690 | $CHF_2$ | OH | phenyl | NH-CH(CH3)-C(O) | —CH2—C(CH3)2—CH2—CH=CH—CH2—O— |
| 691 | $CHF_2$ | OH | phenyl | NH-CH(CH3)-C(O) | —(CH2)3—cyclopropyl—CH2CH2—O— |
| 692 | $CHF_2$ | OH | phenyl | NH-CH(CH3)-C(O) | —(CH2)5—NH— |
| 693 | $CHF_2$ | OH | phenyl | NH-CH(CH3)-C(O) | —(CH2)6—NH— |
| 694 | $CHF_2$ | OH | phenyl | NH-CH(CH3)-C(O) | —(CH2)7—NH— |
| 695 | $CHF_2$ | OH | phenyl | NH-CH(CH3)-C(O) | —(CH2)5—C(O)NH— |

TABLE 4-continued

| Example# | $R^{2a}$ | $R^{2b}$ | $R^6$ | (R⁷)(R⁸ᵃ)(R⁸ᵇ) group | —W—M— |
|---|---|---|---|---|---|
| 696 | $CHF_2$ | OH | phenyl | N-H, alanine-type | —$(CH_2)_6$—C(O)NH— |
| 697 | $CHF_2$ | OH | phenyl | N-H, alanine-type | —$(CH_2)_7$—C(O)NH— |
| 698 | $CHF_2$ | OH | phenyl | N-H, alanine-type | —(CH₂)₃—N(CH₃)—(CH₂)₄—O— |
| 699 | $CHF_2$ | OH | phenyl | N-H, alanine-type | —(CH₂)₃—S—(CH₂)₄—O— |
| 700 | $CHF_2$ | OH | phenyl | N-H, alanine-type | —$(CH_2)_6$—OC(O)NH— |
| 701 | $CHF_2$ | OH | 1-naphthyl | N-H, alanine-type | —$(CH_2)_4$—O— |
| 702 | $CHF_2$ | OH | 1-naphthyl | N-H, alanine-type | —$(CH_2)_5$—O— |
| 703 | $CHF_2$ | OH | 1-naphthyl | N-H, alanine-type | —$(CH_2)_6$—O— |
| 704 | $CHF_2$ | OH | 1-naphthyl | N-H, alanine-type | —$(CH_2)_7$—O— |

TABLE 4-continued
| Example# | $R^{2a}$ | $R^{2b}$ | $R^6$ | | —W—M— |
|---|---|---|---|---|---|
| 705 | $CHF_2$ | OH |  |  | —$(CH_2)_8$—O— |
| 706 | $CHF_2$ | OH |  |  |  |
| 707 | $CHF_2$ | OH | 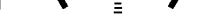 |  |  |
| 708 | $CHF_2$ | OH |  |  | —$(CH_2)_3$—O—$(CH_2)_5$—O— |
| 709 | $CHF_2$ | OH |  |  |  |
| 710 | $CHF_2$ | OH | 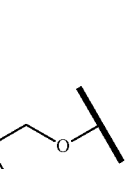 |  | 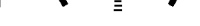 |
| 711 | $CHF_2$ | OH |  |  |  |
| 712 | $CHF_2$ | OH | 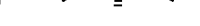 |  | —$(CH_2)_5$—NH— |
| 713 | $CHF_2$ | OH |  | 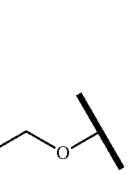 | —$(CH_2)_6$—NH— |

TABLE 4-continued
| Example# | $R^{2a}$ | $R^{2b}$ | $R^6$ | | —W—M— |
|---|---|---|---|---|---|
| 714 | $CHF_2$ | OH | 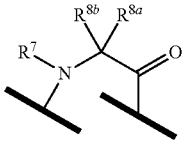 | 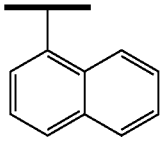 | —$(CH_2)_7$—NH— |
| 715 | $CHF_2$ | OH | 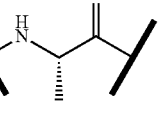 | 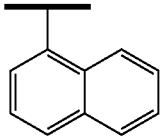 | —$(CH_2)_5$—C(O)NH— |
| 716 | $CHF_2$ | OH | 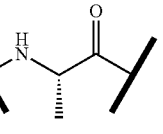 | 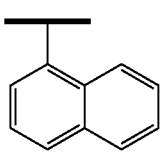 | —$(CH_2)_6$—C(O)NH— |
| 717 | $CHF_2$ | OH | 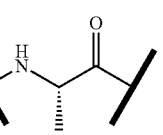 | 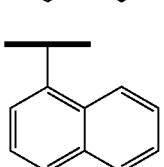 | —$(CH_2)_7$—C(O)NH— |
| 718 | $CHF_2$ | OH | 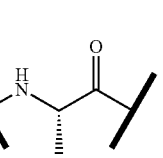 | 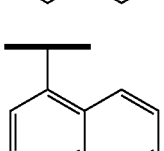 | 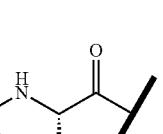 |
| 719 | $CHF_2$ | OH | 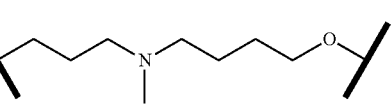 | 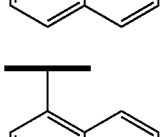 | 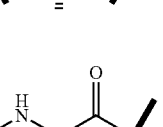 |
| 720 | $CHF_2$ | OH | 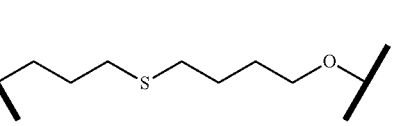 | 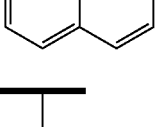 | —$(CH_2)_6$—OC(O)NH— |
| 721 | $CHF_2$ | F | 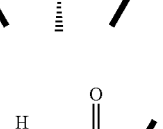 | 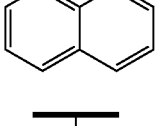 | —$(CH_2)_4$—O— |
| 722 | $CHF_2$ | F | 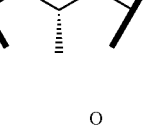 | 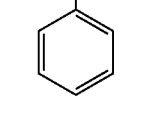 | —$(CH_2)_5$—O— |

TABLE 4-continued

| Example# | $R^{2a}$ | $R^{2b}$ | $R^6$ | | —W—M— |
|---|---|---|---|---|---|
| 723 | $CHF_2$ | F | phenyl | N-H, alanine | —$(CH_2)_6$—O— |
| 724 | $CHF_2$ | F | phenyl | N-H, alanine | —$(CH_2)_7$—O— |
| 725 | $CHF_2$ | F | phenyl | N-H, alanine | —$(CH_2)_8$—O— |
| 726 | $CHF_2$ | F | phenyl | N-H, alanine | gem-dimethyl alkyl-O- |
| 727 | $CHF_2$ | F | phenyl | N-H, alanine | gem-difluoro alkyl-O- |
| 728 | $CHF_2$ | F | phenyl | N-H, alanine | —$(CH_2)_3$—O—$(CH_2)_5$—O— |
| 729 | $CHF_2$ | F | phenyl | N-H, alanine | alkenyl-O- |
| 730 | $CHF_2$ | F | phenyl | N-H, alanine | gem-dimethyl alkenyl-O- |
| 731 | $CHF_2$ | F | phenyl | N-H, alanine | cyclopropyl alkyl-O- |

TABLE 4-continued
| Example# | $R^{2a}$ | $R^{2b}$ | $R^6$ | | —W—M— |
|---|---|---|---|---|---|
| 732 | $CHF_2$ | F | 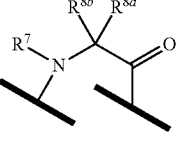 | 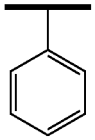 | —$(CH_2)_5$—NH— |
| 733 | $CHF_2$ | F | 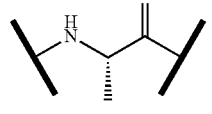 | 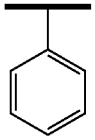 | —$(CH_2)_6$—NH— |
| 734 | $CHF_2$ | F | 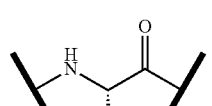 | 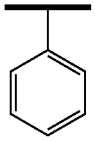 | —$(CH_2)_7$—NH— |
| 735 | $CHF_2$ | F | 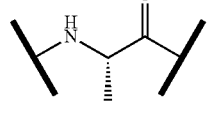 | 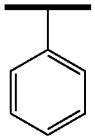 | —$(CH_2)_5$—C(O)NH— |
| 736 | $CHF_2$ | F | 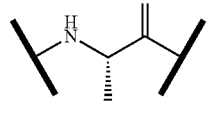 | 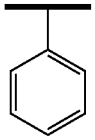 | —$(CH_2)_6$—C(O)NH— |
| 737 | $CHF_2$ | F | 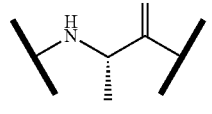 | 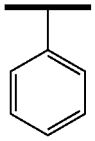 | —$(CH_2)_7$—C(O)NH— |
| 738 | $CHF_2$ | F | 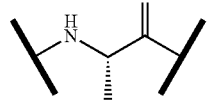 | 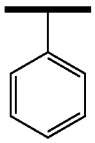 | 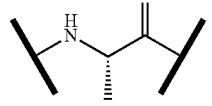 |
| 739 | $CHF_2$ | F | 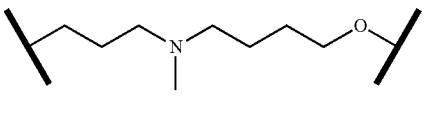 | 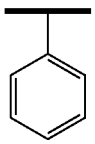 | 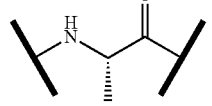 |
| 740 | $CHF_2$ | F | 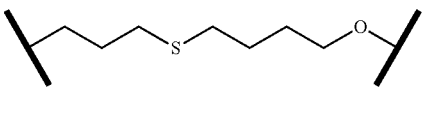 | 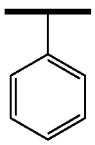 | —$(CH_2)_6$—OC(O)NH— |

TABLE 4-continued

| Example# | $R^{2a}$ | $R^{2b}$ | $R^6$ | (R⁷R⁸ᵇR⁸ᵃN-C-C(=O) group) | —W—M— |
|---|---|---|---|---|---|
| 741 | $CHF_2$ | F | 1-naphthyl | -NH-CH(CH₃)-C(=O)- | —$(CH_2)_4$—O— |
| 742 | $CHF_2$ | F | 1-naphthyl | -NH-CH(CH₃)-C(=O)- | —$(CH_2)_5$—O— |
| 743 | $CHF_2$ | F | 1-naphthyl | -NH-CH(CH₃)-C(=O)- | —$(CH_2)_6$—O— |
| 744 | $CHF_2$ | F | 1-naphthyl | -NH-CH(CH₃)-C(=O)- | —$(CH_2)_7$—O— |
| 745 | $CHF_2$ | F | 1-naphthyl | -NH-CH(CH₃)-C(=O)- | —$(CH_2)_8$—O— |
| 746 | $CHF_2$ | F | 1-naphthyl | -NH-CH(CH₃)-C(=O)- | —C(CH₃)₂(CH₂)₅—O— |
| 747 | $CHF_2$ | F | 1-naphthyl | -NH-CH(CH₃)-C(=O)- | —(CH₂)₅CF₂CH₂—O— |
| 748 | $CHF_2$ | F | 1-naphthyl | -NH-CH(CH₃)-C(=O)- | —$(CH_2)_3$—O—$(CH_2)_5$—O— |
| 749 | $CHF_2$ | F | 1-naphthyl | -NH-CH(CH₃)-C(=O)- | —(CH₂)₄CH=CHCH₂—O— |

TABLE 4-continued

| Example# | R² ͣ | R² ᵇ | R⁶ | [R⁷R⁸ᵇR⁸ᵃ group] | —W—M— |
|---|---|---|---|---|---|
| 750 | CHF₂ | F | 1-naphthyl | NH-CH(CH₃)-C(O) | -C(CH₃)₂-CH=CH-CH₂-O- |
| 751 | CHF₂ | F | 1-naphthyl | NH-CH(CH₃)-C(O) | -CH₂-CH₂-(cyclopropyl)-CH₂-O- |
| 752 | CHF₂ | F | 1-naphthyl | NH-CH(CH₃)-C(O) | —(CH₂)₅—NH— |
| 753 | CHF₂ | F | 1-naphthyl | NH-CH(CH₃)-C(O) | —(CH₂)₆—NH— |
| 754 | CHF₂ | F | 1-naphthyl | NH-CH(CH₃)-C(O) | —(CH₂)₇—NH— |
| 755 | CHF₂ | F | 1-naphthyl | NH-CH(CH₃)-C(O) | —(CH₂)₅—C(O)NH— |
| 756 | CHF₂ | F | 1-naphthyl | NH-CH(CH₃)-C(O) | —(CH₂)₆—C(O)NH— |
| 757 | CHF₂ | F | 1-naphthyl | NH-CH(CH₃)-C(O) | —(CH₂)₇—C(O)NH— |
| 758 | CHF₂ | F | 1-naphthyl | NH-CH(CH₃)-C(O) | -(CH₂)₃-N(CH₃)-(CH₂)₃-O- |

TABLE 4-continued
| Example# | R²ᵃ | R²ᵇ | R⁶ | | —W—M— |
|---|---|---|---|---|---|
| 759 | CHF₂ | F | 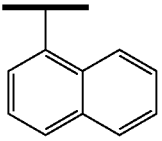 | 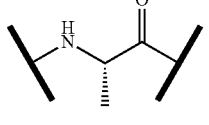 | 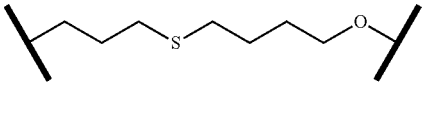 |
| 760 | CHF₂ | F | 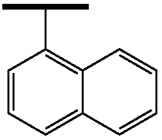 | 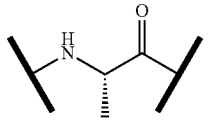 | —(CH₂)₆—OC(O)NH— |
| 761 | Me | OH | 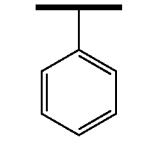 | 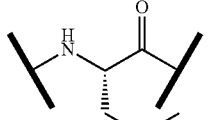 | —(CH₂)₄—O— |
| 762 | Me | OH | 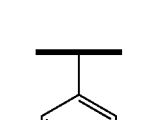 | 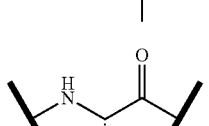 | —(CH₂)₅—O— |
| 763 | Me | OH | 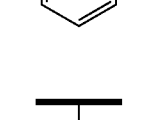 | 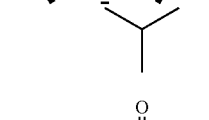 | —(CH₂)₆—O— |
| 764 | Me | OH | 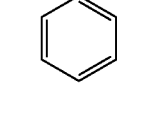 | 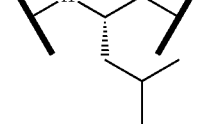 | —(CH₂)₇—O— |
| 765 | Me | OH | 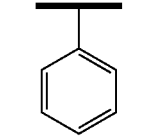 | 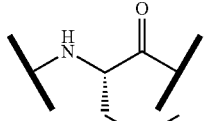 | —(CH₂)₈—O— |
| 766 | Me | OH | 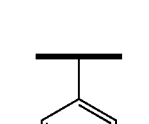 | 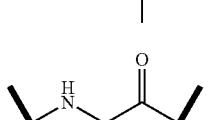 | 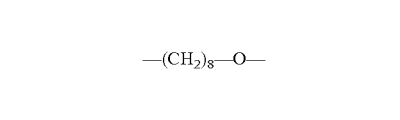 |

TABLE 4-continued

| Example# | R^2a | R^2b | R^6 | (R^7,R^8a,R^8b group) | —W—M— |
|---|---|---|---|---|---|
| 767 | Me | OH | phenyl | Leu-like | alkyl chain with CF$_2$–O |
| 768 | Me | OH | phenyl | Leu-like | —(CH$_2$)$_3$—O—(CH$_2$)$_5$—O— |
| 769 | Me | OH | phenyl | Leu-like | alkenyl chain —O— |
| 770 | Me | OH | phenyl | Leu-like | gem-dimethyl alkenyl —O— |
| 771 | Me | OH | phenyl | Leu-like | alkyl-cyclopropyl-CH$_2$—O— |
| 772 | Me | OH | phenyl | Leu-like | —(CH$_2$)$_5$—NH— |
| 773 | Me | OH | phenyl | Leu-like | —(CH$_2$)$_6$—NH— |

TABLE 4-continued

| Example# | R2a | R2b | R6 | (R7,R8a,R8b,N,C=O group) | —W—M— |
|---|---|---|---|---|---|
| 774 | Me | OH | Ph | Leu-like | —(CH$_2$)$_7$—NH— |
| 775 | Me | OH | Ph | Leu-like | —(CH$_2$)$_5$—C(O)NH— |
| 776 | Me | OH | Ph | Leu-like | —(CH$_2$)$_6$—C(O)NH— |
| 777 | Me | OH | Ph | Leu-like | —(CH$_2$)$_7$—C(O)NH— |
| 778 | Me | OH | Ph | Leu-like | —(CH$_2$)$_3$—N(Me)—(CH$_2$)$_4$—O— |
| 779 | Me | OH | Ph | Leu-like | —(CH$_2$)$_3$—S—(CH$_2$)$_4$—O— |
| 780 | Me | OH | Ph | Leu-like | —(CH$_2$)$_6$—OC(O)NH— |

TABLE 4-continued

| Example# | R2a | R2b | R6 | (R7,R8a,R8b group) | —W—M— |
|---|---|---|---|---|---|
| 781 | Me | F | phenyl | Leu-derived | —(CH2)4—O— |
| 782 | Me | F | phenyl | Leu-derived | —(CH2)5—O— |
| 783 | Me | F | phenyl | Leu-derived | —(CH2)6—O— |
| 784 | Me | F | phenyl | Leu-derived | —(CH2)7—O— |
| 785 | Me | F | phenyl | Leu-derived | —(CH2)8—O— |
| 786 | Me | F | phenyl | Leu-derived | gem-dimethyl alkyl-O— |
| 787 | Me | F | phenyl | Leu-derived | gem-difluoro alkyl-O— |

TABLE 4-continued
| Example# | R2a | R2b | R6 | | —W—M— |
|---|---|---|---|---|---|
| 788 | Me | F | 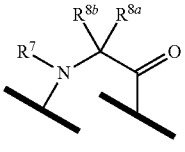 | 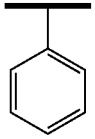 | —(CH₂)₃—O—(CH₂)₅—O— |
| 789 | Me | F | 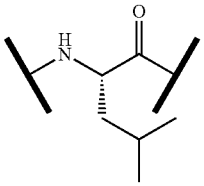 | 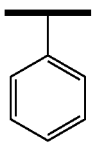 | 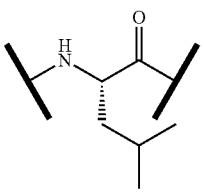 |
| 790 | Me | F | 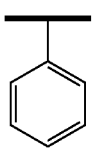 | 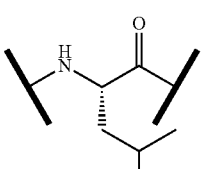 | 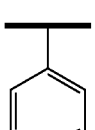 |
| 791 | Me | F | 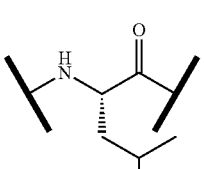 | 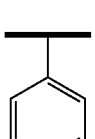 | 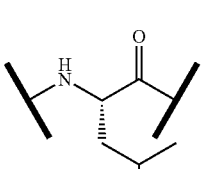 |
| 792 | Me | F | 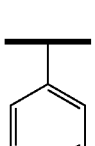 | 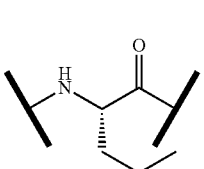 | —(CH₂)₅—NH— |
| 793 | Me | F | 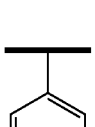 | 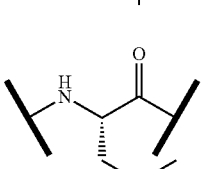 | —(CH₂)₆—NH— |
| 794 | Me | F | | | —(CH₂)₇—NH— |

TABLE 4-continued

| Example# | R²ᵃ | R²ᵇ | R⁶ | R⁷N(R⁸ᵇR⁸ᵃ)C(O) group | —W—M— |
|---|---|---|---|---|---|
| 795 | Me | F | phenyl | N-H Leu-like | —(CH$_2$)$_5$—C(O)NH— |
| 796 | Me | F | phenyl | N-H Leu-like | —(CH$_2$)$_6$—C(O)NH— |
| 797 | Me | F | phenyl | N-H Leu-like | —(CH$_2$)$_7$—C(O)NH— |
| 798 | Me | F | phenyl | N-H Leu-like | —(CH$_2$)$_3$—N(CH$_3$)—(CH$_2$)$_4$—O— |
| 799 | Me | F | phenyl | N-H Leu-like | —(CH$_2$)$_3$—S—(CH$_2$)$_4$—O— |
| 800 | Me | F | phenyl | N-H Leu-like | —(CH$_2$)$_6$—OC(O)NH—. |

In certain embodiments of the compounds of Formulas I-X, $R^1$ is hydrogen.

In certain embodiments of the compounds of Formulas I-X, $R^{2a}$ is methyl or —CHF$_2$.

In certain embodiments of the compounds of Formulas I-X, $R^{2b}$ is —OH or halogen, preferably fluorine.

In certain embodiments of the compounds of Formulas I-X, $R^3$ is hydrogen.

In certain embodiments of the compounds of Formulas I-X, $R^4$ is hydrogen.

In certain embodiments of the compounds of Formulas I-X, $R^{5a}$ is hydrogen.

In certain embodiments of the compounds of Formulas I-X, $R^{5b}$ is hydrogen.

In certain embodiments of the compounds of Formulas I-X, $R^6$ is aryl, preferably phenyl or naphthyl.

In certain embodiments of the compounds of Formulas I-X, $R^7$ is hydrogen.

In certain embodiments of the compounds of Formulas I-X, one of $R^{8a}$ and $R^{8b}$ is hydrogen and the other is normal or branched $C_1$-$C_8$-alkyl, preferably normal or branched $C_1$-$C_6$-alkyl and more preferably normal or branched $C_1$-$C_4$-alkyl.

In certain embodiments of the compounds of Formulas I-X, X is O.

In certain embodiments of the compounds of Formulas I-X, W is $C_4$-$C_{10}$-alkylene or $C_4$-$C_{10}$-alkenylene, each optionally substituted. Preferably, the $C_4$-$C_{10}$-alkylene or $C_4$-$C_{10}$-alkenylene group comprises 0, 1 or 2 substituents selected from $C_1$-$C_4$-alkyl and halogen, preferably fluorine. Alternatively, two adjacent substituents, together with the carbon atoms to which they are attached, form a $C_3$-$C_8$-cycloalkyl group, preferably a $C_3$-$C_6$-cycloalkyl group and more preferably a cyclopropyl group. In other embodiments, M is —$(CH_2)_n$—Y—$(CH_2)_m$—, where Y is O, S, NH or NMe and n and m are each independently 2 to 6.

In certain embodiments of the compounds of Formulas I-X, M is O, NH, OC(O)NH—, or C(O)NH.

In certain embodiments of the compounds of Formulas I-X, $R^1$ is hydrogen; $R^{2a}$ is methyl or —$CHF_2$; $R^{2b}$ is —OH or halogen, preferably fluorine; $R^3$, $R^4$, $R^{5a}$ and $R^{5b}$ are each hydrogen; $R^6$ is aryl, preferably phenyl or naphthyl; $R^7$ is hydrogen; one of $R^{8a}$ and $R^{8b}$ is hydrogen and the other is normal or branched $C_1$-$C_8$-alkyl, preferably normal or branched $C_1$-$C_6$-alkyl, and more preferably normal or branched $C_1$-$C_4$-alkyl; X is O; W is (a) $C_4$-$C_{10}$-alkylene or $C_4$-$C_{10}$-alkenylene, each optionally substituted, preferably with one or two substituents independently selected from $C_1$-$C_4$-alkyl and halogen, preferably fluorine; alternatively two adjacent substituents, together with the carbon atoms to which they are attached, form a $C_3$-$C_8$-cycloalkyl group, preferably a $C_3$-$C_6$-cycloalkyl group and more preferably a cyclopropyl group; or (b) —$(CH_2)_n$—Y—$(CH_2)_m$—, where Y is O, S, NH or NMe and n and m are each independently 2 to 6; and M is O, NH, —OC(O)NH—, or C(O)NH.

In certain embodiments of the compounds of Formulas I-X, one of $R^{8a}$ and $R^{8b}$ is hydrogen and the other is methyl or isobuytl. In one embodiment, the unit represented by

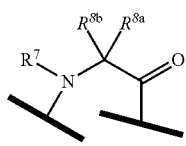

is selected from and

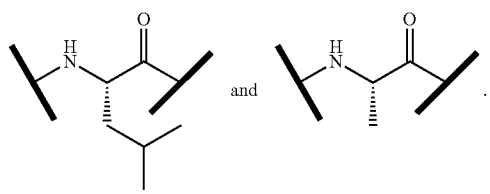

is selected from

In certain embodiments of the compounds of the compounds of Formulas I-X, —W-M- is selected from the groups below.

—$(CH_2)_4$—O—; —$(CH_2)_5$—O—; —$(CH_2)_6$—O—;
—$(CH_2)_7$—O—; —$(CH_2)_8$—O—;

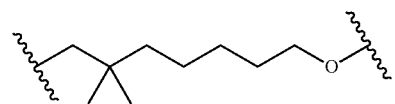

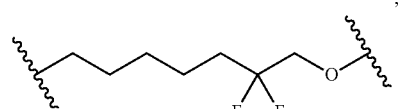

—$(CH_2)_3$—O—$(CH_2)_5$—O—;

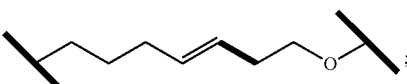

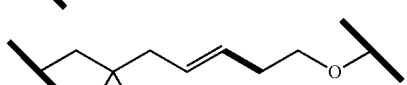

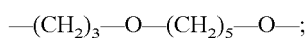

—$(CH_2)_5$—NH—; —$(CH_2)_6$—NH—; —$(CH_2)_7$—NH—;
—$(CH_2)_5$—C(O)NH—; —$(CH_2)_6$—C(O)NH—; —$(CH_2)_7$—C(O)NH—;

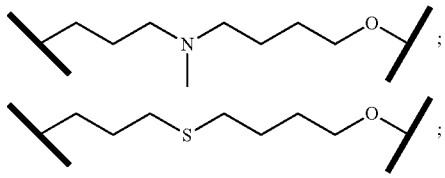

—$(CH_2)_6$—OC(O)NH—.

The present invention also features pharmaceutical compositions comprising a compound of the invention, or a pharmaceutically acceptable salt, ester or prodrug thereof. In one embodiment, the present invention features pharmaceutical compositions comprising a therapeutically effective amount of a compound of the invention, or a pharmaceutically acceptable salt, ester or prodrug thereof, in combination with a pharmaceutically acceptable carrier or excipient. In another embodiment, the invention features methods of treating a hepatitis C infection in a subject in need of such treatment with said pharmaceutical composition.

In addition, the present invention features methods of using compounds of the present invention or pharmaceutically acceptable salts thereof to treat HCV infection. The methods comprise administering to an HCV patient in need thereof an effective amount of a compound of the invention or a pharmaceutically acceptable salt thereof.

It will be appreciated that the compounds of the present invention may contain one or more asymmetric carbon atoms and may exist in racemic, diastereoisomeric, and optically active forms. It should be understood that the compounds encompassed by the present invention are those that are suitably stable for use as pharmaceutical agent.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient. In the methods described herein, a compound of the present invention or a pharmaceutically acceptable salt thereof can be administered alone, or in combination with one or more other anti-HCV agents, such as HCV polymerase inhibitors, HCV protease inhibitors, HCV NS5A inhibitors, CD81 inhibitors, cyclophilin inhibitors, internal ribosome entry site (IRES) inhibitors or any combinations thereof. Interferon, ribavirin or both can also be included in the treatment. For example, the methods described herein can further comprise administering to the patient peginterferon-alpha and ribavirin. Different agents can be administered simultaneously or sequentially. The dosing frequency of each agent in a treatment regimen can be the same or different. For instance, a compound of the invention can be dosed once daily, and ribavirin can be dosed twice daily.

Compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), cyclophilins (e.g., Debio 025), or antiviral compounds that inhibit host cellular functions such as inosine monophosphate dehydrogenase (for example, ribavirin and the like). Also included are cytokines that modulate immune function. Also included are vaccines comprising HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO0190121(A2), or U.S. Pat. No. 6,348,587B1 or WO0160315 or WO0132153 or non-nucleoside inhibitors such as, for example, benzimidazole polymerase inhibitors described in EP 1162196A1 or WO204425 or inhibitors of HCV protease such as, for example, peptidomimetic type inhibitors such as BILN2061 and the like or inhibitors of HCV helicase.

Other agents to be administered in combination with a compound of the present invention include any agent or combination of agents that inhibit the replication of other viruses for co-infected individuals. These agents include but are not limited to therapies for disease caused by hepatitis B (HBV) infection or therapies for disease caused by human immunodeficiency virus (HIV) infection.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

A further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenfovir, or any combination thereof. Example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. An example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to, ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to, interferons conjugated with other proteins including but not limited to, human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to, an NS5A protein and an NS4B protein.

It can occur that a patient may be co-infected with hepatitis C virus and one or more other viruses, including but not limited to, human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the pharmaceutical compositions of the present invention may further comprise another anti-viral, anti-bacterial, anti-fungal or anti-cancer agent, or an immune modulator, or another therapeutic agent.

According to still another embodiment, the present invention includes methods of treating viral infection such as, but not limited to, hepatitis C infections in a subject in need of such treatment by administering to said subject an effective amount of a compound of the present invention or a pharmaceutically acceptable salt, ester, or prodrug thereof.

According to a further embodiment, the present invention includes methods of treating hepatitis C infections in a subject in need of such treatment by administering to said subject an anti-HCV virally effective amount or an inhibitory amount of a pharmaceutical composition of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "anti-cancer agent" refers to a compound or drug capable of preventing or inhibiting the advancement of cancer. Examples of such agents include cis-platin, actinomycin D, doxorubicin, vincristine, vinblastine, etoposide, amsacrine, mitoxantrone, tenipaside, taxol, colchicine, cyclosporin A, phenothiazines or thioxantheres.

The term "anti-fungal agent" shall used to describe a compound which may be used to treat a fungus infection other than 3-AP, 3-AMP or prodrugs of 3-AP and 3-AMP according to the present invention. Anti-fungal agents according to the present invention include, for example, terbinafine, fluconazole, itraconazole, posaconazole, clotrimazole, griseofulvin, nystatin, tolnaftate, caspofungin, amphotericin B, liposomal amphotericin B, and amphotericin B lipid complex.

The term "antibacterial agent" refers to both naturally occurring antibiotics produced by microorganisms to suppress the growth of other microorganisms, and agents synthesized or modified in the laboratory which have either bactericidal or bacteriostatic activity, e.g., β-lactam antibacterial agents, glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term "immune modulator" refers to any substance meant to alter the working of the humoral or cellular immune system of a subject. Such immune modulators include inhibitors of mast cell-mediated inflammation, interferons, interleukins, prostaglandins, steroids, cortico-steroids, colony-stimulating factors, chemotactic factors, etc.

The term "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "$C_2$-$C_6$ alkenyl," or "$C_2$-$C_8$ alkenyl," as used herein, denote a monovalent group derived from a hydrocarbon moiety by the removal of a single hydrogen atom wherein the hydrocarbon moiety has at least one carbon-carbon double bond and contains from two to six, or two to eight carbon atoms, respectively. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety by the removal of a single hydrogen atom wherein the hydrocarbon moiety has at least one carbon-carbon triple bond and contains from two to six, or two to eight carbon atoms, respectively. Representative alkynyl groups include, but are not limited to, for example, ethynyl, 1-propynyl, 1-butynyl, heptynyl, octynyl and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure (such as Z in Formula $I_A$), the carbocycle group can be attached to the two other elements through any two substitutable ring atoms. A $C_4$-$C_6$ carbocycle has 4-6 ring atoms.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom where the saturated carbocyclic ring compound has from 3 to 8, or from 3 to 12, ring atoms, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom where the carbocyclic ring compound has from 3 to 8, or from 3 to 12, ring atoms, respectively. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue residue attached to a heteroaryl ring. Examples include, but are not limited to, pyridinylmethyl, pyrimidinylethyl and the like.

The term "substituted" as used herein, refers to independent replacement of one, two, or three or more of the hydrogen atoms thereon with substituents including, but not limited to, —F, —Cl, —Br, —I, —OH, protected hydroxy, —$NO_2$, —CN, —$NH_2$, $N_3$, protected amino, alkoxy, thioalkoxy, oxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH—$C_1$-$C_{12}$-alkyl, —$SO_2$NH—$C_2$-$C_{12}$-alkenyl, —$SO_2$NH—$C_2$-$C_{12}$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1]heptyl, and bicyclo [2.2.2]octyl. Such alicyclic groups may be further substituted.

The term "heterocycloalkyl" and "heterocyclic" can be used interchangeably and refer to a non-aromatic 3-, 4-, 5-, 6- or 7-membered ring or a bi- or tri-cyclic group fused system, where: (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$). Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.01 mg/Kg to about 500 mg/Kg, alternatively from about 1 to about 100 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, mean a sufficient amount of the compound so as to decrease the viral load in a biological sample or in a subject (e.g., resulting in at least 10%, preferably at least 50%, more preferably at least 80%, and most preferably at least 90% or 95%, reduction in viral load). As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject (e.g., resulting in at least 10%, preferably at least 50%, more preferably at least 80%, and most preferably at least 90% or 95%, reduction in viral load). It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:

ACN for acetonitrile;

BME for 2-mercaptoethanol;

BOP for benzotriazol-1-yloxy-tris(dimethylamino)phosphonium hexafluorophosphate;

CDI for carbonyldiimidazole;

COD for cyclooctadiene;

DABCO for 1,4-diazabicyclo[2.2.2]octane;

DAST for diethylaminosulfur trifluoride;

DABCYL for 6-(N-4'-carboxy-4-(dimethylamino)azobenzene)-aminohexyl-1-O-(2-cyanoethyl)-(N,N-diisopropyl)-phosphoramidite;

DBU for 1,8-Diazabicycloundec-7-ene;

DCC for N,N'-dicyclohexylcarbodiimide;

DCM for dichloromethane;

DIAD for diisopropyl azodicarboxylate;

DIBAL-H for diisobutylaluminum hydride;

DIPEA for diisopropyl ethylamine;

DMAP for N,N-dimethylaminopyridine;

DME for ethylene glycol dimethyl ether;

DMEM for Dulbecco's Modified Eagles Media;

DMF for N,N-dimethyl formamide;

DMSO for dimethylsulfoxide;

DSC for N,N'-disuccinimidyl carbonate;

DUPHOS for

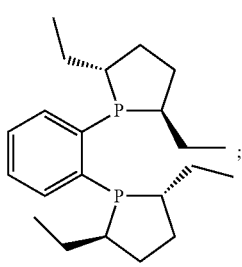 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl)amide;
Ms for mesyl;
NMM for N-4-methylmorpholine;
NMI for N-methylimidazole;
NMO for N-4-methylmorpholine-N-Oxide;
PyBrOP for Bromo-tri-pyrrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TEA for triethyl amine;
$Tf_2O$ for trifluoromethanesulfonic anhydride
TFA for trifluoroacetic acid;
THF for tetrahydrofuran;
TLC for thin layer chromatography;
TMSOTf for trimethylsilyl trifluoromethanesulfonate;
TPAP tetrapropylammonium perruthenate;
TPP or $PPh_3$ for triphenylphosphine;
TrCl for trityl chloride;
DMTrCl for 4,4'-dimethoxytrityl chloride;
tBOC or Boc for tert-butyloxy carbonyl;
Xantphos for 4,5-Bis-diphenylphosphanyl-9,9-dimethyl-9H-xanthene; and
Zhan 1 B for

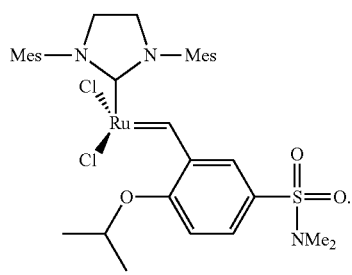

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

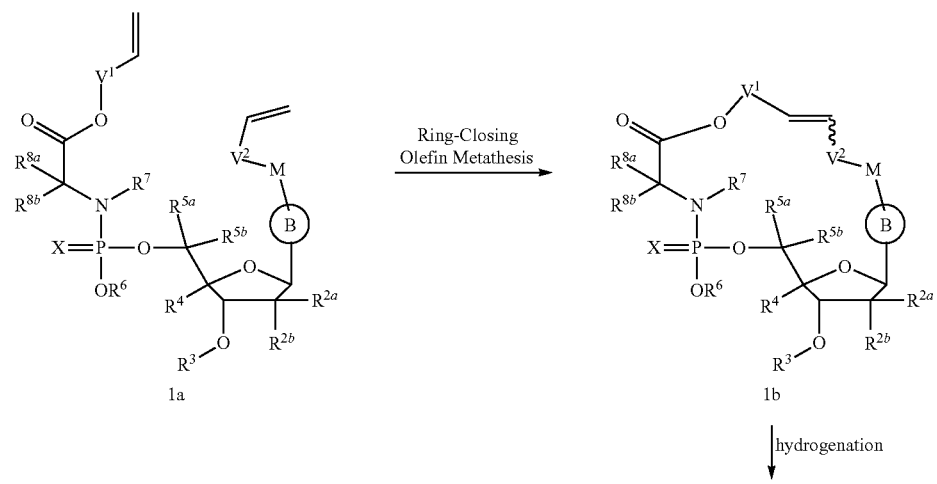

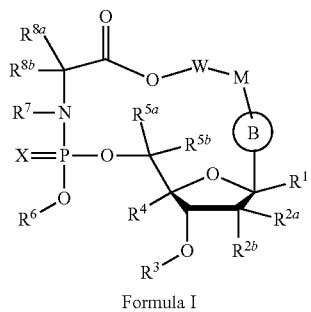

Formula I

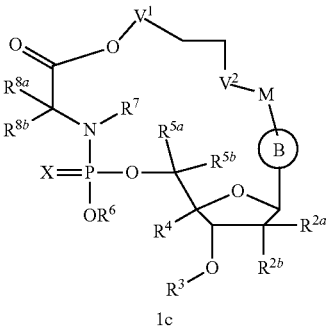

1c

Wherein $R^1$, $R^{2a}$, $R^{2b}$, $R^3$, $R^4$, $R^{5a}$, $R^{5b}$, $R^6$, $R^7$, $R^{8a}$, $R^{8b}$, X, W, M and

re previously defined as in formula I. $V^1$ and $V^2$ are each independently selected from —$C_1$-$C_8$ alkylene, —$C_2$-$C_8$ alkenylene, or —$C_2$-$C_8$ alkynylene each containing 0, 1, 2, or 3 heteroatoms selected from O, S, or N; substituted —$C_1$-$C_8$ alkylene, substituted —$C_2$-$C_8$ alkenylene, or substituted —$C_2$-$C_8$ alkynylene each containing 0, 1, 2, or 3 heteroatoms selected from O, S or N; —$C_3$-$C_8$ cycloalkylene, or substituted —$C_3$-$C_8$ cycloalkylene each containing 0, 1, 2, or 3 heteroatoms selected from O, S, or N; —$C_3$-$C_8$ cycloalkenylene or substituted —$C_3$-$C_8$ cycloalkenylene each containing 0, 1, 2, or 3 heteroatoms selected from O, S or N.

One approach to the synthesis of macrocyclic compounds with Formula I is exemplified in Scheme 1. The macrocyclic compound 1b could be synthesized from the Ring-Closing Olefin Metathesis of diene 1a employing a suitable catalyst such as, but not limited to Zhan 1B. (For further details on ring-closing metathesis see recent reviews: Grubbs et al., *Acc. Chem. Res.*, 1995, 28, 446; Shrock et al., *Tetrahedron* 1999, 55, 8141; Furstner, A. *Angew. Chem. Int. Ed.* 2000, 39, 3012; Trnka et al., *Acc. Chem. Res.* 2001, 34, 18, and Hoveyda et al., *Chem. Eur. J.* 2001, 7, 945; Agrofoglio et al., *Tetrahedron* 2005, 61, 7067; Len et al., *Tetrahedron* 2008, 64, 7475). When hydroxyl group(s) is present on the 2'-position and/or 3'-position, protecting of hydroxyl group(s) might be involved. Acetonide, Silyl, acetyl and phenylboronic ester are known in the art as hydroxyl protecting groups. If needed and/or desired, any amino group present on

can be protected with one or more protecting groups such as, but not limited to, Trityl, 4, 4'-dimethoxytrityl (DMTr), carbamates, and imine derivatives. Upon hydrogenation and deprotection if necessary the olefin 1b could be converted to compounds 1c, which are included in compounds with Formula I. Methods to deprotect and regenerate the free hydroxyl and/or amino groups when needed are known in the art. (For further details on protecting groups see T. H. Greene and P. G., S. M. Wuts, *Protective Groups in Organic Synthesis*, Fourth edition, John Wiley & Sons, New York (2006)).

Scheme 2

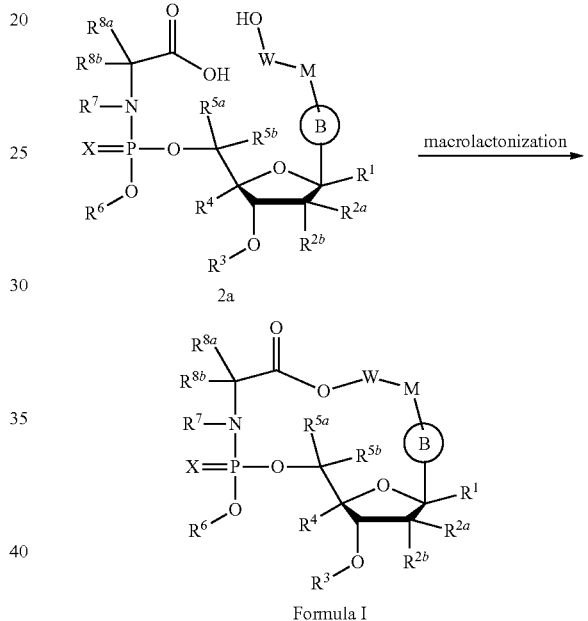

Wherein $R^1$, $R^{2a}$, $R^{2b}$, $R^3$, $R^4$, $R^{5a}$, $R^{5b}$, $R^6$, $R^7$, $R^{8a}$, $R^{8b}$, X, W, M and (B)

are previously defined as in formula I.

Another approach for the synthesis of macrocyclic compounds with Formula I is the macrolactonization of compounds 2a as exemplified in Scheme 2. The macrolactonization could be achieved employing coupling reagent (the coupling reagent can be selected from, but not limited to, HATU, DCC, EDCI, and Yamaguchi reagent in the presence of organic/inorganic base such as, but not limited to, DIEPA, TEA, DMAP; (For further details on macrolactonization see recent articles: Campagne et al., *Chem. Rev.* 2006, 106, 911; Clausen et al., *Eur. J. Org. Chem.* 2011, 17, 3107; Swamy et al., *Chem. Rev.* 2009, 109, 2551; Yamaguchi et al., *Bull. chem. Soc. Jpn.* 1979, 52, 1989).

Scheme 3

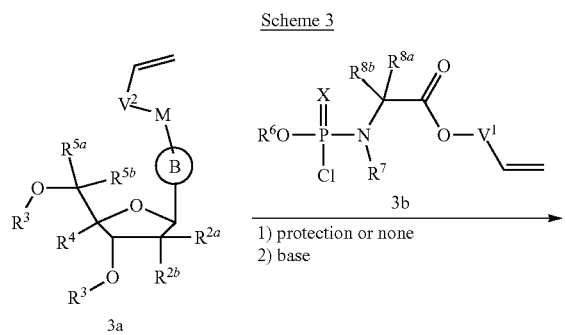

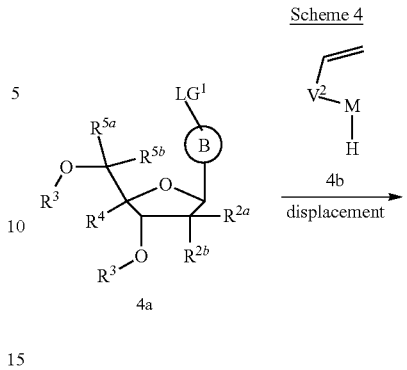

Wherein $R^1$, $R^{2a}$, $R^{2b}$, $R^3$, $R^4$, $R^{5a}$, $R^{5b}$, $R^6$, $R^7$, $R^{8a}$, $R^{8b}$, X, M and

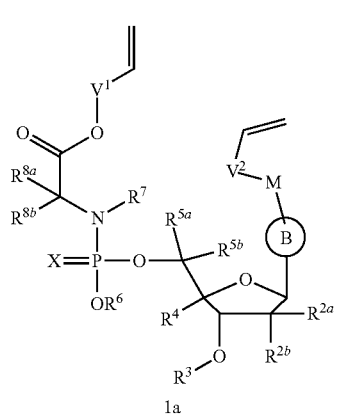

are previously defined as in formula I. $V^2$ is as previously defined.

The compounds 1a could be synthesized from the coupling of nucleoside (appropriately protected if necessary) 3a and 3b in the presence of organic/inorganic base such as, but not limited to, NMI, DIEPA, TEA, DMAP, as exemplified in Scheme 3. In some embodiment, when a hydroxyl group is present on the 2'-position and/or 3'-position, protecting of hydroxyl group(s) might be involved. Acetonide, Silyl, acetyl and phenylboronic ester are known in the art as hydroxyl protecting groups. If needed and/or desired, any amino group present on

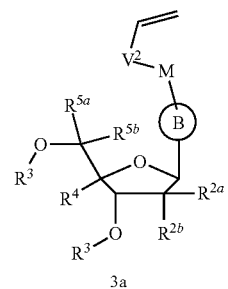

can be protected with one or a combination of the following protecting groups such as, but not limited to, Trityl, 4,4'-dimethoxytrityl (DMTr), carbamates, and imine derivatives.

Wherein $R^1$, $R^{2a}$, $R^{2b}$, $R^3$, $R^4$, $R^{5a}$, $R^{5b}$, M and

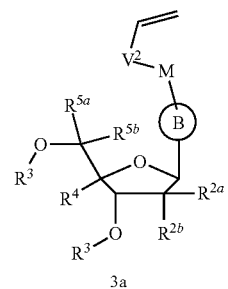

are previously defined as in formula I. $V^2$ is as previously defined. $LG^1$ is defined as leaving group such as, but not limited to, —Cl, —Br, —I, —F, —OTs, —OCOCF$_3$, —OSO$_2$CF$_3$, —NR$_3^+$.

The synthesis of compounds 3a is exemplified in Scheme 4. The displacement of $LG^1$ in 4a by 4b could be achieved in the presence of a base such as, but not limited to, NaH, n-BuLi, DBU, DIEPA, TEA or DMAP. Alternatively, this displacement of $LG^1$ in 4a by 4b could be achieved employing the Pd-catalyzed carbon-heteroatom bond formation method, (for further details on this method see recent articles: Hartwig J., *Acc. Chem. Res.* 1998, 31, 852; Hartwig J., *Nature* 2008, 455, 314).

Scheme 5

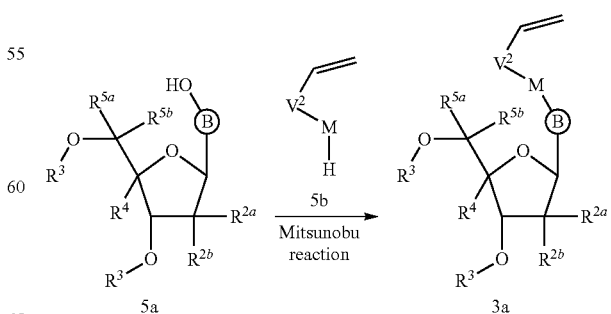

Wherein $R^1$, $R^{2a}$, $R^{2b}$, $R^3$, $R^4$, $R^{5a}$, $R^{5b}$, M and (B)

are previously defined as in formula I. $V^2$ is as previously defined.

The synthesis of compounds 3a could also be achieved via the Mitsunobu reaction between 5a and 5b as exemplified in Scheme 5. A typical reaction condition employs reagents such as, but not limited to, PPh₃, DIAD. (For further details on Mitsunobu reaction, see recent articles: Swamy et al., *Chem. Rev.* 2009, 109, 2551; Dembinski et al., *Eur. J. Org. Chem.* 2004, 13, 2763).

Scheme 6

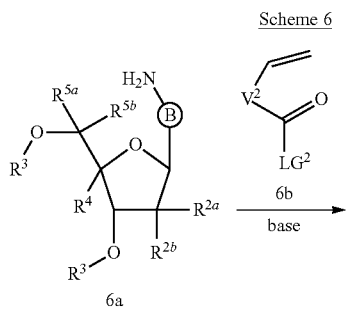

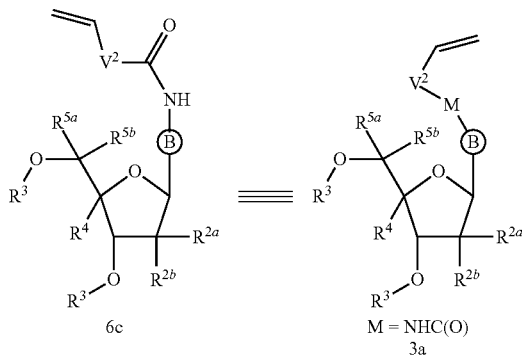

Wherein $R^1$, $R^{2a}$, $R^{2b}$, $R^3$, $R^4$, $R^{5a}$, $R^{5b}$ and (B)

are previously defined as in formula I. $V^2$ is as previously defined. $LG^2$ is defined as leaving group such as, but not limited to, —Cl, —Br, —I, —F, —OTs, —OCOCF3, —OSO₂CF₃, —NR₃⁺.

Another synthetic approach to compounds 3a is exemplified as in Scheme 6. The condensation between 6a and 6b employing amide coupling reagent (the coupling reagent can be selected from, but not limited to, HATU, DCC and HOBT in the presence of organic base such as, but not limited to, DIEPA, TEA, DMAP; for further details on amide formation see recent review: Christian A. G. N. Montalbetti et al., *Tetrahedron* 2005, 61, 10827).

Scheme 7

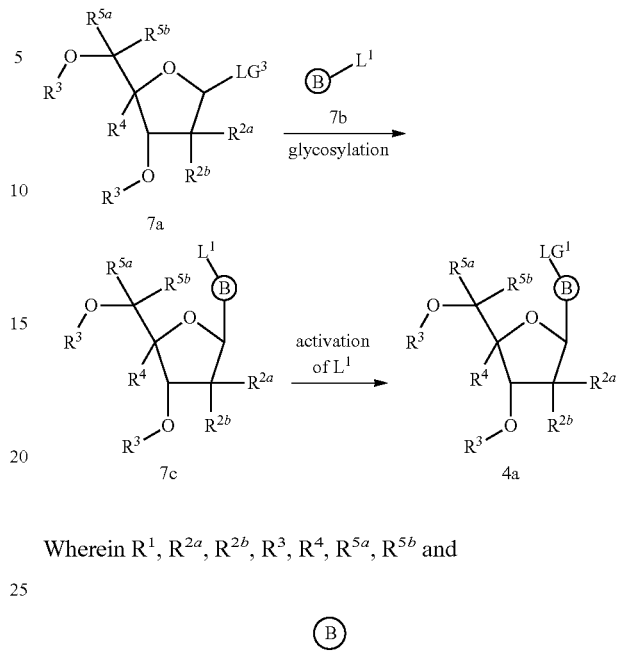

Wherein $R^1$, $R^{2a}$, $R^{2b}$, $R^3$, $R^4$, $R^{5a}$, $R^{5b}$ and (B)

are previously defined. $LG^1$ and $LG^3$ is defined as leaving group such as, but not limited to, —Cl, —Br, —I, —F, —OTs, —OCOCF₃, —OSO₂CF₃, —NR₃⁺. $L^1$ at each occurrence is each independently selected from the group(s) consisting of either one or a combination of the following: hydrogen, free hydroxyl or amino group, halogen, —N₃, —OR⁹, —NHR⁹, —NR⁹₂. R⁹ is previously defined.

The compounds 7c could be synthesized from the glycosylation between an optionally substituted heterocyclic base (or its derivatives) 7b and 7a employing a suitable catalyst such as, but not limited to TMSOTf or SnCl₄ with or without the presence of a suitable base, exemplified as in Scheme 7. Examples of suitable base includes, but not limited to, triethylamine, DBU, and DABCO. In some embodiment, deprotection and/or protection steps are involved to convert $L^1$ to the free hydroxyl or amino group. In some embodiment when $L^1$ is —OH, it could be activated to a leaving group $LG^1$ in the presence of a suitable base. Activation reagents include, but not limited to, POCl₃, TsCl, MsCl, Tf₂O, Mesitylsulfonyl chloride.

Scheme 8

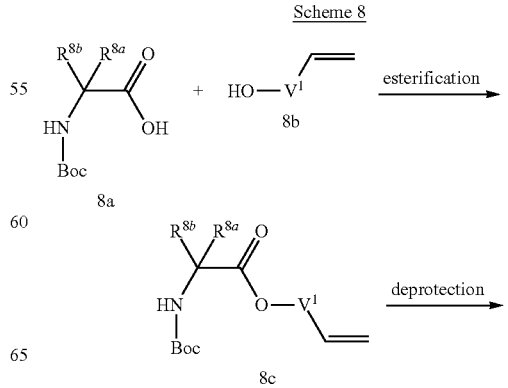

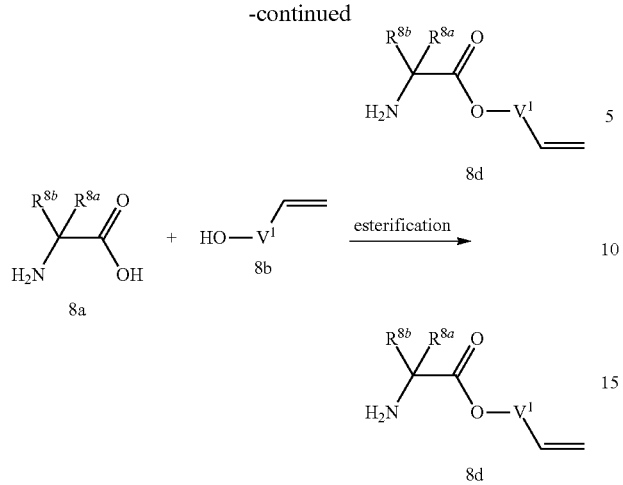

Wherein $R^{8a}$, $R^{8b}$ and $V^1$ are previously defined.

The amino ester 8d could be prepared from a two-step sequence exemplified as in Scheme 8. The condensation between N-Boc amino acid 8a and alcohol 8b under esterification conditions employing coupling reagent such as, but not limited to, EDCI, HATU, DCC and HOBT in the presence of organic base such as, but not limited to, DIEPA, TEA, DMAP. Followed with deprotection of Boc group under acidic condition such as, but not limited to, TFA or HCl in dioxane afforded the amino ester 8d (as a corresponding salt). Alternatively, amino ester 8d could be obtained from direct coupling between amino acid 8a and alcohol 8b in the presence of suitable reagent such as, but not limited to, SOCl$_2$, TMSCl, HCl, H$_2$SO$_4$, PTSA and ion-exchange resins.

Scheme 9

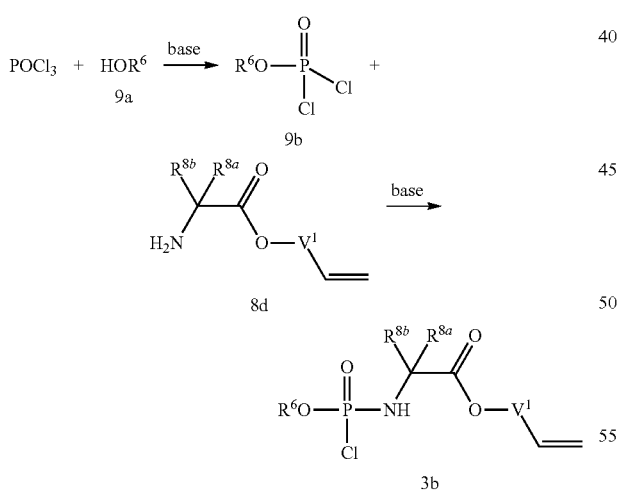

Wherein $V^1$, $R^6$, $R^{8a}$ and $R^{8b}$ are previously defined as in formula I.

The synthesis of phosphoramidate 3b is exemplified as in Scheme 9. Condensation of alcohol 9a and POCl$_3$ in the presence of base such as Et$_3$N or NMI affords the phosphodichloridate 9b, which is then treated with amino ester 8d in the presence of a base such as, but not limited to, NMI and Et$_3$N to afford the phosphoramidate 3b.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Compound of Formula III, wherein $R^1$=H, $R^{2a}$=Me, $R^{2b}$=OH, $R^3$=H, $R^4$=H, $R^{5a}$=$R^{5b}$=H, $R^6$=

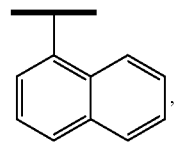

X=O, $R^7$=H, $R^{8a}$=Me, $R^{8b}$=H, W–M=

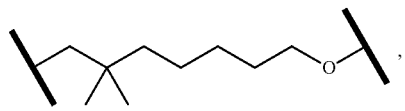

$R^{14}$=NH$_2$.

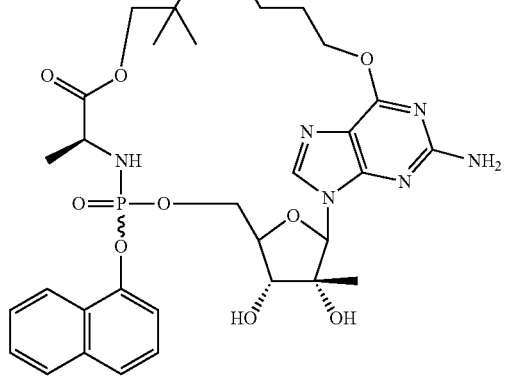

Step 1A

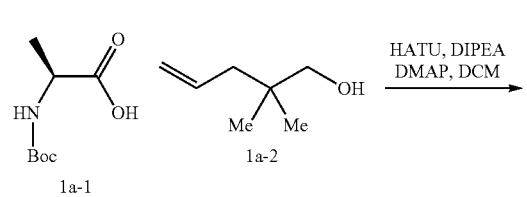

-continued

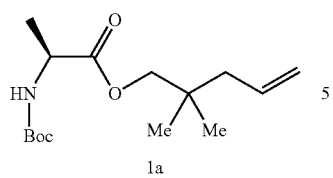
1a

To a solution of N-Boc-L-alanine 1a-1 (9.52 g, 50.3 mmol) and the alcohol 1a-2 (5.46 g, 47.9 mmol) in DCM (80 mL) at 0° C. was added HATU (21.86 g, 57.5 mmol), DIPEA (16.7 mL, 95.8 mmol) and DMAP (292 mg, 2.39 mmol). The resulted mixture was stirred at RT fro 14 h, and diluted with DCM. The organic layer was washed with 1 N HCl, water and brine, dried ($Na_2SO_4$), filtered and evaporated. The residue was purified by flash column chromatography (hexane to 40% acetone in hexane) to afford the product 1a (12.78 g, 93%). MS (ESI): m/e 308.2 (M+Na). Alcohol 1a-2 could be synthesized through a two steps sequence from methyl isobutyrate elaborated by Andrade et al (*Org. Lett.* 2009, 11, 3594).

Step 1B

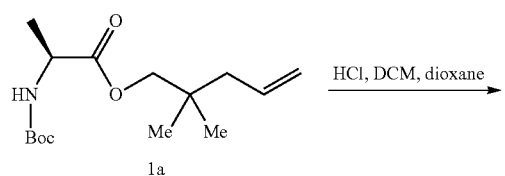

To compound 1a (6.3 g, 22.1 mmol) in DCM (20 mL) was added HCl (4N in dioxane, 55 mL) and the resulted solution was stirred at RT for 2 h. The solution was concentrated in vacuo to give the product 1b as white solid (5.262 g). MS (ESI): m/z 186.2 (M+H).

Step 1C

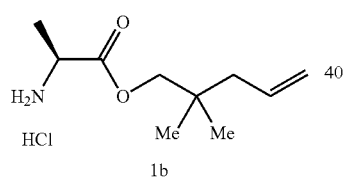

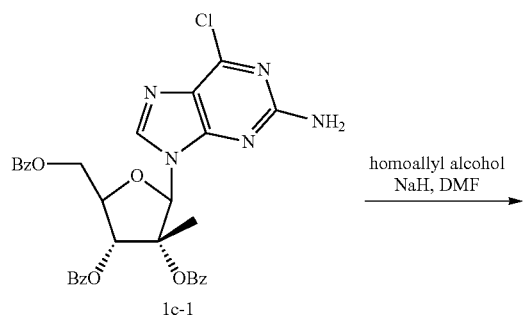

-continued

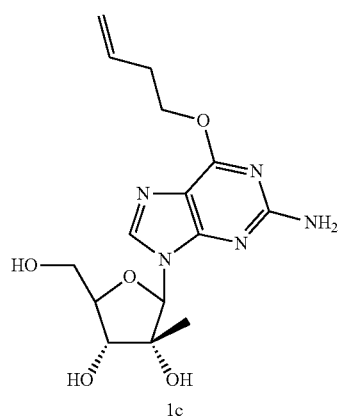
1c

To homoallyl alcohol (82 mL) in DMF (64 mL) at 0° C. was added NaH (3.83 g, 95.7 mmol) in portions and the mixture was stirred for 1 h at 0° C. Compound 1c-1 (4.0 g, 6.38 mmol) in DMF (64 mL) was added, and the mixture was allowed to warm up and stirred for 14 h at RT. The mixture was cooled down to 0° C. and quenched with saturated $NH_4Cl$ solution (18 mL). The mixture was filtered through celite, and filtrate was collected and concentrated in vacuo. The residue was purified by silica gel chromatography (DCM to 10% MeOH in DCM) to afford product 1c (1.65 g, 74%). MS (ESI): m/e 352.4 (M+H). $^1$H NMR ($CD_3OD$) 8.25 (s, 1H), 5.98 (s, 1H), 5.95 (m, 1H), 5.17 (d, J=15.5 Hz, 1H), 5.08 (d, J=12.0 Hz, 1H), 4.52 (t, J=6.5 Hz, 1H), 4.22 (d, J=9.5 Hz, 1H), 4.02 (m, 2H), 3.31 (s, 2H), 2.59 (q, J=7.5 Hz, 2H), 0.94 (s, 3H).

Step 1D

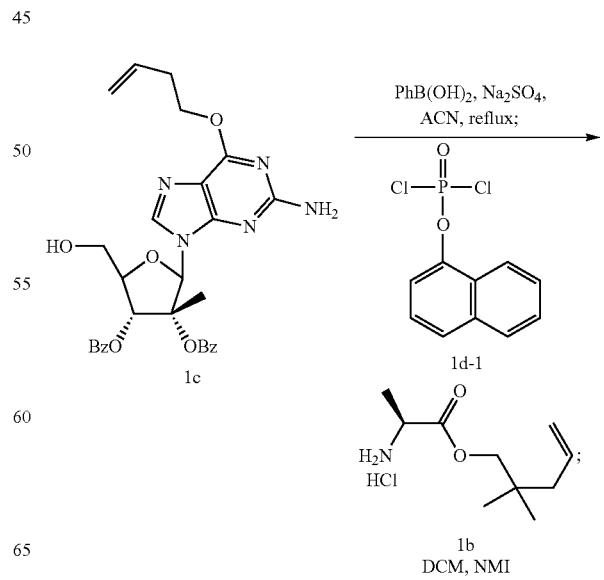

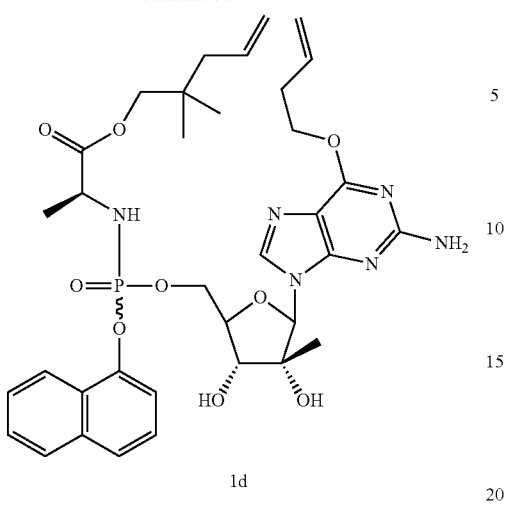

1d

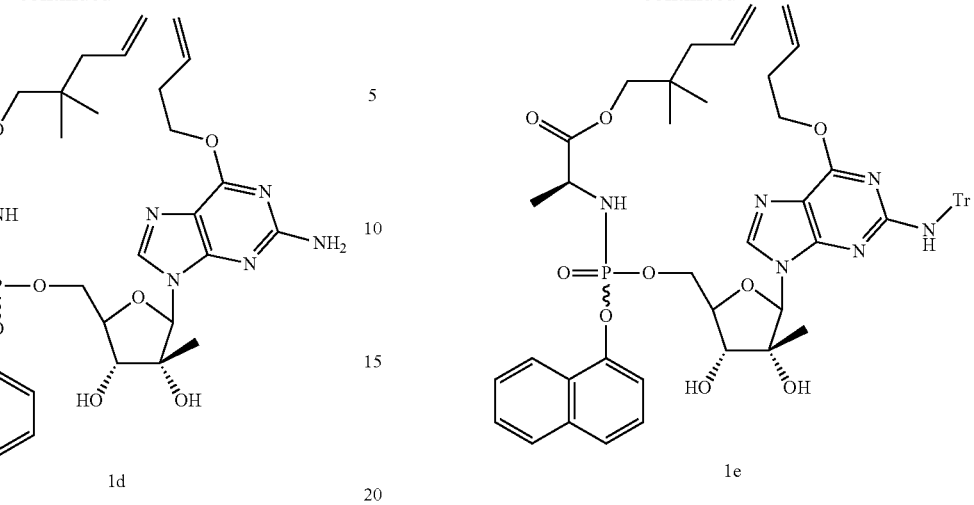

1e

To a solution of naphthyl dichlorophosphate id-1 (446 mg, 1.708 mmol) and the aminoester 1b (378 mg, 1.708 mmol) in DCM at 0° C. was added NMI (0.41 mL, 5.124 mmol) dropwise and the resulted solution was stirred at 0° C. for 1 h to form chlorophosphoramidate solution.

To compound 1c (150 mg, 0.427 mmol), benzeneboronic acid (57.3 mg, 0.47 mmol) in anhydrous acetonitrile (5 mL) was added Na$_2$SO$_4$ (182 mg, 1.281 mmol). The mixture was heated up to reflux for 14 h. The mixture was cooled down to RT and transferred to the freshly synthesized chlorophosphoramidate solution and the resulted mixture was stirred at RT for 8 h. The mixture was concentrated in vacuo and the residue was purified by silica gel chromatography (DCM to 6% MeOH in DCM) to afford the product 1d (385 mg, containing NMI). MS (ESI): m/e 725.48 (M+H). This material was used to next step without further purification.

To diene 1d (385 mg, ~0.427 mmol) in DCM (2 mL) was added TrCl (238 mg, 0.854 mmol) and pyridine (6 mL), and the resulted mixture was stirred at 60° C. for 14 h. The mixture was concentrated in vacuo and the residue was dissolved in DCM and washed with water, brine, dried and concentrated in vacuo. The residue was purified by silica gel chromatography (DCM to 50% acetone in DCM) to afford the product 1e (370 mg, 90% over 2 steps). MS (ESI): m/e 967.54 (M+H).

Step 1F

Step 1E

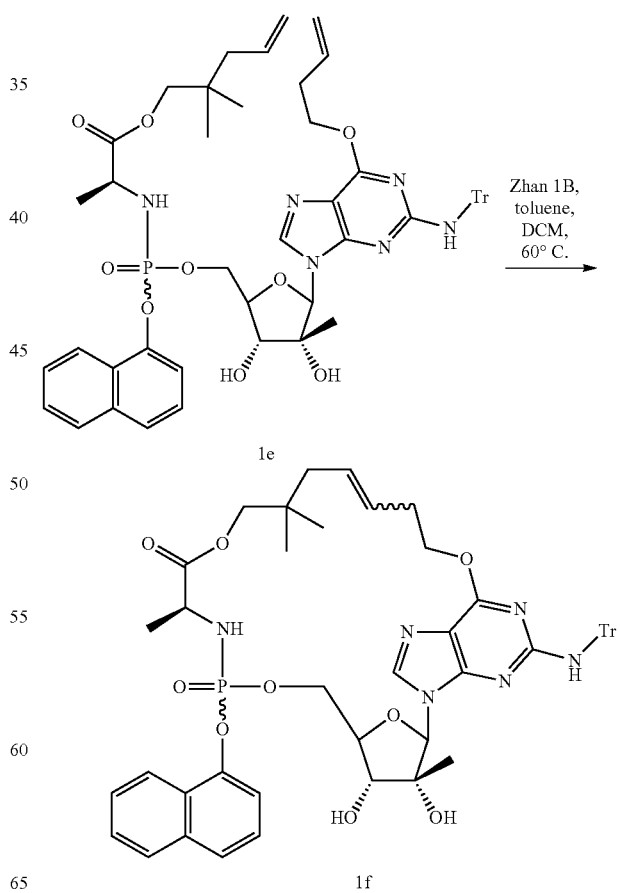

To diene 1e (180 mg, 0.186 mmol) in DCM (2 mL) and toluene (7.3 mL) was added Zhan 1B catalyst (13.6 mg, 0.0186 mmol). The resulted mixture was degassed and filled with $N_2$ and stirred at 60° C. for 2 h. Another portion of Zhan 1B catalyst (6.5 mg, 0.0093 mmol) was added, and continues stirring for 1.5 h. The solution was purified by a short wash column to give the product 1f (108 mg, 62%). MS (ESI): m/e 939.60 (M+H).

Step 1G

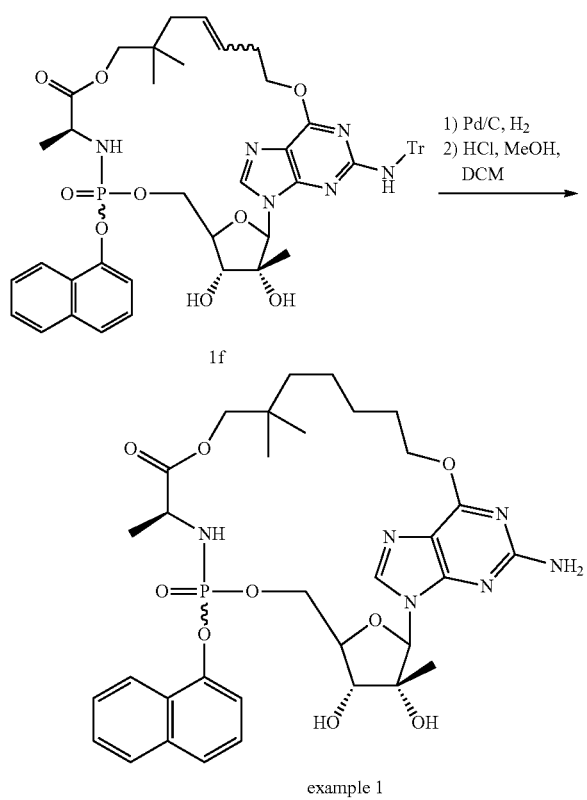

A mixture of compound 1f (108 mg), Pd—C (10%, 25 mg) and ethyl acetate (4 ml) was hydrogenated at 60 PSI for 60 h, and ~50% conversion was observed by MS. The mixture was filtered, washed with ethyl acetate. The filtrate was concentrated and dissolved in EtOH (5 mL). The resulted solution was hydrogenated at 60 PSI for 24 h in the presence of Pd—C (10%, 25 mg). The mixture was filtered, washed with ethyl acetate. The filtrate was concentrated in vacuo to afford the hydrogenation product (101 mg). MS (ESI): m/z 941.55 (M+H).

To the solution of hydrogenation product (101 mg) in DCM (3 mL) was added HCl (1.25 M in MeOH, 0.5 mL), and the resulted solution was stirred at RT for 1.5 h until starting material was consumed. The mixture concentrated in vacuo and dissolved in DCM with addition of one drop of $NH_3$ (7M in MeOH), and the volatile was removed in vacuo. The residue was purified by a short wash column and further purified by HPLC to give the title compound of example 1 (32 mg). MS (ESI): m/z 699.45 (M+H).

Example 2

Compound of Formula III, wherein $R^1$=H, $R^{2a}$=Me, $R^{2b}$=OH, $R^3$=H, $R^4$=H, $R^{5a}$=$R^{5b}$=H, $R^6$=

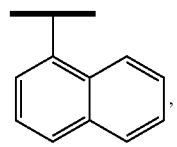

$X$=O, $R^7$=H, $R^{8a}$=Me, $R^{8b}$=H, W–M=

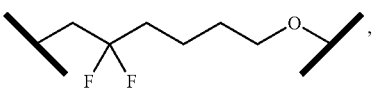

$R^{17}$=$NH_2$.

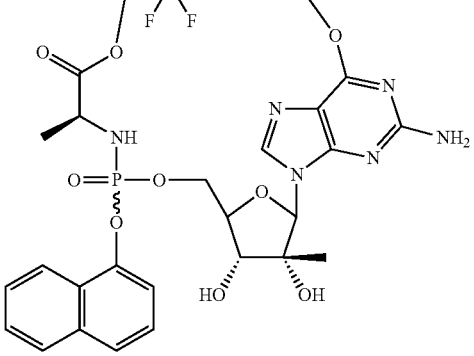

Step 2A

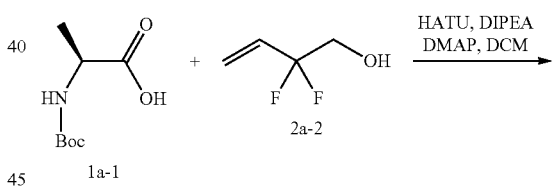

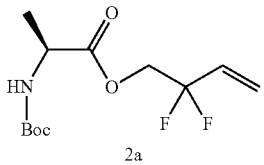

To N-Boc-L-alanine 1a-1 (3.568 g, 18.8 mmol) and alcohol 2a-2 (1.456 g, 13.5 mmol) in DCM (40 mL) was added HATU (7.7 g, 20.2 mmol), DIPEA (4.7 mL, 27 mmol) and DMAP (82 mg, 0.675 mmol). The resulted mixture was stirred at RT for 14 h, and was diluted with DCM, washed with 1N HCl, H2O and brine sequentially. The organic layer was dried ($Na_2SO_4$) and concentrated in vacuo and the residue was purified by silica gel chromatography (hexane to 35% acetone in hexane) to afford the product (2.04 g, 53%). $^1$H NMR (CDCl$_3$) 5.94 (m, 1H), 5.76 (d, J=17.5 Hz, 1H), 5.58 (d, J=11.0 Hz, 1H), 5.00 (b, 1H), 4.49 (q, J=12 Hz, 1H), 4.39 (m, 1H), 4.30 (q, J=12 Hz, 1H), 1.47 (s, 9H), 1.42 (d, J=7.0 Hz, 3H). Alcohol 2a-2 could be synthesized from reported procedure by Saksena et al (US 2007/0032433 A1).

Step 2B

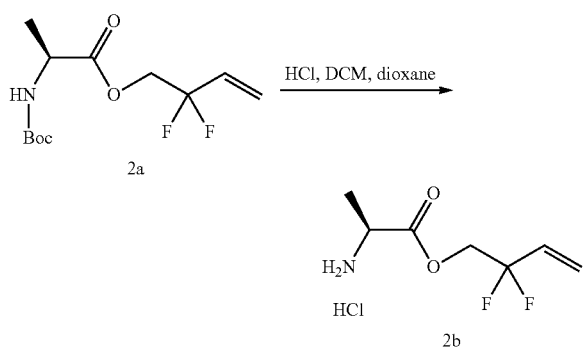

To compound 2a (2.04 g, 7.304 mmol) in DCM (10 mL) was added HCl (4N in dioxane, 18.3 mL) and the resulted solution was stirred at RT for 2 h. The solution was concentrated in vacuo to give the product 2b as white solid. MS (ESI): m/z 180.1 (M+H). $^1$H NMR (CD$_3$OD) 6.07 (m, 1H), 5.79 (d, J=18.5 Hz, 1H), 5.66 (d, J=10.5 Hz, 1H), 4.66 (q, J=10.5 Hz, 1H), 4.50 (q, J=13.0 Hz, 1H), 4.25 (q, J=7.5 Hz, 1H), 1.60 (d, J=7.5 Hz, 3H).

Step 2C

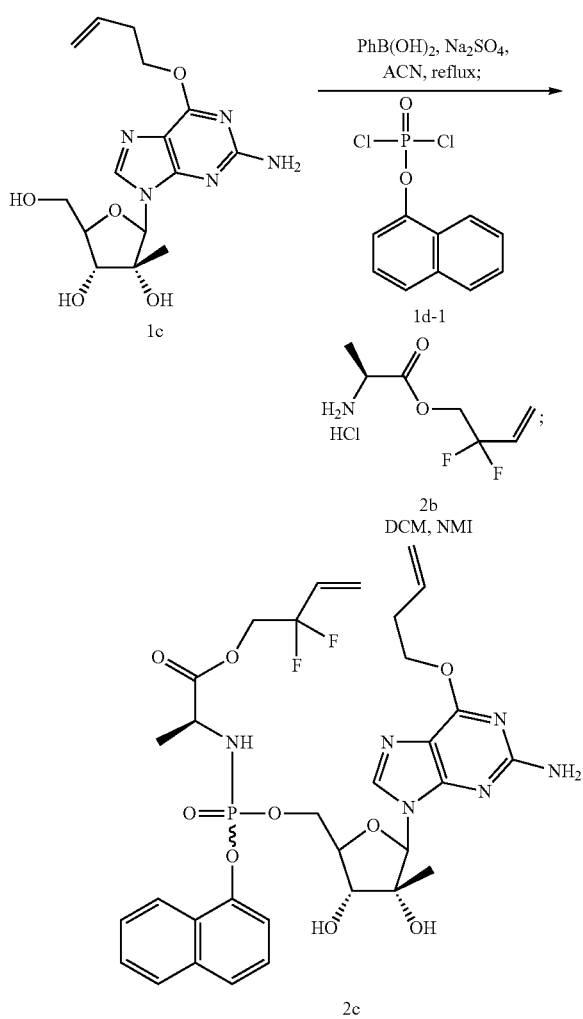

To a solution of naphthyl dichlorophosphate 1d-1 (368.8 mg, 1.252 mmol) and the aminoester 2b (278 mg, 1.252 mmol) in DCM (4 mL) at 0° C. was added NMI (0.3 mL, 3.756 mmol) dropwise and the resulted solution was stirred at 0° C. for 1 h to form chlorophosphoramidate solution.

To compound 1c (110 mg, 0.313 mmol), benzeneboronic acid (42 mg, 0.344 mmol) in anhydrous acetonitrile (4 mL) was added Na$_2$SO$_4$ (178 mg, 1.252 mmol). The mixture was heated up to reflux for 14 h. The mixture was cooled down to RT and transferred to the freshly synthesized chlorophosphoramidate solution and the resulted mixture was stirred at RT for 8 h. The mixture was concentrated in vacuo and the residue was purified by silica gel chromatography (DCM to 8% MeOH in DCM) to afford the product 2c (202 mg). MS (ESI): m/e 719.33 (M+H). This material was used to next step without further purification.

Step 2D

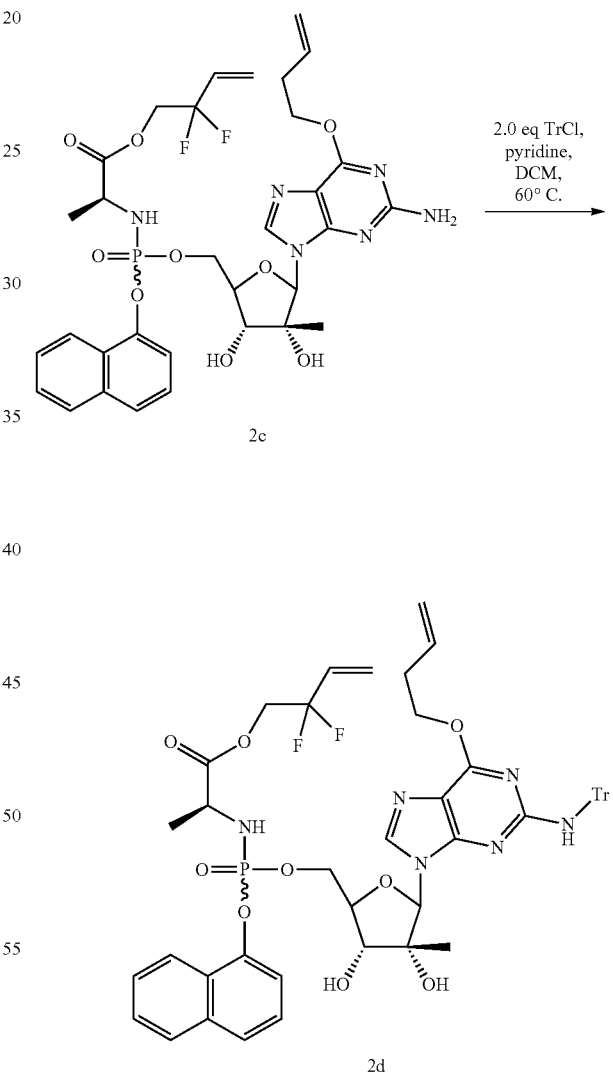

SM 2c (202 mg, 0.281 mmol) in DCM (1 mL) was added TrCl (156.7 mg, 0.562 mmol) and pyridine (4 mL), and the resulted mixture was stirred at 60° C. for 14 h. The mixture was concentrated in vacuo and the residue was purified by silica gel chromatography (DCM to 6% MeOH in DCM) to afford the product 2d (136 mg, 50%). MS (ESI): m/e 961.32 (M+H).

Step 2E

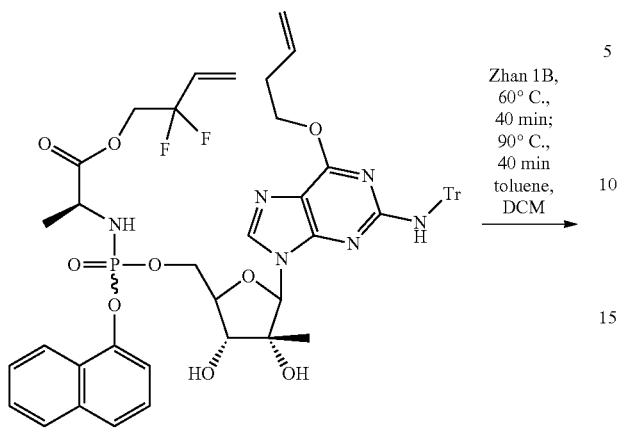

2d

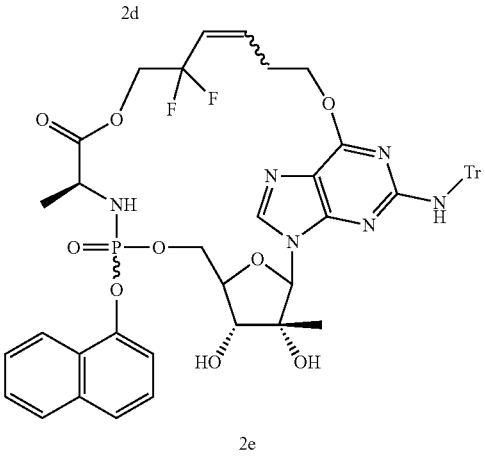

2e

To diene 2d (136 mg, 0.142 mmol) in DCM (1.5 mL) and toluene (5.6 mL) was added Zhan 1B catalyst (10.4 mg, 0.00142 mmol). The resulted mixture was degassed and filled with N₂ and stirred at 60° C. for 40 min. Another portion of Zhan 1B catalyst (5.2 mg) was added, and the solution was heated up to 90° C. and stirred for 40 min. The solution was purified by a short wash column to give the product 2e (46 mg, 25%). MS (ESI): m/e 961.36 (M+H).

Step 2F

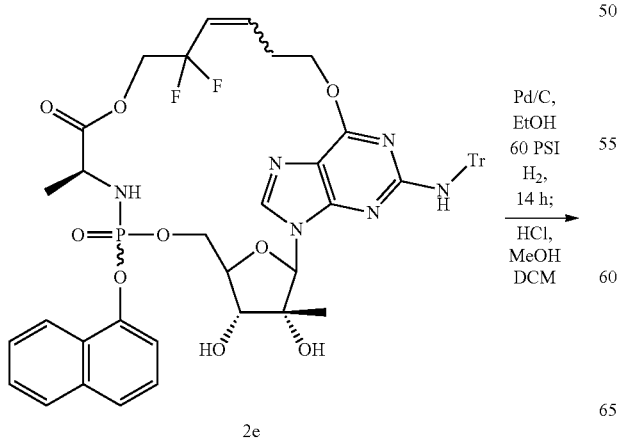

2e example 2

A mixture of compound 2e (32.7 mg, 0.0351 mmol), Pd—C (10%, 8 mg) and EtOH (3 ml) was hydrogenated at 60 PSI for 14 h. The mixture was filtered, washed with DCM. The filtrate was concentrated in vacuo. The residue was dissolved in DCM (2 mL) was added HCl (1.25 M in MeOH, 0.5 mL), and the resulted solution was stirred at RT for 1.5 h until starting material was consumed. The mixture concentrated in vacuo and dissolved in DCM with addition of one drop of NH₃ (7M in MeOH), and the volatile was removed in vacuo. The residue was purified by a short wash column and further purified by HPLC to give the title compound of example 2 (6.3 mg). MS (ESI): m/z 693.31 (M+H).

Example 3

Compound of Formula III, wherein $R^1$=H, $R^{2a}$=Me, $R^{2b}$=OH, $R^3$=H, $R^4$=H, $R^{5a}$=$R^{5b}$=H, $R^6$=

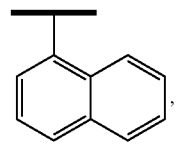

$X$=O, $R^7$=H, $R^{8a}$=Me, $R^{8b}$=H, W-M=—(CH₂)₇—O—, $R^{14}$=NH₂.

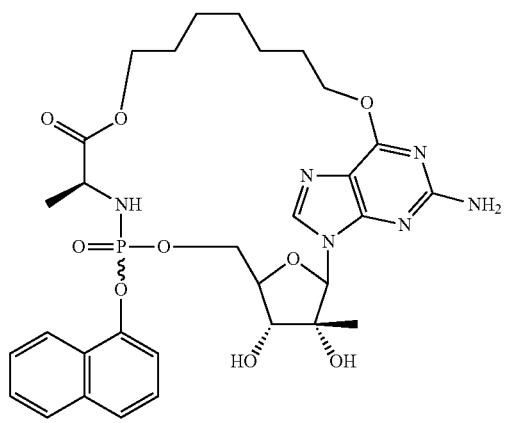 [SMILES: C[C@@H]1NP(=O)(Oc2cccc3ccccc23)OCC2OC(n3cnc4c(nc(N)nc43)OCCCCCCCOC1=O)[C@](C)(O)[C@@H]2O]

Step 3A
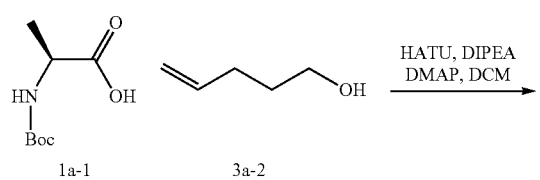
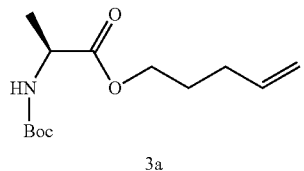
Compound 3a was synthesized according a similar procedure as in Step 1A. MS (ESI): m/z 280.33 (M+Na).
Step 3B
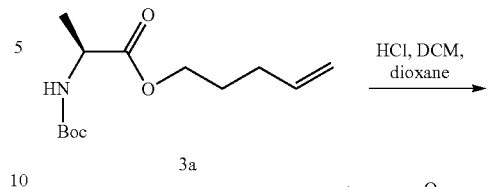
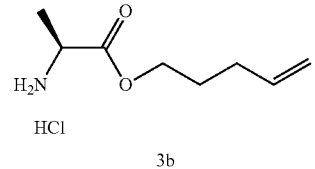
Compound 3b was synthesized according a similar procedure as in Step 1B. MS (ESI): m/z 158.22 (M+H).
Step 3C
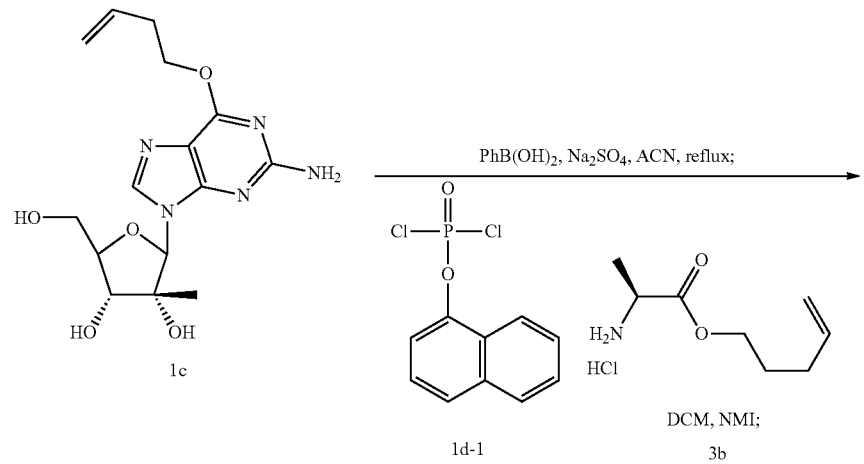
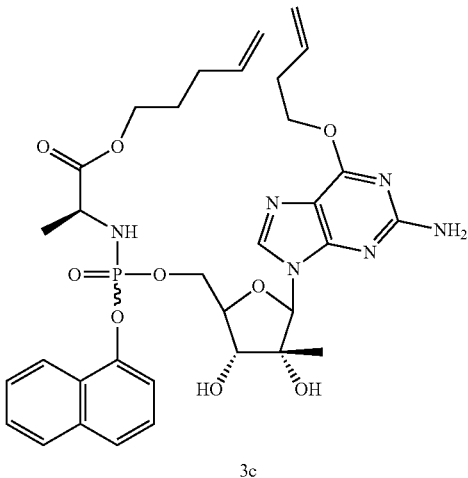

To a solution of naphthyl dichlorophosphate 1d-1 (158 mg, 0.604 mmol) and the aminoester 3b (117 mg, 0.604 mmol) in DCM at 0° C. was added NMI (0.14 mL, 1.812 mmol) dropwise and the resulted solution was stirred at 0° C. for 1 h to form chlorophosphoramidate solution.

To 1c (53 mg, 0.151 mmol), benzeneboronic acid (22 mg, 0.181 mmol) in anhydrous acetonitrile (3 mL) was added $Na_2SO_4$ (64 mg, 0.453 mmol). The mixture was heated up to reflux for 14 h. The mixture was cooled down to 0° C. and transferred to the freshly synthesized chlorophosphoramidate solution and the resulted mixture was stirred at RT for 7 h. The mixture was quenched with MeOH (0.5 mL) and stir for 20 min. The mixture was concentrated in vacuo and the residue was purified by silica gel chromatography (DCM to 6% MeOH in DCM) to afford the product 3c (126 mg). MS (ESI): m/e 697.49 (M+H). This material was used to next step without further purification.

Step 3D

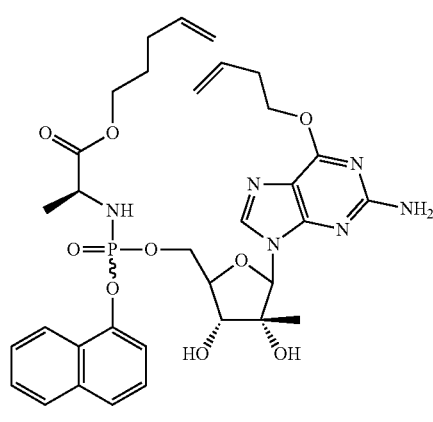

3c

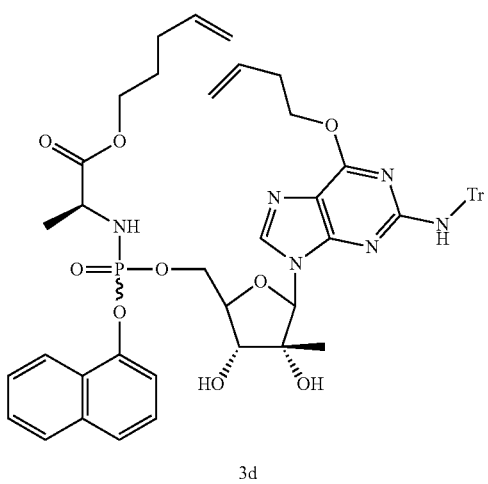

3d

To a solution of 3c (50 mg, 0.0718 mmol) in DCM (2 mL) and pyridine (1 mL) was added TrCl (100 mg, 0.358 mmol). The resulted mixture was heated up to 60° C. for 5 h, and concentrated in vacuo. The residue was purified by silica gel chromatography (DCM to 8% MeOH in DCM) to afford the product 3d (38 mg). MS (ESI): m/e 940.11 (M+H).

Step 3E

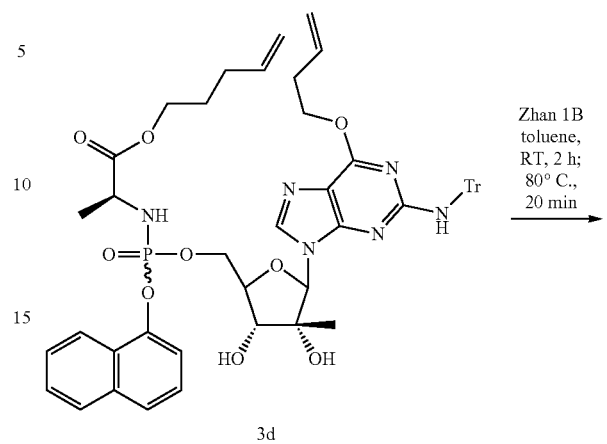

3d

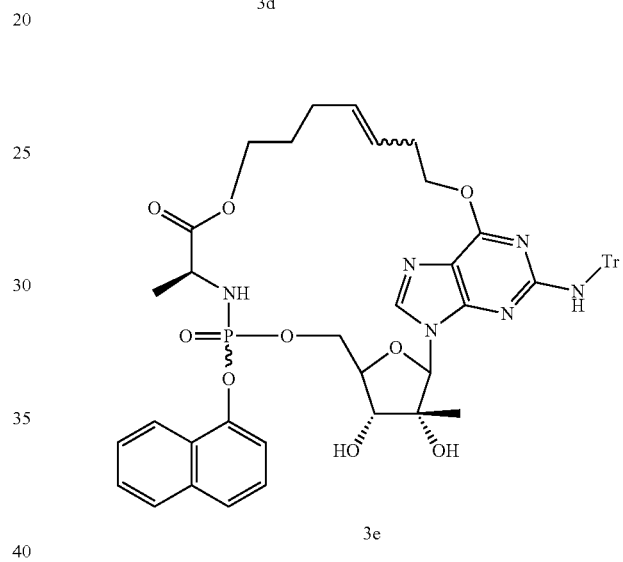

3e

To a solution of diene 3d (81 mg, 0.116 mmol) in DCM (2.3 mL) and toluene (9.3 mL) was added Zhan 1B catalyst (8.5 mg, 0.0116 mmol), the resulted solution was degassed and heated up in a 80° C. oil bath for 20 min under N2 atmosphere. The mixture was passed through a short wash column to give the alkene 3e (61 mg). MS (ESI): m/e 911.29 (M+H).

Step 3F

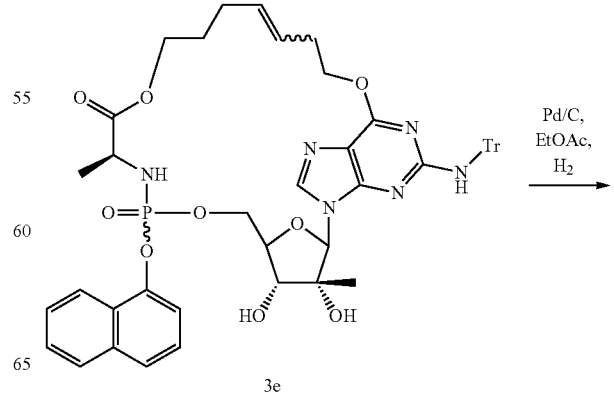

3e

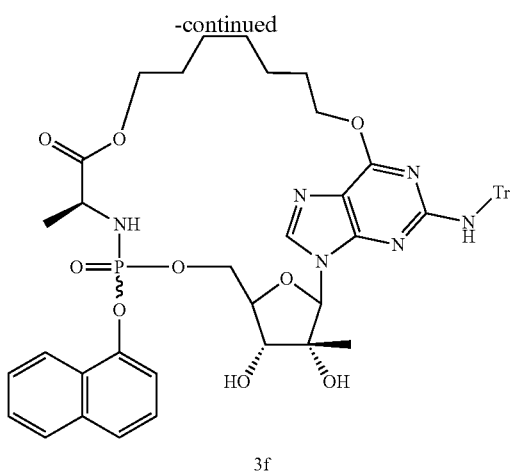

3f

A mixture of compound 3e (61 mg), Pd—C (10%, 10 mg) and ethyl acetate (4 ml) was hydrogenated under atmospheric pressure for 22 h. The mixture was filtered, washed with ethyl acetate. The filtrate was concentrated to afford the product 3f (61 mg). MS (ESI): m/z 913.41 (M+H).

Step 3G passed through a short wash column followed by HPLC purification to give the title compound of example 3 (34.8 mg), MS (ESI): m/z 671.3 (M+H).

Example 4

Compound of Formula III, wherein $R^1$=H, $R^{2a}$=Me, $R^{2b}$=OH, $R^3$=H, $R^4$=H, $R^{5a}$=$R^{5b}$=H, $R^6$=

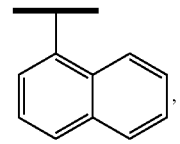

X=O, $R^7$=H, $R^{8a}$=

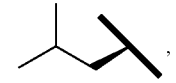

$R^{8b}$=H, W-M=—(CH$_2$)$_7$—O—, $R^{14}$=NH$_2$.

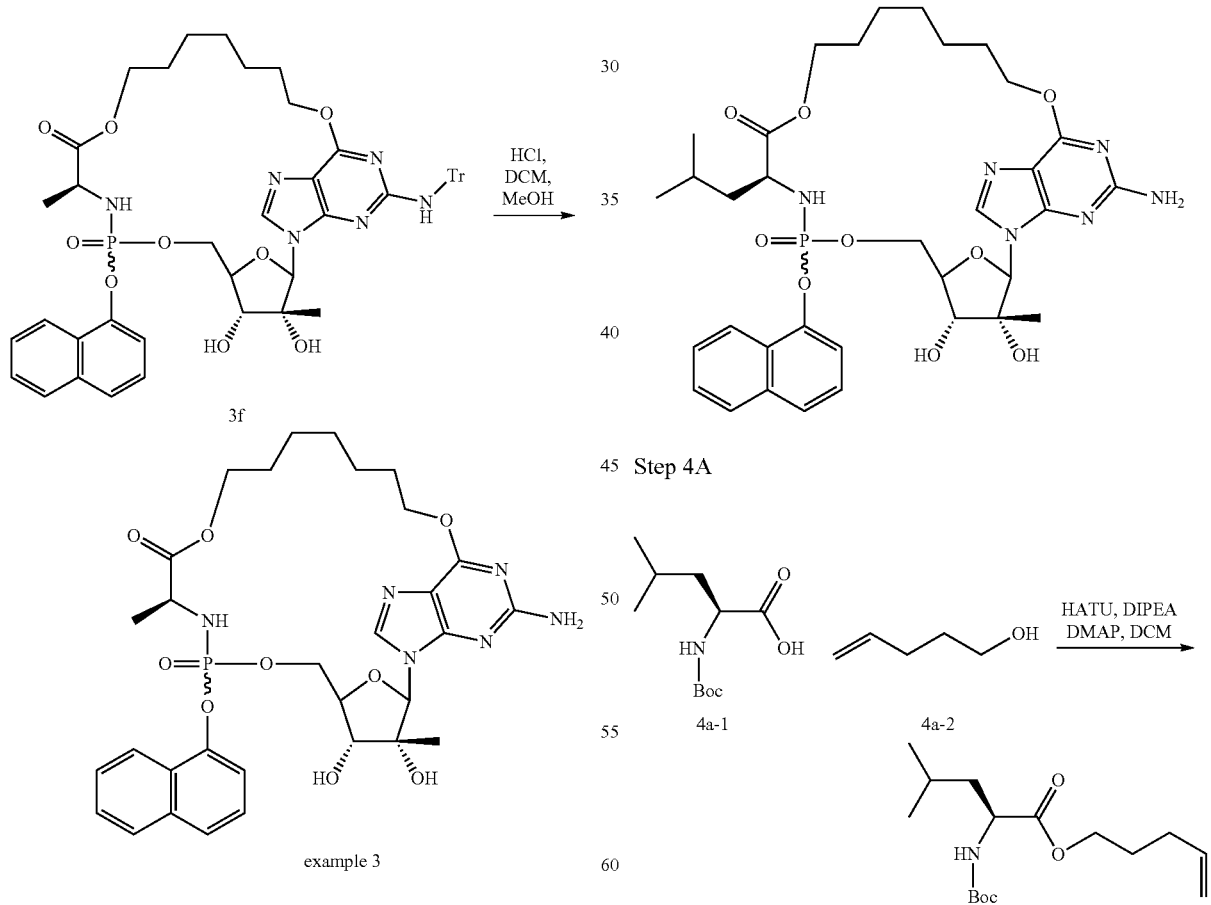

To a solution of compound 3f (108 mg, 0.118 mmol) in DCM (5 mL) was added HCl (1.25 M in MeOH), and the resulted solution was stirred at RT for 2 h. The solvents was removed, and residue dissolved in DCM added NH$_3$ (7N in MeOH, 2 drops). The volatile was removed and residue To N-Boc-L-leucine 4a-1 (3.05 g, 12.234 mmol) and alcohol (1.58 g, 18.35 mmol) in DCM (20 mL) was added HATU (5.582 g, 14.681 mmol), DIPEA (4.3 mL, 24.468 mmol) and DMAP (75 mg, 0.612 mmol). The resulted mixture was stirred at RT for 14 h, and was diluted with DCM, washed with 1N HCl, H₂O and brine sequentially. The organic layer was dried (Na₂SO₄) and concentrated in vacuo and the residue was purified by silica gel chromatography (hexane to 30% acetone in hexane) to afford the product 4a (3.25 g, 89%). MS (ESI): m/z 322.24 (M+Na).

Step 4B

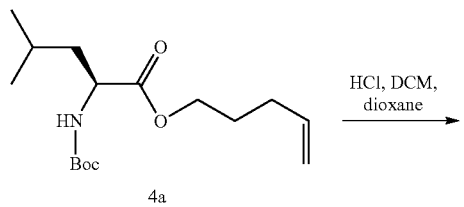

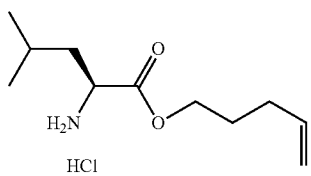

To compound 4a (3.25 g, 10.9 mmol) in DCM (10 mL) was added HCl (4N in dioxane, 27 mL) and the resulted solution was stirred at RT for 2 h. The solution was concentrated in vacuo to give the product 4b as yellow foam. MS (ESI): m/z 200.23 (M+H).

Step 4C

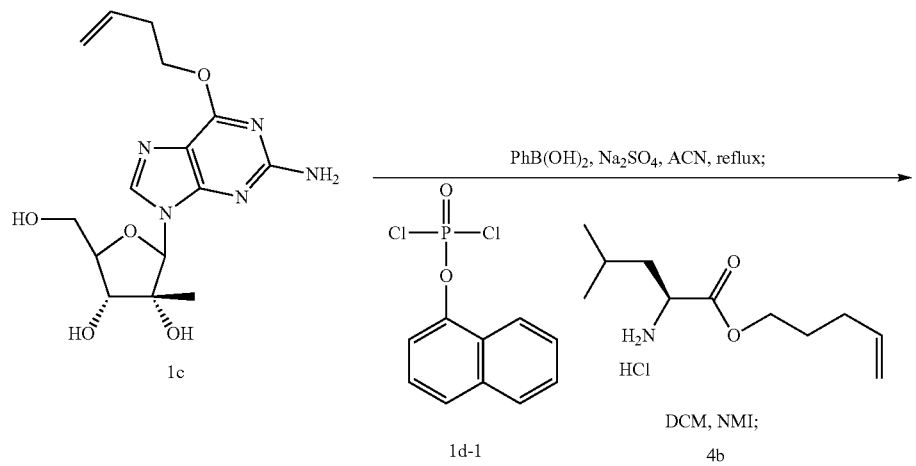

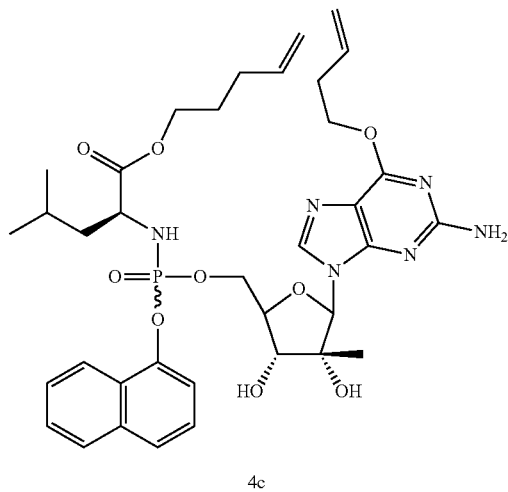

Compound 4c was synthesized according a similar procedure as in step 1D. MS (ESI): m/z 739.3 (M+H).

Step 4D

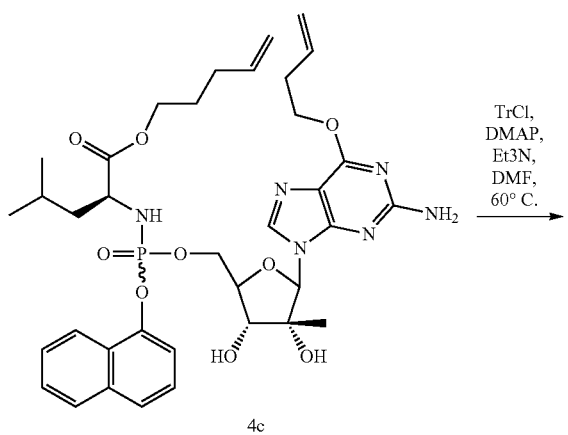

4c

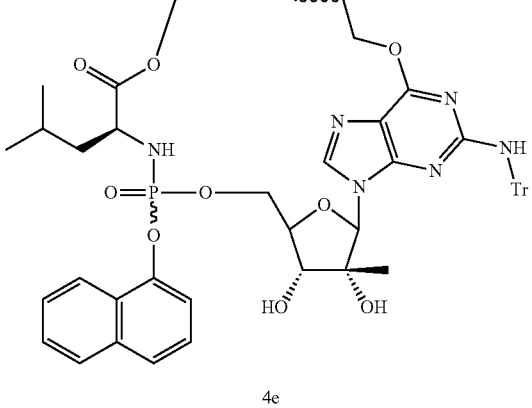

4e

Compound 4e was synthesized according a similar procedure as in step 1F. MS (ESI): m/z 953.5 (M+H).

Step 4F

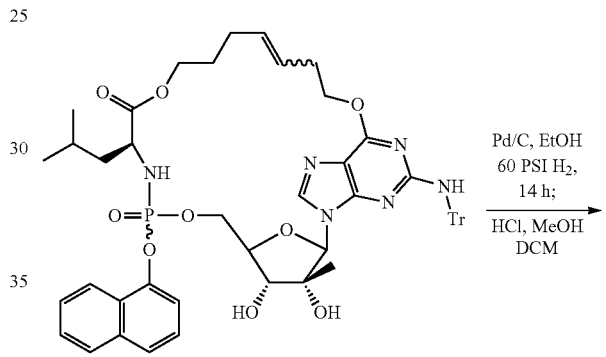

4e

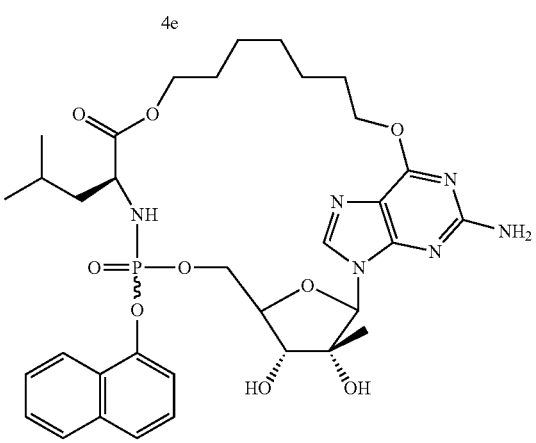

example 4

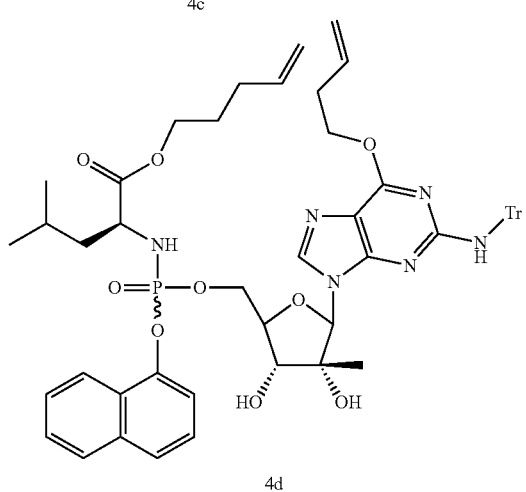

4d

To a solution of 4c (80 mg, 0.108 mmol) in DMF (4 mL) and Et$_3$N (0.15 mL) was added TrCl (60 mg, 0.217 mmol) and DMAP (2.6 mg, 0.0217 mmol). The resulted mixture was heated up to 60° C. for 4 h, and reaction mixture was cooled down to RT and diluted with EtOAc. The organic layer was washed with water (4×), brine, dried (Na$_2$SO$_4$) and concentrated in vacuo. The residue was purified by silica gel chromatography (hexane to 90% acetone in hexane) to afford the product 4d (74 mg, 70%). MS (ESI): m/e 981.5 (M+H).

Step 4E

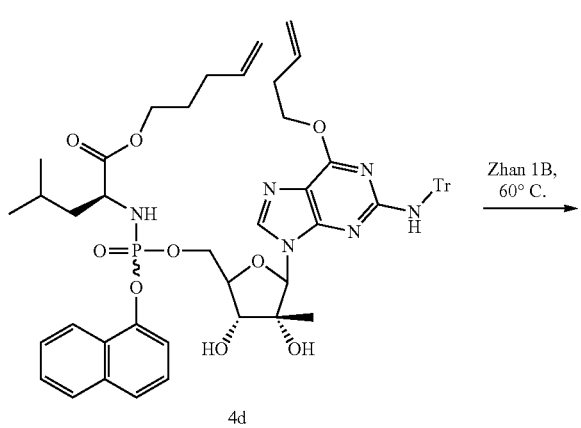

4d

The title compound of example 4 was synthesized according a similar procedure as in step 1G while EtOH was used instead of EtOAc as solvent for the hydrogenation step. MS (ESI): m/z 713.5 (M+H).

Example 5

Compound of Formula III, wherein $R^1$=H, $R^{2a}$=Me, $R^{2b}$=OH, $R^3$=H, $R^4$=H, $R^{5a}$=$R^{5b}$=H, $R^6$=

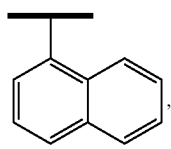
X=O, R⁷=H, R⁸ᵃ=Me, R⁸ᵇ=H, W-M=—(CH₂)₃—O—(CH₂)₅—O—, R¹⁴=NH₂.
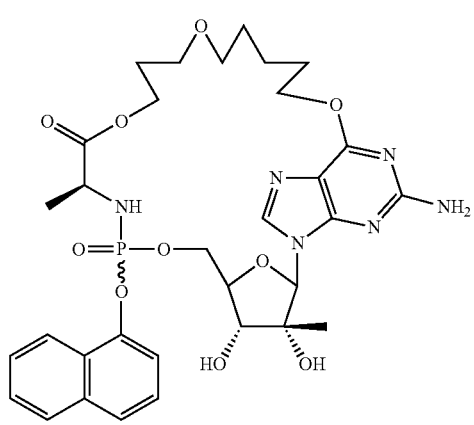 [SMILES: C[C@@H]1NP(=O)(Oc2cccc3ccccc23)OCC2OC(n3cnc4c(nc(N)nc43)OCCCCCOCCCOC1=O)[C@](C)(O)[C@@H]2O]
Step 5A
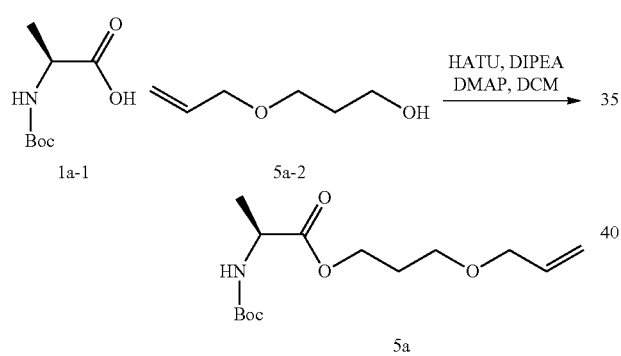
Alcohol 5a-2 could be synthesized according to procedure reported by Liu et al (*Org. Lett.*, 2011, 13, 1702). Compound 5a was synthesized according a similar procedure as in step 1A. MS (ESI): m/z 310.2 (M+Na).
Step 5B
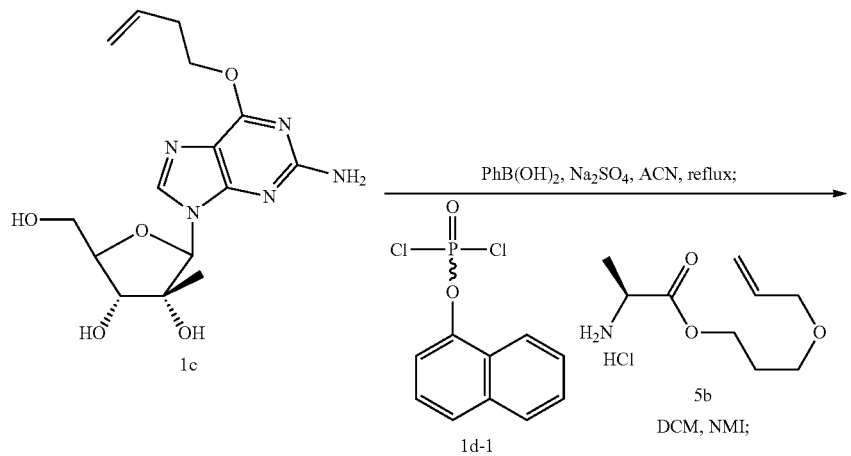
Compound 5b was synthesized according a similar procedure as in step 1B. MS (ESI): m/z 188.2 (M+H).
Step 5C

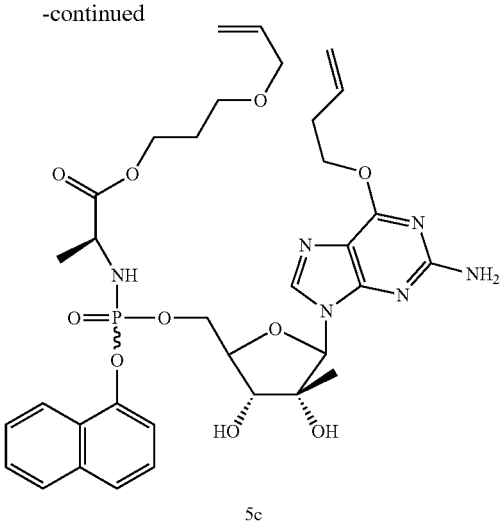
5c
Compound 5c was synthesized according a similar procedure as in step 1D. MS (ESI): m/z 727.4 (M+H).
Step 5D
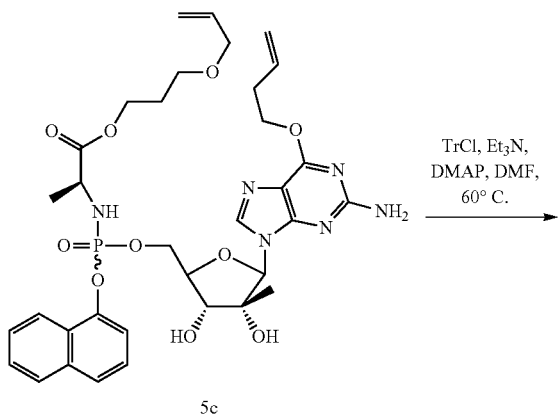
5c
TrCl, Et₃N, DMAP, DMF, 60° C.
Step 5E
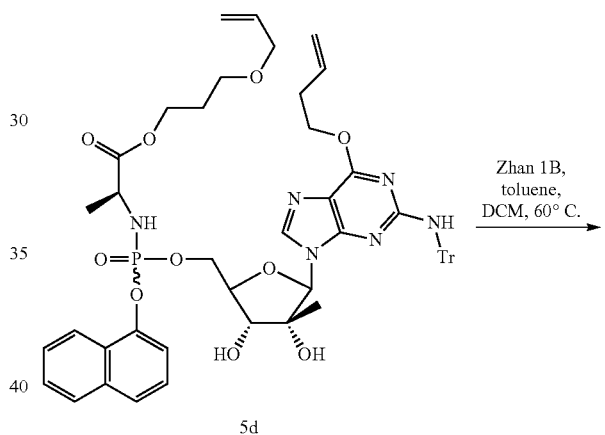
5d
Zhan 1B, toluene, DCM, 60° C.
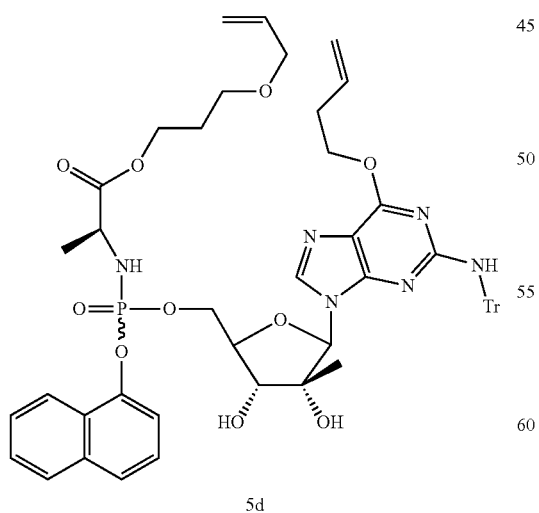
5d
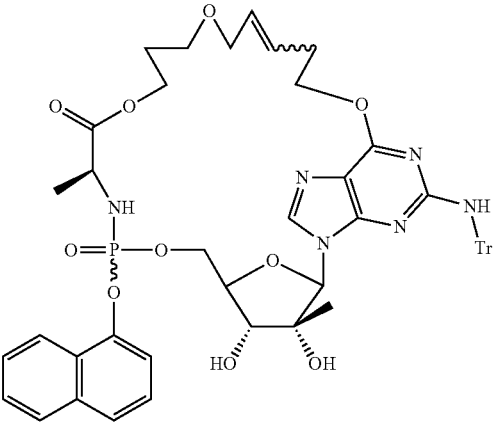
5e
Compound 5d was synthesized according a similar procedure as in step 4D. MS (ESI): m/z 969.1 (M+H).
Compound 5e was synthesized according a similar procedure as in step 1F. MS (ESI): m/z 941.3 (M+H).

Step 5F

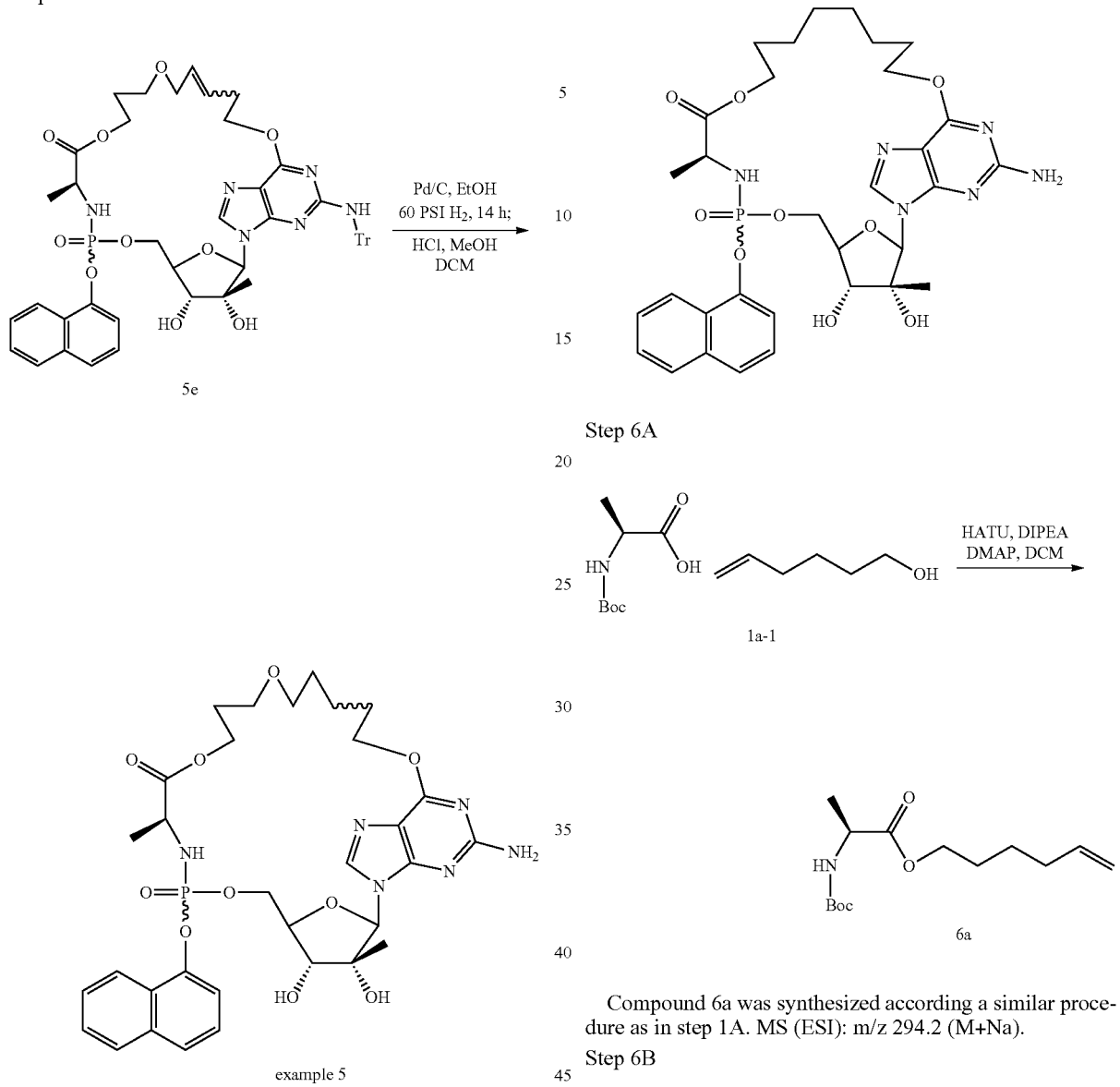

The title compound of example 5 was synthesized according a similar procedure as in step 1G. MS (ESI): m/z 701.2 (M+H).

Example 6

Compound of Formula III, wherein $R^1$=H, $R^{2a}$=Me, $R^{2b}$=OH, $R^3$=H, $R^4$=H, $R^{5a}$=$R^{5b}$=H, $R^6$=

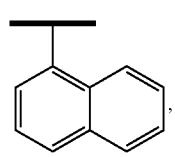

X=O, $R^7$=H, $R^{8a}$=Me, $R^{8b}$=H, W-M=—(CH$_2$)$_8$—O—, $R^{14}$=NH$_2$.

Compound 6a was synthesized according a similar procedure as in step 1A. MS (ESI): m/z 294.2 (M+Na).

Step 6B

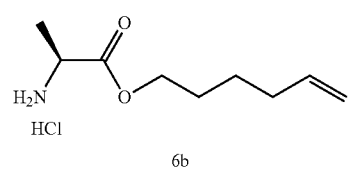

Compound 6b was synthesized according a similar procedure as in step 1B. MS (ESI): m/z 172.2 (M+H).

Step 6C
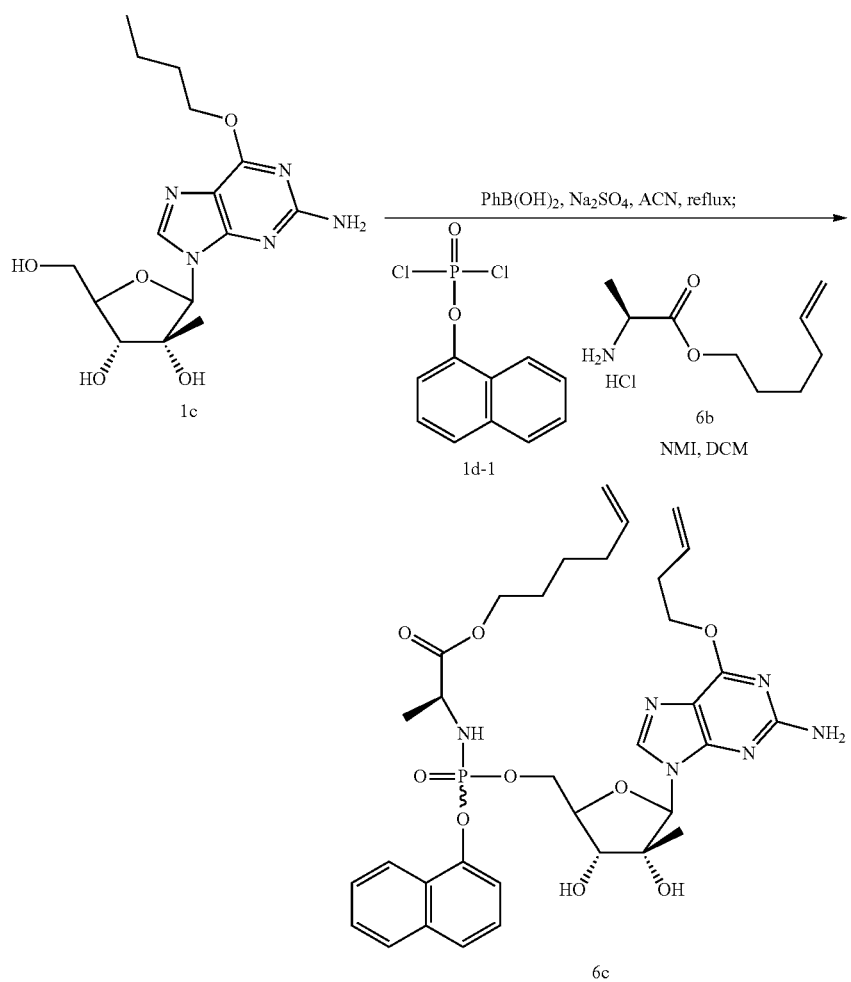
Compound 6c was synthesized according a similar procedure as in step 1D. MS (ESI): m/z 711.2 (M+H).
Step 6D
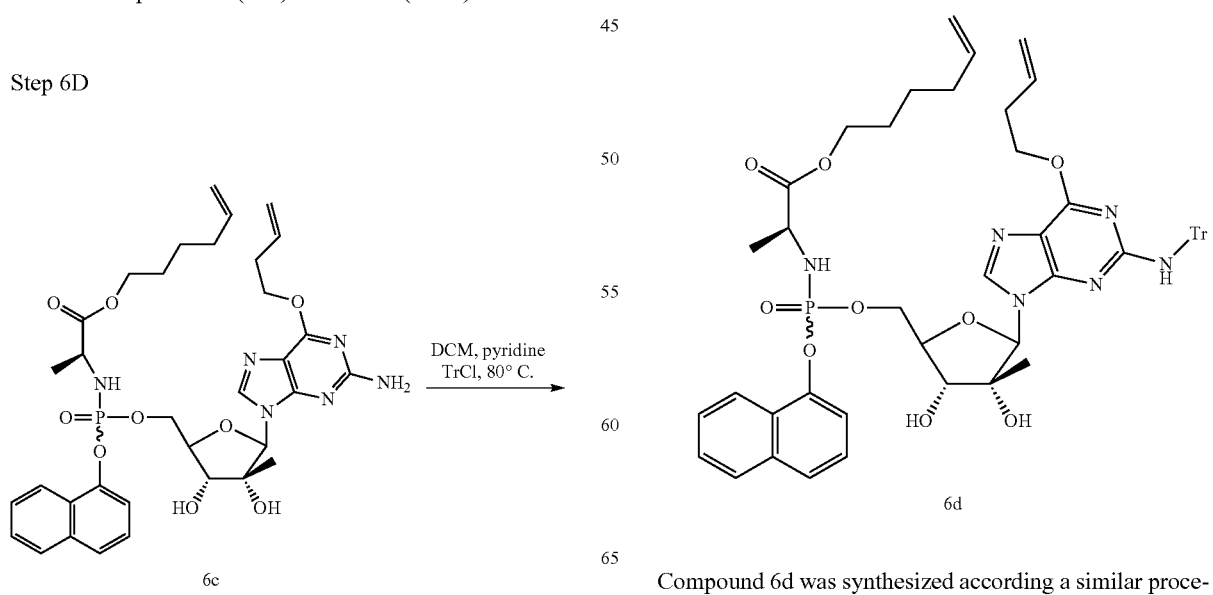
Compound 6d was synthesized according a similar procedure as in step 1E. MS (ESI): m/z 953.5 (M+H).

Step 6E

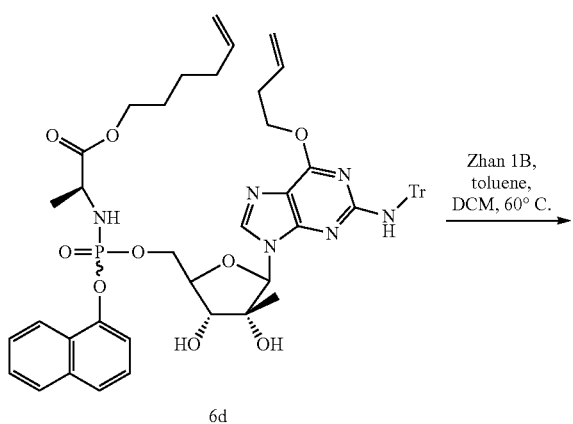

6d

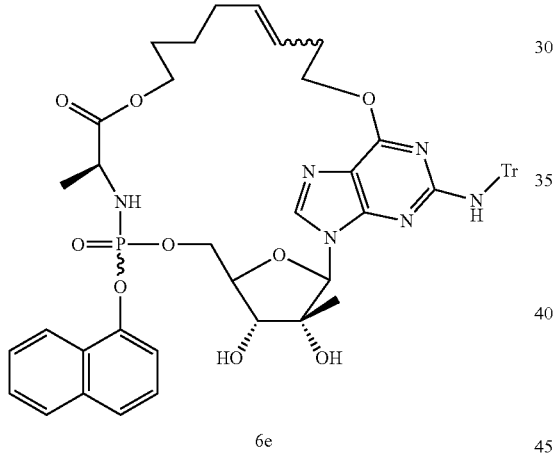

6e

Compound 6e was synthesized according a similar procedure as in step 1F. MS (ESI): m/z 925.6 (M+H).

Step 6F

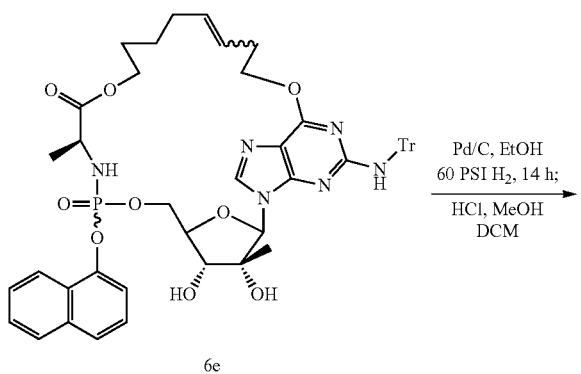

6e

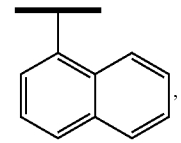

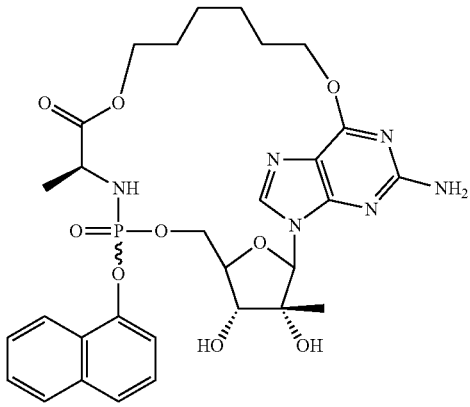 [SMILES: C[C@@H]1NP(=O)(Oc2cccc3ccccc23)OCC2OC(n3cnc4c(nc(N)nc43)OCCCCCCOC1=O)[C@](C)(O)[C@@H]2O]

example 6

The title compound of example 6 was synthesized according a similar procedure as in step 1G. MS (ESI): m/z 685.4 (M+H).

Example 7

Compound of Formula III, wherein $R^1$=H, $R^{2a}$=Me, $R^{2b}$=OH, $R^3$=H, $R^4$=H, $R^{5a}$=$R^{5b}$=H, $R^6$=

$X$=O, $R^7$=H, $R^{8a}$=Me, $R^{8b}$=H, W–M=—(CH$_2$)$_6$—O—, $R^{14}$=NH$_2$.

Step 7A
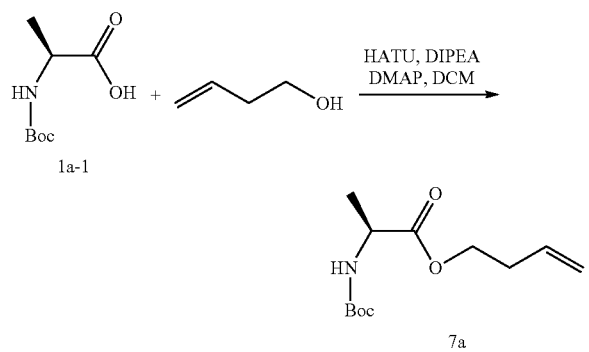
Compound 7a was synthesized according a similar procedure as in step 1A. MS (ESI): m/z 266.2 (M+Na).
Step 7B
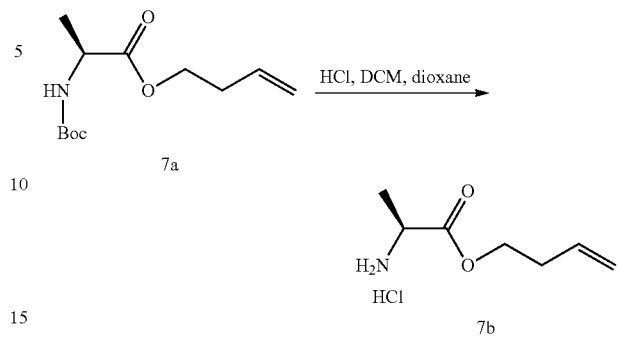
Compound 7a was synthesized according a similar procedure as in step 1B. MS (ESI): m/z 144.1 (M+Na).
Step 7C
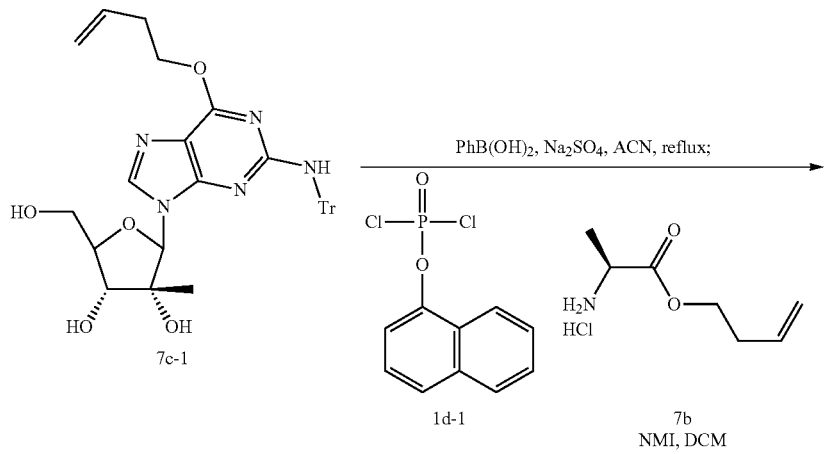
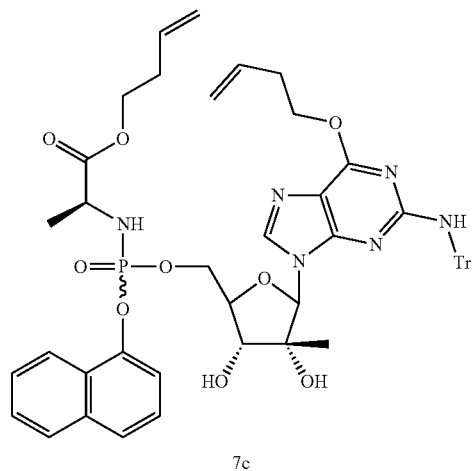

Compound 7c was synthesized according a similar procedure as in step 1D. MS (ESI): m/z 925.2 (M+H).

Step 7D

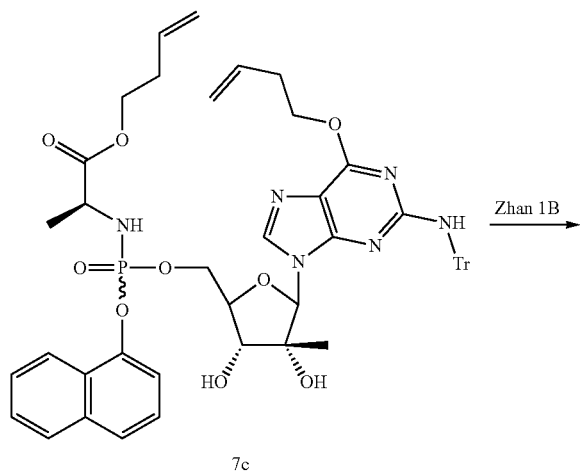

7c

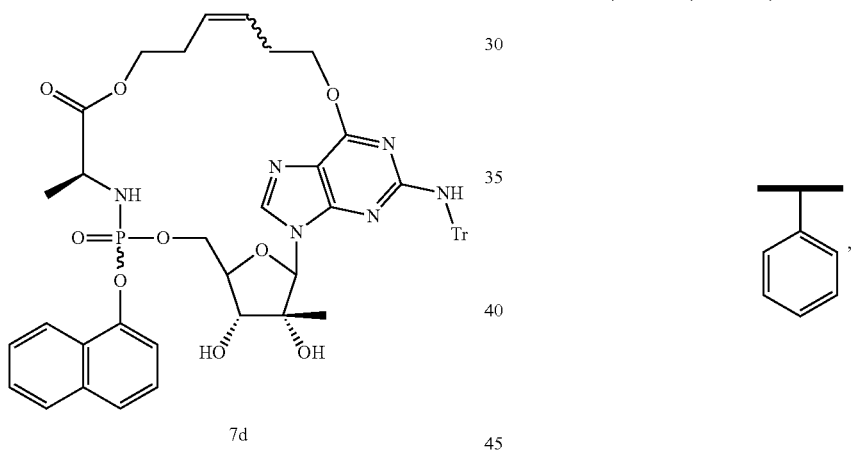

7d

Compound 7d was synthesized according a similar procedure as in step 1F. MS (ESI): m/z 897.5 (M+H).

Step 7E

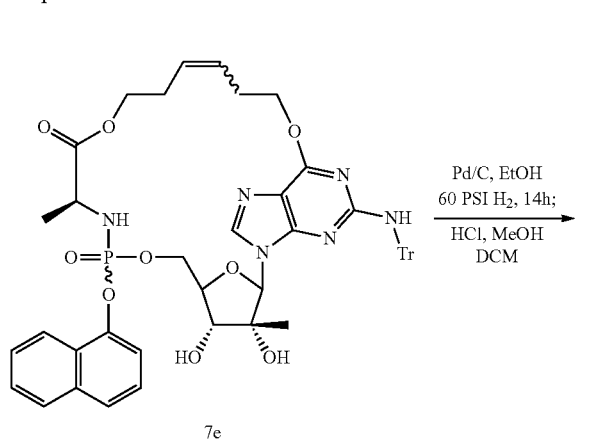

7e

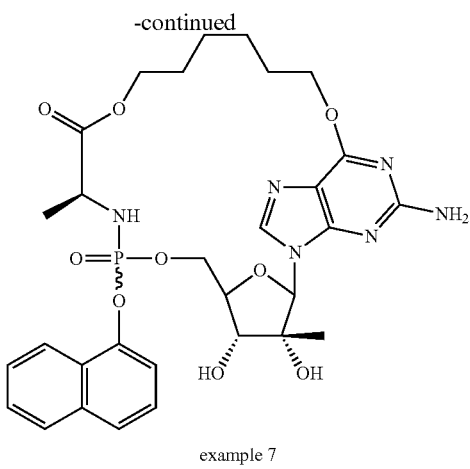

example 7

Compound of example 7 was synthesized from the compound of 7e according to a similar procedure as in step 1G. MS (ESI): m/z 657.3 (M+H).

Example 8

Compound of Formula III, wherein $R^1$=H, $R^{2a}$=Me, $R^{2b}$=OH, $R^3$=H, $R^4$=H, $R^{5a}$=$R^{5b}$=H, $R^6$=

X=O, $R^7$=H, $R^{8a}$=Me, $R^{8b}$=H, W-M=—(CH$_2$)$_7$—O—, $R^{14}$=NH$_2$.

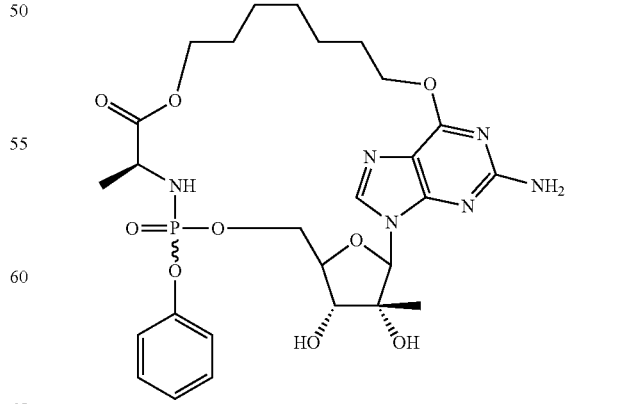

Step 8A
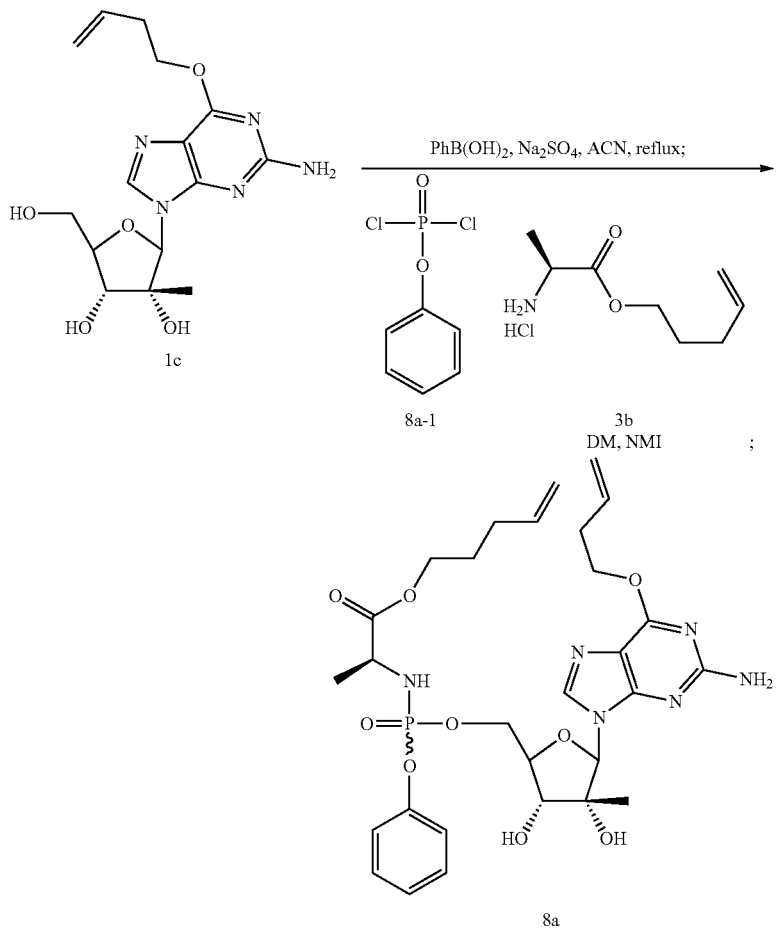
Compound 8a was synthesized according a similar procedure as in step 1D while phenyl dichlorophosphate 8a-1 was used instead of naphthyl dichlorophosphate id-1. MS (ESI): m/z 647.4 (M+H).
Step 8B
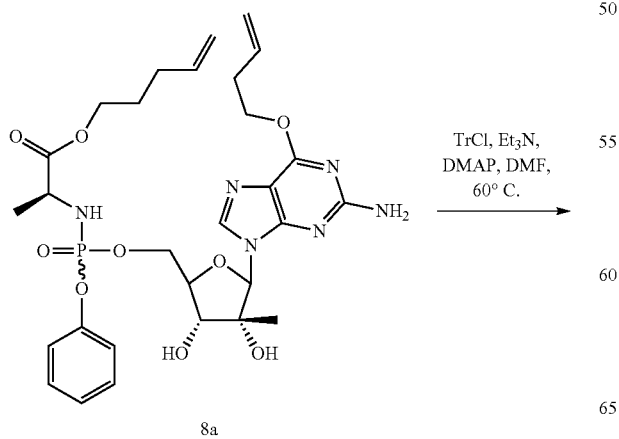
Compound 8b was synthesized from the compound of 8a according to a similar procedure as in step 4D. MS (ESI): m/z 889.4 (M+H).

Step 8C

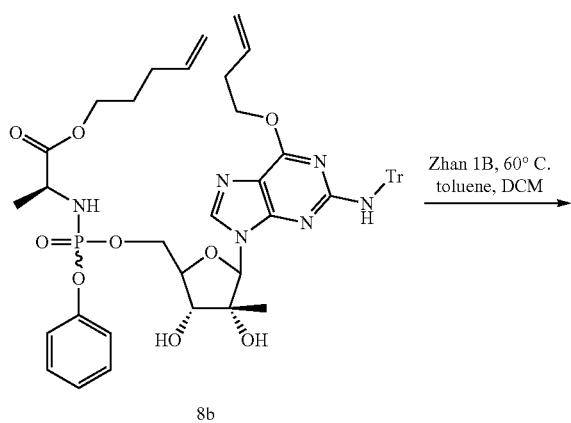

8b

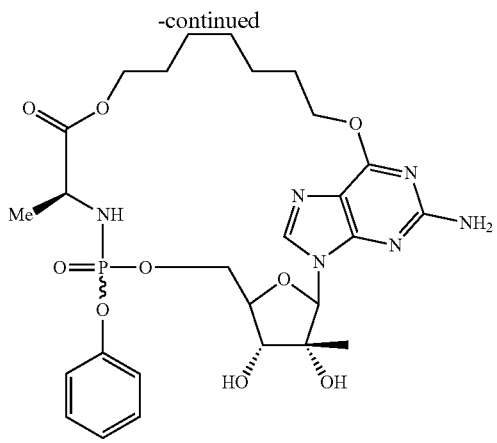

example 8

A mixture of compound 8b (160 mg, 0.186 mmol), Pd—C (10%, 40 mg) and EtOH (8 ml) was hydrogenated at 60 PSI for 14 h. The mixture was filtered, washed with DCM. The filtrate was concentrated in vacuo to afford the hydrogenation product (162 mg). MS (ESI): m/z 863.2 (M+H).

To the solution of hydrogenation product (70 mg) in DCM (3 mL) was added $H_2O$ (7.5 uL) and TFA (15 uL), and the resulted solution was stirred at RT for 1.5 h. Another portion of $H_2O$ (7.5 uL) and TFA (15 uL) was added, and stirred for 1.5 h until starting material was consumed. To the mixture was added EtOH (0.1 mL) and $NH_3$ (80 uL, 7N in MeOH). The mixture concentrated in vacuo. The residue was purified by a short wash column and further purified by HPLC to give the title compound of example 8. MS (ESI): m/z 621.4 (M+H).

Example 9

Compound of Formula III, wherein $R^1$=H, $R^{2a}$=Me, $R^{2b}$=OH, $R^3$=H, $R^4$=H, $R^{5a}$=$R^{5b}$=H, $R^6$=

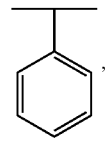

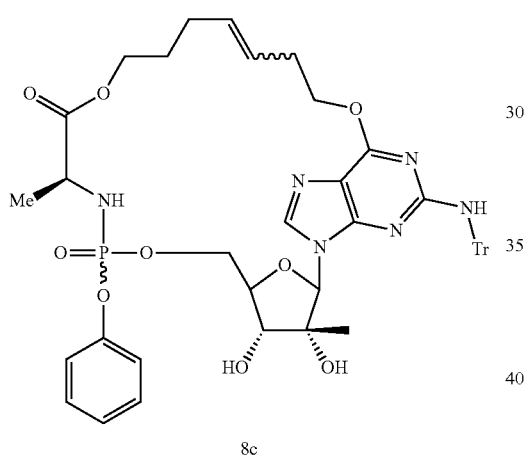

8c

Compound 8c was synthesized from compound of 8b according to a similar procedure as in step 1F. MS (ESI): m/z 861.4 (M+H).

Step 8D

X=O, $R^7$=H, $R^{8a}$=Me, $R^{8b}$=H, W-M=—(CH$_2$)—O—, $R^{14}$=NH$_2$.

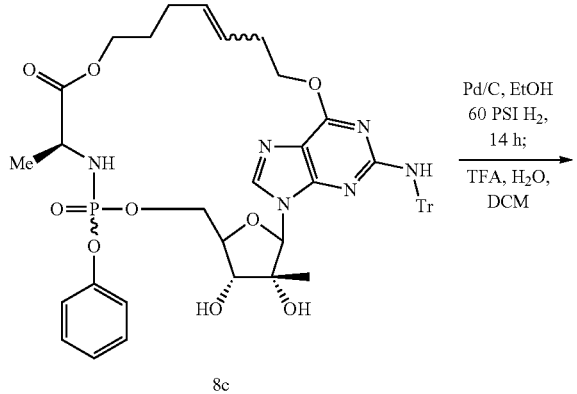

8c

Step 9A
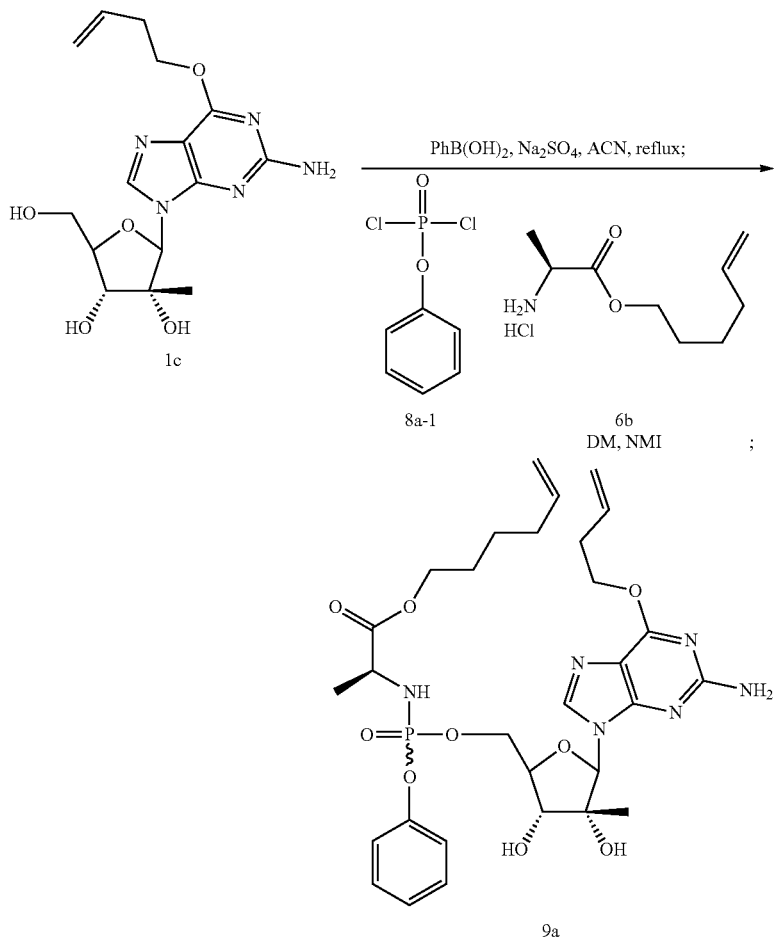
Compound of 9a was synthesized according a similar procedure as in step 1D while phenyl dichlorophosphate 8a-1 was used instead of naphthyl dichlorophosphate 1d-1. MS (ESI): m/z 661.4 (M+H).
Step 9B
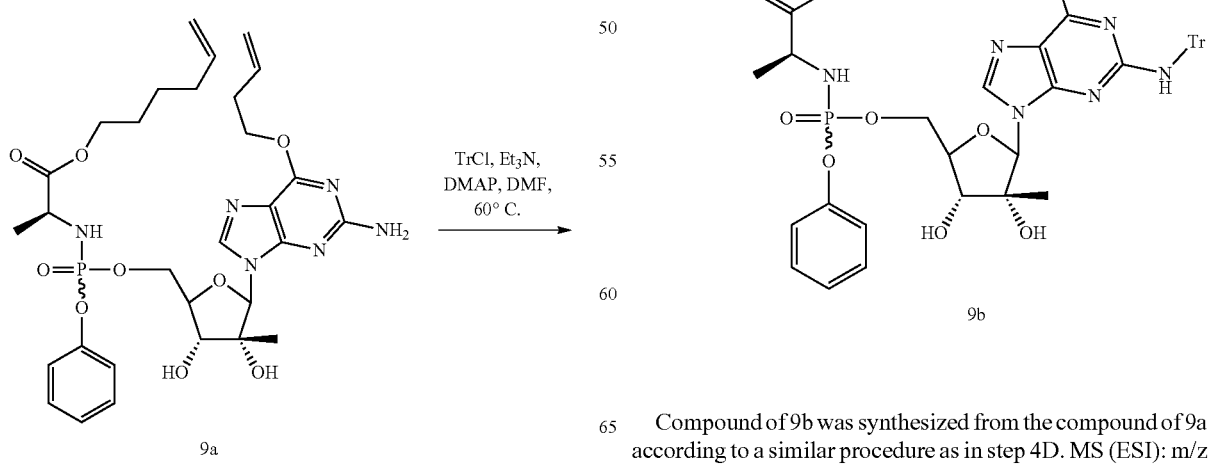
Compound of 9b was synthesized from the compound of 9a according to a similar procedure as in step 4D. MS (ESI): m/z 903.3 (M+H).

Step 9C

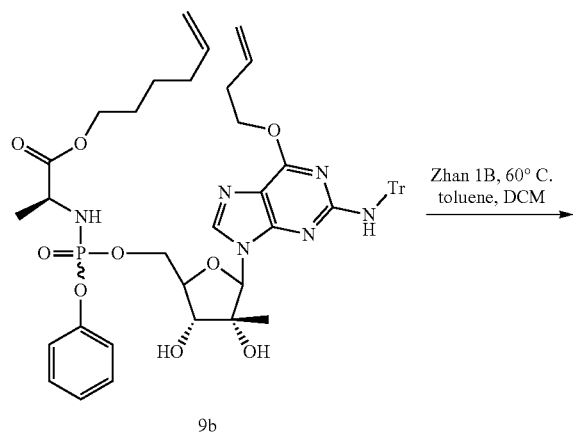

9b

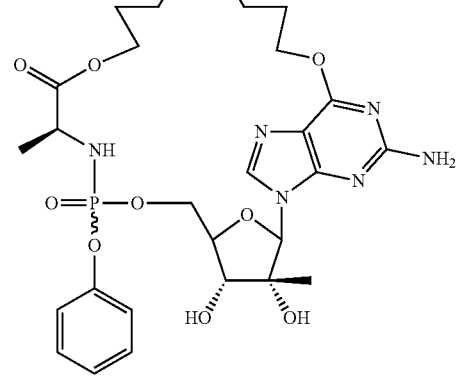

example 9

Compound of example 9 was synthesized from compound of 9c according to a similar procedure as in step 8D. MS (ESI): m/z 635.1 (M+H).

Example 10

Compound of Formula III, wherein $R^1$=H, $R^{2a}$=Me, $R^{2b}$=OH, $R^3$=H, $R^4$=H, $R^{5a}$=$R^{5b}$=H, $R^6$=

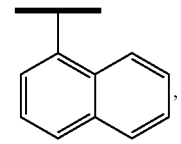

, $X$=O, $R^7$=H, $R^{8a}$=Me, $R^{8b}$=H, W–M=

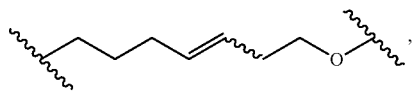

, $R^{14}$=$NH_2$.

Step 10A

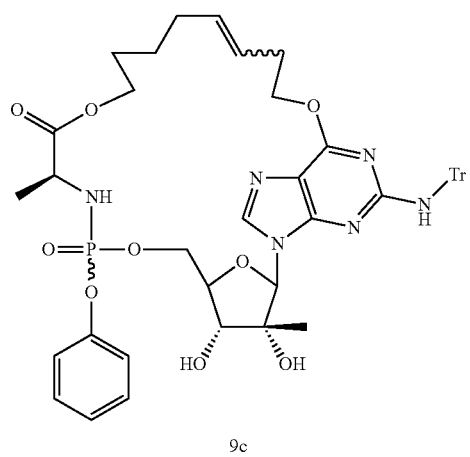

9c

Compound of 9c was synthesized from the compound of 9b according to a similar procedure as in step 1F. MS (ESI): m/z 875.5 (M+H).

Step 9D

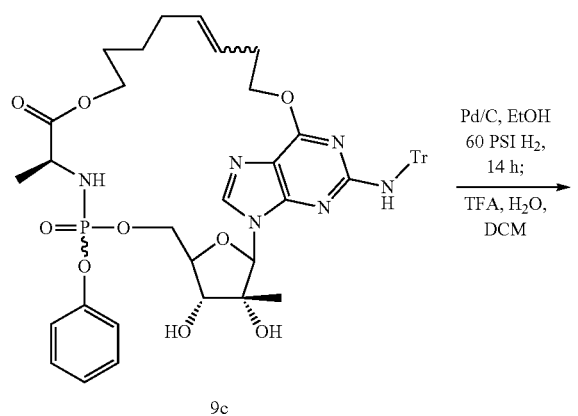

9c

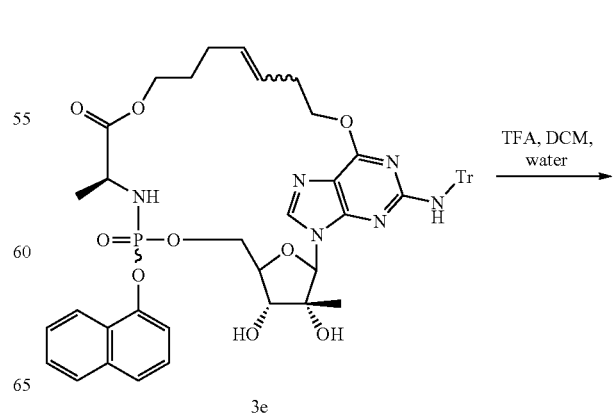

3e

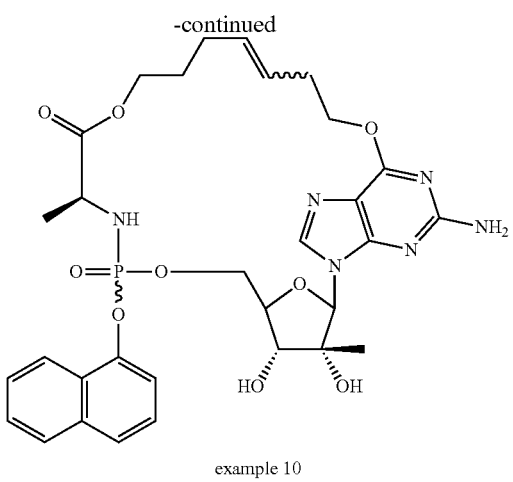

example 10

Compound of example 10 was synthesized from compound of 3e according to a similar procedure as in step 8D. MS (ESI): m/z 669.2 (M+H).

Example 11

Compound of Formula III, wherein $R^1$=H, $R^{2a}$=Me, $R^{2b}$=OH, $R^3$=H, $R^4$=H, $R^{5a}$=$R^{5b}$=H, $R^6$=H, X=O, $R^7$=H, $R^{8a}$=Me, $R^{8b}$=H, W-M=—(CH$_2$)$_7$—O—, $R^{14}$=NH$_2$.

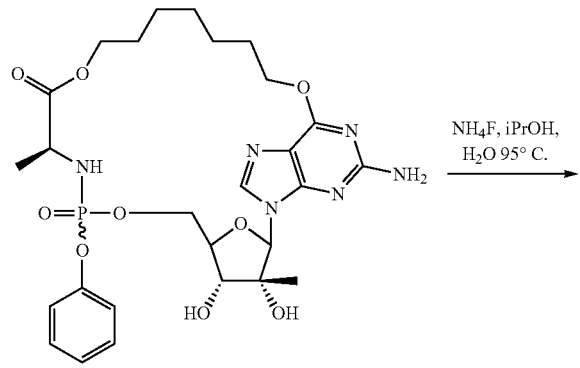

Example 8

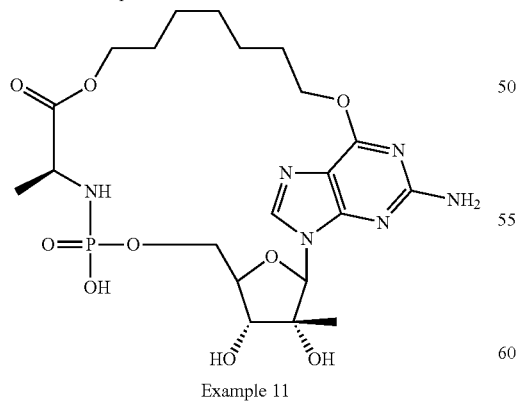

Example 11

To a mixture of compound of example 8 (26 mg) in i-PrOH (0.5 mL) and H$_2$O (0.5 mL) was added NH$_4$F (50 mg), and the resulted mixture was heated up to 95° C. for 1 h. The volatiles were evaporated and residue was extracted with 20% MeOH in DCM and filtered through celite. The filtrate was concentrated in vacuo and the residue was purified by column chromatography (silica, DCM to 20% MeOH in DCM) to give the desired compound of example 11 (8 mg). MS (ESI): m/z 545.2 (M+H).

Example 12

Compound of Formula II, wherein $R^1$=H, $R^{2a}$=Me, $R^{2b}$=F, $R^3$=H, $R^4$=H, $R^{5a}$=$R^{5b}$=H, $R^6$=

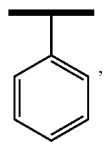

,

X=O, $R^7$=H, $R^{8a}$=Me, $R^{8b}$=H, W-M=—(CH$_2$)$_7$—(CO)NH—, $R^{12}$=$R^{13}$=H.

Step 12A

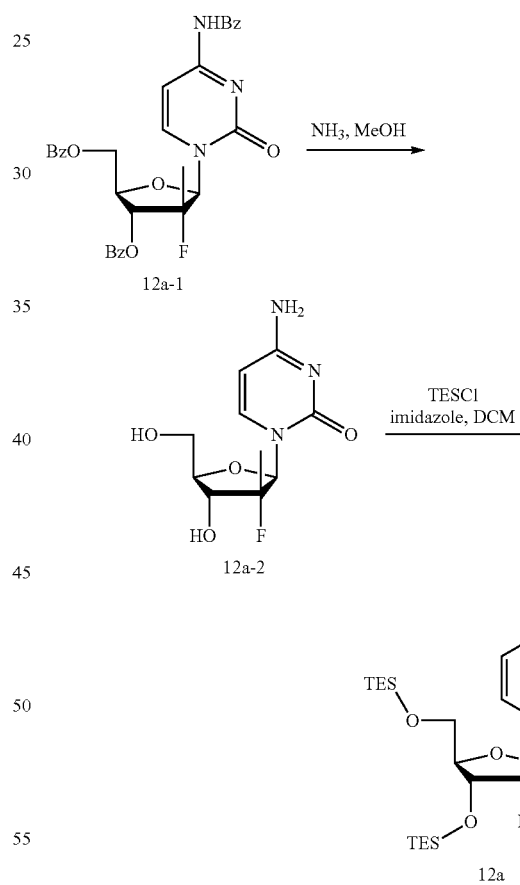

To compound 12a-1 (940 mg, 1.645 mmol) was added NH$_3$ in MeOH (7 N, 10 mL) and the resulted suspension was stirred at room temperature for 3 days to form a clear solution. The volatiles were evaporated and the residue was triturated with EtOAc and THF. The solid was collected by filtration and further washed with Et$_2$O and air dried to give compound 12a-2 as white solid (452 mg).

To the suspension of compound 12a-2 (452 mg) in DCM (10 mL) and acetonitrile (2 mL) was added imidazole (448 mg, 6.58 mmol), and to the resulted mixture was added TESCl (0.83 mL, 4.935 mmol) dropwise. The mixture resulted was stirred at room temperature for 2 h, and quenched with MeOH. The volatiles were evaporated and residue was purified by column chromatography (silica, hexane to EtOAc to 10% MeOH in DCM) to give the desired compound 12a as white solid (537 mg). MS (ESI): m/z 488.45 (M+H).

Step 12B chromatography (silica, hexane to 50% EtOAc in hexane) to give the desired compound 12b (96 mg). MS (ESI): m/z 570.37 (M+H).

Step 12C

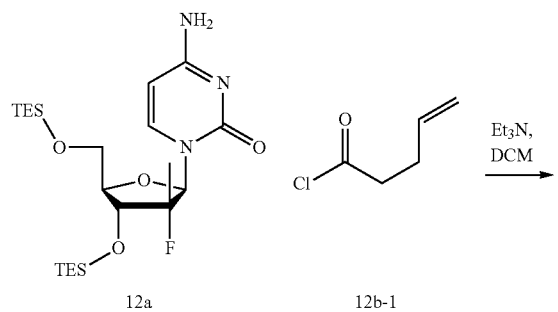

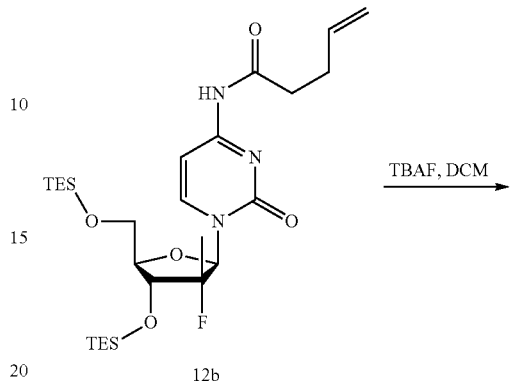

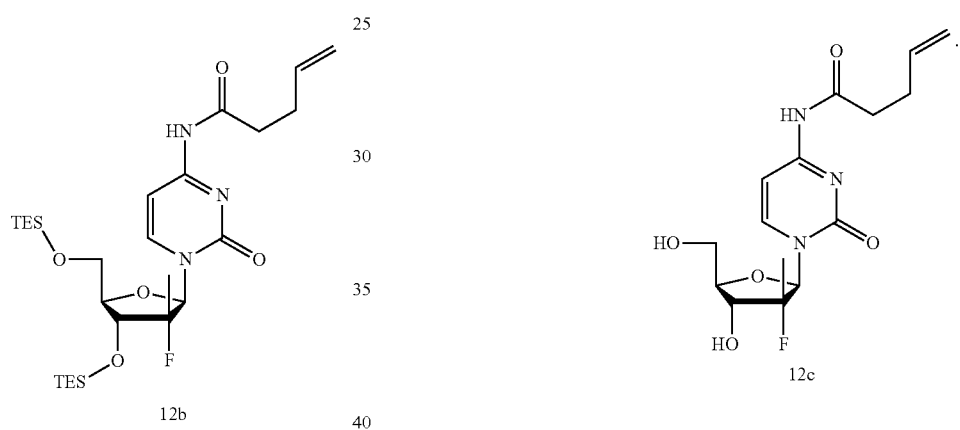

To the solution of compound 12a (100 mg, 0.205 mmol) in DCM (3 mL) was added Et$_3$N (0.11 mL, 0.82 mmol) and compound 12b-1 (34 µL). The mixture was stirred at room temperature for 45 min and then quenched with MeOH. The volatiles were evaporated and residue was purified by column To the solution of compound 12b (96 mg, 0.168 mmol) in DCM (4 mL) was added TBAF (0.5 mL, 0.504 mmol). The mixture was stirred at room temperature for 40 min, and the volatiles were evaporated. The residue was purified by column chromatography (silica, DCM to 10% MeOH in DCM) to give the diol 12c (46 mg). MS (ESI): m/z 342.26 (M+H).

Step 12D

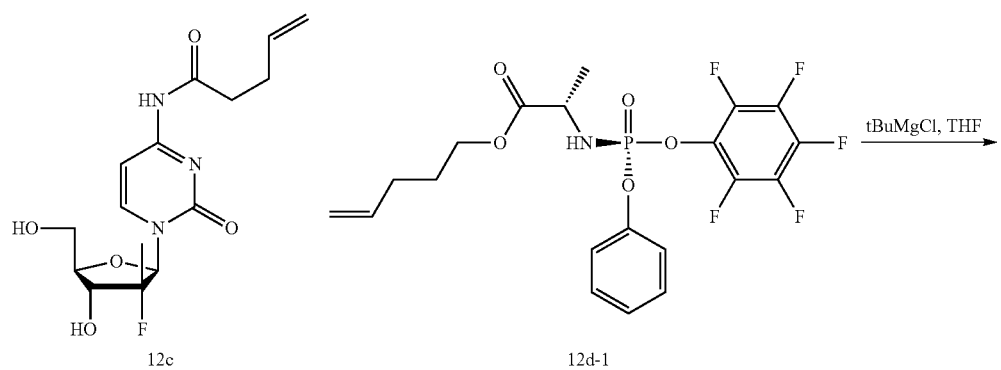

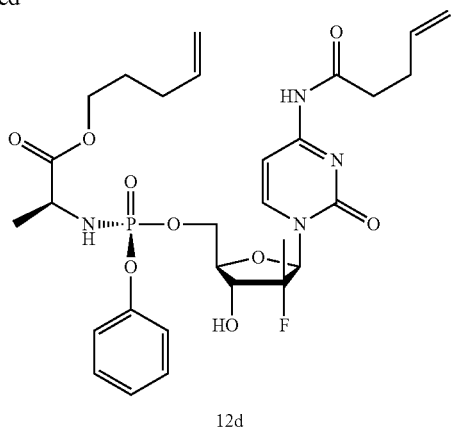

12d

To the solution of compound 12c (88 mg, 0.258 mmol) in THF (6 mL) at 0° C. was added tBuMgCl (0.39 ml, 0.987 mmol, 1.0 M in THF) dropwise. The mixture resulted was stirred at room temperature for 30 min and to this mixture was added compound 12d-1 (186 mg, 0.387 mmol) in THF (3 mL) dropwise and the resulted mixture was stirred at room temperature for 14 h. The reaction was quenched with 1N HCl, and the volatiles were evaporated in vacuo. The residue was purified by column chromatography (silica, DCM to 8% MeOH in DCM) to give the diene 12d (83 mg). MS (ESI): m/z 637.41 (M+H).

Step 12E

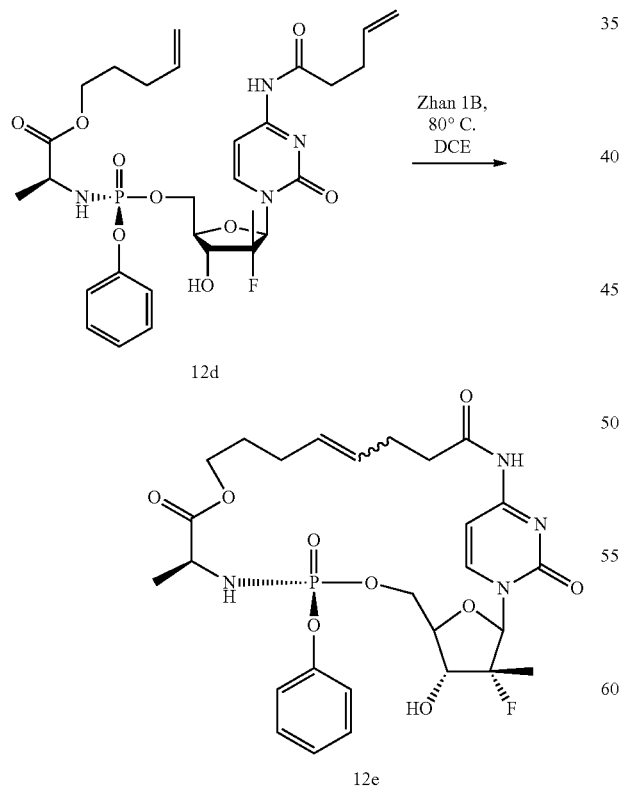

12d

12e

To a solution of diene 12d (57 mg, 0.0895 mmol) in DCE (9 mL was added Zhan 1B catalyst (9.9 mg, 0.0134 mmol), the resulted solution was degassed and heated up in a 80° C. oil bath for 45 min under N$_2$ atmosphere. The volatiles were evaporated in vacuo and the residue was purified by column chromatography (silica, DCM to 8% MeOH in DCM) to give the desired compound 12e (36.8 mg). MS (ESI): m/z 609.43 (M+H).

Step 12F

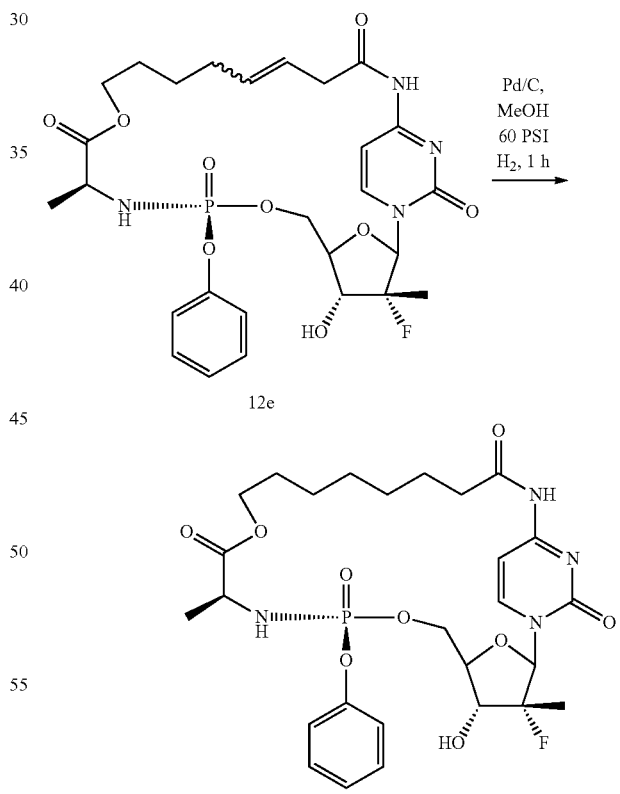

12e example 12

A mixture of compound 12e (30 mg, 0.0493 mmol), Pd—C (10%, 8 mg) and MeOH (2.5 ml) was hydrogenated at 60 PSI for 1 h. The mixture was filtered, washed with DCM. The filtrate was concentrated in vacuo to give the compound of example 12 (30 mg). MS (ESI): m/z 611.42 (M+H).

Step 12G

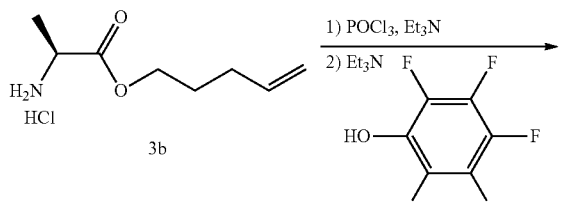

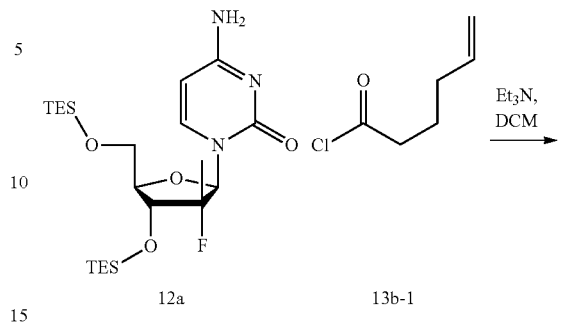

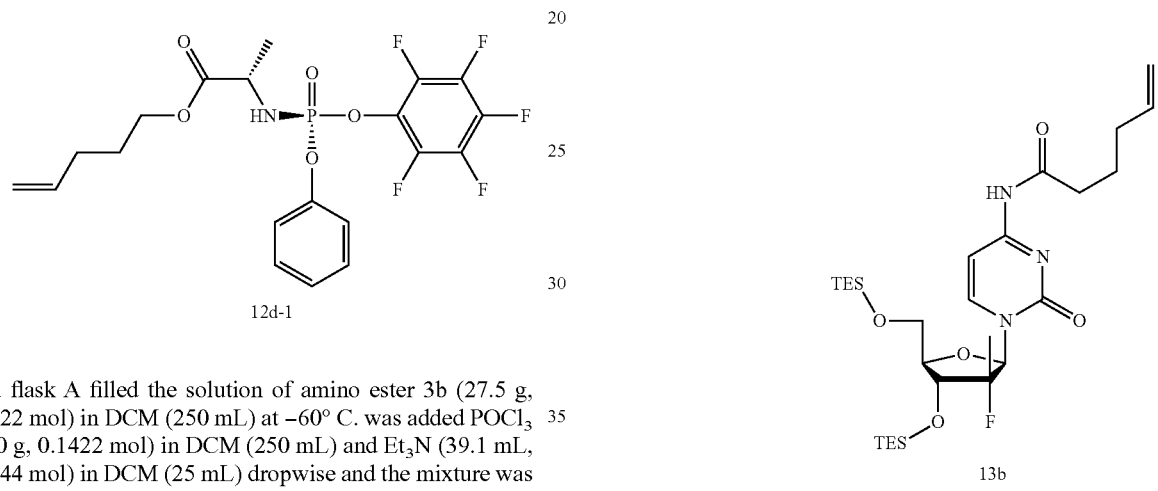

To a flask A filled the solution of amino ester 3b (27.5 g, 0.1422 mol) in DCM (250 mL) at −60° C. was added POCl$_3$ (30.0 g, 0.1422 mol) in DCM (250 mL) and Et$_3$N (39.1 mL, 0.2844 mol) in DCM (25 mL) dropwise and the mixture was slowly warmed up to 0° C. over 2 h. To another flask B filled pentafluorophenol (26.2 g, 0.1422 mol) in DCM (25 mL) at 0° C. was added Et$_3$N (21.5 mL, 0.1564 mol) slowly and the resulted mixture was slowly transferred to the flask A. The mixture was stirred at 0° C. for 4 h and filtered through celite. The filtrate was collected and the volatiles were evaporated. To this mixture was added a solution of hexane/EtOAc (6:1) and the mixture was stirred at room temperature for 8 h. The solid was collected by filtration, and then partitioned between EtOAc and water. The organic layer was dried and concentrated in vacuo to give the phosphoramidate 12d-1 (20.4 g). Another portion of product 12d-1 (10.8 g) was obtained from the filtrate after similar purification process.

Example 13

Compound of Formula II, wherein $R^1$=H, $R^{2a}$=Me, $R^{2b}$=F, $R^3$=H, $R^4$=H, $R^{5a}$=$R^{5b}$=H, $R^6$=

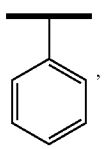

X=O, $R^7$=H, $R^{8a}$=Me, $R^{8b}$=H, W-M=—(CH$_2$)$_8$—O(CO)NH—, $R^{12}$=$R^{13}$=H.

Step 13B

To the solution of compound 12a (200 mg, 0.41 mmol) in DCM (6 mL) was added Et$_3$N (0.17 mL, 1.23 mmol) and compound 13b-1 (81.6 mg) in DCM (0.3 mL) dropwise. The mixture was stirred at room temperature for 1 h and then quenched with MeOH. The volatiles were evaporated and residue was purified by column chromatography (silica, DCM to 6% MeOH in DCM) to give the desired compound 13b (151 mg). MS (ESI): m/z 584.47 (M+H).

Step 13C

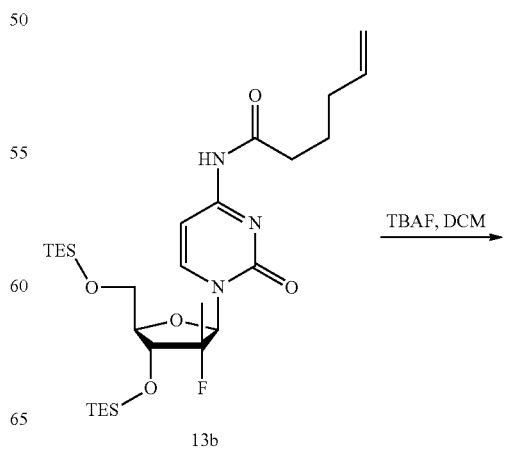

-continued
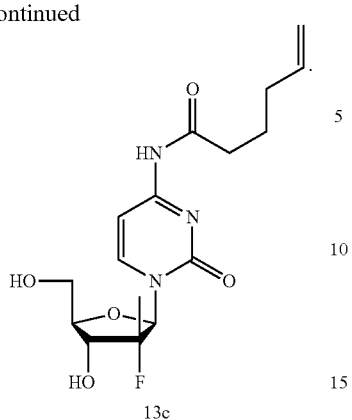
13c
To the solution of compound 13b (151 mg, 0.241 mmol) in DCM (6 mL) was added TBAF (0.7 mL, 0.724 mmol). The mixture was stirred at room temperature for 1.5 h, and the volatiles were evaporated. The residue was purified by column chromatography (silica, DCM to 10% MeOH in DCM) to give the desired compound 13c (54 mg). MS (ESI): m/z 378.27 (M+Na).
Step 13D
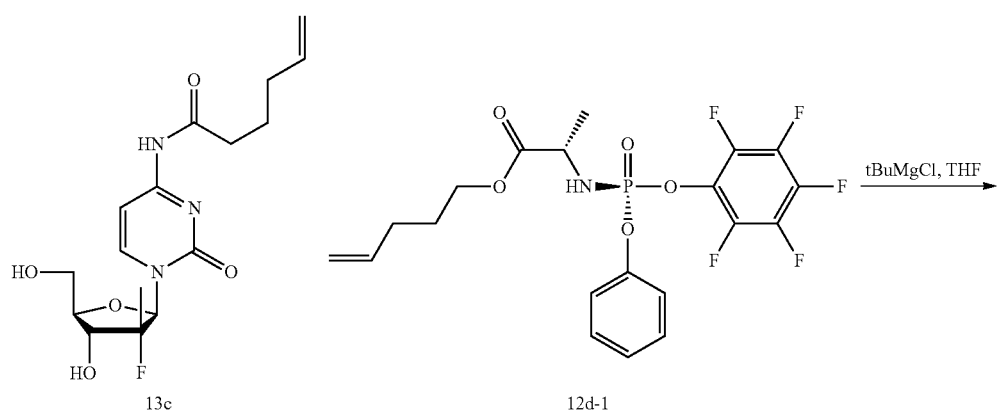
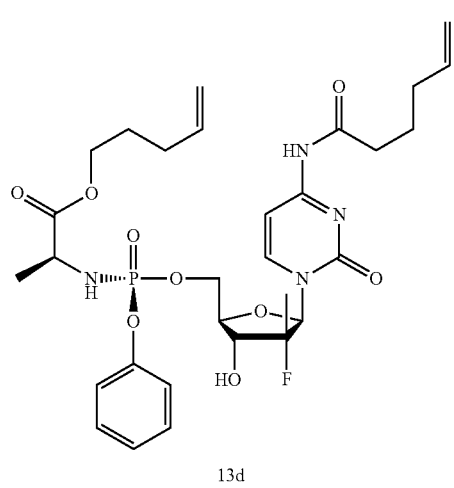
13d To the solution of compound 13c (54 mg, 0.152 mmol) in THF (4 mL) at 0° C. was added tBuMgCl (0.23 ml, 0.228 mmol, 1.0 M in THF) dropwise. The mixture resulted was stirred at room temperature for 30 min and to this mixture was added compound 12d-1 (109 mg, 0.228 mmol) in THF (2 mL) dropwise and the resulted mixture was stirred at room temperature for 14 h. The reaction was quenched with 1N HCl, and the volatiles were evaporated in vacuo. The residue was purified by column chromatography (silica, DCM to 8% MeOH in DCM) to give the desired compound 13d (42 mg). MS (ESI): m/z 651.43 (M+H).

Step 13E

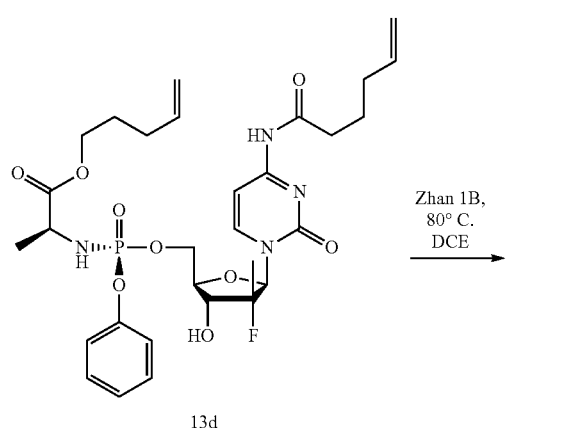

13d

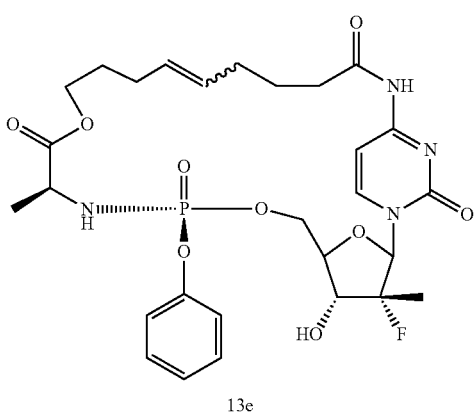

13e

To a solution of diene 13d (42 mg, 0.0646 mmol) in DCE (6.5 mL) was added Zhan 1B catalyst (4.5 mg, 0.00613 mmol), the resulted solution was degassed and heated up to 45° C. for 30 min under $N_2$ atmosphere. Another portion of Zhan 1B catalyst (4.5 mg, 0.00613 mmol) was added, and the mixture was stirred at 80° C. for 45 min. The volatiles were evaporated in vacuo and the residue was purified by column chromatography (silica, DCM to 10% MeOH in DCM) to give the desired compound 13e (9.6 mg). MS (ESI): m/z 623.4 (M+H).

Step 13F

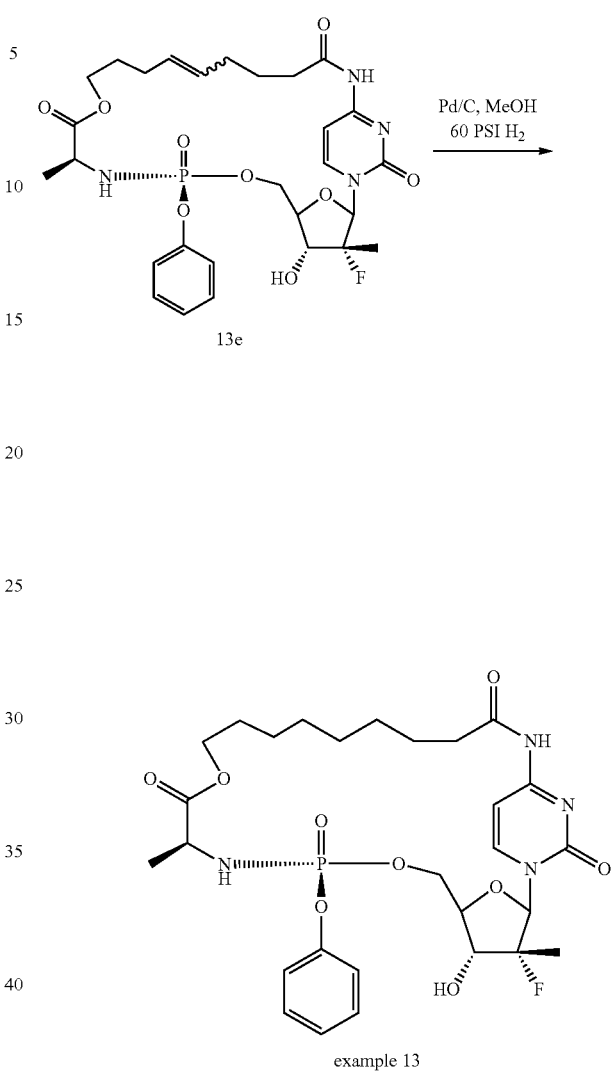

A mixture of compound 13e (7.0 mg, 0.0112 mmol), Pd—C (10%, 3 mg) and MeOH (0.7 mL) was hydrogenated at 60 PSI for 1 h. The mixture was filtered, washed with DCM. The filtrate was concentrated in vacuo to give the compound of example 13 (6 mg). MS (ESI): m/z 625.46 (M+H).

Example 14

Compound of Formula II, wherein $R^1$=H, $R^{2a}$=Me, $R^{2b}$=F, $R^3$=H, $R^4$=H, $R^{5a}$=$R^{5b}$=H, $R^6$=

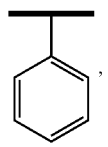

,

X=O, $R^7$=H, $R^{8a}$=Me, $R^{8b}$=H, W-M=—$(CH_2)_6$—O(CO)NH—, $R^{12}$=$R^{13}$=H.

Step 14D
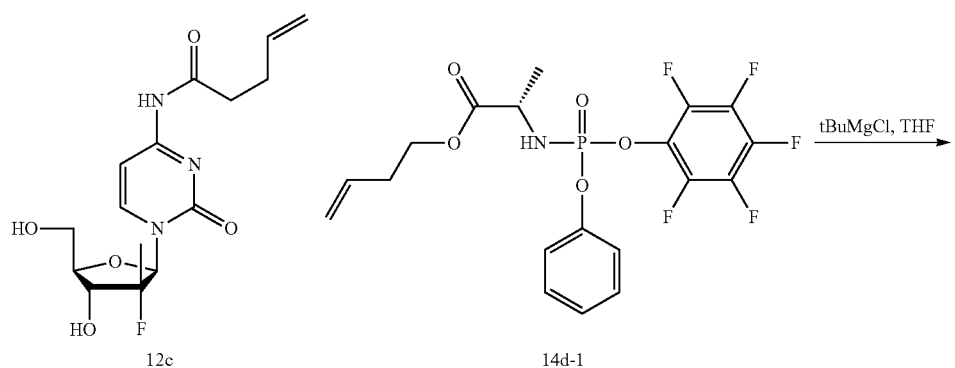
Diene 14d was synthesized according a similar procedure as in step 12D. MS (ESI): m/z 625.4 (M+H). Phosphoramidate 14d-1 was obtained as a mixture of diastereomers according a similar procedure as in step 12G.
Step 14E
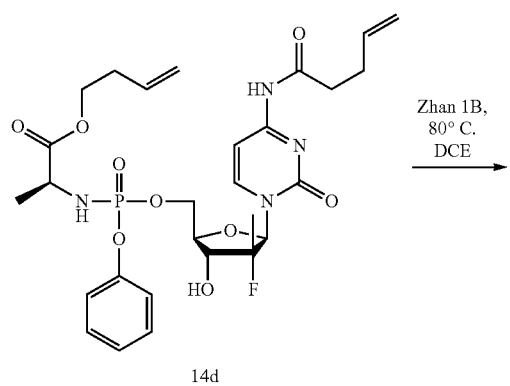
-continued
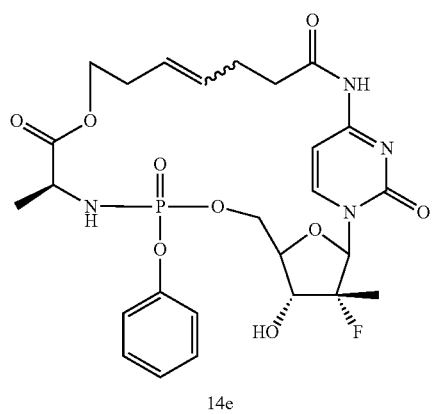
Olefin 14e was synthesized according a similar procedure as in step 12E. MS (ESI): m/z 595.4 (M+H).

Step 14F
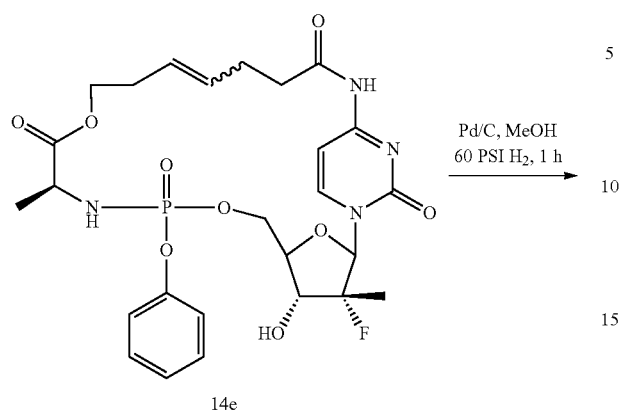
14e
Pd/C, MeOH
60 PSI H₂, 1 h
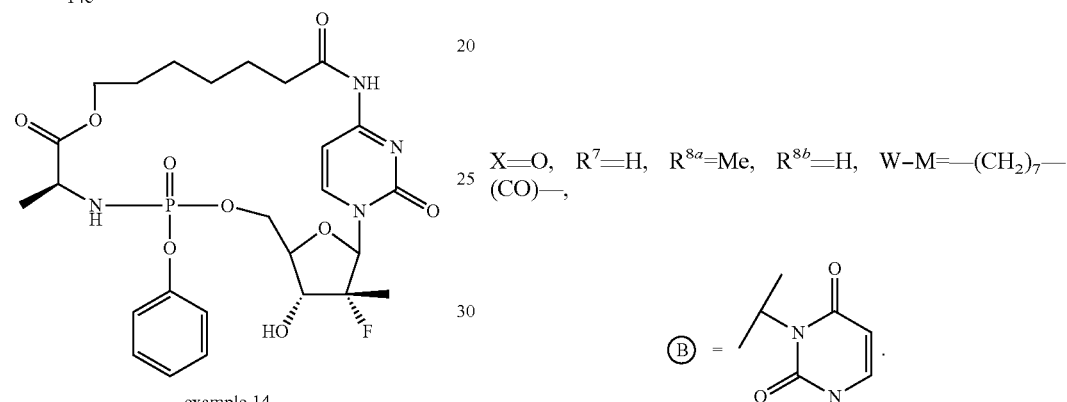
example 14
Compound of example 14 was synthesized according a similar procedure as in step 12F. MS (ESI): m/z 597.4 (M+H).
Example 15
Compound of Formula I, wherein $R^1$=H, $R^{2a}$=Me, $R^{2b}$=F, $R^3$=H, $R^4$=H, $R^{5a}$=$R^{5b}$=H, $R^6$=
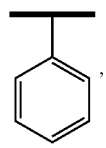,
X=O, $R^7$=H, $R^{8a}$=Me, $R^{8b}$=H, W-M=—(CH₂)₇—(CO)—,
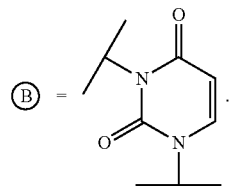
Step 15A
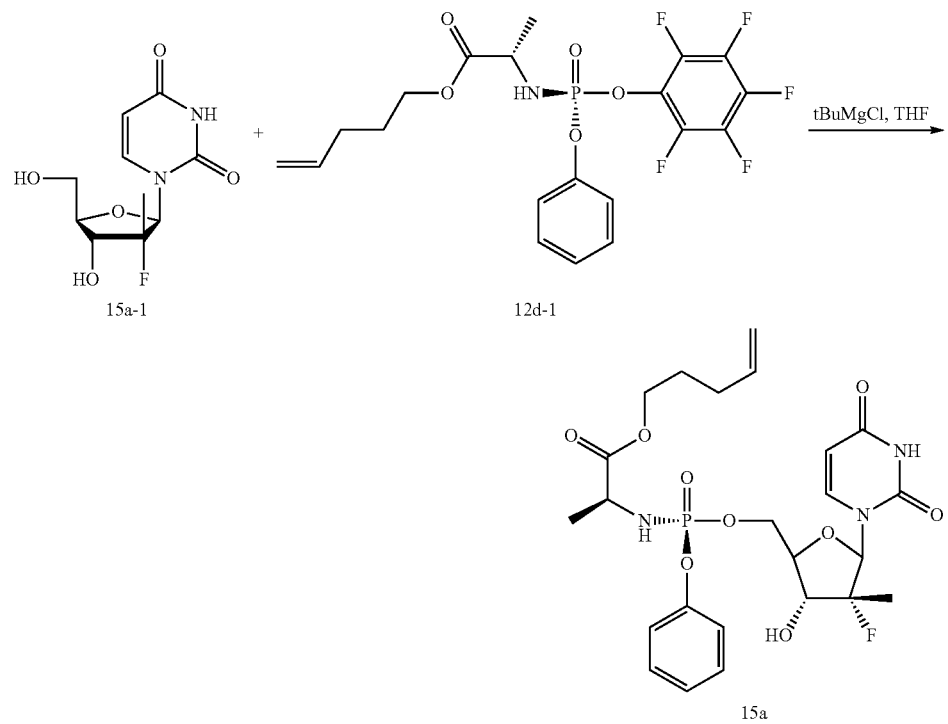

To Nucleoside 15a-1 (138 mg, 0.53 mmol) in THF (9 mL) at 0° C. was added t-BuMgCl (1.1 mL, 1.06 mmol, 1.0 M in THF) dropwise. The mixture resulted was stirred at room temperature for 30 min and to this mixture was added compound 12d-1 (457 mg, 0.954 mmol) in THF (3 mL) dropwise and the resulted mixture was stirred at room temperature for 14 h. The reaction was quenched with NaHCO$_3$ solution, and the volatiles were evaporated in vacuo. The residue was purified by column chromatography (silica, Hexane to 80% acetone in hexane) to give the desired compound 15a (170 mg). MS (ESI): m/z 556.34 (M+H).

(For synthesis of Nucleoside 15a-1 sees: Clark, J. L. et al., *J. Med. chem.* 2005, 48, 5504.)

Step 15B

Step 15C

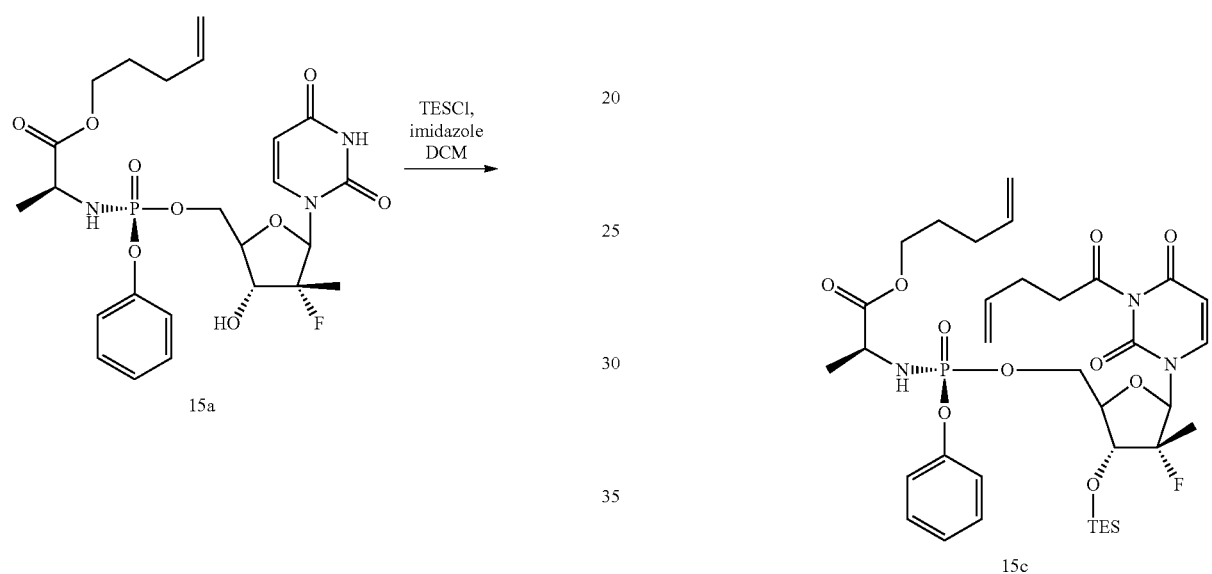

To a solution of alcohol 15a (62 mg, 0.107 mmol) and imidazole (21.8 mg, 0.321 mmol) in DCM (2 mL) was added TESCl (36 μL, 0.214 mmol). The mixture resulted was stirred at room temperature for 4 h. The volatiles were evaporated in vacuo and the residue was purified by column chromatography (silica, DCM to 8% MeOH in DCM) to give the desired compound 15b (71 mg). MS (ESI): m/z 692.19 (M+Na).

To the solution of compound 15b (71 mg, 0.106 mmol) in DCM (3 mL) was added Et$_3$N (44 μL, 0.318 mmol) and acid chloride 12b-1 (23 μL, 0.212 mmol) and the mixture was stirred at room temperature for 1 h. The volatiles were evaporated and residue was purified by column chromatography (silica, hexane to 80% EtOAc in hexane) to give the diene 15c (62 mg). MS (ESI): m/z 774.63 (Manna).

Step 15D

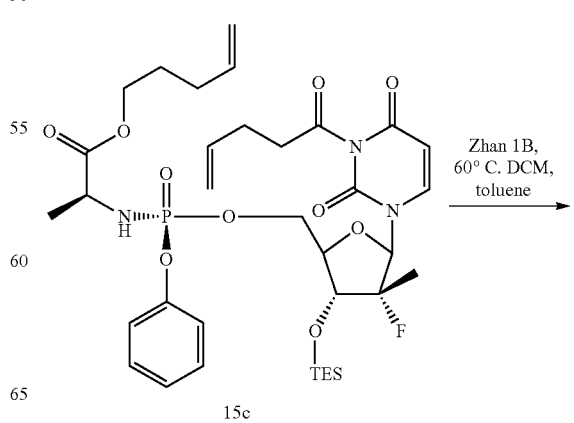

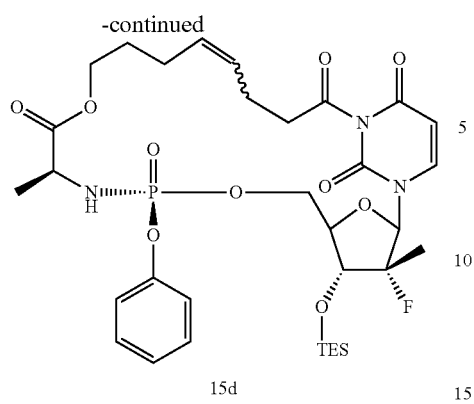

15d

To a solution of diene 15c (62 mg, 0.0819 mmol) in DCM (2 mL) and toluene (6 mL) was added Zhan 1B catalyst (12 mg, 0.0164 mmol), the resulted solution was degassed and heated up to 60° C. for 40 min under $N_2$ atmosphere. The volatiles were evaporated in vacuo and the residue was purified by column chromatography (silica, hexane to 60% acetone in hexane) to give the olefin 15d (51 mg). MS (ESI): m/z 746.61 (M+Na).

Step 15E

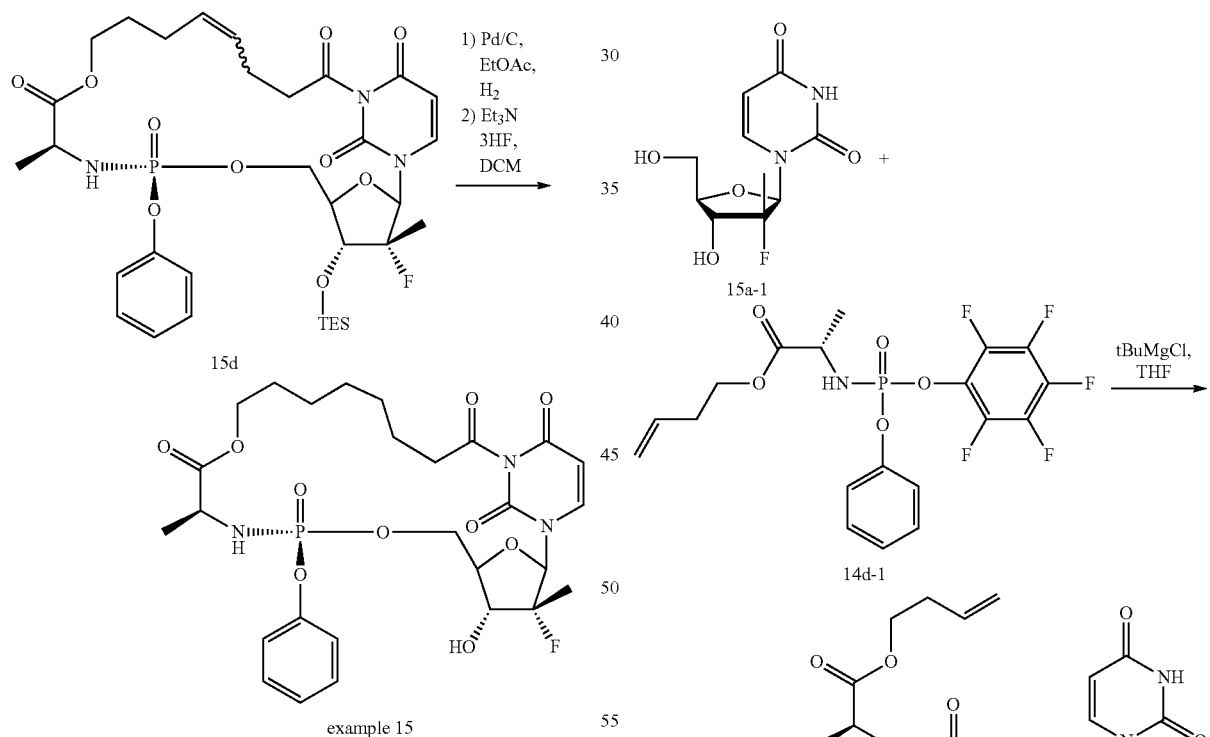

A mixture of compound 15d (51 mg, 0.07 mmol), Pd—C (10%, 15 mg, 0.014 mmol) and EtOAc (2 mL) was hydrogenated under $H_2$ balloon for 3 h. The mixture was filtered, washed with DCM and the filtrate was concentrated in vacuo. To the residue was added DCM (3 mL) and $Et_3N \cdot 3HF$ (91 µL, 0.56 mmol) and the mixture was stirred at room temperature for 1 h. The reaction was quenched with EtOTMS, and stirred for 15 min. The volatiles were evaporated and residue was purified by HPLC to give the compound of example 15 (7 mg). MS (ESI): m/z 634.5 (M+Na).

Example 16

Compound of Formula I, wherein $R^1$=H, $R^{2a}$=Me, $R^{2b}$=F, $R^3$=H, $R^4$=H, $R^{5a}$=$R^{5b}$=H, $R^6$=

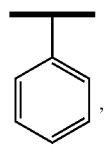,

X=O, $R^7$=H, $R^{8a}$=Me, $R^{8b}$=H, W-M=—$(CH_2)_6$—(CO)—,

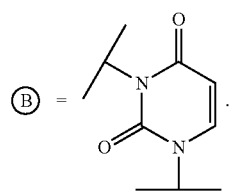

Step 16A

Olefin 16a was synthesized according a similar procedure as in step 15A. MS (ESI): m/z 593.96 (M+Na). Phosphoramidate 14d-1 was obtained as a mixture of diastereomers according a similar procedure as in step 12G.

Step 16B

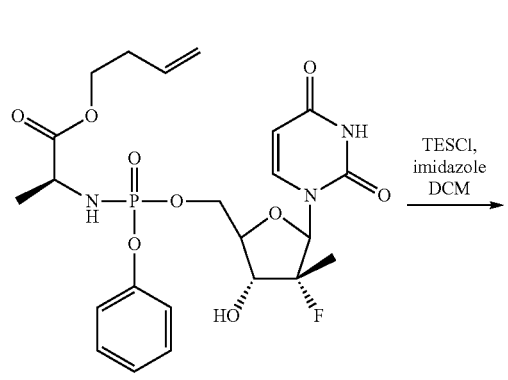

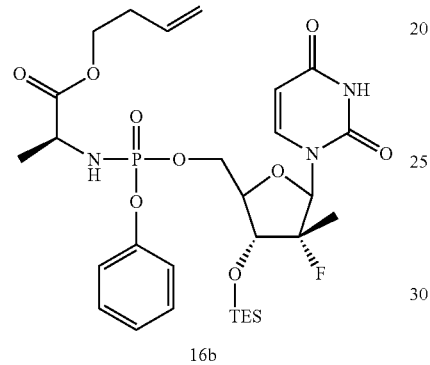

Olefin 16b was synthesized according a similar procedure as in step 15B. MS (ESI): m/z 656.2 (M+H).

Step 16C

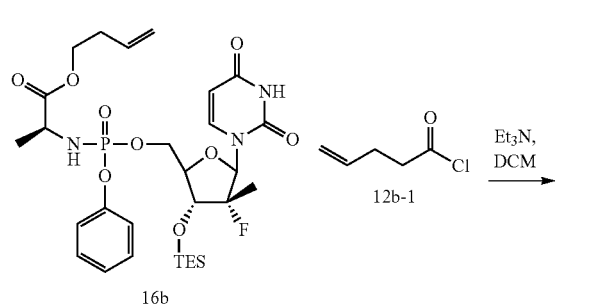

Diene 16c was synthesized according a similar procedure as in step 15C. MS (ESI): m/z 760.54 (M+Na).

Step 16D

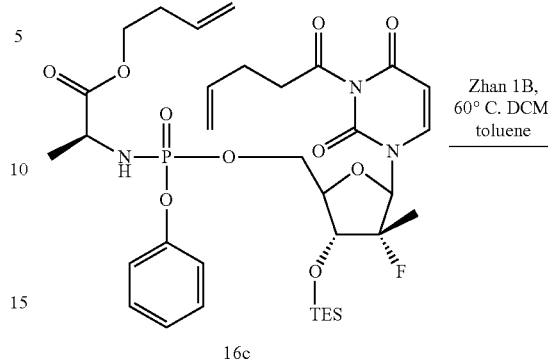

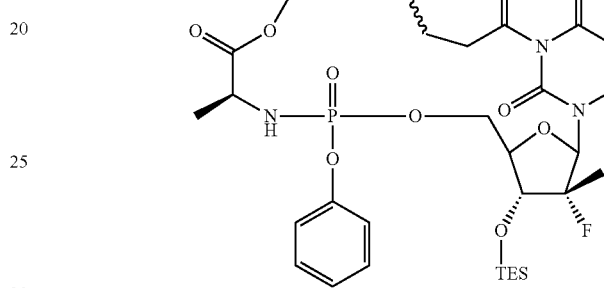

Olefin 16d was synthesized according a similar procedure as in step 15D. MS (ESI): m/z 732.55 (M+Na).

Step 16E

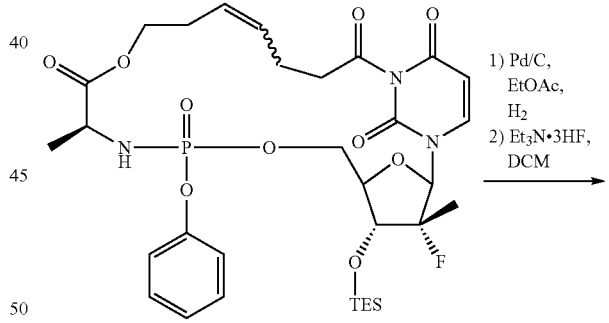

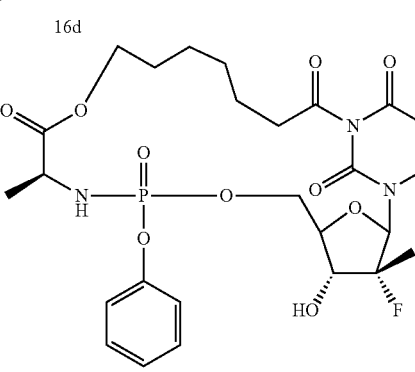

example 16

The compound of example 16 was synthesized according a similar procedure as in step 16E. MS (ESI): m/z 598.54 (M+Na).

Example 17

Compound of Formula III, wherein $R^1$=H, $R^{2a}$=Me, $R^{2b}$=OH, $R^3$=H, $R^4$=H, $R^{5a}$=$R^{5b}$=H, $R^6$=

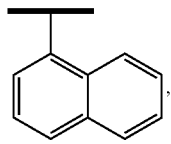

X=O, $R^7$=H, $R^{8a}$=Me, $R^{8b}$=H, W–M=—(CH$_2$)$_7$—NH—, $R^{14}$=NH$_2$.

Step 17A

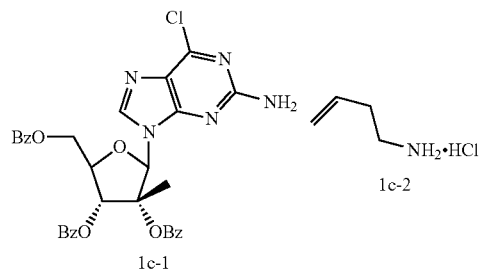

To a mixture of Compound 1c-1 (100 mg, 0.159 mmol) and amine 1c-2 (34.3 mg, 0.319 mmol) in EtOH (3 mL) was added DIPEA (0.11 mL, 0.636 mmol) and DMAP (1.9 mg, 0.0159 mmol), and the resulted solution was heated up to reflux for 16 h. The volatiles were evaporated in vacuo and the residue was dissolved in EtOAc. The organics were washed with 1 N HCl, water, brine sequentially, dried (Na$_2$SO$_4$), filtered and evaporated to give the olefin 17a (107 mg). MS (ESI): m/z 663.23 (M+H).

(For synthesis of Compound 1c-1 see: Eldrup, A. B. et al., *J. Med. chem.* 2004, 47, 2283.)

Step 17B

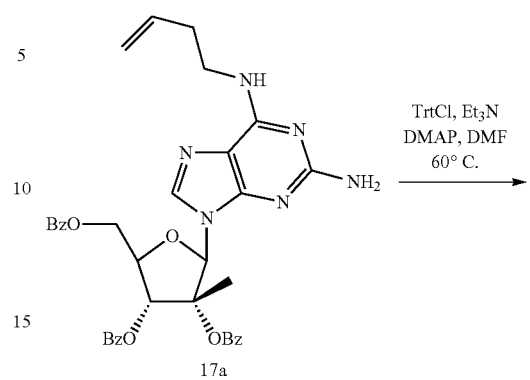

To a mixture of Compound 17a (100 mg, 0.151 mmol) in DMF (3 mL) was added TrtCl (84 mg, 0.302 mmol), Et$_3$N (0.21 mL, 1.51 mmol) and DMAP (3.7 mg, 0.0302 mmol), and the resulted mixture was heated up to 60° C. for 2 h. The mixture was diluted in EtOAc and washed with water, brine sequentially, dried (Na$_2$SO$_4$), filtered and evaporated. The residue was purified by column chromatography (silica, hexane to 60% EtOAc in hexane) to give the compound 17b (102 mg). MS (ESI): m/z 905.44, 906.49 (M+H).

Step 17C

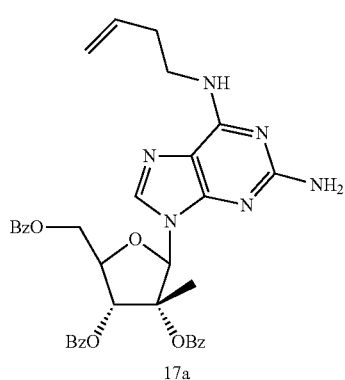

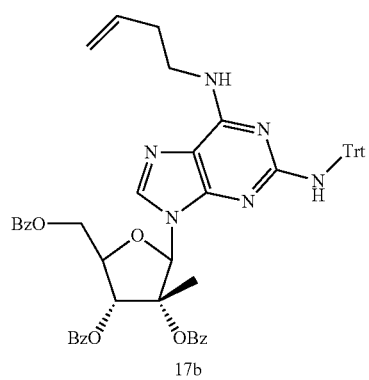

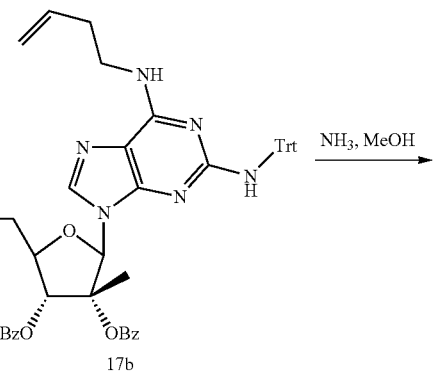

-continued

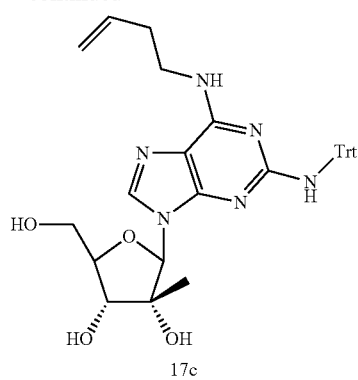

17c

To tribenzoate 17b (1.055 g, 1.166 mmol) was added NH₃ (40 mL, 7 N in MeOH), and the resulted mixture was stirred at room temperature for 62 h. The volatiles were evaporated in vacuo and the residue was purified by column chromatography (silica, DCM to 10% MeOH in DCM) to give the triol 17c (531 mg). MS (ESI): m/z 593.23 (M+H).

Step 17D

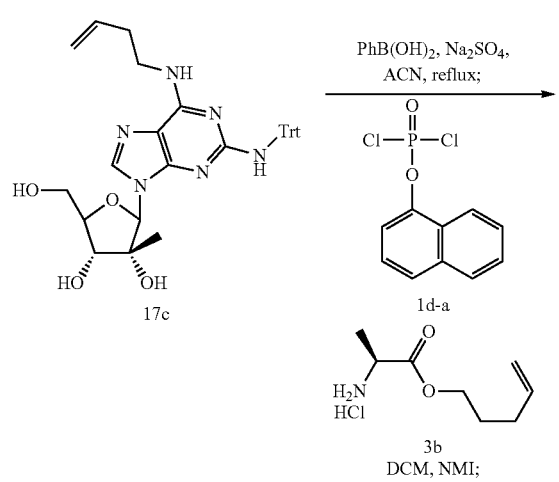

The diene 17d was synthesized according a similar procedure as in step 3C. MS (ESI): m/z 938.25 (M+H).

Step 17E

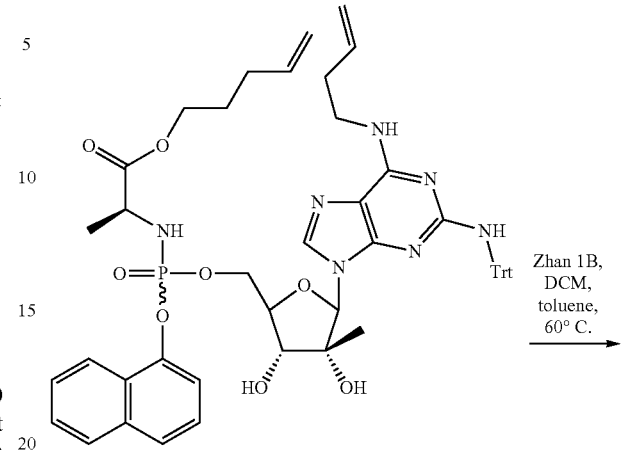

To a solution of diene 17d (185 mg, 0.197 mmol) in DCM (2 mL) and toluene (17.7 mL) was added Zhan 1B catalyst (14.5 mg, 0.0197 mmol), the resulted solution was degassed and heated up to 60° C. for 1 h under N2 atmosphere. Another portion of Zhan 1B catalyst (7.0 mg, 0.0098 mmol) was added and the mixture was stirred for another 30 min. The mixture was passed through a short wash column to give the alkene 17e (115 mg). MS (ESI): m/e 910.35 (M+H).

Step 17D

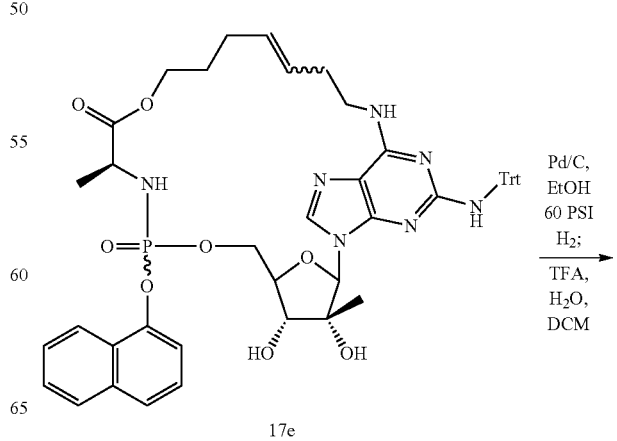

17e

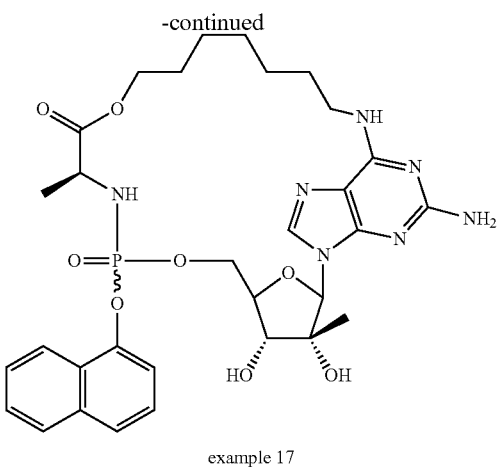

example 17

The compound of example 17 was synthesized according a similar procedure as in step 8D. MS (ESI): m/z 670.15 (M+H).

Biological Activity

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. One of the HCV replicon cell lines (strain Con1, genotype 1b) has the nucleic acid sequence set forth in EMBL Accession No.: AJ242651, the coding sequence of which is from nucleotides 1801 to 8406. Another replicon cell line (strain H77, genotype 1a) was constructed as described by Yi et. al. (Yi et. al. (2004) Journal of Virology 78(15):7904-15). The coding sequences of the published HCV replicons were synthesized and subsequently assembled in plasmids using standard molecular biology techniques.

One replicon cell line ("SGR 11-7") stably expresses HCV replicon RNA, genotype 1b, which consists of (i) the HCV 5'UTR fused to the first 12 amino acids of the capsid protein, (ii) the neomycin phosphotransferase gene (neo), (iii) the IRES from encephalomyocarditis virus (EMCV) and (iv) HCV NS2 to NS5B genes and the HCV 3'UTR. Another replicon cell line ("Huh-1a7") described by Yi et. al. (Yi et. al. (2004) Journal of Virology 78(15):7904-15, expressly incorporated by reference in its entirety) stably expresses HCV replicon RNA, genotype 1a, which consists of (i) the HCV 5'UTR fused to the first 12 amino acids of the capsid protein, (ii) the HIV tat protein, (iii) the neomycin phosphotransferase gene (neo), (iv) the IRES from encephalomyocarditis virus (EMCV) and (vi) HCV NS3 to NS5B genes that harbor cell culture adaptive mutations (Q1067R, K1691R, S2204I) and the HCV 3'UTR.

These cell lines are maintained at 37° C., 5% $CO_2$, 100% relative humidity in DMEM (Cat#11965-084, Invitrogen), with 10% fetal calf serum ("FCS", Invitrogen), 1% non-essential amino acids (Invitrogen), 1% of Glutamax (Invitrogen), 1% of 10× penicillin/streptomycin (Cat#15140-122, Invitrogen) and Geneticin (Cat#10131-027, Invitrogen) at 0.75 mg/ml or 0.25 mg/ml for 11-7 and Huh-1a7 cells, respectively.

2. HCV Replicon Assay—qRT-PCR.

$EC_{50}$ values of single agent compounds were determined by HCV RNA detection using quantitative RT-PCR, according to the manufacturer's instructions, with a TAQMAN® One-Step RT-PCR Master Mix Reagents Kit (Cat#AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat#AM1812). Chemical agent cytotoxicity is evaluated using an MTS assay according to the manufacturer's directions (Promega).

The compounds of the present invention can be effective against the HCV 1a and 1b genotypes. It should also be understood that the compounds of the present invention can inhibit multiple genotypes of HCV. In one embodiment, compounds of the present invention are active against the 1a, 1b, 2a, 2b, 3a, 4a, and 5a genotypes. Table 5 shows the $EC_{50}$ values of representative compounds of the present invention against the HCV 1a and 1b genotypes from the above described qRT-PCR. $EC_{50}$ ranges against HCV 1a or 1b are as follows: A>1 μM; B 0.1-1 μM; C<0.1 μM.

TABLE 5

| | Genotype-1a or 1b replicon $EC_{50}$ | | |
|---|---|---|---|
| Example | Structures | 1a $EC_{50}$ | 1b $EC_{50}$ |
| 1 | | B | A |

TABLE 5-continued
| | | Genotype-1a or 1b replicon EC$_{50}$ | |
|---|---|---|---|
| Example | Structures | 1a EC$_{50}$ | 1b EC$_{50}$ |
| 2 | 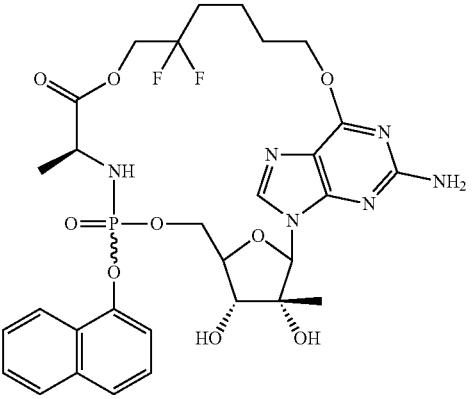 [SMILES: C[C@@H]1NP(=O)(Oc2cccc3ccccc23)OCC2OC(n3cnc4c(nc(N)nc43)OCCCCC(F)(F)COC1=O)[C@](C)(O)[C@@H]2O] | B | B |
| 3 | 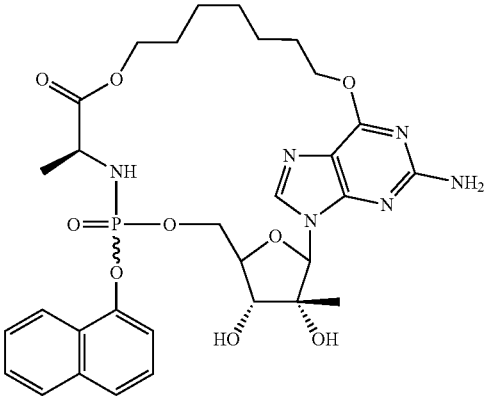 [SMILES: C[C@@H]1NP(=O)(Oc2cccc3ccccc23)OCC2OC(n3cnc4c(nc(N)nc43)OCCCCCCCOC1=O)[C@](C)(O)[C@@H]2O] | C | B |
| 4 | 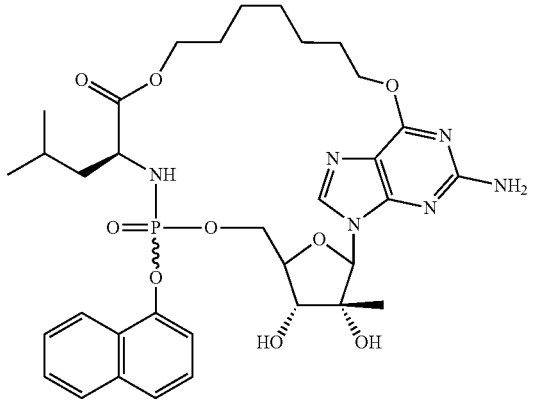 [SMILES: CC(C)C[C@@H]1NP(=O)(Oc2cccc3ccccc23)OCC2OC(n3cnc4c(nc(N)nc43)OCCCCCCCOC1=O)[C@](C)(O)[C@@H]2O] | B | A |

TABLE 5-continued

| | Genotype-1a or 1b replicon EC$_{50}$ | | |
|---|---|---|---|
| Example | Structures | 1a EC$_{50}$ | 1b EC$_{50}$ |
| 5 | | B | A |
| 6 | | B | B |
| 7 | | C | B |

TABLE 5-continued
| | Genotype-1a or 1b replicon EC$_{50}$ | | |
|---|---|---|---|
| Example | Structures | 1a EC$_{50}$ | 1b EC$_{50}$ |
| 8 |  | B | B |
| 9 | 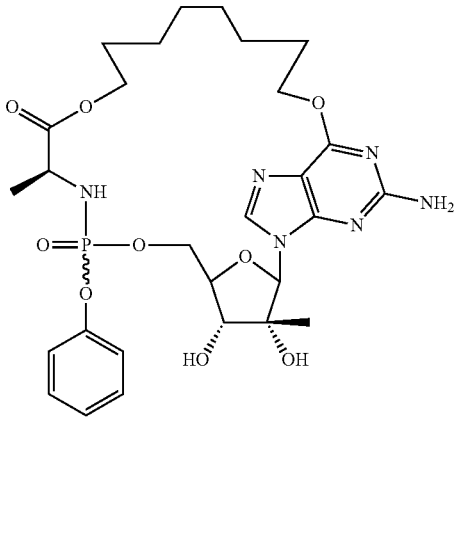 [SMILES: C[C@@H]1NP(=O)(Oc2ccccc2)OCC2OC(n3cnc4c(nc(N)nc43)OCCCCCCCCCOC1=O)[C@](C)(O)[C@@H]2O] | B | B |
| 10 | 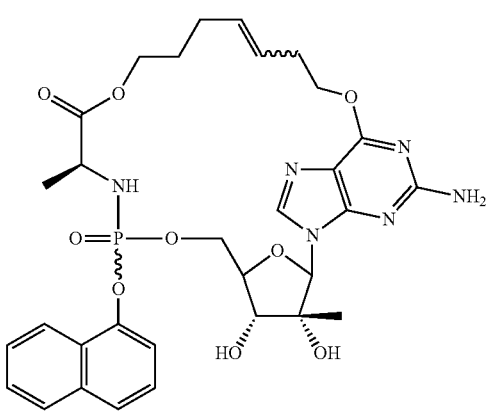 [SMILES: C[C@@H]1NP(=O)(Oc2cccc3ccccc23)OCC2OC(n3cnc4c(nc(N)nc43)OCCC=CCCCOC1=O)[C@](C)(O)[C@@H]2O] | B | B |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula I or a pharmaceutically acceptable salt, ester, stereoisomer, tautomer, solvate, or combination thereof:

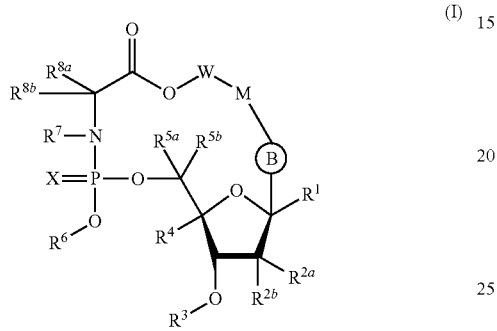
(I)

wherein:
$R^1$ and $R^4$ are each independently selected from the group consisting of:
1) hydrogen;
2) —CN;
3) halogen;
4) —$N_3$;
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R^{2a}$ is selected from the group consisting of:
1) hydrogen;
2) halogen;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;

$R^{2b}$ at each occurrence is selected from the group consisting of:
1) hydrogen;
2) halogen;
3) —CN;
4) —$N_3$; and
5) $OR^9$;

$R^3$ and $R^9$ are each independently selected from the group consisting of: hydrogen, hydroxy protecting group, $R^{10}$, $C(O)R^{10}$, —$C(O)_{OR}{}^{10}$, and —$C(O)NR^{11a}R^{11b}$; wherein $R^{10}$ at each occurrence is independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic;

$R^{11a}$ and $R^{11b}$ at each occurrence are each independently selected from the group consisting of: hydrogen and $R^{10}$; or alternatively $R^{11a}$ and $R^{11b}$ taken together with the nitrogen atom to which they are attached form a heterocyclic ring;

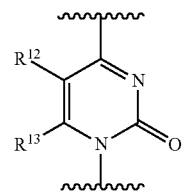

is selected from the following structures:

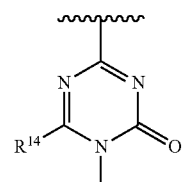
(B1)

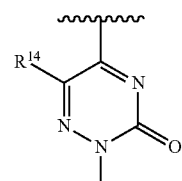
(B2)

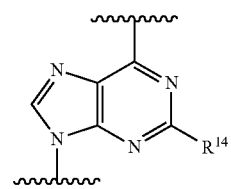
(B3)

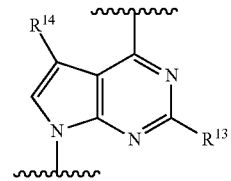
(B4)

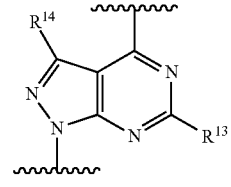
(B5)

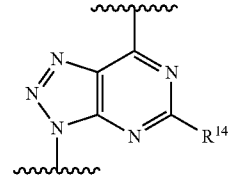
(B6)

(B7)

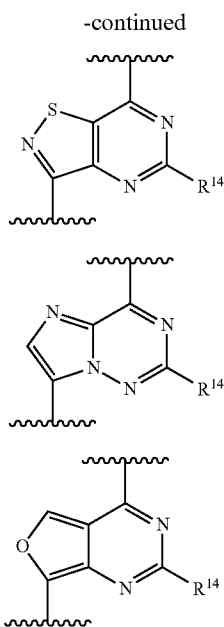

(B8)

(B9)

(B10)

wherein $R^{12}$, $R^{13}$ and $R^{14}$ are each independently selected from the group consisting of: hydrogen, halogen, —CN, $N_3$, —C(O)$NR^{11a}R^{11b}$, —$NO_2$, —$OR^9$, —$SR^9$, —$NR^{11a}R^{11b}$, —NHC(O)$R^{10}$, —NHC(O)$OR^{10}$ and —NHC(O)$NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl;

$R^{5a}$ and $R^{5b}$ are each independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;
or $R^{5a}$ and $R^{5b}$ are taken together with the carbon atom to which they are attached to form a group selected from —$C_3$-$C_8$ cycloalkyl, —$C_3$-$C_8$ cycloalkenyl, and —$C_3$-$C_8$ cycloalkynyl;

$R^6$ is selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;
or $R^7$ and $R^{8a}$ or $R^{8b}$ together form —$(CH_2)_n$— so as to form a cyclic ring which includes the adjoining N and C; wherein n is 2 to 6;

$R^{8a}$ and $R^{8b}$ are each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;

or $R^{8a}$ and $R^{8b}$ combined together form —$(CH_2)_m$—, so as to form a spiro ring with the carbon to which they are attached; wherein m is 2 to 5;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—; and W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_8$ alkynylene each containing 0, 1, 2, or 3 heteroatoms selected from 0, S or N; —$C_4$-$C_{12}$ cycloalkylene, or substituted —$C_4$-$C_{12}$ cycloalkylene each containing 0, 1, 2, or 3 heteroatoms selected from O, S or N; —$C_4$-$C_{12}$ and cycloalkenylene or substituted —$C_3$-$C_{12}$ cycloalkenylene each containing 0, 1, 2, or 3 heteroatoms selected from O, S or N.

2. The compound of claim 1, wherein:
$R^1$ is hydrogen;
$R^{2a}$ is methyl or —$CHF_2$;
$R^{2b}$ is —OH or halogen;
$R^3$, $R^4$, $R^{5a}$ and $R^{5b}$ are each hydrogen;
$R^6$ is aryl;
$R^7$ is hydrogen;
one of $R^{8a}$ and $R^{8b}$ is hydrogen and the other is normal or branched $C_1$-$C_8$-alkyl;
X is O;
W is optionally substituted $C_4$-$C_{10}$-alkylene, optionally substituted $C_4$-$C_{10}$-alkenylene, or —$(CH_2)_n$—Y—$(CH_2)_m$—, where Y is O, S, NH or NMe and n and m are each independently 2 to 6; and
M is O, NH, —OC(O)NH—, or C(O)NH.

3. The compound of claim 1, represented by Formula II or a pharmaceutically acceptable salt, ester or solvate thereof,

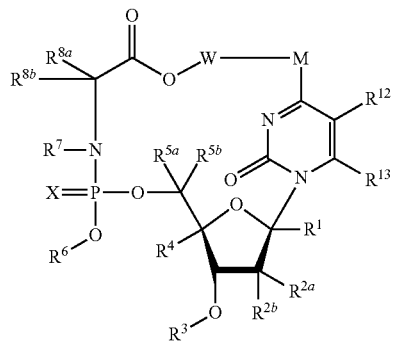

(II)

wherein:
$R^1$ and $R^4$ are each independently selected from the group consisting of:
1) hydrogen;
2) —CN;
3) halogen;
4) —$N_3$;
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R^{2a}$ is selected from the group consisting of:
1) hydrogen;
2) halogen;

3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;

$R^{2b}$ is selected from the group consisting of:
1) hydrogen;
2) halogen;
3) —CN;
4) —$N_3$; and
5) $OR^9$;

$R^3$ and $R^9$ are each independently selected from the group consisting of: hydrogen, hydroxy protecting group, $R^{10}$, —$C(O)R^{10}$, —$C(O)OR^{10}$, and —$C(O)NR^{11a}R^{11b}$; wherein $R^{10}$ at each occurrence is each independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic;

$R^{11a}$ and $R^{11b}$ at each occurrence are each independently selected from the group consisting of: hydrogen and $R^{10}$; or alternatively $R^{11a}$ and $R^{11b}$ taken together with the nitrogen atom to which they are attached form a heterocyclic ring;

$R^{5a}$ and $R^{5b}$ are each independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;
or $R^{5a}$ and $R^{5b}$ together with the carbon atom to which they are attached form a group selected from —$C_3$-$C_8$ cycloalkyl, —$C_3$-$C_8$ cycloalkenyl, and —$C_3$-$C_8$ cycloalkynyl;

$R^6$ is selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;
or $R^7$ and $R^{8a}$ or $R^{8b}$ together form —$(CH_2)_n$— so as to form a cyclic ring which includes the adjoining N and C; wherein n is 2 to 6;

$R^{8a}$ and $R^{8b}$ are each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;
or $R^{8a}$ and $R^{8b}$ are taken together to form —$(CH_2)_m$—, so as to form a spiro ring with the carbon to which they are attached; wherein m is 2 to 5;

$R^{12}$ and $R^{13}$ are each independently selected from a group consisting of: hydrogen, halogen, —CN, $N_3$, —$C(O)NR^{11a}R^{11b}$, —$NO_2$, —$OR^9$, —$SR^9$, —$NR^{11a}R^{11b}$, —$NHC(O)R^{10}$, —$NHC(O)OR^{10}$ and —$NHC(O)NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—; and W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_8$ alkynylene each containing 0, 1, 2, or 3 heteroatoms selected from O, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_3$-$C_{12}$ cycloalkenylene each containing 0, 1, 2, or 3 heteroatoms selected from O, S or N.

4. The compound of claim 1, represented by Formula III, or a pharmaceutically acceptable salt, ester or solvate thereof, (III)

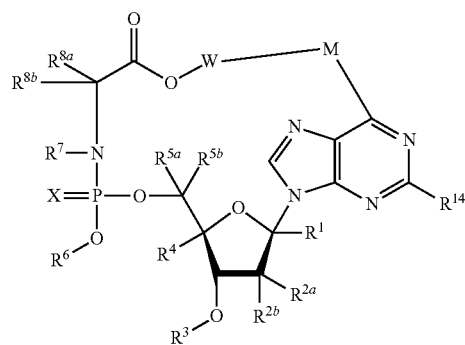

wherein:

$R^1$ and $R^4$ are each independently selected from the group consisting of:
1) hydrogen;
2) —CN;
3) halogen;
4) —$N_3$; and
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R^{2a}$ is selected from the group consisting of:
1) hydrogen;
2) halogen;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;

$R^{2b}$ is selected from the group consisting of:
1) hydrogen;
2) halogen;
3) —CN;
4) —$N_3$; and
5) $OR^9$;

$R^3$ and $R^9$ are each independently selected from the group consisting of: hydrogen, hydroxy protecting group, $R^{10}$, —$C(O)R^{10}$, —$C(O)OR^{10}$, and —$C(O)NR^{11a}R^{11b}$; wherein $R^{10}$ at each occurrence is each independently selected from the group consisting of: substituted or unsubstituted —$C_1$-$C_8$ alkyl, substituted or unsubstituted —C$_2$-C$_8$ alkenyl, substituted or unsubstituted —C$_2$-C$_8$ alkynyl, substituted or unsubstituted aryl, substituted or unsubstituted heteroaryl, and substituted or unsubstituted heterocyclic;

R$^{11a}$ and R$^{11b}$ at each occurrence is each independently selected from the group consisting of: hydrogen and R$^{10}$; or alternatively R$^{11a}$ and R$^{11b}$ taken together with the nitrogen atom to which they are attached form a heterocyclic ring;

R$^{5a}$ and R$^{5b}$ are each independently selected from the group consisting of:
1) hydrogen;
2) substituted or unsubstituted —C$_1$-C$_8$ alkyl;
3) substituted or unsubstituted —C$_2$-C$_8$ alkenyl; and
4) substituted or unsubstituted —C$_2$-C$_8$ alkynyl;
or R$^{5a}$ and R$^{5b}$ are taken together with the carbon atom to which they are attached to form a group selected from —C$_3$-C$_8$ cycloalkyl, —C$_3$-C$_8$ cycloalkenyl, and —C$_3$-C$_8$ cycloalkynyl;

R$^6$ is selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; such as, but not limited to, phenyl or naphthyl; and
5) Substituted or unsubstituted heteroaryl;

X is O or S;

R$^7$ is selected from the group consisting of:
1) hydrogen; and
2) Substituted or unsubstituted —C$_1$-C$_8$ alkyl;
or R$^7$ and R$^{8a}$ or R$^{8b}$ together form —(CH$_2$)$_n$— so as to form a cyclic ring which includes the adjoining N and C; wherein n is 2 to 6;

R$^{8a}$ and R$^{8b}$ are each independently selected from the group consisting of:
1) hydrogen;
2) Substituted or unsubstituted —C$_1$-C$_8$ alkyl;
3) Substituted or unsubstituted —C$_3$-C$_8$ cycloalkyl;
4) Substituted or unsubstituted aryl; and
5) Substituted or unsubstituted heteroaryl;
or R$^{8a}$ and R$^{8b}$ taken together form —(CH$_2$)$_m$—, so as to form a spiro ring with the carbon to which they are attached; wherein m is 2 to 5;

R$^{14}$ is selected from the group consisting of: hydrogen, halogen, —CN, N$_3$, —C(O)NR$^{11a}$R$^{11b}$, —NO$_2$, —OR$^9$, —SR$^9$, —NR$^{11a}$R$^{11b}$, —NHC(O)R$^{10}$, —NHC(O)OR$^{10}$ and —NHC(O)NR$^{11a}$R$^{11b}$, substituted or unsubstituted aryl, substituted or unsubstituted heteroaryl, substituted or unsubstituted heterocyclic, substituted or unsubstituted —C$_1$-C$_8$ alkyl, substituted or unsubstituted —C$_2$-C$_8$ alkenyl, and substituted or unsubstituted —C$_2$-C$_8$ alkynyl;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—; and W is selected from —C$_4$-C$_{12}$ alkylene, —C$_4$-C$_{12}$ alkenylene, or —C$_4$-C$_{12}$ alkynylene each containing 0, 1, 2, or 3 heteroatoms selected from O, S, or N; substituted —C$_4$-C$_{12}$ alkylene, substituted —C$_4$-C$_{12}$ alkenylene, or substituted —C$_4$-C$_8$ alkynylene each containing 0, 1, 2, or 3 heteroatoms selected from O, S or N; —C$_4$-C$_{12}$ cycloalkylene, or substituted —C$_4$-C$_{12}$ cycloalkylene each containing 0, 1, 2, or 3 heteroatoms selected from O, S or N; and —C$_4$-C$_{12}$ cycloalkenylene or substituted —C$_3$-C$_{12}$ cycloalkenylene each containing 0, 1, 2, or 3 heteroatoms selected from O, S or N.

5. The compound of claim 1 represented by Formula IV or a pharmaceutically acceptable salt, ester or solvate thereof,

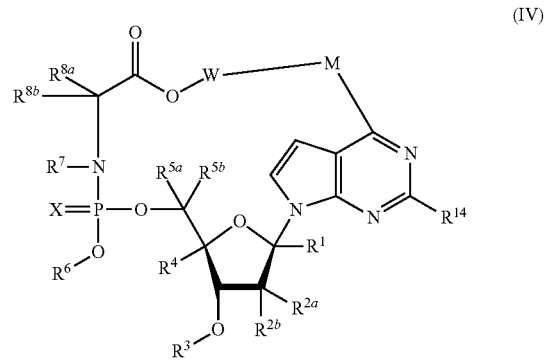

(IV)

wherein:

R$^1$ and R$^4$ are each independently selected from the group consisting of:
1) hydrogen;
2) —CN;
3) halogen;
4) —N$_3$; and
5) Substituted or unsubstituted —C$_1$-C$_8$ alkyl;
6) Substituted or unsubstituted —C$_2$-C$_8$ alkenyl; and
7) Substituted or unsubstituted —C$_2$-C$_8$ alkynyl;

R$^{2a}$ is selected from the group consisting of:
1) hydrogen;
2) halogen;
3) Substituted or unsubstituted —C$_1$-C$_8$ alkyl;
4) Substituted or unsubstituted —C$_2$-C$_8$ alkenyl; and
5) Substituted or unsubstituted —C$_2$-C$_8$ alkynyl;

R$^{2b}$ is selected from the group consisting of:
1) hydrogen;
2) halogen;
3) —CN;
4) —N$_3$; and
5) OR$^9$;

R$^3$ and R$^9$ are each independently selected from the group consisting of: hydrogen, hydroxy protecting group, R$^{10}$, —C(O)R$^{10}$, —C(O)OR$^{10}$, and —C(O)NR$^{11a}$R$^{11b}$; wherein R$^{10}$ at each occurrence is each independently selected from the group consisting of: substituted or unsubstituted —C$_1$-C$_8$ alkyl, substituted or unsubstituted —C$_2$-C$_8$ alkenyl, substituted or unsubstituted —C$_2$-C$_8$ alkynyl, substituted or unsubstituted aryl, substituted or unsubstituted heteroaryl, and substituted or unsubstituted heterocyclic;

R$^{11a}$ and R$^{11b}$ at each occurrence are each independently selected from the group consisting of: hydrogen and R$^{10}$; or alternatively R$^{11a}$ and R$^{11b}$ taken together with the nitrogen atom to which they are attached form a heterocyclic ring;

R$^{5a}$ and R$^{5b}$ are each independently selected from the group consisting of:
1) hydrogen;
2) substituted or unsubstituted —C$_1$-C$_8$ alkyl;

3) substituted or unsubstituted —$C_2$-$C_8$ alkenyl; and
4) substituted or unsubstituted —$C_2$-$C_8$ alkynyl;
or $R^{5a}$ and $R^{5b}$ are taken together with the carbon atom to which they are attached to form a group selected from —$C_3$-$C_8$ cycloalkyl, —$C_3$-$C_8$ cycloalkenyl, and —$C_3$-$C_8$ cycloalkynyl;

$R^6$ is selected from a group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;
or $R^7$ and $R^{8a}$ or $R^{8b}$ together form —$(CH_2)_n$— so as to form a cyclic ring which includes the adjoining N and C; wherein n is 2 to 6;

$R^{8a}$ and $R^{8b}$ are each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;
or $R^{8a}$ and $R^{8b}$ are taken together to form —$(CH_2)_m$—, so as to form a spiro ring with the carbon to which they are attached; wherein m is 2 to 5;

$R^{14}$ is selected from the group consisting of: hydrogen, halogen, —CN, $N_3$, —C(O)$NR^{11a}R^{11b}$, —$NO_2$, —$OR^9$, —$SR^9$, —$NR^{11a}R^{11b}$, —NHC(O)$R^{10}$, —NHC(O)$OR^{10}$ and —NHC(O)$NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—; and W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_8$ alkynylene each containing 0, 1, 2, or 3 heteroatoms selected from O, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_3$-$C_{12}$ cycloalkenylene each containing 0, 1, 2, or 3 heteroatoms selected from O, S or N.

6. The compound of claim 1, represented by Formula V or a pharmaceutically acceptable salt, ester or solvate thereof,

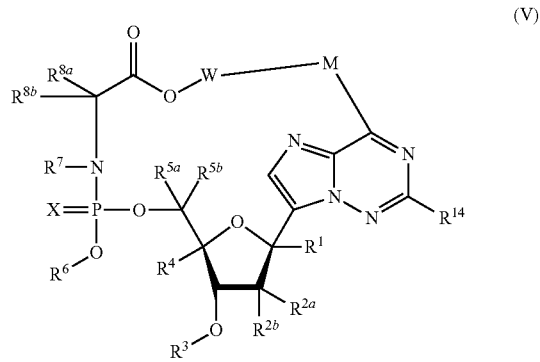

(V)

wherein:
$R^1$ and $R^4$ are each independently selected from the group consisting of:
1) hydrogen;
2) —CN;
3) halogen;
4) —$N_3$; and
5) Substituted or unsubstituted —$C_1$-$C_8$ alkyl;
6) Substituted or unsubstituted —$C_2$-$C_8$ alkenyl; and
7) Substituted or unsubstituted —$C_2$-$C_8$ alkynyl;

$R^{2a}$ is selected from the group consisting of:
1) hydrogen;
2) halogen;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;

$R^{2b}$ is selected from the group consisting of:
1) hydrogen;
2) halogen;
3) —CN;
4) —$N_3$; and
5) $OR^9$;

$R^3$ and $R^9$ are each independently selected from the group consisting of: hydrogen, hydroxy protecting group, $R^{10}$, —C(O)$R^{10}$, —C(O)$OR^{10}$, and —C(O)$NR^{11a}R^{11b}$; wherein
$R^{10}$ at each occurrence is each independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic;
$R^{11a}$; and $R^{11b}$ at each occurrence is each independently selected from the group consisting of: hydrogen and $R^{10}$; or alternatively $R^{11a}$ and $R^{11b}$ taken together with the nitrogen atom to which they are attached form a heterocyclic ring;

$R^{5a}$ and $R^{5b}$ are each independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;
or $R^{5a}$ and $R^{5b}$ are taken together with the carbon atom to which they are attached to form a group selected from —$C_3$-$C_8$ cycloalkyl, —$C_3$-$C_8$ cycloalkenyl, and —$C_3$-$C_8$ cycloalkynyl;

$R^6$ is selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;

or $R^7$ and $R^{8a}$ or $R^{8b}$ together form —$(CH_2)_n$— so as to form a cyclic ring which includes the adjoining N and C; wherein n is 2 to 6;

$R^{8a}$ and $R^{8b}$ are each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;

or $R^{8a}$ and $R^{8b}$ are taken together to form —$(CH_2)_m$—, so as to form a spiro ring with the carbon to which they are attached; wherein m is 2 to 5;

$R^{14}$ is selected from the group consisting of: hydrogen, halogen, —CN, $N_3$, —C(O)$NR^{11a}R^{11b}$, —$NO_2$, —$OR^9$, —$SR^9$, —$NR^{11a}R^{11b}$, —NHC(O)$R^{10}$, —NHC(O)$OR^{10}$ and —NHC(O)$NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)—, —NHC(O)O—, and —NHC(O)NH—; and W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_8$ alkynylene each containing 0, 1, 2, or 3 heteroatoms selected from 0, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_3$-$C_{12}$ cycloalkenylene each containing 0, 1, 2, or 3 heteroatoms selected from O, S or N.

7. The compound of claim 1, represented by Formula VI, or a pharmaceutically acceptable salt, ester or solvate thereof,

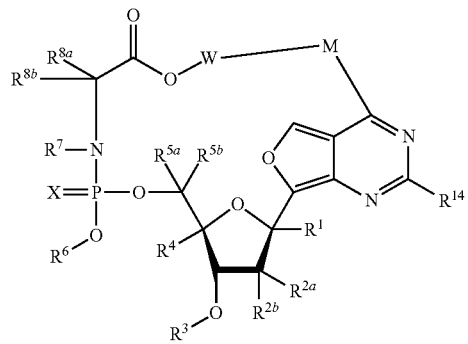

(VI)

wherein:
$R^1$ and $R^4$ are each independently selected from the group consisting of:
1) hydrogen;
2) —CN;
3) halogen;
4) —$N_3$; and
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;

$R^{2a}$ is selected from the group consisting of:
1) hydrogen;
2) halogen;
3) Substituted or unsubstituted —$C_1$-$C_8$ alkyl;
4) Substituted or unsubstituted —$C_2$-$C_8$ alkenyl; and
5) Substituted or unsubstituted —$C_2$-$C_8$ alkynyl;

$R^{2b}$ is selected from the group consisting of:
1) hydrogen;
2) halogen;
3) —CN;
4) —$N_3$; and
5) $OR^9$;

$R^3$ and $R^9$ are each independently selected from the group consisting of: hydrogen, hydroxy protecting group, $R^{10}$, —C(O)$R^{10}$, —C(O)$_{OR}{}^{10}$, and —C(O)$NR^{11a}R^{11b}$; wherein $R^{10}$ at each occurrence is each independently selected from the group consisting of: substituted or unsubstituted —$C_1$-$C_8$ alkyl, substituted or unsubstituted —$C_2$-$C_8$ alkenyl, substituted or unsubstituted —$C_2$-$C_8$ alkynyl, substituted or unsubstituted aryl, substituted or unsubstituted heteroaryl, and substituted or unsubstituted heterocyclic;

$R^{11a}$ and $R^{11b}$ at each occurrence is each independently selected from the group consisting of: hydrogen and $R^{10}$; or alternatively $R^{11a}$ and $R^{11b}$ taken together with the nitrogen atom to which they are attached form a heterocyclic ring;

$R^{5a}$ and $R^{5b}$ are each independently selected from the group consisting of:
1) hydrogen;
2) substituted or unsubstituted —$C_1$-$C_8$ alkyl;
3) substituted or unsubstituted —$C_2$-$C_8$ alkenyl; and
4) substituted or unsubstituted —$C_2$-$C_8$ alkynyl;

or $R^{5a}$ and $R^{5b}$ are taken together with the carbon atom to which they are attached to form a group selected from —$C_3$-$C_8$ cycloalkyl, —$C_3$-$C_8$ cycloalkenyl, and —$C_3$-$C_8$ cycloalkynyl;

$R^6$ is selected from the group consisting of:
1) hydrogen;
2) Substituted or unsubstituted —$C_1$-$C_8$ alkyl;

3) Substituted or unsubstituted —$C_3$-$C_8$ cycloalkyl;
4) Substituted or unsubstituted aryl; such as, but not limited to, phenyl or naphthyl; and
5) Substituted or unsubstituted heteroaryl;

X is O or S;

$R^7$ is selected from the group consisting of:
1) hydrogen; and
2) Substituted or unsubstituted —$C_1$-$C_8$ alkyl;
or $R^7$ and $R^{8a}$ or $R^{8b}$ together form —$(CH_2)_n$— so as to form a cyclic ring which includes the adjoining N and C; wherein n is 2 to 6;

$R^{8a}$ and $R^{8b}$ are each independently selected from the group consisting of:
1) hydrogen;
2) Substituted or unsubstituted —$C_1$-$C_8$ alkyl;
3) Substituted or unsubstituted —$C_3$-$C_8$ cycloalkyl;
4) Substituted or unsubstituted aryl; and
5) Substituted or unsubstituted heteroaryl;
or $R^{8a}$ and $R^{8b}$ together form —$(CH_2)_m$—, so as to form a spiro ring with the carbon to which they are attached; wherein m is 2 to 5;

$R^{14}$ is selected from a group consisting of: hydrogen, halogen, —CN, $N_3$, —C(O)$NR^{11a}R^{11b}$, —$NO_2$, —$OR^9$, —$SR^9$, —$NR^{11a}R^{11b}$, —NHC(O)$R^{10}$, —NHC(O)$OR^{10}$ and —NHC(O)$NR^{11a}R^{11b}$, substituted or unsubstituted aryl, substituted or unsubstituted heteroaryl, substituted or unsubstituted heterocyclic, substituted or unsubstituted —$C_1$-$C_8$ alkyl, substituted or unsubstituted —$C_2$-$C_8$ alkenyl, and substituted or unsubstituted —$C_2$-$C_8$ alkynyl;

M is selected from the group consisting of O, S, —NH—, —O(CO)O—, —O(CO)—, —O(CO)S—, —O(CO)NH—, —S(CO)—, —SC(O)O—, —S(CO)S—, —SC(O)NH—, —NHC(O)—, —NHC(O)S—, —NHC(O)O—, —NHC(O)O—, and —NHC(O)NH—; and W is selected from —$C_4$-$C_{12}$ alkylene, —$C_4$-$C_{12}$ alkenylene, or —$C_4$-$C_{12}$ alkynylene each containing 0, 1, 2, or 3 heteroatoms selected from O, S, or N; substituted —$C_4$-$C_{12}$ alkylene, substituted —$C_4$-$C_{12}$ alkenylene, or substituted —$C_4$-$C_2$ alkynylene each containing 0, 1, 2, or 3 heteroatoms selected from O, S or N; —$C_4$-$C_{12}$ cycloalkylene, or substituted —$C_4$-$C_{12}$ cycloalkylene each containing 0, 1, 2, or 3 heteroatoms selected from O, S or N; and —$C_4$-$C_{12}$ cycloalkenylene or substituted —$C_4$-$C_{12}$ cycloalkenylene each containing 0, 1, 2, or 3 heteroatoms selected from O, S or N.

8. The compound of claim 1, which is selected from (a) compounds of Formula VII, wherein, $R^{2a}$, $R^{2b}$, $R^6$, $R^7$, $R^{8a}$, $R^{8b}$ and —W-M- are delineated for each compound Table 1,

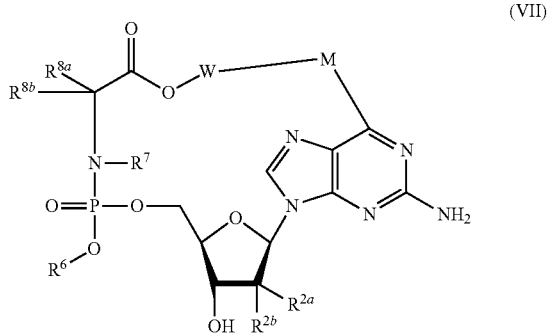

(VII)

or a pharmaceutically acceptable salt, ester or solvate thereof,

TABLE 1

| Example# | $R^{2a}$ | $R^{2b}$ | $R^6$ | (center structure) | —W—M— |
|---|---|---|---|---|---|
| 1 | Me | OH | phenyl | NH-CH(Me)-C(O) | —$(CH_2)_4$—O— |
| 2 | Me | OH | phenyl | NH-CH(Me)-C(O) | —$(CH_2)_5$—O— |
| 3 | Me | OH | phenyl | NH-CH(Me)-C(O) | —$(CH_2)_6$—O— |
| 4 | Me | OH | phenyl | NH-CH(Me)-C(O) | —$(CH_2)_7$—O— |

TABLE 1-continued

| Example# | R²ᵃ | R²ᵇ | R⁶ | [R⁷R⁸ᵇR⁸ᵃ group] | —W—M— |
|---|---|---|---|---|---|
| 5 | Me | OH | phenyl | NH-CH(Me)-C(O) | —(CH₂)₈—O— |
| 6 | Me | OH | phenyl | NH-CH(Me)-C(O) | gem-dimethyl alkyl-O- |
| 7 | Me | OH | phenyl | NH-CH(Me)-C(O) | CF₂-containing alkyl-O- |
| 8 | Me | OH | phenyl | NH-CH(Me)-C(O) | —(CH₂)₃—O—(CH₂)₅—O— |
| 9 | Me | OH | phenyl | NH-CH(Me)-C(O) | alkenyl-O- |
| 10 | Me | OH | phenyl | NH-CH(Me)-C(O) | gem-dimethyl alkenyl-O- |
| 11 | Me | OH | phenyl | NH-CH(Me)-C(O) | cyclopropyl-containing alkyl-O- |
| 12 | Me | OH | phenyl | NH-CH(Me)-C(O) | —(CH₂)₅—NH— |
| 13 | Me | OH | phenyl | NH-CH(Me)-C(O) | —(CH₂)₆—NH— |

TABLE 1-continued

| Example# | R$^{2a}$ | R$^{2b}$ | R$^6$ | | —W—M— |
|---|---|---|---|---|---|
| 14 | Me | OH | phenyl | Ala | —(CH$_2$)$_7$—NH— |
| 15 | Me | OH | phenyl | Ala | —(CH$_2$)$_5$—C(O)NH— |
| 16 | Me | OH | phenyl | Ala | —(CH$_2$)$_6$—C(O)NH— |
| 17 | Me | OH | phenyl | Ala | —(CH$_2$)$_7$—C(O)NH— |
| 18 | Me | OH | phenyl | Ala | —(CH$_2$)$_3$—N(CH$_3$)—(CH$_2$)$_4$—O— |
| 19 | Me | OH | phenyl | Ala | —(CH$_2$)$_3$—S—(CH$_2$)$_4$—O— |
| 20 | Me | OH | phenyl | Ala | —(CH$_2$)$_6$—OC(O)NH— |
| 21 | Me | OH | 1-naphthyl | Ala | —(CH$_2$)$_4$—O— |
| 22 | Me | OH | 1-naphthyl | Ala | —(CH$_2$)$_5$—O— |

TABLE 1-continued
| Example# | R²ᵃ | R²ᵇ | R⁶ | 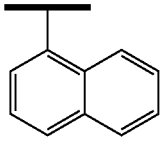 (R⁷, R⁸ᵃ, R⁸ᵇ group) | —W—M— |
|---|---|---|---|---|---|
| 23 | Me | OH | 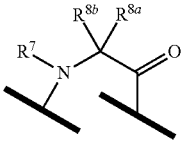 | 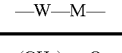 | —(CH₂)₆—O— |
| 24 | Me | OH | 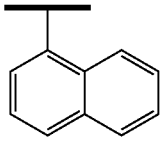 | 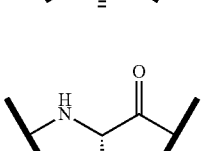 | —(CH₂)₇—O— |
| 25 | Me | OH | 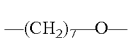 | 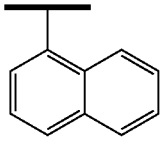 | —(CH₂)₈—O— |
| 26 | Me | OH | 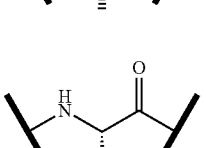 | 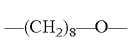 | 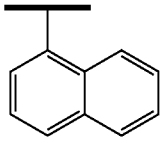 |
| 27 | Me | OH | 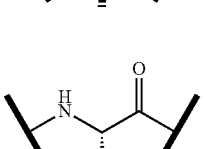 | 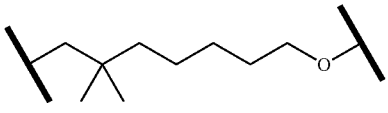 | 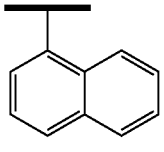 |
| 28 | Me | OH | 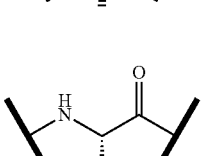 | 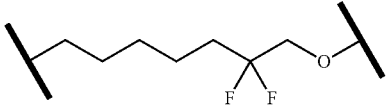 | —(CH₂)₃—O—(CH₂)₅—O— |
| 29 | Me | OH | 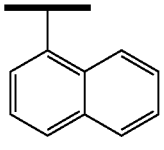 | 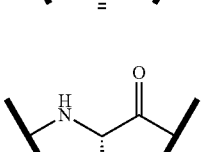 | 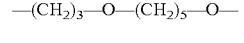 |
| 30 | Me | OH | 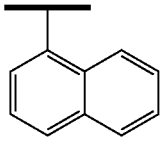 | 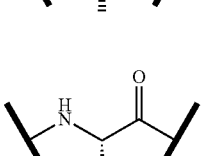 | 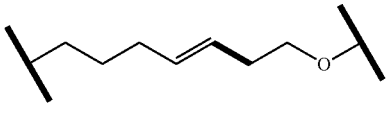 |
| 31 | Me | OH | 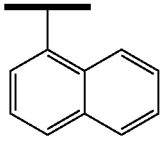 | 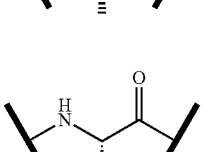 | 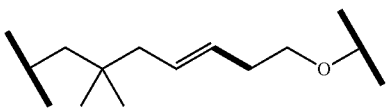 |

TABLE 1-continued
| Example# | $R^{2a}$ | $R^{2b}$ | $R^6$ | | —W—M— |
|---|---|---|---|---|---|
| 32 | Me | OH | 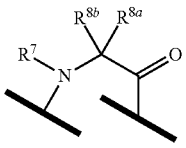 | 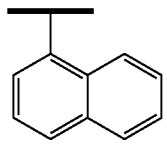 | —(CH$_2$)$_5$—NH— |
| 33 | Me | OH | 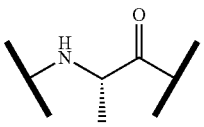 | 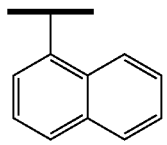 | —(CH$_2$)$_6$—NH— |
| 34 | Me | OH | 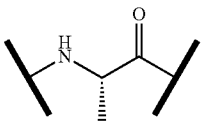 | 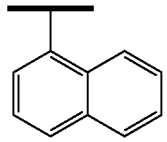 | —(CH$_2$)$_7$—NH— |
| 35 | Me | OH | 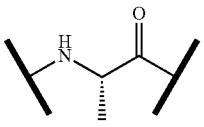 | 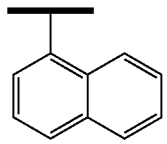 | —(CH$_2$)$_5$—C(O)NH— |
| 36 | Me | OH | 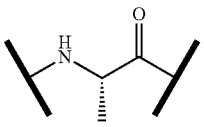 | 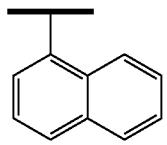 | —(CH$_2$)$_6$—C(O)NH— |
| 37 | Me | OH | 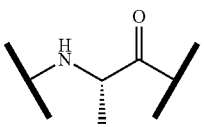 | 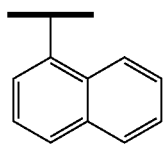 | —(CH$_2$)$_7$—C(O)NH— |
| 38 | Me | OH | 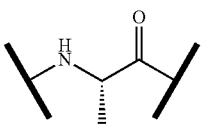 | 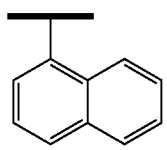 | 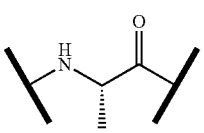 |
| 39 | Me | OH | 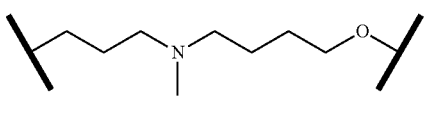 | 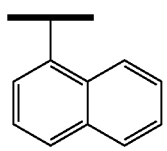 | 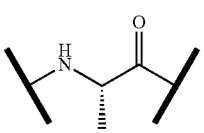 |
| 40 | Me | OH | 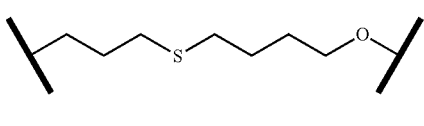 | 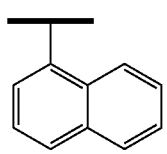 | —(CH$_2$)$_6$—OC(O)NH— |

TABLE 1-continued

| Example# | $R^{2a}$ | $R^{2b}$ | $R^6$ | $R^7$,$R^{8a}$,$R^{8b}$ group | —W—M— |
|---|---|---|---|---|---|
| 41 | Me | F | phenyl | NH-CH(Me)-C(O) | —(CH$_2$)$_4$—O— |
| 42 | Me | F | phenyl | NH-CH(Me)-C(O) | —(CH$_2$)$_5$—O— |
| 43 | Me | F | phenyl | NH-CH(Me)-C(O) | —(CH$_2$)$_6$—O— |
| 44 | Me | F | phenyl | NH-CH(Me)-C(O) | —(CH$_2$)$_7$—O— |
| 45 | Me | F | phenyl | NH-CH(Me)-C(O) | —(CH$_2$)$_8$—O— |
| 46 | Me | F | phenyl | NH-CH(Me)-C(O) | —C(Me)$_2$(CH$_2$)$_4$CH$_2$—O— |
| 47 | Me | F | phenyl | NH-CH(Me)-C(O) | —(CH$_2$)$_5$CF$_2$CH$_2$—O— |
| 48 | Me | F | phenyl | NH-CH(Me)-C(O) | —(CH$_2$)$_3$—O—(CH$_2$)$_5$—O— |
| 49 | Me | F | phenyl | NH-CH(Me)-C(O) | —(CH$_2$)$_3$CH=CHCH$_2$—O— |

TABLE 1-continued
| Example# | R2a | R2b | R6 | (R7, R8a, R8b group) | —W—M— |
|---|---|---|---|---|---|
| 50 | Me | F | 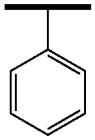 | 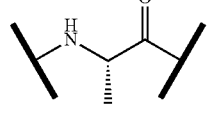 | 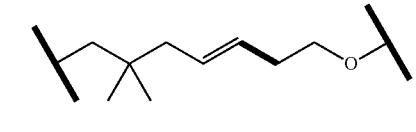 |
| 51 | Me | F | 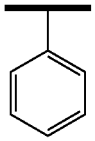 | 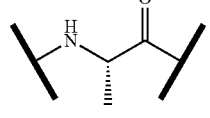 | 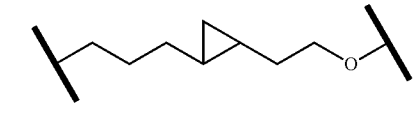 |
| 52 | Me | F | 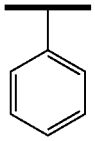 | 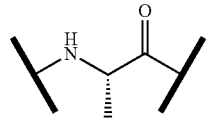 | —(CH$_2$)$_5$—NH— |
| 53 | Me | F | 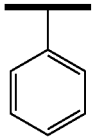 | 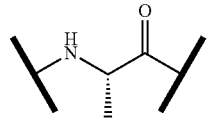 | —(CH$_2$)$_6$—NH— |
| 54 | Me | F | 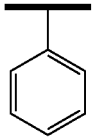 | 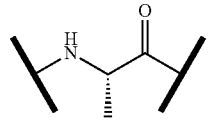 | —(CH$_2$)$_7$—NH— |
| 55 | Me | F | 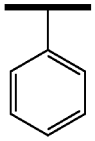 | 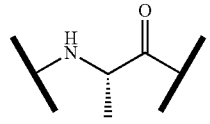 | —(CH$_2$)$_5$—C(O)NH— |
| 56 | Me | F | 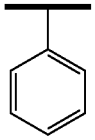 | 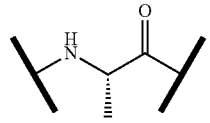 | —(CH$_2$)$_6$—C(O)NH— |
| 57 | Me | F | 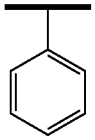 | 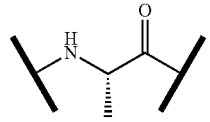 | —(CH$_2$)$_7$—C(O)NH— |
| 58 | Me | F | 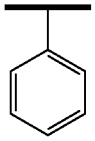 | 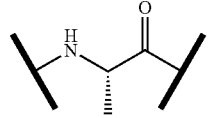 | 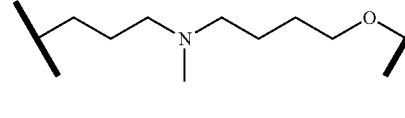 |

TABLE 1-continued
| Example# | R²ᵃ | R²ᵇ | R⁶ | 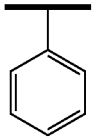 | —W—M— |
|---|---|---|---|---|---|
| 59 | Me | F | 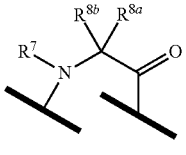 |  | 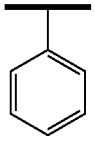 |
| 60 | Me | F | 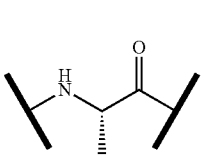 | 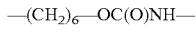 | —(CH₂)₆—OC(O)NH— |
| 61 | Me | F | 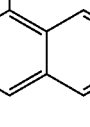 | 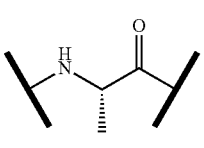 | —(CH₂)₄—O— |
| 62 | Me | F | 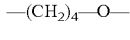 | 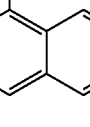 | —(CH₂)₅—O— |
| 63 | Me | F | 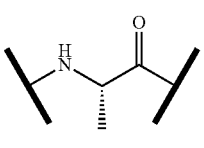 | 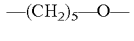 | —(CH₂)₆—O— |
| 64 | Me | F | 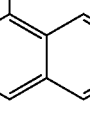 | 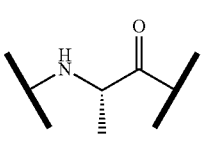 | —(CH₂)₇—O— |
| 65 | Me | F | 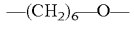 | 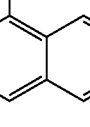 | —(CH₂)₈—O— |
| 66 | Me | F | 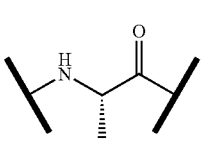 | 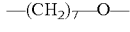 | 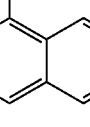 |
| 67 | Me | F | 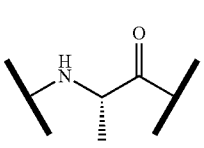 | 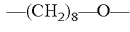 | 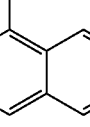 |

TABLE 1-continued

| Example# | R²ᵃ | R²ᵇ | R⁶ | [R⁷R⁸ᵇR⁸ᵃN-C(=O) group] | —W—M— |
|---|---|---|---|---|---|
| 68 | Me | F | 1-naphthyl | N-H, α-Me (S) alanyl | —(CH$_2$)$_3$—O—(CH$_2$)$_5$—O— |
| 69 | Me | F | 1-naphthyl | N-H, α-Me (S) alanyl | —CH$_2$CH$_2$CH=CHCH$_2$O— |
| 70 | Me | F | 1-naphthyl | N-H, α-Me (S) alanyl | —C(CH$_3$)$_2$CH$_2$CH=CHCH$_2$O— |
| 71 | Me | F | 1-naphthyl | N-H, α-Me (S) alanyl | —(CH$_2$)$_3$-cyclopropyl-CH$_2$CH$_2$O— |
| 72 | Me | F | 1-naphthyl | N-H, α-Me (S) alanyl | —(CH$_2$)$_5$—NH— |
| 73 | Me | F | 1-naphthyl | N-H, α-Me (S) alanyl | —(CH$_2$)$_6$—NH— |
| 74 | Me | F | 1-naphthyl | N-H, α-Me (S) alanyl | —(CH$_2$)$_7$—NH— |
| 75 | Me | F | 1-naphthyl | N-H, α-Me (S) alanyl | —(CH$_2$)$_5$—C(O)NH— |
| 76 | Me | F | 1-naphthyl | N-H, α-Me (S) alanyl | —(CH$_2$)$_6$—C(O)NH— |

TABLE 1-continued
| Example# | $R^{2a}$ | $R^{2b}$ | $R^6$ | 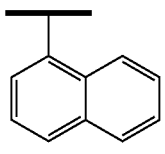 | —W—M— |
|---|---|---|---|---|---|
| 77 | Me | F | 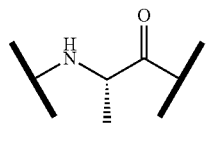 | 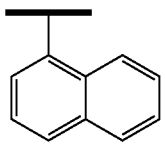 | —(CH$_2$)$_7$—C(O)NH— |
| 78 | Me | F | 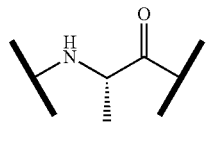 | 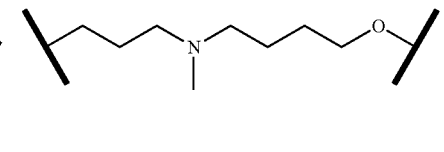 | 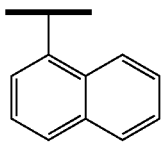 |
| 79 | Me | F | 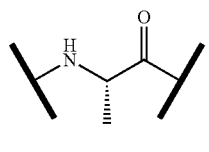 | 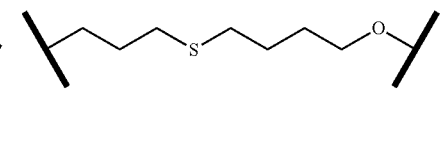 | 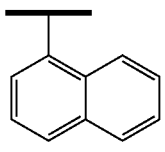 |
| 80 | Me | F | 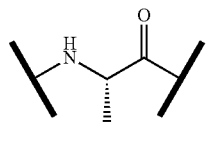 | 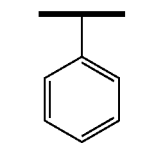 | —(CH$_2$)$_6$—OC(O)NH— |
| 81 | CHF$_2$ | OH | 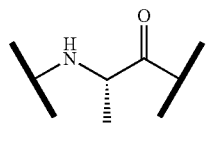 | 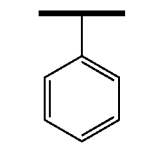 | —(CH$_2$)$_4$—O— |
| 82 | CHF$_2$ | OH | 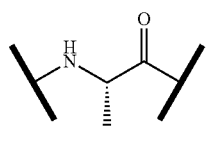 | 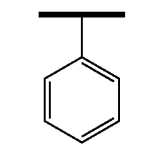 | —(CH$_2$)$_5$—O— |
| 83 | CHF$_2$ | OH | 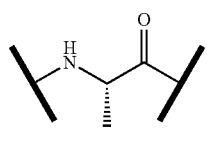 | 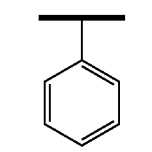 | —(CH$_2$)$_6$—O— |
| 84 | CHF$_2$ | OH | 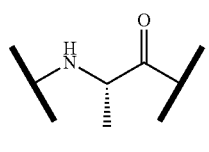 | 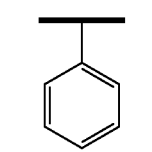 | —(CH$_2$)$_7$—O— |
| 85 | CHF$_2$ | OH | 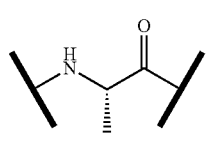 |  | —(CH$_2$)$_8$—O— |

TABLE 1-continued

| Example# | R²ᵃ | R²ᵇ | R⁶ | (R⁷,R⁸ᵃ,R⁸ᵇ amino acid) | —W—M— |
|---|---|---|---|---|---|
| 86 | CHF₂ | OH | phenyl | Ala | (CH₃)₂C-(CH₂)₄-O |
| 87 | CHF₂ | OH | phenyl | Ala | -(CH₂)₅-CF₂-CH₂-O- |
| 88 | CHF₂ | OH | phenyl | Ala | —(CH₂)₃—O—(CH₂)₅—O— |
| 89 | CHF₂ | OH | phenyl | Ala | -(CH₂)₄-CH=CH-CH₂-O- |
| 90 | CHF₂ | OH | phenyl | Ala | (CH₃)₂C-CH₂-CH=CH-CH₂-O- |
| 91 | CHF₂ | OH | phenyl | Ala | -(CH₂)₃-cyclopropyl-CH₂-O- |
| 92 | CHF₂ | OH | phenyl | Ala | —(CH₂)₅—NH— |
| 93 | CHF₂ | OH | phenyl | Ala | —(CH₂)₆—NH— |
| 94 | CHF₂ | OH | phenyl | Ala | —(CH₂)₇—NH— |

TABLE 1-continued

| Example# | $R^{2a}$ | $R^{2b}$ | $R^6$ | $R^7,N,R^{8b},R^{8a}$ group | —W—M— |
|---|---|---|---|---|---|
| 95 | $CHF_2$ | OH | phenyl | NH-CH(CH3)-C(O) | —$(CH_2)_5$—C(O)NH— |
| 96 | $CHF_2$ | OH | phenyl | NH-CH(CH3)-C(O) | —$(CH_2)_6$—C(O)NH— |
| 97 | $CHF_2$ | OH | phenyl | NH-CH(CH3)-C(O) | —$(CH_2)_7$—C(O)NH— |
| 98 | $CHF_2$ | OH | phenyl | NH-CH(CH3)-C(O) | —(CH2)3—N(CH3)—(CH2)4—O— |
| 99 | $CHF_2$ | OH | phenyl | NH-CH(CH3)-C(O) | —(CH2)3—S—(CH2)4—O— |
| 100 | $CHF_2$ | OH | phenyl | NH-CH(CH3)-C(O) | —$(CH_2)_6$—OC(O)NH— |
| 101 | $CHF_2$ | OH | 1-naphthyl | NH-CH(CH3)-C(O) | —$(CH_2)_4$—O— |
| 102 | $CHF_2$ | OH | 1-naphthyl | NH-CH(CH3)-C(O) | —$(CH_2)_5$—O— |
| 103 | $CHF_2$ | OH | 1-naphthyl | NH-CH(CH3)-C(O) | —$(CH_2)_6$—O— |

TABLE 1-continued

| Example# | R²ᵃ | R²ᵇ | R⁶ | (R⁷,R⁸ᵃ,R⁸ᵇ group) | —W—M— |
|---|---|---|---|---|---|
| 104 | CHF₂ | OH | 1-naphthyl | N-H, α-methyl (Ala) | —(CH₂)₇—O— |
| 105 | CHF₂ | OH | 1-naphthyl | N-H, α-methyl (Ala) | —(CH₂)₈—O— |
| 106 | CHF₂ | OH | 1-naphthyl | N-H, α-methyl (Ala) | gem-dimethyl alkyl-O— |
| 107 | CHF₂ | OH | 1-naphthyl | N-H, α-methyl (Ala) | gem-difluoro alkyl-O— |
| 108 | CHF₂ | OH | 1-naphthyl | N-H, α-methyl (Ala) | —(CH₂)₃—O—(CH₂)₅—O— |
| 109 | CHF₂ | OH | 1-naphthyl | N-H, α-methyl (Ala) | alkenyl-O— |
| 110 | CHF₂ | OH | 1-naphthyl | N-H, α-methyl (Ala) | gem-dimethyl alkenyl-O— |
| 111 | CHF₂ | OH | 1-naphthyl | N-H, α-methyl (Ala) | cyclopropyl-containing alkyl-O— |
| 112 | CHF₂ | OH | 1-naphthyl | N-H, α-methyl (Ala) | —(CH₂)₅—NH— |

TABLE 1-continued
| Example# | $R^{2a}$ | $R^{2b}$ | $R^6$ | 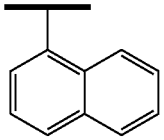 | —W—M— |
|---|---|---|---|---|---|
| 113 | $CHF_2$ | OH | 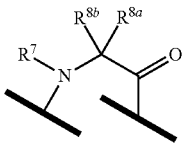 | 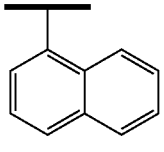 | —$(CH_2)_6$—NH— |
| 114 | $CHF_2$ | OH | 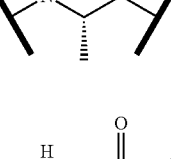 | 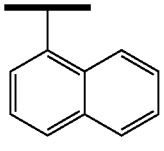 | —$(CH_2)_7$—NH— |
| 115 | $CHF_2$ | OH | 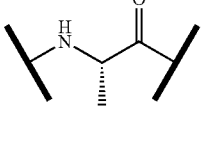 | 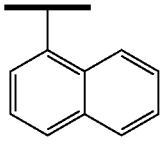 | —$(CH_2)_5$—C(O)NH— |
| 116 | $CHF_2$ | OH | 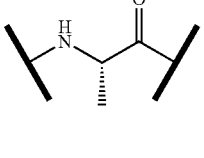 | 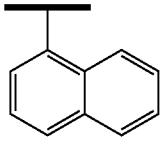 | —$(CH_2)_6$—C(O)NH— |
| 117 | $CHF_2$ | OH | 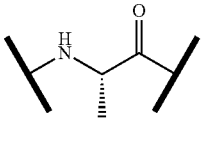 | 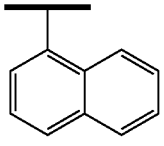 | —$(CH_2)_7$—C(O)NH— |
| 118 | $CHF_2$ | OH | 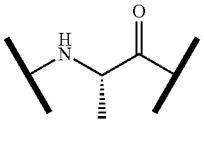 | 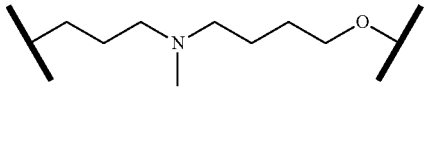 | 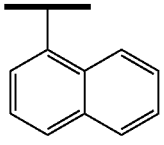 |
| 119 | $CHF_2$ | OH | 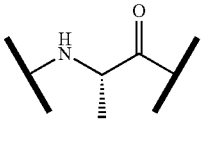 | 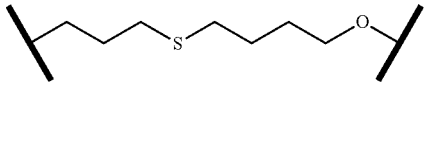 | 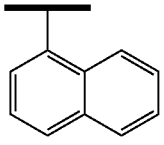 |
| 120 | $CHF_2$ | OH | 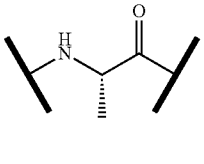 | 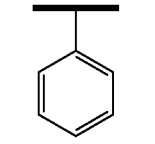 | —$(CH_2)_6$—OC(O)NH— |
| 121 | $CHF_2$ | F | 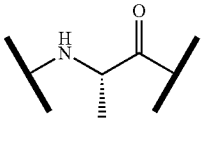 | | —$(CH_2)_4$—O— |

TABLE 1-continued
| Example# | $R^{2a}$ | $R^{2b}$ | $R^6$ | | —W—M— |
|---|---|---|---|---|---|
| 122 | $CHF_2$ | F | 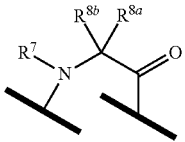 | 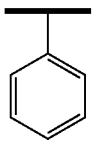 | —$(CH_2)_5$—O— |
| 123 | $CHF_2$ | F | 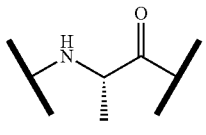 | 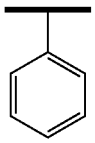 | —$(CH_2)_6$—O— |
| 124 | $CHF_2$ | F | 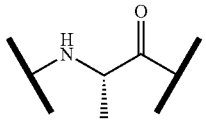 | 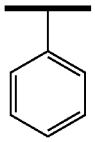 | —$(CH_2)_7$—O— |
| 125 | $CHF_2$ | F | 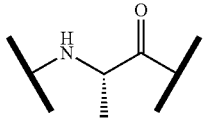 | 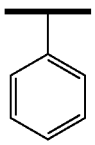 | —$(CH_2)_8$—O— |
| 126 | $CHF_2$ | F | 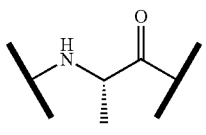 | 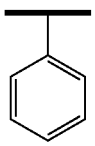 | 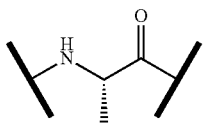 |
| 127 | $CHF_2$ | F | 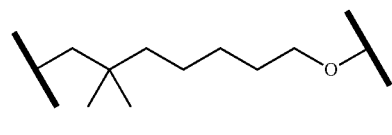 | 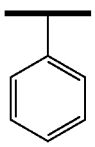 | 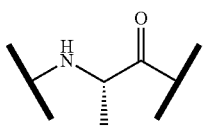 |
| 128 | $CHF_2$ | F | 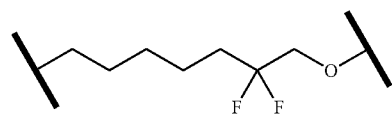 | 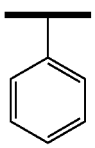 | —$(CH_2)_3$—O—$(CH_2)_5$—O— |
| 129 | $CHF_2$ | F | 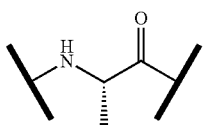 | 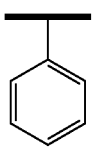 | 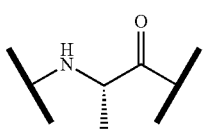 |
| 130 | $CHF_2$ | F | 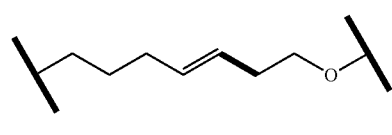 | 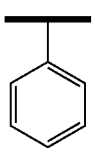 | 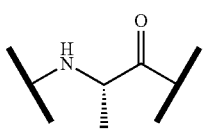 |

TABLE 1-continued

| Example# | $R^{2a}$ | $R^{2b}$ | $R^6$ | (R7,R8a,R8b,N group) | —W—M— |
|---|---|---|---|---|---|
| 131 | $CHF_2$ | F | phenyl | NH-CH(CH3)-C(O) | cyclopropyl-CH2CH2-O linker |
| 132 | $CHF_2$ | F | phenyl | NH-CH(CH3)-C(O) | $-(CH_2)_5-NH-$ |
| 133 | $CHF_2$ | F | phenyl | NH-CH(CH3)-C(O) | $-(CH_2)_6-NH-$ |
| 134 | $CHF_2$ | F | phenyl | NH-CH(CH3)-C(O) | $-(CH_2)_7-NH-$ |
| 135 | $CHF_2$ | F | phenyl | NH-CH(CH3)-C(O) | $-(CH_2)_5-C(O)NH-$ |
| 136 | $CHF_2$ | F | phenyl | NH-CH(CH3)-C(O) | $-(CH_2)_6-C(O)NH-$ |
| 137 | $CHF_2$ | F | phenyl | NH-CH(CH3)-C(O) | $-(CH_2)_7-C(O)NH-$ |
| 138 | $CHF_2$ | F | phenyl | NH-CH(CH3)-C(O) | -(CH2)3-N(CH3)-(CH2)3-O- |
| 139 | $CHF_2$ | F | phenyl | NH-CH(CH3)-C(O) | -(CH2)3-S-(CH2)3-O- |

TABLE 1-continued

| Example# | $R^{2a}$ | $R^{2b}$ | $R^6$ | (R7R8bR8a N-C-C(O) group) | —W—M— |
|---|---|---|---|---|---|
| 140 | $CHF_2$ | F | phenyl-CH | NH-CH(CH3)-C(O) (S) | $-(CH_2)_6-OC(O)NH-$ |
| 141 | $CHF_2$ | F | 1-naphthyl-CH | NH-CH(CH3)-C(O) (S) | $-(CH_2)_4-O-$ |
| 142 | $CHF_2$ | F | 1-naphthyl-CH | NH-CH(CH3)-C(O) (S) | $-(CH_2)_5-O-$ |
| 143 | $CHF_2$ | F | 1-naphthyl-CH | NH-CH(CH3)-C(O) (S) | $-(CH_2)_6-O-$ |
| 144 | $CHF_2$ | F | 1-naphthyl-CH | NH-CH(CH3)-C(O) (S) | $-(CH_2)_7-O-$ |
| 145 | $CHF_2$ | F | 1-naphthyl-CH | NH-CH(CH3)-C(O) (S) | $-(CH_2)_8-O-$ |
| 146 | $CHF_2$ | F | 1-naphthyl-CH | NH-CH(CH3)-C(O) (S) | $-C(CH_3)_2-(CH_2)_5-O-$ |
| 147 | $CHF_2$ | F | 1-naphthyl-CH | NH-CH(CH3)-C(O) (S) | $-(CH_2)_6-CF_2-CH_2-O-$ |
| 148 | $CHF_2$ | F | 1-naphthyl-CH | NH-CH(CH3)-C(O) (S) | $-(CH_2)_3-O-(CH_2)_5-O-$ |

TABLE 1-continued

| Example# | R²ᵃ | R²ᵇ | R⁶ | (R⁷,R⁸ᵃ,R⁸ᵇ amino acid) | —W—M— |
|---|---|---|---|---|---|
| 149 | CHF₂ | F | 1-naphthyl | L-Ala | —CH₂CH₂CH₂—CH=CH—CH₂—O— |
| 150 | CHF₂ | F | 1-naphthyl | L-Ala | —C(CH₃)₂CH₂—CH=CH—CH₂—O— |
| 151 | CHF₂ | F | 1-naphthyl | L-Ala | —CH₂CH₂CH₂—cyclopropyl—CH₂CH₂—O— |
| 152 | CHF₂ | F | 1-naphthyl | L-Ala | —(CH₂)₅—NH— |
| 153 | CHF₂ | F | 1-naphthyl | L-Ala | —(CH₂)₆—NH— |
| 154 | CHF₂ | F | 1-naphthyl | L-Ala | —(CH₂)₇—NH— |
| 155 | CHF₂ | F | 1-naphthyl | L-Ala | —(CH₂)₅—C(O)NH— |
| 156 | CHF₂ | F | 1-naphthyl | L-Ala | —(CH₂)₆—C(O)NH— |
| 157 | CHF₂ | F | 1-naphthyl | L-Ala | —(CH₂)₇—C(O)NH— |

TABLE 1-continued
| Example# | $R^{2a}$ | $R^{2b}$ | $R^6$ | 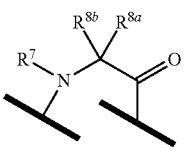 | —W—M— |
|---|---|---|---|---|---|
| 158 | $CHF_2$ | F | 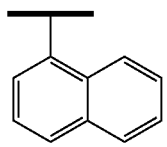 | 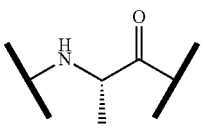 | 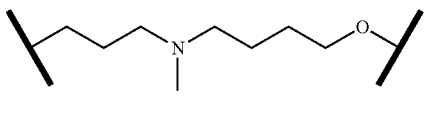 |
| 159 | $CHF_2$ | F | 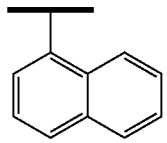 | 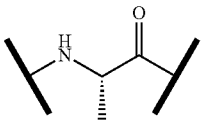 | 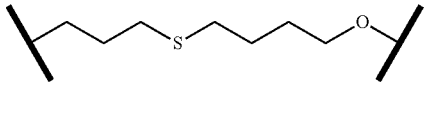 |
| 160 | $CHF_2$ | F | 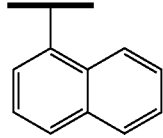 | 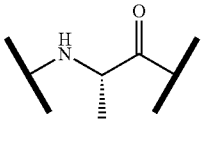 | —(CH$_2$)$_6$—OC(O)NH— |
| 161 | Me | OH | 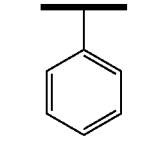 | 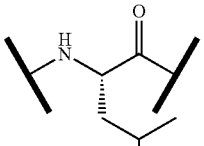 | —(CH$_2$)$_4$—O— |
| 162 | Me | OH | 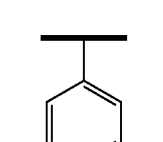 | 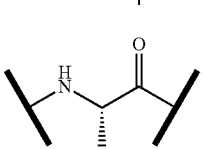 | —(CH$_2$)$_5$—O— |
| 163 | Me | OH | 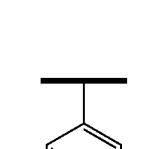 | 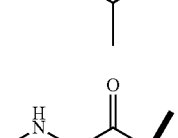 | —(CH$_2$)$_6$—O— |
| 164 | Me | OH | 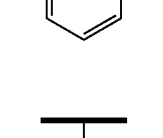 | 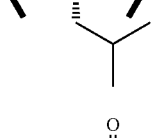 | —(CH$_2$)$_7$—O— |
| 165 | Me | OH | 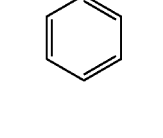 | 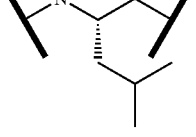 | —(CH$_2$)$_8$—O— |

TABLE 1-continued
| Example# | R2a | R2b | R6 | | —W—M— |
|---|---|---|---|---|---|
| 166 | Me | OH | 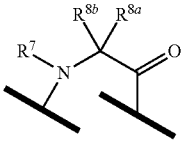 | 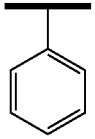 | 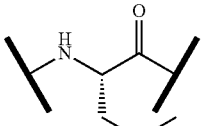 |
| 167 | Me | OH | 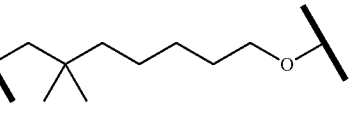 | 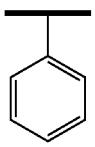 | 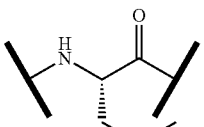 |
| 168 | Me | OH | 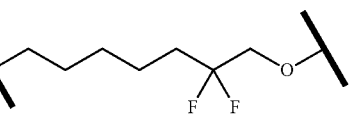 | 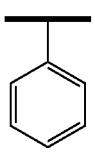 | —(CH$_2$)$_3$—O—(CH$_2$)$_5$—O— |
| 169 | Me | OH | 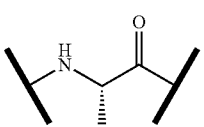 | 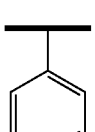 | 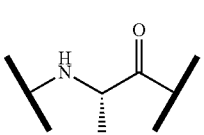 |
| 170 | Me | OH | 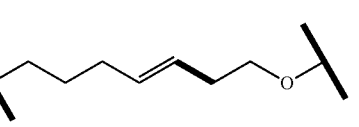 | 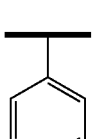 | 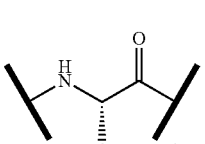 |
| 171 | Me | OH | 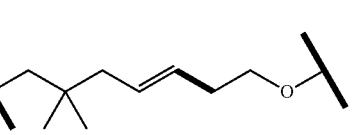 |  | 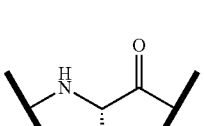 |
| 172 | Me | OH | 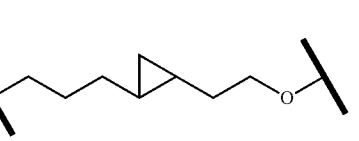 | 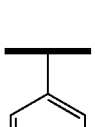 | —(CH$_2$)$_5$—NH— |

TABLE 1-continued

| Example# | $R^{2a}$ | $R^{2b}$ | $R^6$ | | —W—M— |
|---|---|---|---|---|---|
| 173 | Me | OH | phenyl | Leu | —(CH$_2$)$_6$—NH— |
| 174 | Me | OH | phenyl | Leu | —(CH$_2$)$_7$—NH— |
| 175 | Me | OH | phenyl | Leu | —(CH$_2$)$_5$—C(O)NH— |
| 176 | Me | OH | phenyl | Leu | —(CH$_2$)$_6$—C(O)NH— |
| 177 | Me | OH | phenyl | Leu | —(CH$_2$)$_7$—C(O)NH— |
| 178 | Me | OH | phenyl | Leu | —(CH$_2$)$_3$N(CH$_3$)(CH$_2$)$_4$O— |
| 179 | Me | OH | phenyl | Leu | —(CH$_2$)$_3$S(CH$_2$)$_4$O— |

TABLE 1-continued
| Example# | $R^{2a}$ | $R^{2b}$ | $R^6$ | | —W—M— |
|---|---|---|---|---|---|
| 180 | Me | OH | 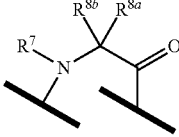 | 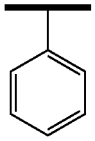 | —(CH$_2$)$_6$—OC(O)NH— |
| 181 | Me | F | 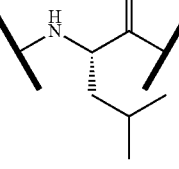 | 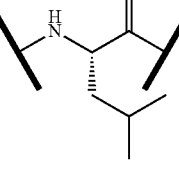 | —(CH$_2$)$_4$—O— |
| 182 | Me | F | 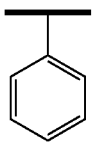 | 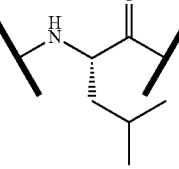 | —(CH$_2$)$_5$—O— |
| 183 | Me | F | 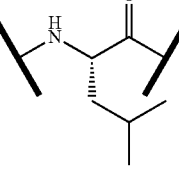 | 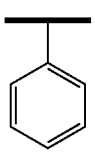 | —(CH$_2$)$_6$—O— |
| 184 | Me | F | 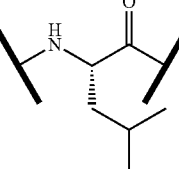 | 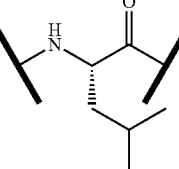 | —(CH$_2$)$_7$—O— |
| 185 | Me | F | 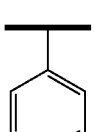 | 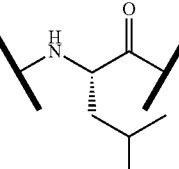 | —(CH$_2$)$_8$—O— |
| 186 | Me | F | 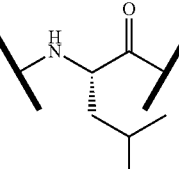 | 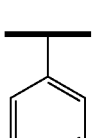 | 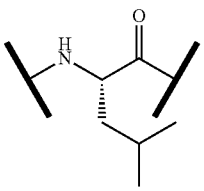 |

TABLE 1-continued
| Example# | R2a | R2b | R6 | | —W—M— |
|---|---|---|---|---|---|
| 187 | Me | F | 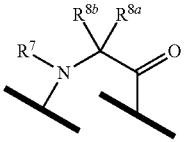 |  | 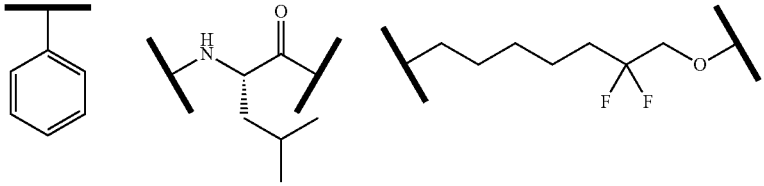 |
| 188 | Me | F | 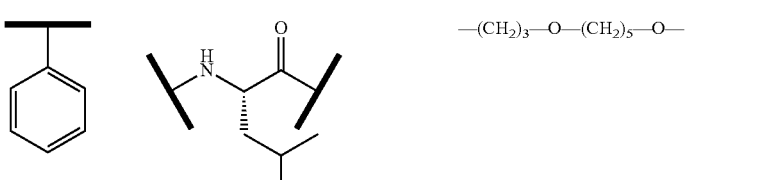 | 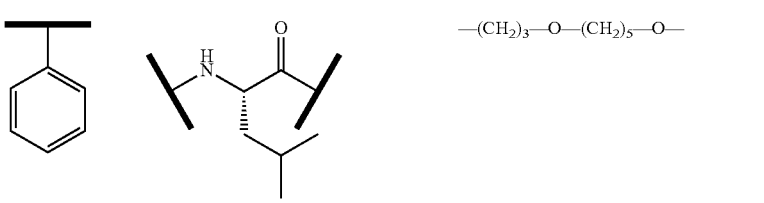 | —(CH$_2$)$_3$—O—(CH$_2$)$_5$—O— |
| 189 | Me | F | 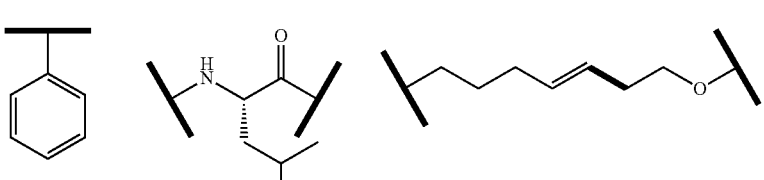 | 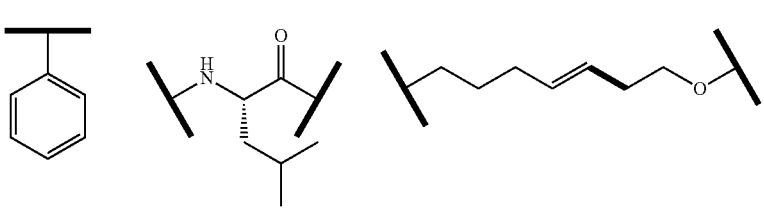 | 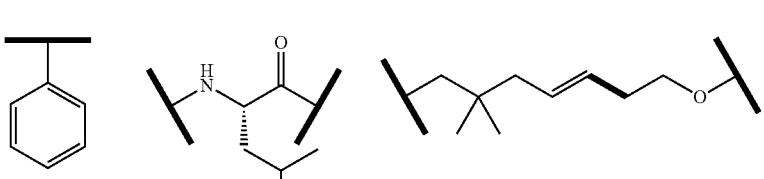 |
| 190 | Me | F | 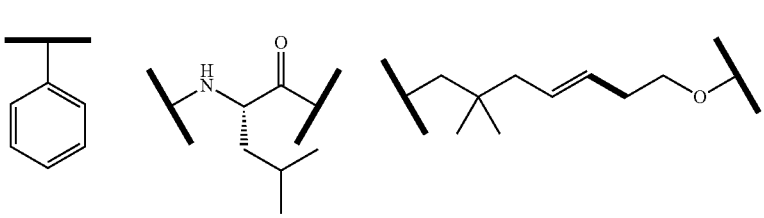 | 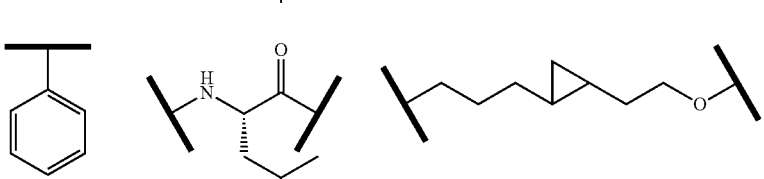 | 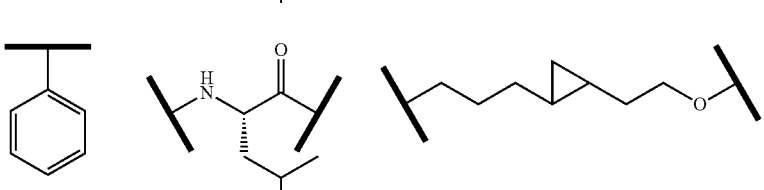 |
| 191 | Me | F | 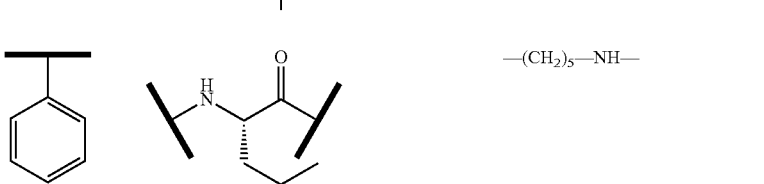 | 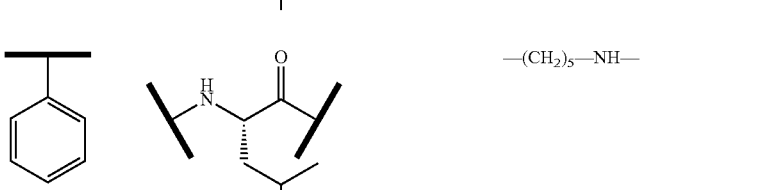 |  |
| 192 | Me | F | | 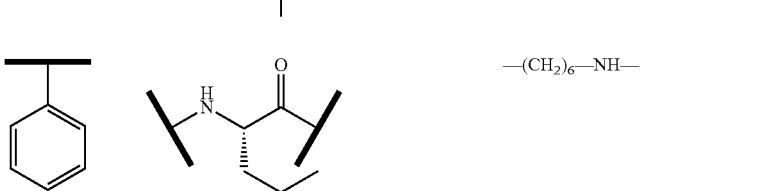 | —(CH$_2$)$_5$—NH— |
| 193 | Me | F | |  | —(CH$_2$)$_6$—NH— |

TABLE 1-continued

| Example# | R$^{2a}$ | R$^{2b}$ | R$^6$ | | —W—M— |
|---|---|---|---|---|---|
| 194 | Me | F | phenyl | Leu | —(CH$_2$)$_7$—NH— |
| 195 | Me | F | phenyl | Leu | —(CH$_2$)$_5$—C(O)NH— |
| 196 | Me | F | phenyl | Leu | —(CH$_2$)$_6$—C(O)NH— |
| 197 | Me | F | phenyl | Leu | —(CH$_2$)$_7$—C(O)NH— |
| 198 | Me | F | phenyl | Leu | —(CH$_2$)$_3$N(CH$_3$)(CH$_2$)$_4$O— |
| 199 | Me | F | phenyl | Leu | —(CH$_2$)$_3$S(CH$_2$)$_4$O— |
| 200 | Me | F | phenyl | Leu | —(CH$_2$)$_6$—OC(O)NH— |

(b) compounds of Formula VIII,

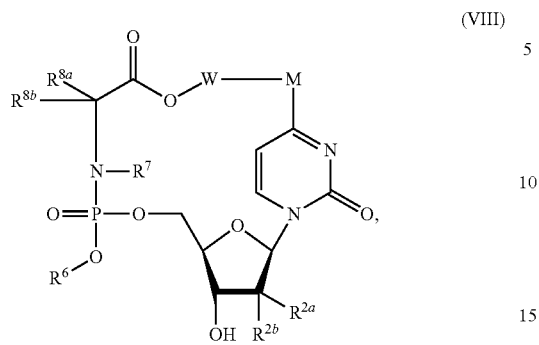

wherein, $R^{2a}$, $R^{2b}$, $R^6$, $R^7$, $R^{8a}$, $R^{8b}$ and —W-M- are delineated for each compound Table 2, or a pharmaceutically acceptable salt, ester or solvate thereof,

TABLE 2

| Example# | $R^{2a}$ | $R^{2b}$ | $R^6$ | $R^{8b}\,R^{8a}$ on $R^7$-N—C—C(=O) | —W—M— |
|---|---|---|---|---|---|
| 201 | Me | OH | phenyl | NH-CH(Me)-C(=O) | —(CH$_2$)$_4$—O— |
| 202 | Me | OH | phenyl | NH-CH(Me)-C(=O) | —(CH$_2$)$_5$—O— |
| 203 | Me | OH | phenyl | NH-CH(Me)-C(=O) | —(CH$_2$)$_6$—O— |
| 204 | Me | OH | phenyl | NH-CH(Me)-C(=O) | —(CH$_2$)$_7$—O— |
| 205 | Me | OH | phenyl | NH-CH(Me)-C(=O) | —(CH$_2$)$_8$—O— |
| 206 | Me | OH | phenyl | NH-CH(Me)-C(=O) | —C(Me)$_2$(CH$_2$)$_5$—O— |

TABLE 2-continued

| Example# | $R^{2a}$ | $R^{2b}$ | $R^6$ | $R^7R^{8b}R^{8a}$ group | —W—M— |
|---|---|---|---|---|---|
| 207 | Me | OH | phenyl | NH-CH(CH₃)-C(O) | —(CH₂)₆—C(CF₂)—CH₂—O— |
| 208 | Me | OH | phenyl | NH-CH(CH₃)-C(O) | —(CH₂)₃—O—(CH₂)₅—O— |
| 209 | Me | OH | phenyl | NH-CH(CH₃)-C(O) | —(CH₂)₃—CH=CH—CH₂—O— |
| 210 | Me | OH | phenyl | NH-CH(CH₃)-C(O) | —C(CH₃)₂—(CH₂)₂—CH=CH—CH₂—O— |
| 211 | Me | OH | phenyl | NH-CH(CH₃)-C(O) | —(CH₂)₃—cyclopropyl—(CH₂)₂—O— |
| 212 | Me | OH | phenyl | NH-CH(CH₃)-C(O) | —(CH₂)₅—NH— |
| 213 | Me | OH | phenyl | NH-CH(CH₃)-C(O) | —(CH₂)₆—NH— |
| 214 | Me | OH | phenyl | NH-CH(CH₃)-C(O) | —(CH₂)₇—NH— |
| 215 | Me | OH | phenyl | NH-CH(CH₃)-C(O) | —(CH₂)₅—C(O)NH— |

TABLE 2-continued

| Example# | R2a | R2b | R6 | | —W—M— |
|---|---|---|---|---|---|
| 216 | Me | OH | phenyl | NH-CH(CH3)-C(O) | —(CH2)6—C(O)NH— |
| 217 | Me | OH | phenyl | NH-CH(CH3)-C(O) | —(CH2)7—C(O)NH— |
| 218 | Me | OH | phenyl | NH-CH(CH3)-C(O) | —(CH2)3—N(CH3)—(CH2)3—O— |
| 219 | Me | OH | phenyl | NH-CH(CH3)-C(O) | —(CH2)3—S—(CH2)3—O— |
| 220 | Me | OH | phenyl | NH-CH(CH3)-C(O) | —(CH2)6—OC(O)NH— |
| 221 | Me | OH | 1-naphthyl | NH-CH(CH3)-C(O) | —(CH2)4—O— |
| 222 | Me | OH | 1-naphthyl | NH-CH(CH3)-C(O) | —(CH2)5—O— |
| 223 | Me | OH | 1-naphthyl | NH-CH(CH3)-C(O) | —(CH2)6—O— |
| 224 | Me | OH | 1-naphthyl | NH-CH(CH3)-C(O) | —(CH2)7—O— |

TABLE 2-continued
| Example# | R²ᵃ | R²ᵇ | R⁶ | 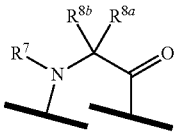 | —W—M— |
|---|---|---|---|---|---|
| 225 | Me | OH | 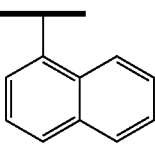 | 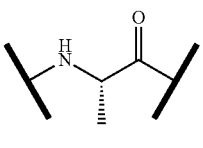 | —(CH₂)₈—O— |
| 226 | Me | OH | 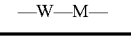 | 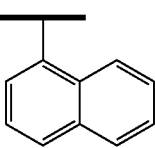 | 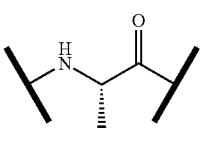 |
| 227 | Me | OH | 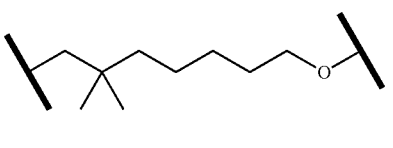 | 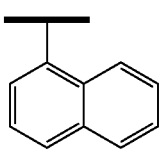 | 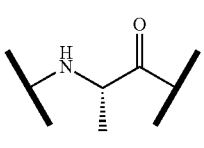 |
| 228 | Me | OH | 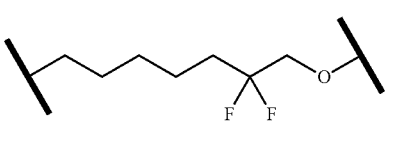 | 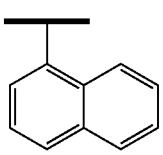 | —(CH₂)₃—O—(CH₂)₅—O— |
| 229 | Me | OH | 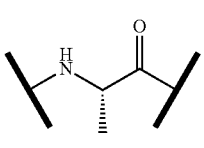 | 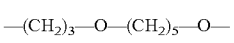 | 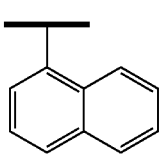 |
| 230 | Me | OH | 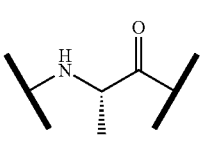 | 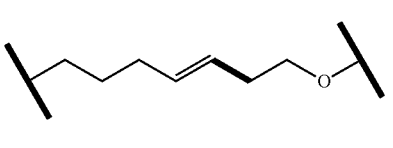 | 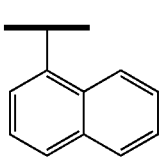 |
| 231 | Me | OH | 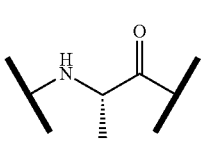 | 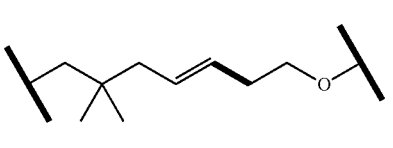 | 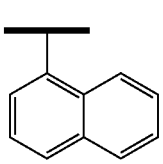 |
| 232 | Me | OH | 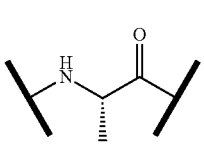 | 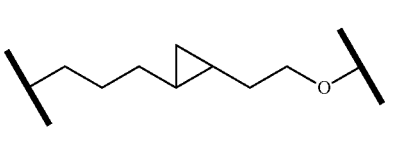 | —(CH₂)₅—NH— |
| 233 | Me | OH | 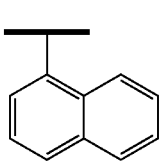 | 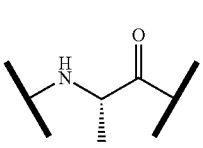 | —(CH₂)₆—NH— |

TABLE 2-continued
| Example# | R²ᵃ | R²ᵇ | R⁶ | 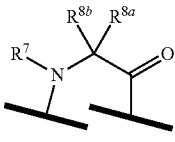 | —W—M— |
|---|---|---|---|---|---|
| 234 | Me | OH | 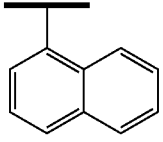 | 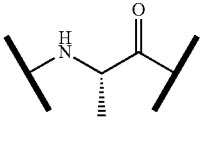 | —(CH₂)₇—NH— |
| 235 | Me | OH | 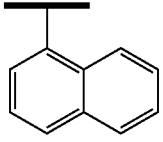 | 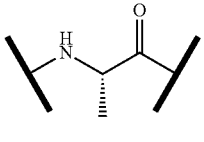 | —(CH₂)₅—C(O)NH— |
| 236 | Me | OH | 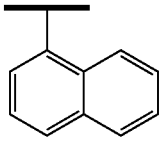 | 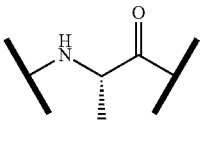 | —(CH₂)₆—C(O)NH— |
| 237 | Me | OH | 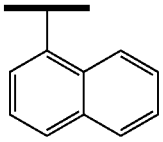 | 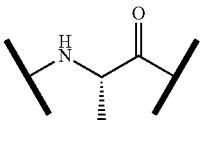 | —(CH₂)₇—C(O)NH— |
| 238 | Me | OH | 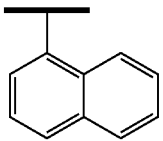 | 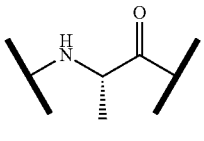 | 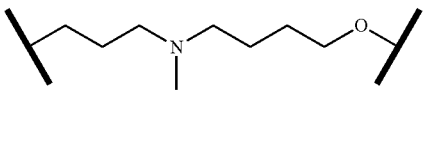 |
| 239 | Me | OH | 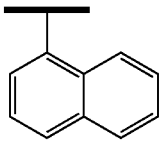 | 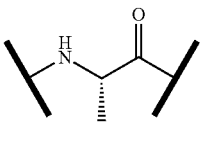 | 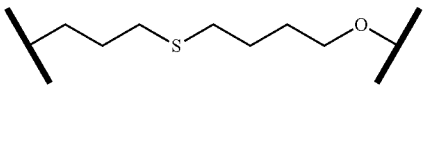 |
| 240 | Me | OH | 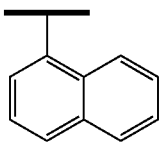 | 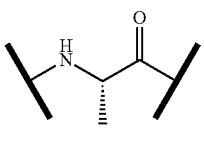 | —(CH₂)₆—OC(O)NH— |
| 241 | Me | F | 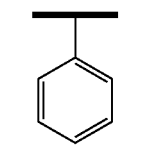 | 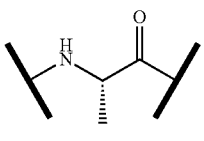 | —(CH₂)₄—O— |
| 242 | Me | F | 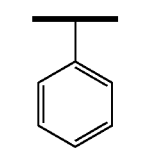 | 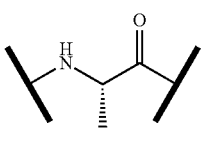 | —(CH₂)₅—O— |

TABLE 2-continued

| Example# | $R^{2a}$ | $R^{2b}$ | $R^6$ | $R^7/R^{8a}/R^{8b}$ group | —W—M— |
|---|---|---|---|---|---|
| 243 | Me | F | phenyl | NH-CH(CH₃)-C(O) | —(CH$_2$)$_6$—O— |
| 244 | Me | F | phenyl | NH-CH(CH₃)-C(O) | —(CH$_2$)$_7$—O— |
| 245 | Me | F | phenyl | NH-CH(CH₃)-C(O) | —(CH$_2$)$_8$—O— |
| 246 | Me | F | phenyl | NH-CH(CH₃)-C(O) | gem-dimethyl alkyl ether |
| 247 | Me | F | phenyl | NH-CH(CH₃)-C(O) | CF$_2$ alkyl ether |
| 248 | Me | F | phenyl | NH-CH(CH₃)-C(O) | —(CH$_2$)$_3$—O—(CH$_2$)$_5$—O— |
| 249 | Me | F | phenyl | NH-CH(CH₃)-C(O) | alkenyl ether |
| 250 | Me | F | phenyl | NH-CH(CH₃)-C(O) | gem-dimethyl alkenyl ether |
| 251 | Me | F | phenyl | NH-CH(CH₃)-C(O) | cyclopropyl alkyl ether |

TABLE 2-continued

| Example# | R$^{2a}$ | R$^{2b}$ | R$^6$ | R$^7$N(R$^{8b}$)(R$^{8a}$)C(O) | —W—M— |
|---|---|---|---|---|---|
| 252 | Me | F | phenyl | NH-CH(CH$_3$)-C(O) | —(CH$_2$)$_5$—NH— |
| 253 | Me | F | phenyl | NH-CH(CH$_3$)-C(O) | —(CH$_2$)$_6$—NH— |
| 254 | Me | F | phenyl | NH-CH(CH$_3$)-C(O) | —(CH$_2$)$_7$—NH— |
| 255 | Me | F | phenyl | NH-CH(CH$_3$)-C(O) | —(CH$_2$)$_5$—C(O)NH— |
| 256 | Me | F | phenyl | NH-CH(CH$_3$)-C(O) | —(CH$_2$)$_6$—C(O)NH— |
| 257 | Me | F | phenyl | NH-CH(CH$_3$)-C(O) | —(CH$_2$)$_7$—C(O)NH— |
| 258 | Me | F | phenyl | NH-CH(CH$_3$)-C(O) | —(CH$_2$)$_3$—N(CH$_3$)—(CH$_2$)$_3$—O— |
| 259 | Me | F | phenyl | NH-CH(CH$_3$)-C(O) | —(CH$_2$)$_3$—S—(CH$_2$)$_3$—O— |
| 260 | Me | F | phenyl | NH-CH(CH$_3$)-C(O) | —(CH$_2$)$_6$—OC(O)NH— |

TABLE 2-continued

| Example# | R²ᵃ | R²ᵇ | R⁶ | R⁷N(R⁸ᵇ)(R⁸ᵃ)C(=O) group | —W—M— |
|---|---|---|---|---|---|
| 261 | Me | F | 1-naphthyl-CH₂– | –NH-CH(Me)-C(=O)– | —(CH₂)₄—O— |
| 262 | Me | F | 1-naphthyl-CH₂– | –NH-CH(Me)-C(=O)– | —(CH₂)₅—O— |
| 263 | Me | F | 1-naphthyl-CH₂– | –NH-CH(Me)-C(=O)– | —(CH₂)₆—O— |
| 264 | Me | F | 1-naphthyl-CH₂– | –NH-CH(Me)-C(=O)– | —(CH₂)₇—O— |
| 265 | Me | F | 1-naphthyl-CH₂– | –NH-CH(Me)-C(=O)– | —(CH₂)₈—O— |
| 266 | Me | F | 1-naphthyl-CH₂– | –NH-CH(Me)-C(=O)– | —CH₂C(Me)₂(CH₂)₄CH₂—O— |
| 267 | Me | F | 1-naphthyl-CH₂– | –NH-CH(Me)-C(=O)– | —(CH₂)₅CF₂CH₂—O— |
| 268 | Me | F | 1-naphthyl-CH₂– | –NH-CH(Me)-C(=O)– | —(CH₂)₃—O—(CH₂)₅—O— |
| 269 | Me | F | 1-naphthyl-CH₂– | –NH-CH(Me)-C(=O)– | —CH₂CH₂CH=CHCH₂—O— |

TABLE 2-continued

| Example# | R2a | R2b | R6 | R7,R8a,R8b group | —W—M— |
|---|---|---|---|---|---|
| 270 | Me | F | naphthalen-1-yl | —NH—CH(Me)—C(O)— | —CH2C(Me)2CH=CHCH2O— |
| 271 | Me | F | naphthalen-1-yl | —NH—CH(Me)—C(O)— | —(CH2)2-cyclopropyl-CH2O— |
| 272 | Me | F | naphthalen-1-yl | —NH—CH(Me)—C(O)— | —(CH2)5—NH— |
| 273 | Me | F | naphthalen-1-yl | —NH—CH(Me)—C(O)— | —(CH2)6—NH— |
| 274 | Me | F | naphthalen-1-yl | —NH—CH(Me)—C(O)— | —(CH2)7—NH— |
| 275 | Me | F | naphthalen-1-yl | —NH—CH(Me)—C(O)— | —(CH2)5—C(O)NH— |
| 276 | Me | F | naphthalen-1-yl | —NH—CH(Me)—C(O)— | —(CH2)6—C(O)NH— |
| 277 | Me | F | naphthalen-1-yl | —NH—CH(Me)—C(O)— | —(CH2)7—C(O)NH— |
| 278 | Me | F | naphthalen-1-yl | —NH—CH(Me)—C(O)— | —(CH2)3N(Me)(CH2)4O— |

TABLE 2-continued

| Example# | $R^{2a}$ | $R^{2b}$ | $R^6$ | $R^7\text{N}(R^{8b})(R^{8a})$—C(O)— | —W—M— |
|---|---|---|---|---|---|
| 279 | Me | F | 1-naphthyl | NH-CH(CH$_3$)-C(O) | —(CH$_2$)$_3$—S—(CH$_2$)$_4$—O— |
| 280 | Me | F | 1-naphthyl | NH-CH(CH$_3$)-C(O) | —(CH$_2$)$_6$—OC(O)NH— |
| 281 | CHF$_2$ | OH | phenyl | NH-CH(CH$_3$)-C(O) | —(CH$_2$)$_4$—O— |
| 282 | CHF$_2$ | OH | phenyl | NH-CH(CH$_3$)-C(O) | —(CH$_2$)$_5$—O— |
| 283 | CHF$_2$ | OH | phenyl | NH-CH(CH$_3$)-C(O) | —(CH$_2$)$_6$—O— |
| 284 | CHF$_2$ | OH | phenyl | NH-CH(CH$_3$)-C(O) | —(CH$_2$)$_7$—O— |
| 285 | CHF$_2$ | OH | phenyl | NH-CH(CH$_3$)-C(O) | —(CH$_2$)$_8$—O— |
| 286 | CHF$_2$ | OH | phenyl | NH-CH(CH$_3$)-C(O) | —C(CH$_3$)$_2$(CH$_2$)$_5$—O— |
| 287 | CHF$_2$ | OH | phenyl | NH-CH(CH$_3$)-C(O) | —(CH$_2$)$_5$CF$_2$CH$_2$—O— |

TABLE 2-continued

| Example# | R$^{2a}$ | R$^{2b}$ | R$^6$ | [R$^7$R$^{8b}$R$^{8a}$ group] | —W—M— |
|---|---|---|---|---|---|
| 288 | CHF$_2$ | OH | phenyl | NH-CH(CH$_3$)-C(O) | —(CH$_2$)$_3$—O—(CH$_2$)$_5$—O— |
| 289 | CHF$_2$ | OH | phenyl | NH-CH(CH$_3$)-C(O) | —CH$_2$CH$_2$CH$_2$CH=CHCH$_2$—O— |
| 290 | CHF$_2$ | OH | phenyl | NH-CH(CH$_3$)-C(O) | —C(CH$_3$)$_2$CH$_2$CH=CHCH$_2$—O— |
| 291 | CHF$_2$ | OH | phenyl | NH-CH(CH$_3$)-C(O) | —(CH$_2$)$_3$-cyclopropyl-(CH$_2$)$_2$—O— |
| 292 | CHF$_2$ | OH | phenyl | NH-CH(CH$_3$)-C(O) | —(CH$_2$)$_5$—NH— |
| 293 | CHF$_2$ | OH | phenyl | NH-CH(CH$_3$)-C(O) | —(CH$_2$)$_6$—NH— |
| 294 | CHF$_2$ | OH | phenyl | NH-CH(CH$_3$)-C(O) | —(CH$_2$)$_7$—NH— |
| 295 | CHF$_2$ | OH | phenyl | NH-CH(CH$_3$)-C(O) | —(CH$_2$)$_5$—C(O)NH— |
| 296 | CHF$_2$ | OH | phenyl | NH-CH(CH$_3$)-C(O) | —(CH$_2$)$_6$—C(O)NH— |

TABLE 2-continued
| Example# | $R^{2a}$ | $R^{2b}$ | $R^6$ | 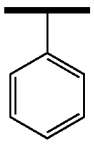 | —W—M— |
|---|---|---|---|---|---|
| 297 | $CHF_2$ | OH | 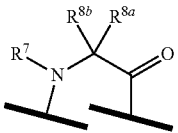 | 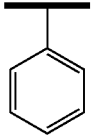 | —$(CH_2)_7$—C(O)NH— |
| 298 | $CHF_2$ | OH | 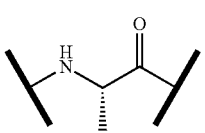 | 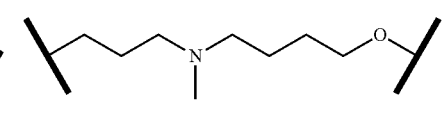 | 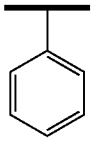 |
| 299 | $CHF_2$ | OH | 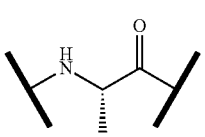 | 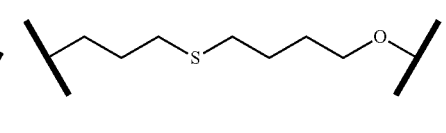 | 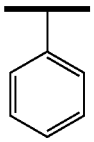 |
| 300 | $CHF_2$ | OH | 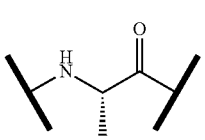 | 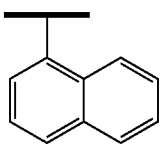 | —$(CH_2)_6$—OC(O)NH— |
| 301 | $CHF_2$ | OH | 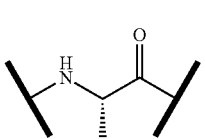 | 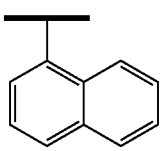 | —$(CH_2)_4$—O— |
| 302 | $CHF_2$ | OH | 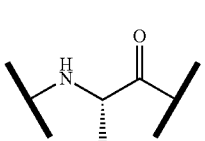 | 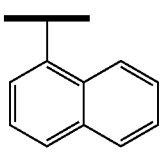 | —$(CH_2)_5$—O— |
| 303 | $CHF_2$ | OH | 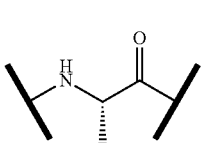 | 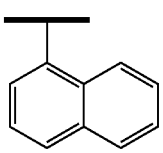 | —$(CH_2)_6$—O— |
| 304 | $CHF_2$ | OH | 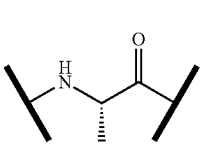 | 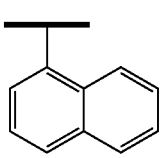 | —$(CH_2)_7$—O— |
| 305 | $CHF_2$ | OH | 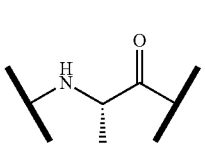 |  | —$(CH_2)_8$—O— |

TABLE 2-continued

| Example# | R²ᵃ | R²ᵇ | R⁶ | R⁷R⁸ᵇR⁸ᵃ group | —W—M— |
|---|---|---|---|---|---|
| 306 | CHF₂ | OH | 1-naphthyl | NH-CH(CH₃)-C(=O) | gem-dimethyl alkyl-O- |
| 307 | CHF₂ | OH | 1-naphthyl | NH-CH(CH₃)-C(=O) | alkyl-CF₂-CH₂-O- |
| 308 | CHF₂ | OH | 1-naphthyl | NH-CH(CH₃)-C(=O) | —(CH₂)₃—O—(CH₂)₅—O— |
| 309 | CHF₂ | OH | 1-naphthyl | NH-CH(CH₃)-C(=O) | alkenyl-CH₂-O- |
| 310 | CHF₂ | OH | 1-naphthyl | NH-CH(CH₃)-C(=O) | gem-dimethyl alkenyl-O- |
| 311 | CHF₂ | OH | 1-naphthyl | NH-CH(CH₃)-C(=O) | cyclopropyl-containing alkyl-O- |
| 312 | CHF₂ | OH | 1-naphthyl | NH-CH(CH₃)-C(=O) | —(CH₂)₅—NH— |
| 313 | CHF₂ | OH | 1-naphthyl | NH-CH(CH₃)-C(=O) | —(CH₂)₆—NH— |
| 314 | CHF₂ | OH | 1-naphthyl | NH-CH(CH₃)-C(=O) | —(CH₂)₇—NH— |

TABLE 2-continued
| Example# | R²ᵃ | R²ᵇ | R⁶ | 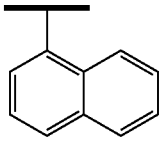 | —W—M— |
|---|---|---|---|---|---|
| 315 | CHF₂ | OH | 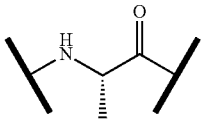 | 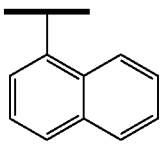 | —(CH₂)₅—C(O)NH— |
| 316 | CHF₂ | OH | 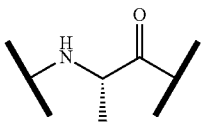 | 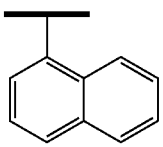 | —(CH₂)₆—C(O)NH— |
| 317 | CHF₂ | OH | 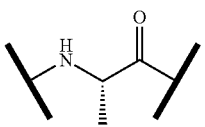 | 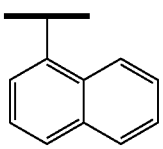 | —(CH₂)₇—C(O)NH— |
| 318 | CHF₂ | OH | 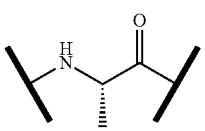 | 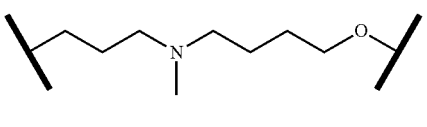 | 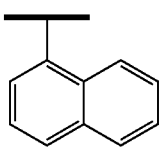 |
| 319 | CHF₂ | OH | 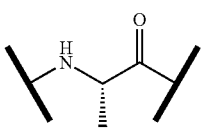 | 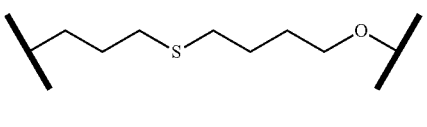 | 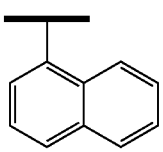 |
| 320 | CHF₂ | OH | 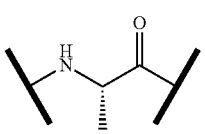 | 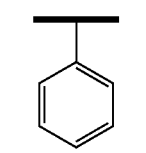 | —(CH₂)₆—OC(O)NH— |
| 321 | CHF₂ | F | 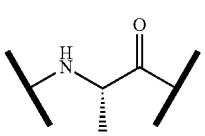 | 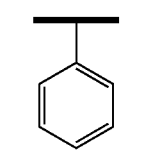 | —(CH₂)₄—O— |
| 322 | CHF₂ | F | 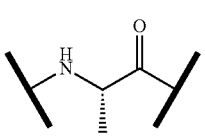 | 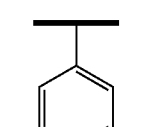 | —(CH₂)₅—O— |
| 323 | CHF₂ | F | 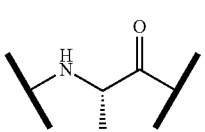 | | —(CH₂)₆—O— |

TABLE 2-continued

| Example# | $R^{2a}$ | $R^{2b}$ | $R^6$ | $R^7,R^{8a},R^{8b}$ group | —W—M— |
|---|---|---|---|---|---|
| 324 | $CHF_2$ | F | phenyl | NH-CH(CH3)-C(O) | $-(CH_2)_7-O-$ |
| 325 | $CHF_2$ | F | phenyl | NH-CH(CH3)-C(O) | $-(CH_2)_8-O-$ |
| 326 | $CHF_2$ | F | phenyl | NH-CH(CH3)-C(O) | gem-dimethyl alkyl-O- |
| 327 | $CHF_2$ | F | phenyl | NH-CH(CH3)-C(O) | gem-difluoro alkyl-O- |
| 328 | $CHF_2$ | F | phenyl | NH-CH(CH3)-C(O) | $-(CH_2)_3-O-(CH_2)_5-O-$ |
| 329 | $CHF_2$ | F | phenyl | NH-CH(CH3)-C(O) | alkenyl-O- |
| 330 | $CHF_2$ | F | phenyl | NH-CH(CH3)-C(O) | gem-dimethyl alkenyl-O- |
| 331 | $CHF_2$ | F | phenyl | NH-CH(CH3)-C(O) | cyclopropyl alkyl-O- |
| 332 | $CHF_2$ | F | phenyl | NH-CH(CH3)-C(O) | $-(CH_2)_5-NH-$ |

TABLE 2-continued

| Example# | $R^{2a}$ | $R^{2b}$ | $R^6$ | $R^7$N-C($R^{8b}$)($R^{8a}$)-C(O) | —W—M— |
|---|---|---|---|---|---|
| 333 | $CHF_2$ | F | phenyl | NH-CH(CH₃)-C(O) | —(CH₂)₆—NH— |
| 334 | $CHF_2$ | F | phenyl | NH-CH(CH₃)-C(O) | —(CH₂)₇—NH— |
| 335 | $CHF_2$ | F | phenyl | NH-CH(CH₃)-C(O) | —(CH₂)₅—C(O)NH— |
| 336 | $CHF_2$ | F | phenyl | NH-CH(CH₃)-C(O) | —(CH₂)₆—C(O)NH— |
| 337 | $CHF_2$ | F | phenyl | NH-CH(CH₃)-C(O) | —(CH₂)₇—C(O)NH— |
| 338 | $CHF_2$ | F | phenyl | NH-CH(CH₃)-C(O) | —(CH₂)₃—N(CH₃)—(CH₂)₄—O— |
| 339 | $CHF_2$ | F | phenyl | NH-CH(CH₃)-C(O) | —(CH₂)₃—S—(CH₂)₄—O— |
| 340 | $CHF_2$ | F | phenyl | NH-CH(CH₃)-C(O) | —(CH₂)₆—OC(O)NH— |
| 341 | $CHF_2$ | F | naphthyl | NH-CH(CH₃)-C(O) | —(CH₂)₄—O— |

TABLE 2-continued

| Example# | $R^{2a}$ | $R^{2b}$ | $R^6$ | (R7,R8a,R8b,N,O group) | —W—M— |
|---|---|---|---|---|---|
| 342 | $CHF_2$ | F | 1-naphthyl-CH | NH-CH(CH3)-C(=O) | —(CH$_2$)$_5$—O— |
| 343 | $CHF_2$ | F | 1-naphthyl-CH | NH-CH(CH3)-C(=O) | —(CH$_2$)$_6$—O— |
| 344 | $CHF_2$ | F | 1-naphthyl-CH | NH-CH(CH3)-C(=O) | —(CH$_2$)$_7$—O— |
| 345 | $CHF_2$ | F | 1-naphthyl-CH | NH-CH(CH3)-C(=O) | —(CH$_2$)$_8$—O— |
| 346 | $CHF_2$ | F | 1-naphthyl-CH | NH-CH(CH3)-C(=O) | gem-dimethyl alkyl-O— |
| 347 | $CHF_2$ | F | 1-naphthyl-CH | NH-CH(CH3)-C(=O) | CF$_2$-containing alkyl-O— |
| 348 | $CHF_2$ | F | 1-naphthyl-CH | NH-CH(CH3)-C(=O) | —(CH$_2$)$_3$—O—(CH$_2$)$_5$—O— |
| 349 | $CHF_2$ | F | 1-naphthyl-CH | NH-CH(CH3)-C(=O) | alkenyl-CH$_2$—O— |
| 350 | $CHF_2$ | F | 1-naphthyl-CH | NH-CH(CH3)-C(=O) | gem-dimethyl alkenyl-CH$_2$—O— |

TABLE 2-continued

| Example# | R²ᵃ | R²ᵇ | R⁶ | R⁷R⁸ᵇR⁸ᵃ (N-C-C=O group) | —W—M— |
|---|---|---|---|---|---|
| 351 | CHF₂ | F | naphthyl | NH-CH(CH₃)-C(O) | —(CH₂)₃—cyclopropyl—(CH₂)₂—O— |
| 352 | CHF₂ | F | naphthyl | NH-CH(CH₃)-C(O) | —(CH₂)₅—NH— |
| 353 | CHF₂ | F | naphthyl | NH-CH(CH₃)-C(O) | —(CH₂)₆—NH— |
| 354 | CHF₂ | F | naphthyl | NH-CH(CH₃)-C(O) | —(CH₂)₇—NH— |
| 355 | CHF₂ | F | naphthyl | NH-CH(CH₃)-C(O) | —(CH₂)₅—C(O)NH— |
| 356 | CHF₂ | F | naphthyl | NH-CH(CH₃)-C(O) | —(CH₂)₆—C(O)NH— |
| 357 | CHF₂ | F | naphthyl | NH-CH(CH₃)-C(O) | —(CH₂)₇—C(O)NH— |
| 358 | CHF₂ | F | naphthyl | NH-CH(CH₃)-C(O) | —(CH₂)₃—N(CH₃)—(CH₂)₃—O— |
| 359 | CHF₂ | F | naphthyl | NH-CH(CH₃)-C(O) | —(CH₂)₃—S—(CH₂)₃—O— |

TABLE 2-continued

| Example# | $R^{2a}$ | $R^{2b}$ | $R^6$ | $R^7R^8{}^bR^{8a}$ group | —W—M— |
|---|---|---|---|---|---|
| 360 | $CHF_2$ | F | naphthyl | Ala | $-(CH_2)_6-OC(O)NH-$ |
| 361 | Me | OH | phenyl | Leu | $-(CH_2)_4-O-$ |
| 362 | Me | OH | phenyl | Leu | $-(CH_2)_5-O-$ |
| 363 | Me | OH | phenyl | Leu | $-(CH_2)_6-O-$ |
| 364 | Me | OH | phenyl | Leu | $-(CH_2)_7-O-$ |
| 365 | Me | OH | phenyl | Leu | $-(CH_2)_8-O-$ |
| 366 | Me | OH | phenyl | Leu | (gem-dimethyl alkyl ether linker) |

TABLE 2-continued
| Example# | R<sup>2a</sup> | R<sup>2b</sup> | R<sup>6</sup> | | —W—M— |
|---|---|---|---|---|---|
| 367 | Me | OH | 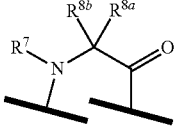 | 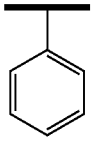 | 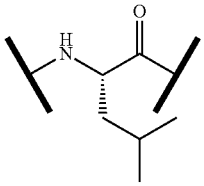 |
| 368 | Me | OH | 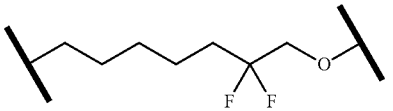 | 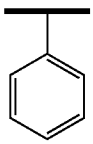 | —(CH$_2$)$_3$—O—(CH$_2$)$_5$—O— |
| 369 | Me | OH | 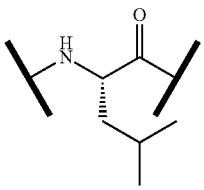 | 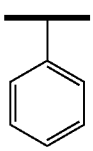 | 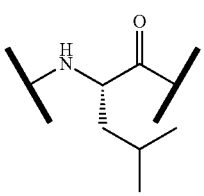 |
| 370 | Me | OH | 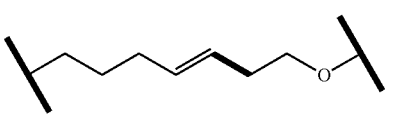 | 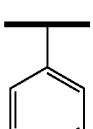 | 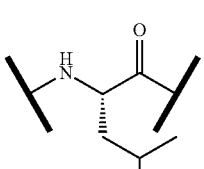 |
| 371 | Me | OH | 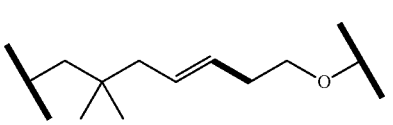 | 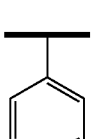 | 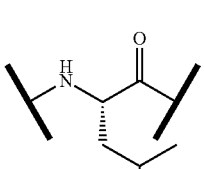 |
| 372 | Me | OH | 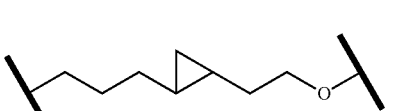 | 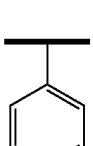 | —(CH$_2$)$_5$—NH— |
| 373 | Me | OH | 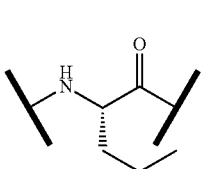 | 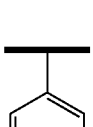 | —(CH$_2$)$_6$—NH— |

TABLE 2-continued
| Example# | R²ᵃ | R²ᵇ | R⁶ | R⁷\N(R⁸ᵇ)(R⁸ᵃ)C(=O) | —W—M— |
|---|---|---|---|---|---|
| 374 | Me | OH | 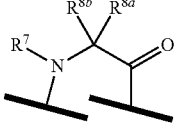 | 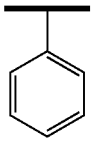 | —(CH₂)₇—NH— |
| 375 | Me | OH | 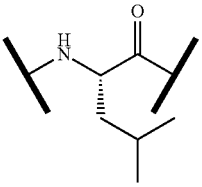 | 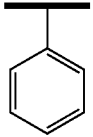 | —(CH₂)₅—C(O)NH— |
| 376 | Me | OH | 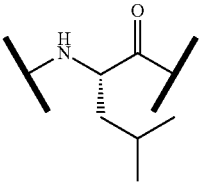 | 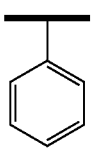 | —(CH₂)₆—C(O)NH— |
| 377 | Me | OH | 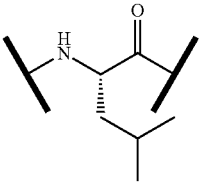 | 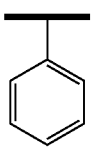 | —(CH₂)₇—C(O)NH— |
| 378 | Me | OH | 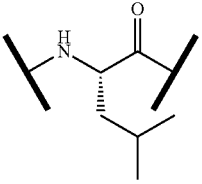 | 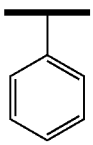 | 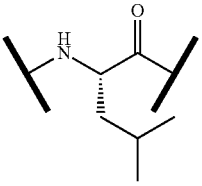 |
| 379 | Me | OH | 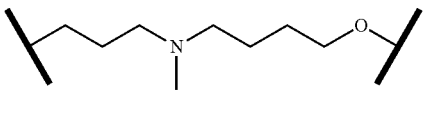 | 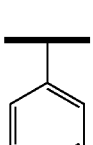 | 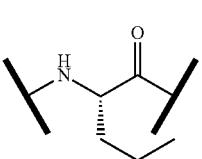 |
| 380 | Me | OH | 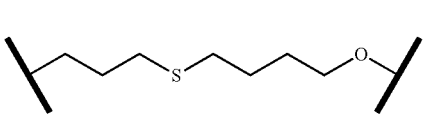 | 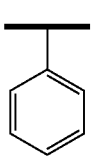 | —(CH₂)₆—OC(O)NH— |

TABLE 2-continued

| Example# | R2a | R2b | R6 | R7,R8a,R8b group | —W—M— |
|---|---|---|---|---|---|
| 381 | Me | F | phenyl | leucine-derived | —(CH2)4—O— |
| 382 | Me | F | phenyl | leucine-derived | —(CH2)5—O— |
| 383 | Me | F | phenyl | leucine-derived | —(CH2)6—O— |
| 384 | Me | F | phenyl | leucine-derived | —(CH2)7—O— |
| 385 | Me | F | phenyl | leucine-derived | —(CH2)8—O— |
| 386 | Me | F | phenyl | leucine-derived | gem-dimethyl alkyl ether |
| 387 | Me | F | phenyl | leucine-derived | gem-difluoro alkyl ether |

TABLE 2-continued
| Example# | R²ᵃ | R²ᵇ | R⁶ | 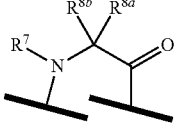 | —W—M— |
|---|---|---|---|---|---|
| 388 | Me | F | 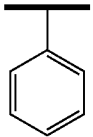 | 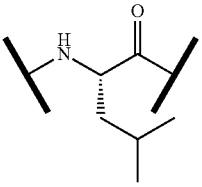 | —(CH₂)₃—O—(CH₂)₅—O— |
| 389 | Me | F | 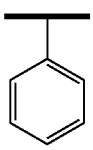 | 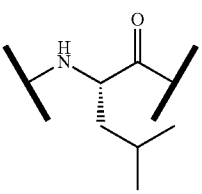 | 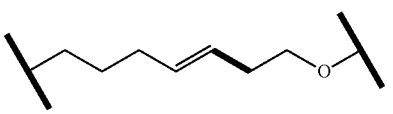 |
| 390 | Me | F | 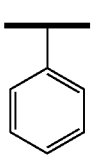 | 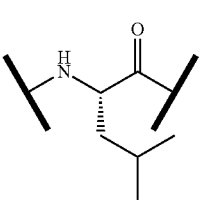 | 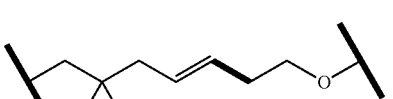 |
| 391 | Me | F | 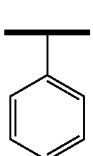 | 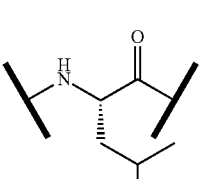 | 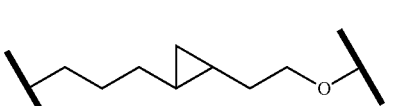 |
| 392 | Me | F | 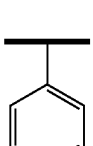 | 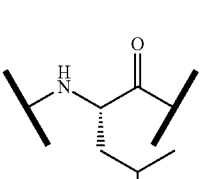 | —(CH₂)₅—NH— |
| 393 | Me | F | 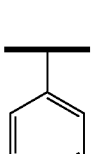 | 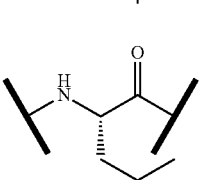 | —(CH₂)₆—NH— |
| 394 | Me | F | 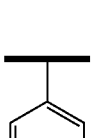 | 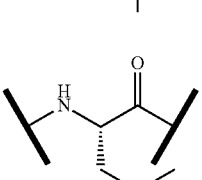 | —(CH₂)₇—NH— |

TABLE 2-continued
| Example# | R2a | R2b | R6 | (R7,R8a,R8b group) | —W—M— |
|---|---|---|---|---|---|
| 395 | Me | F | 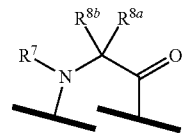 | 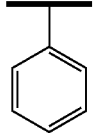 | —(CH₂)₅—C(O)NH— |
| 396 | Me | F | 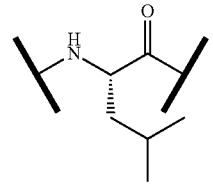 | 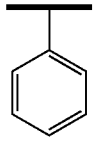 | —(CH₂)₆—C(O)NH— |
| 397 | Me | F | 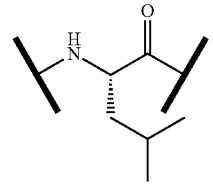 | 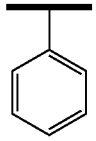 | —(CH₂)₇—C(O)NH— |
| 398 | Me | F | 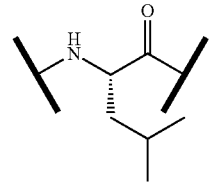 | 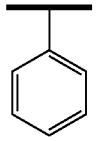 | 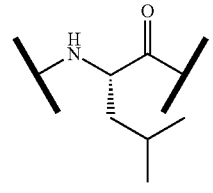 |
| 399 | Me | F | 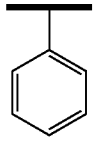 | 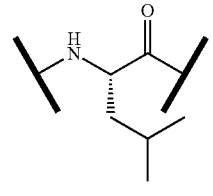 | 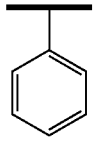 |
| 400 | Me | F | 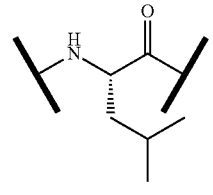 |  | —(CH₂)₆—OC(O)NH— |

(c) compounds of Formula IX,

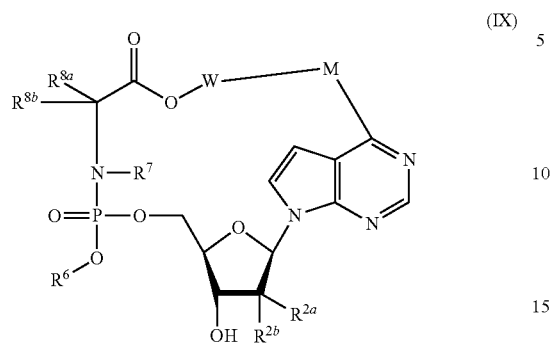

(IX)

wherein, $R^{2a}$, $R^{2b}$, $R^6$, $R^7$, $R^{8a}$, $R^{8b}$ and —W-M- are delineated for each compound Table 3, or a pharmaceutically acceptable salt, ester or solvate thereof,

TABLE 3

| Example# | $R^{2a}$ | $R^{2b}$ | $R^6$ | $R^7\text{-N}(R^{8b})(R^{8a})\text{-C(=O)-}$ | —W—M— |
|---|---|---|---|---|---|
| 401 | Me | OH | Ph | NH-CH(Me)-C(=O) (S) | —(CH$_2$)$_4$—O— |
| 402 | Me | OH | Ph | NH-CH(Me)-C(=O) (S) | —(CH$_2$)$_5$—O— |
| 403 | Me | OH | Ph | NH-CH(Me)-C(=O) (S) | —(CH$_2$)$_6$—O— |
| 404 | Me | OH | Ph | NH-CH(Me)-C(=O) (S) | —(CH$_2$)$_7$—O— |
| 405 | Me | OH | Ph | NH-CH(Me)-C(=O) (S) | —(CH$_2$)$_8$—O— |
| 406 | Me | OH | Ph | NH-CH(Me)-C(=O) (S) | —C(Me)$_2$(CH$_2$)$_4$—O— |

TABLE 3-continued

| Example# | R² ͣ | R²ᵇ | R⁶ | $\begin{smallmatrix}R^{8b} & R^{8a}\\ R^7\diagdown_N\diagdown\diagdown_O\end{smallmatrix}$ | —W—M— |
|---|---|---|---|---|---|
| 407 | Me | OH | Ph | NH-CH(Me)-C(O) | —CH₂(CH₂)₅C(F)₂CH₂O— |
| 408 | Me | OH | Ph | NH-CH(Me)-C(O) | —(CH₂)₃—O—(CH₂)₅—O— |
| 409 | Me | OH | Ph | NH-CH(Me)-C(O) | —(CH₂)₄CH=CHCH₂O— |
| 410 | Me | OH | Ph | NH-CH(Me)-C(O) | —CH₂C(Me)₂CH=CHCH₂O— |
| 411 | Me | OH | Ph | NH-CH(Me)-C(O) | —(CH₂)₃-cyclopropyl-(CH₂)₂O— |
| 412 | Me | OH | Ph | NH-CH(Me)-C(O) | —(CH₂)₅—NH— |
| 413 | Me | OH | Ph | NH-CH(Me)-C(O) | —(CH₂)₆—NH— |
| 414 | Me | OH | Ph | NH-CH(Me)-C(O) | —(CH₂)₇—NH— |
| 415 | Me | OH | Ph | NH-CH(Me)-C(O) | —(CH₂)₅—C(O)NH— |

TABLE 3-continued

| Example# | R²ᵃ | R²ᵇ | R⁶ | (R⁷R⁸ᵇR⁸ᵃN-C-C(O)) | —W—M— |
|---|---|---|---|---|---|
| 416 | Me | OH | benzyl | NH-CH(CH₃)-C(O) | —(CH₂)₆—C(O)NH— |
| 417 | Me | OH | benzyl | NH-CH(CH₃)-C(O) | —(CH₂)₇—C(O)NH— |
| 418 | Me | OH | benzyl | NH-CH(CH₃)-C(O) | —(CH₂)₃—N(CH₃)—(CH₂)₄—O— |
| 419 | Me | OH | benzyl | NH-CH(CH₃)-C(O) | —(CH₂)₃—S—(CH₂)₄—O— |
| 420 | Me | OH | benzyl | NH-CH(CH₃)-C(O) | —(CH₂)₆—OC(O)NH— |
| 421 | Me | OH | 1-naphthylmethyl | NH-CH(CH₃)-C(O) | —(CH₂)₄—O— |
| 422 | Me | OH | 1-naphthylmethyl | NH-CH(CH₃)-C(O) | —(CH₂)₅—O— |
| 423 | Me | OH | 1-naphthylmethyl | NH-CH(CH₃)-C(O) | —(CH₂)₆—O— |
| 424 | Me | OH | 1-naphthylmethyl | NH-CH(CH₃)-C(O) | —(CH₂)₇—O— |

TABLE 3-continued

| Example# | R²ᵃ | R²ᵇ | R⁶ | R⁷-N(R⁸ᵇ)(R⁸ᵃ)-C(=O) | —W—M— |
|---|---|---|---|---|---|
| 425 | Me | OH | 1-naphthyl-CH₂ | N-H-Ala | —(CH₂)₈—O— |
| 426 | Me | OH | 1-naphthyl-CH₂ | N-H-Ala | —C(CH₃)₂(CH₂)₅—O— |
| 427 | Me | OH | 1-naphthyl-CH₂ | N-H-Ala | —(CH₂)₅C(F)₂CH₂—O— |
| 428 | Me | OH | 1-naphthyl-CH₂ | N-H-Ala | —(CH₂)₃—O—(CH₂)₅—O— |
| 429 | Me | OH | 1-naphthyl-CH₂ | N-H-Ala | —(CH₂)₃CH=CHCH₂—O— |
| 430 | Me | OH | 1-naphthyl-CH₂ | N-H-Ala | —C(CH₃)₂(CH₂)₂CH=CHCH₂—O— |
| 431 | Me | OH | 1-naphthyl-CH₂ | N-H-Ala | —(CH₂)₃-(cyclopropyl)-CH₂CH₂—O— |
| 432 | Me | OH | 1-naphthyl-CH₂ | N-H-Ala | —(CH₂)₅—NH— |
| 433 | Me | OH | 1-naphthyl-CH₂ | N-H-Ala | —(CH₂)₆—NH— |

TABLE 3-continued

| Example# | R2a | R2b | R6 | (R7,R8a,R8b group) | —W—M— |
|---|---|---|---|---|---|
| 434 | Me | OH | 1-naphthyl | NH-CH(Me)-C(O) | —(CH2)7—NH— |
| 435 | Me | OH | 1-naphthyl | NH-CH(Me)-C(O) | —(CH2)5—C(O)NH— |
| 436 | Me | OH | 1-naphthyl | NH-CH(Me)-C(O) | —(CH2)6—C(O)NH— |
| 437 | Me | OH | 1-naphthyl | NH-CH(Me)-C(O) | —(CH2)7—C(O)NH— |
| 438 | Me | OH | 1-naphthyl | NH-CH(Me)-C(O) | —(CH2)3N(Me)(CH2)4O— |
| 439 | Me | OH | 1-naphthyl | NH-CH(Me)-C(O) | —(CH2)3S(CH2)4O— |
| 440 | Me | OH | 1-naphthyl | NH-CH(Me)-C(O) | —(CH2)6—OC(O)NH— |
| 441 | Me | F | phenyl | NH-CH(Me)-C(O) | —(CH2)4—O— |
| 442 | Me | F | phenyl | NH-CH(Me)-C(O) | —(CH2)5—O— |

TABLE 3-continued

| Example# | R2a | R2b | R6 | (R7,R8a,R8b group) | —W—M— |
|---|---|---|---|---|---|
| 443 | Me | F | phenyl | NH-CH(Me)-C(O) | —(CH2)6—O— |
| 444 | Me | F | phenyl | NH-CH(Me)-C(O) | —(CH2)7—O— |
| 445 | Me | F | phenyl | NH-CH(Me)-C(O) | —(CH2)8—O— |
| 446 | Me | F | phenyl | NH-CH(Me)-C(O) | gem-dimethyl alkyl-O |
| 447 | Me | F | phenyl | NH-CH(Me)-C(O) | gem-difluoro alkyl-O |
| 448 | Me | F | phenyl | NH-CH(Me)-C(O) | —(CH2)3—O—(CH2)5—O— |
| 449 | Me | F | phenyl | NH-CH(Me)-C(O) | alkenyl-O |
| 450 | Me | F | phenyl | NH-CH(Me)-C(O) | gem-dimethyl alkenyl-O |
| 451 | Me | F | phenyl | NH-CH(Me)-C(O) | cyclopropyl-containing alkyl-O |

TABLE 3-continued

| Example# | R$^{2a}$ | R$^{2b}$ | R$^6$ | R$^7$N(R$^{8b}$)(R$^{8a}$)C(O) | —W—M— |
|---|---|---|---|---|---|
| 452 | Me | F | phenyl | NH-CH(CH$_3$)-C(O) | —(CH$_2$)$_5$—NH— |
| 453 | Me | F | phenyl | NH-CH(CH$_3$)-C(O) | —(CH$_2$)$_6$—NH— |
| 454 | Me | F | phenyl | NH-CH(CH$_3$)-C(O) | —(CH$_2$)$_7$—NH— |
| 455 | Me | F | phenyl | NH-CH(CH$_3$)-C(O) | —(CH$_2$)$_5$—C(O)NH— |
| 456 | Me | F | phenyl | NH-CH(CH$_3$)-C(O) | —(CH$_2$)$_6$—C(O)NH— |
| 457 | Me | F | phenyl | NH-CH(CH$_3$)-C(O) | —(CH$_2$)$_7$—C(O)NH— |
| 458 | Me | F | phenyl | NH-CH(CH$_3$)-C(O) | —(CH$_2$)$_3$N(CH$_3$)(CH$_2$)$_4$O— |
| 459 | Me | F | phenyl | NH-CH(CH$_3$)-C(O) | —(CH$_2$)$_3$S(CH$_2$)$_4$O— |
| 460 | Me | F | phenyl | NH-CH(CH$_3$)-C(O) | —(CH$_2$)$_6$—OC(O)NH— |

TABLE 3-continued

| Example# | R²ᵃ | R²ᵇ | R⁶ | R⁷-N(R⁸ᵇ)(R⁸ᵃ)-C(=O) | —W—M— |
|---|---|---|---|---|---|
| 461 | Me | F | 1-naphthyl-CH₂- | -NH-CH(Me)-C(=O)- | —(CH₂)₄—O— |
| 462 | Me | F | 1-naphthyl-CH₂- | -NH-CH(Me)-C(=O)- | —(CH₂)₅—O— |
| 463 | Me | F | 1-naphthyl-CH₂- | -NH-CH(Me)-C(=O)- | —(CH₂)₆—O— |
| 464 | Me | F | 1-naphthyl-CH₂- | -NH-CH(Me)-C(=O)- | —(CH₂)₇—O— |
| 465 | Me | F | 1-naphthyl-CH₂- | -NH-CH(Me)-C(=O)- | —(CH₂)₈—O— |
| 466 | Me | F | 1-naphthyl-CH₂- | -NH-CH(Me)-C(=O)- | —C(Me)₂(CH₂)₅—O— |
| 467 | Me | F | 1-naphthyl-CH₂- | -NH-CH(Me)-C(=O)- | —(CH₂)₅CF₂CH₂—O— |
| 468 | Me | F | 1-naphthyl-CH₂- | -NH-CH(Me)-C(=O)- | —(CH₂)₃—O—(CH₂)₅—O— |
| 469 | Me | F | 1-naphthyl-CH₂- | -NH-CH(Me)-C(=O)- | —(CH₂)₃CH=CHCH₂—O— |

TABLE 3-continued

| Example# | R²ᵃ | R²ᵇ | R⁶ | (R⁷R⁸ᵇR⁸ᵃN-CH-C(O)) | —W—M— |
|---|---|---|---|---|---|
| 470 | Me | F | 1-naphthyl | NH-CH(Me)-C(O) | |
| 471 | Me | F | 1-naphthyl | NH-CH(Me)-C(O) | |
| 472 | Me | F | 1-naphthyl | NH-CH(Me)-C(O) | —(CH$_2$)$_5$—NH— |
| 473 | Me | F | 1-naphthyl | NH-CH(Me)-C(O) | —(CH$_2$)$_6$—NH— |
| 474 | Me | F | 1-naphthyl | NH-CH(Me)-C(O) | —(CH$_2$)$_7$—NH— |
| 475 | Me | F | 1-naphthyl | NH-CH(Me)-C(O) | —(CH$_2$)$_5$—C(O)NH— |
| 476 | Me | F | 1-naphthyl | NH-CH(Me)-C(O) | —(CH$_2$)$_6$—C(O)NH— |
| 477 | Me | F | 1-naphthyl | NH-CH(Me)-C(O) | —(CH$_2$)$_7$—C(O)NH— |
| 478 | Me | F | 1-naphthyl | NH-CH(Me)-C(O) | |

TABLE 3-continued

| Example# | R²ᵃ | R²ᵇ | R⁶ | R⁷,R⁸ᵃ,R⁸ᵇ group | —W—M— |
|---|---|---|---|---|---|
| 479 | Me | F | 1-naphthyl | NH-CH(Me)-C(O) | —(CH₂)₃—S—(CH₂)₄—O— |
| 480 | Me | F | 1-naphthyl | NH-CH(Me)-C(O) | —(CH₂)₆—OC(O)NH— |
| 481 | CHF₂ | OH | phenyl | NH-CH(Me)-C(O) | —(CH₂)₄—O— |
| 482 | CHF₂ | OH | phenyl | NH-CH(Me)-C(O) | —(CH₂)₅—O— |
| 483 | CHF₂ | OH | phenyl | NH-CH(Me)-C(O) | —(CH₂)₆—O— |
| 484 | CHF₂ | OH | phenyl | NH-CH(Me)-C(O) | —(CH₂)₇—O— |
| 485 | CHF₂ | OH | phenyl | NH-CH(Me)-C(O) | —(CH₂)₈—O— |
| 486 | CHF₂ | OH | phenyl | NH-CH(Me)-C(O) | —C(Me)₂(CH₂)₅—O— |
| 487 | CHF₂ | OH | phenyl | NH-CH(Me)-C(O) | —(CH₂)₅C(F)₂CH₂—O— |

TABLE 3-continued

| Example# | R²ᵃ | R²ᵇ | R⁶ | R⁷R⁸ᵇR⁸ᵃ group | —W—M— |
|---|---|---|---|---|---|
| 488 | CHF₂ | OH | phenyl | alanine-type | —(CH₂)₃—O—(CH₂)₅—O— |
| 489 | CHF₂ | OH | phenyl | alanine-type | —(CH₂)₃—CH=CH—CH₂—O— |
| 490 | CHF₂ | OH | phenyl | alanine-type | —C(CH₃)₂—CH₂—CH=CH—CH₂—O— |
| 491 | CHF₂ | OH | phenyl | alanine-type | —(CH₂)₃—cyclopropyl—(CH₂)₂—O— |
| 492 | CHF₂ | OH | phenyl | alanine-type | —(CH₂)₅—NH— |
| 493 | CHF₂ | OH | phenyl | alanine-type | —(CH₂)₆—NH— |
| 494 | CHF₂ | OH | phenyl | alanine-type | —(CH₂)₇—NH— |
| 495 | CHF₂ | OH | phenyl | alanine-type | —(CH₂)₅—C(O)NH— |
| 496 | CHF₂ | OH | phenyl | alanine-type | —(CH₂)₆—C(O)NH— |

TABLE 3-continued

| Example# | R²ᵃ | R²ᵇ | R⁶ | R⁷,R⁸ᵃ,R⁸ᵇ,N,C(O) group | —W—M— |
|---|---|---|---|---|---|
| 497 | CHF₂ | OH | phenyl | NH-CH(CH₃)-C(O) | —(CH₂)₇—C(O)NH— |
| 498 | CHF₂ | OH | phenyl | NH-CH(CH₃)-C(O) | —(CH₂)₃—N(CH₃)—(CH₂)₄—O— |
| 499 | CHF₂ | OH | phenyl | NH-CH(CH₃)-C(O) | —(CH₂)₃—S—(CH₂)₄—O— |
| 500 | CHF₂ | OH | phenyl | NH-CH(CH₃)-C(O) | —(CH₂)₆—OC(O)NH— |
| 501 | CHF₂ | OH | 1-naphthyl | NH-CH(CH₃)-C(O) | —(CH₂)₄—O— |
| 502 | CHF₂ | OH | 1-naphthyl | NH-CH(CH₃)-C(O) | —(CH₂)₅—O— |
| 503 | CHF₂ | OH | 1-naphthyl | NH-CH(CH₃)-C(O) | —(CH₂)₆—O— |
| 504 | CHF₂ | OH | 1-naphthyl | NH-CH(CH₃)-C(O) | —(CH₂)₇—O— |
| 505 | CHF₂ | OH | 1-naphthyl | NH-CH(CH₃)-C(O) | —(CH₂)₈—O— |

TABLE 3-continued

| Example# | R²ᵃ | R²ᵇ | R⁶ | R⁷R⁸ᵇR⁸ᵃ group | —W—M— |
|---|---|---|---|---|---|
| 506 | CHF₂ | OH | 1-naphthyl | NH-CH(CH₃)-C(=O) | gem-dimethyl alkyl-O |
| 507 | CHF₂ | OH | 1-naphthyl | NH-CH(CH₃)-C(=O) | CF₂-containing alkyl-O |
| 508 | CHF₂ | OH | 1-naphthyl | NH-CH(CH₃)-C(=O) | —(CH₂)₃—O—(CH₂)₅—O— |
| 509 | CHF₂ | OH | 1-naphthyl | NH-CH(CH₃)-C(=O) | alkenyl-O |
| 510 | CHF₂ | OH | 1-naphthyl | NH-CH(CH₃)-C(=O) | gem-dimethyl alkenyl-O |
| 511 | CHF₂ | OH | 1-naphthyl | NH-CH(CH₃)-C(=O) | cyclopropyl-containing alkyl-O |
| 512 | CHF₂ | OH | 1-naphthyl | NH-CH(CH₃)-C(=O) | —(CH₂)₅—NH— |
| 513 | CHF₂ | OH | 1-naphthyl | NH-CH(CH₃)-C(=O) | —(CH₂)₆—NH— |
| 514 | CHF₂ | OH | 1-naphthyl | NH-CH(CH₃)-C(=O) | —(CH₂)₇—NH— |

TABLE 3-continued
| Example # | $R^{2a}$ | $R^{2b}$ | $R^6$ | 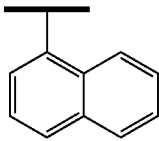 | —W—M— |
|---|---|---|---|---|---|
| 515 | $CHF_2$ | OH | 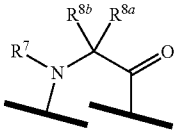 | 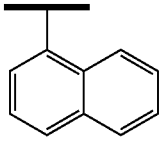 | —$(CH_2)_5$—C(O)NH— |
| 516 | $CHF_2$ | OH | 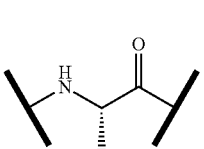 | 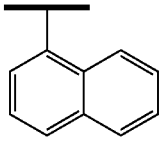 | —$(CH_2)_6$—C(O)NH— |
| 517 | $CHF_2$ | OH | 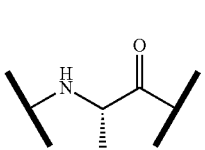 | 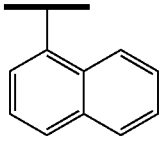 | —$(CH_2)_7$—C(O)NH— |
| 518 | $CHF_2$ | OH | 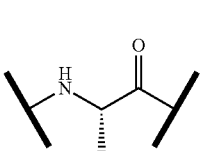 | 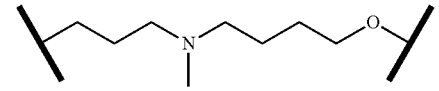 | 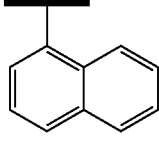 |
| 519 | $CHF_2$ | OH | 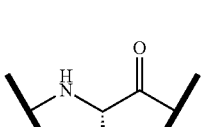 | 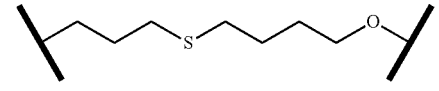 | 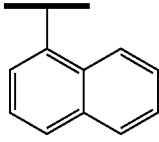 |
| 520 | $CHF_2$ | OH | 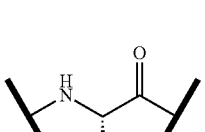 | 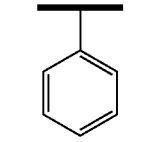 | —$(CH_2)_6$—OC(O)NH— |
| 521 | $CHF_2$ | F | 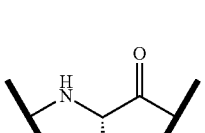 | 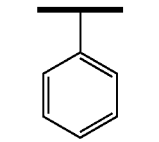 | —$(CH_2)_4$—O— |
| 522 | $CHF_2$ | F | 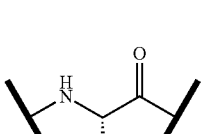 | 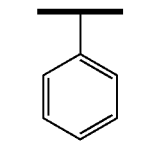 | —$(CH_2)_5$—O— |
| 523 | $CHF_2$ | F | 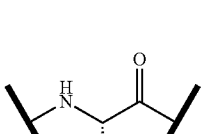 | | —$(CH_2)_6$—O— |

TABLE 3-continued
| Example# | R²ᵃ | R²ᵇ | R⁶ | 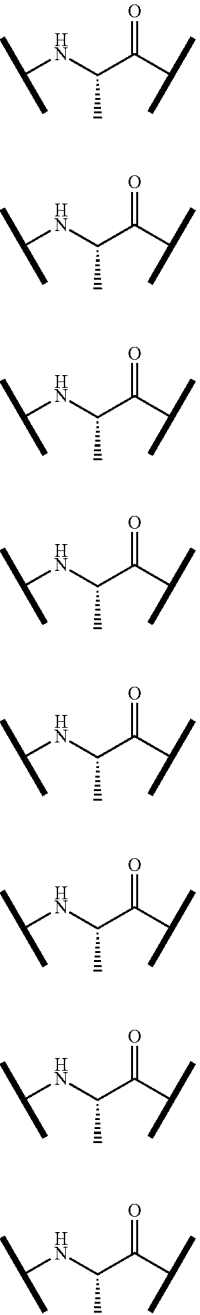 | —W—M— |
|---|---|---|---|---|---|
| 524 | CHF₂ | F | 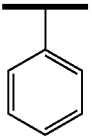 | 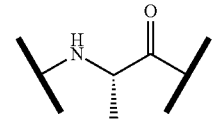 | —(CH₂)₇—O— |
| 525 | CHF₂ | F | 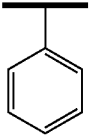 | 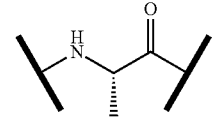 | —(CH₂)₈—O— |
| 526 | CHF₂ | F | 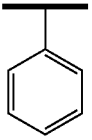 | 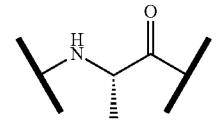 | 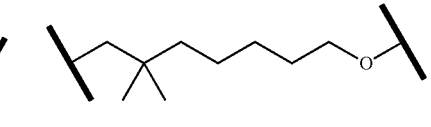 |
| 527 | CHF₂ | F | 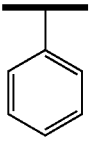 | 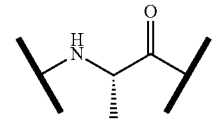 | 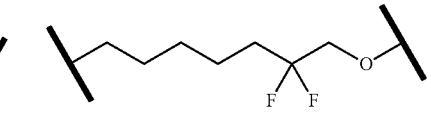 |
| 528 | CHF₂ | F | 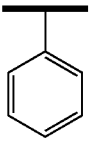 | 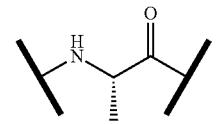 | —(CH₂)₃—O—(CH₂)₅—O— |
| 529 | CHF₂ | F | 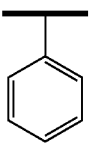 | 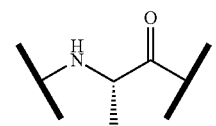 | 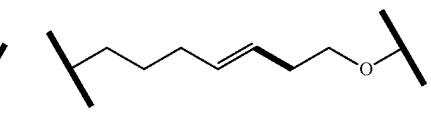 |
| 530 | CHF₂ | F | 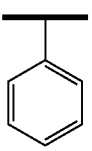 | 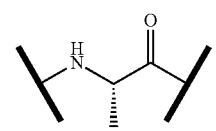 | 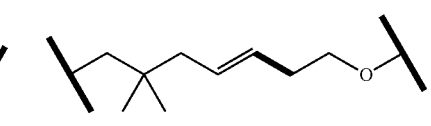 |
| 531 | CHF₂ | F | 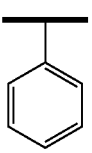 | 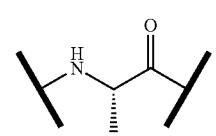 | 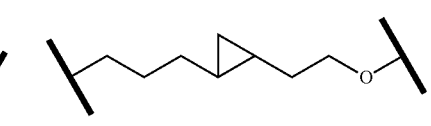 |
| 532 | CHF₂ | F | 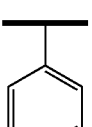 | 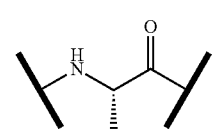 | —(CH₂)₅—NH— |

TABLE 3-continued

| Example# | $R^{2a}$ | $R^{2b}$ | $R^6$ | (R⁷R⁸ᵇR⁸ᵃ N-C-C(=O) group) | —W—M— |
|---|---|---|---|---|---|
| 533 | $CHF_2$ | F | phenyl | NH-CH(CH₃)-C(O) | —$(CH_2)_6$—NH— |
| 534 | $CHF_2$ | F | phenyl | NH-CH(CH₃)-C(O) | —$(CH_2)_7$—NH— |
| 535 | $CHF_2$ | F | phenyl | NH-CH(CH₃)-C(O) | —$(CH_2)_5$—C(O)NH— |
| 536 | $CHF_2$ | F | phenyl | NH-CH(CH₃)-C(O) | —$(CH_2)_6$—C(O)NH— |
| 537 | $CHF_2$ | F | phenyl | NH-CH(CH₃)-C(O) | —$(CH_2)_7$—C(O)NH— |
| 538 | $CHF_2$ | F | phenyl | NH-CH(CH₃)-C(O) | —(CH₂)₃—N(CH₃)—(CH₂)₃—O— |
| 539 | $CHF_2$ | F | phenyl | NH-CH(CH₃)-C(O) | —(CH₂)₃—S—(CH₂)₃—O— |
| 540 | $CHF_2$ | F | phenyl | NH-CH(CH₃)-C(O) | —$(CH_2)_6$—OC(O)NH— |
| 541 | $CHF_2$ | F | naphthyl | NH-CH(CH₃)-C(O) | —$(CH_2)_4$—O— |

TABLE 3-continued
| Example# | $R^{2a}$ | $R^{2b}$ | $R^6$ | $R^7, R^{8a}, R^{8b}$ group | —W—M— |
|---|---|---|---|---|---|
| 542 | $CHF_2$ | F | 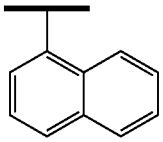 | 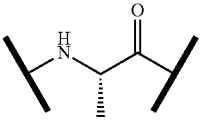 | $-(CH_2)_5-O-$ |
| 543 | $CHF_2$ | F | 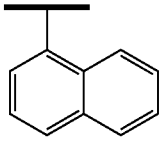 | 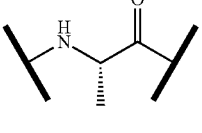 | $-(CH_2)_6-O-$ |
| 544 | $CHF_2$ | F | 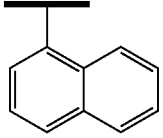 | 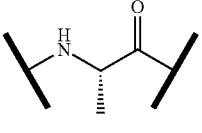 | $-(CH_2)_7-O-$ |
| 545 | $CHF_2$ | F | 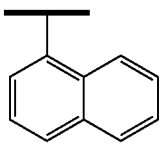 | 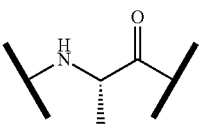 | $-(CH_2)_8-O-$ |
| 546 | $CHF_2$ | F | 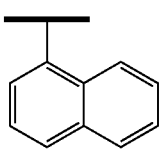 | 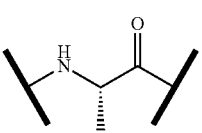 | 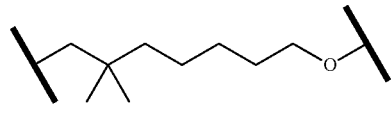 |
| 547 | $CHF_2$ | F | 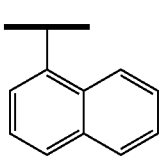 | 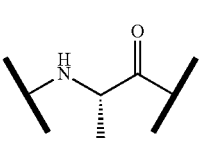 | 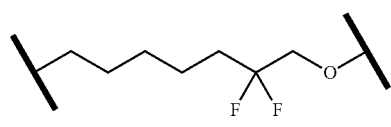 |
| 548 | $CHF_2$ | F | 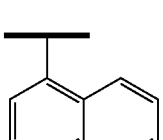 | 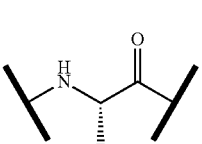 | $-(CH_2)_3-O-(CH_2)_5-O-$ |
| 549 | $CHF_2$ | F | 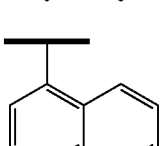 | 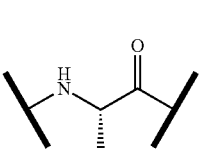 | 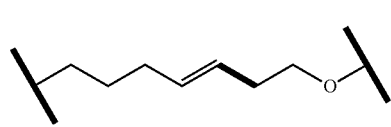 |
| 550 | $CHF_2$ | F | 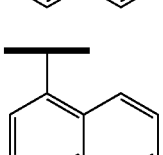 | 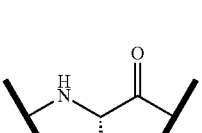 | 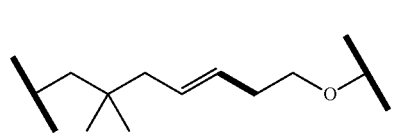 |

TABLE 3-continued

| Example# | R2a | R2b | R6 | (R7, R8a, R8b group) | —W—M— |
|---|---|---|---|---|---|
| 551 | CHF2 | F | 1-naphthyl | NH-CH(CH3)-C(O) | cyclopropyl-containing chain with O |
| 552 | CHF2 | F | 1-naphthyl | NH-CH(CH3)-C(O) | —(CH2)5—NH— |
| 553 | CHF2 | F | 1-naphthyl | NH-CH(CH3)-C(O) | —(CH2)6—NH— |
| 554 | CHF2 | F | 1-naphthyl | NH-CH(CH3)-C(O) | —(CH2)7—NH— |
| 555 | CHF2 | F | 1-naphthyl | NH-CH(CH3)-C(O) | —(CH2)5—C(O)NH— |
| 556 | CHF2 | F | 1-naphthyl | NH-CH(CH3)-C(O) | —(CH2)6—C(O)NH— |
| 557 | CHF2 | F | 1-naphthyl | NH-CH(CH3)-C(O) | —(CH2)7—C(O)NH— |
| 558 | CHF2 | F | 1-naphthyl | NH-CH(CH3)-C(O) | —(CH2)3—N(CH3)—(CH2)4—O— |
| 559 | CHF2 | F | 1-naphthyl | NH-CH(CH3)-C(O) | —(CH2)3—S—(CH2)3—O— |

TABLE 3-continued
| Example# | $R^{2a}$ | $R^{2b}$ | $R^6$ | 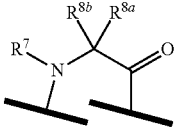 | —W—M— |
|---|---|---|---|---|---|
| 560 | CHF$_2$ | F | 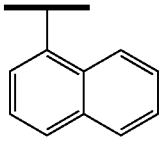 | 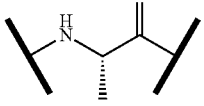 | —(CH$_2$)$_6$—OC(O)NH— |
| 561 | Me | OH | 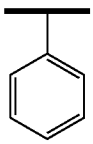 | 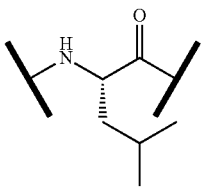 | —(CH$_2$)$_4$—O— |
| 562 | Me | OH | 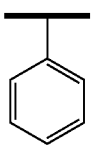 | 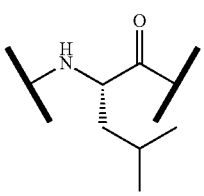 | —(CH$_2$)$_5$—O— |
| 563 | Me | OH | 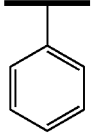 | 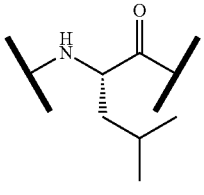 | —(CH$_2$)$_6$—O— |
| 564 | Me | OH | 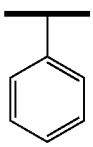 | 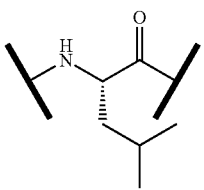 | —(CH$_2$)$_7$—O— |
| 565 | Me | OH | 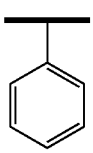 | 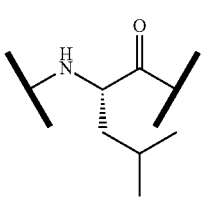 | —(CH$_2$)$_8$—O— |
| 566 | Me | OH | 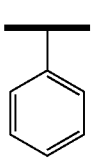 | 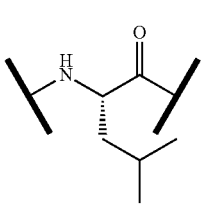 | 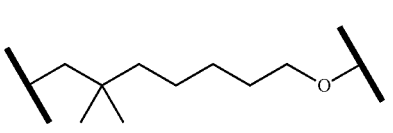 |

TABLE 3-continued
| Example# | $R^{2a}$ | $R^{2b}$ | $R^6$ | (R⁷R⁸ᵇR⁸ᵃ N-C-C(=O) group) | —W—M— |
|---|---|---|---|---|---|
| 567 | Me | OH | 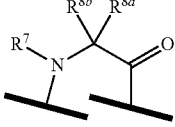 | 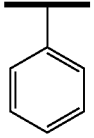 | 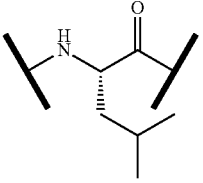 |
| 568 | Me | OH | 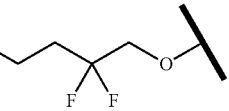 | 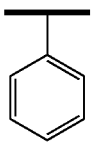 | —(CH$_2$)$_3$—O—(CH$_2$)$_5$—O— |
| 569 | Me | OH | 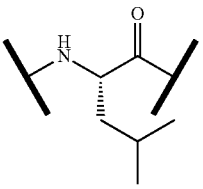 | 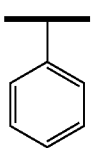 | 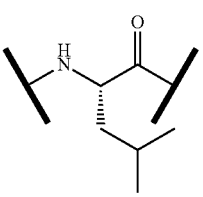 |
| 570 | Me | OH | 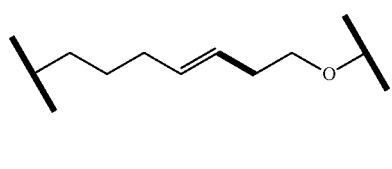 | 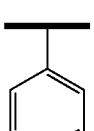 | 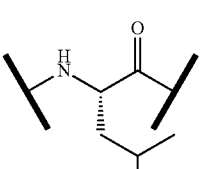 |
| 571 | Me | OH | 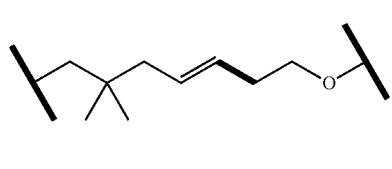 | 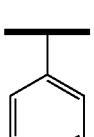 | 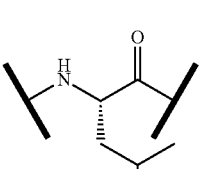 |
| 572 | Me | OH | 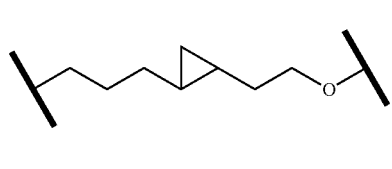 | 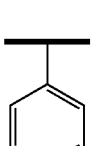 | —(CH$_2$)$_5$—NH— |
| 573 | Me | OH | 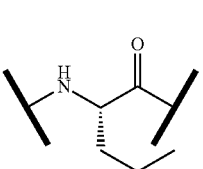 | 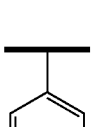 | —(CH$_2$)$_6$—NH— |

TABLE 3-continued
| Example# | $R^{2a}$ | $R^{2b}$ | $R^6$ | $R^7R^{8b}R^{8a}$ structure | —W—M— |
|---|---|---|---|---|---|
| 574 | Me | OH | 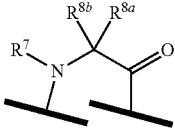 | 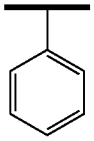 | —(CH$_2$)$_7$—NH— |
| 575 | Me | OH | 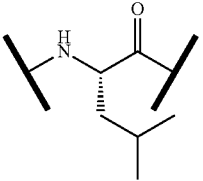 | 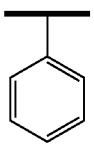 | —(CH$_2$)$_5$—C(O)NH— |
| 576 | Me | OH | 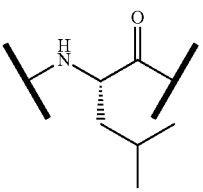 | 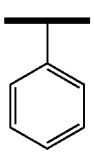 | —(CH$_2$)$_6$—C(O)NH— |
| 577 | Me | OH | 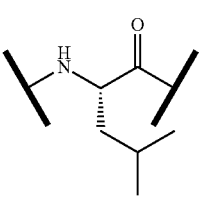 | 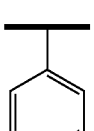 | —(CH$_2$)$_7$—C(O)NH— |
| 578 | Me | OH | 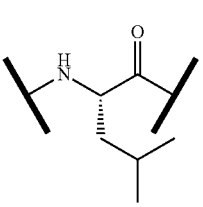 | 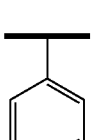 | 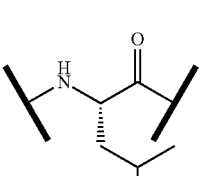 |
| 579 | Me | OH | 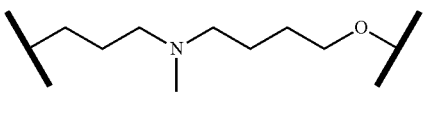 |  | 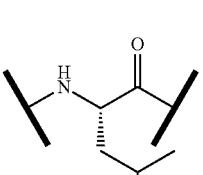 |
| 580 | Me | OH | 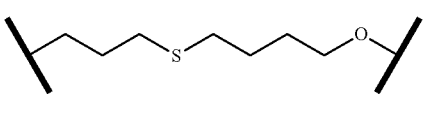 | 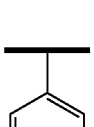 | —(CH$_2$)$_6$—OC(O)NH— |

TABLE 3-continued

| Example# | R2a | R2b | R6 | (R7R8bR8a N-CO group) | —W—M— |
|---|---|---|---|---|---|
| 581 | Me | F | phenyl | leucine | —(CH$_2$)$_4$—O— |
| 582 | Me | F | phenyl | leucine | —(CH$_2$)$_5$—O— |
| 583 | Me | F | phenyl | leucine | —(CH$_2$)$_6$—O— |
| 584 | Me | F | phenyl | leucine | —(CH$_2$)$_7$—O— |
| 585 | Me | F | phenyl | leucine | —(CH$_2$)$_8$—O— |
| 586 | Me | F | phenyl | leucine | gem-dimethyl alkyl-O— |
| 587 | Me | F | phenyl | leucine | gem-difluoro alkyl-O— |

TABLE 3-continued
| Example# | R$^{2a}$ | R$^{2b}$ | R$^6$ | $\underset{R^7}{\overset{R^{8b}}{\underset{N}{\bigvee}}}\overset{R^{8a}}{\underset{}{\bigvee}}\overset{O}{\underset{}{\bigvee}}$ | —W—M— |
|---|---|---|---|---|---|
| 588 | Me | F | 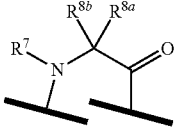 | 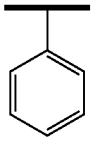 | —(CH$_2$)$_3$—O—(CH$_2$)$_5$—O— |
| 589 | Me | F | 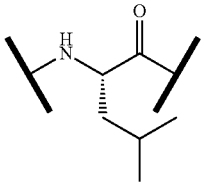 | 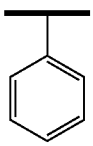 | 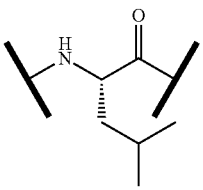 |
| 590 | Me | F | 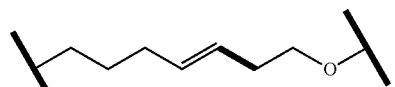 | 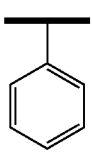 | 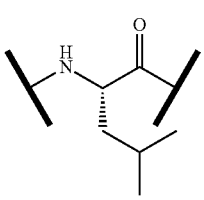 |
| 591 | Me | F | 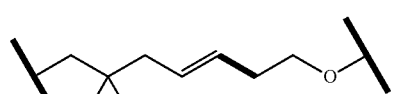 | 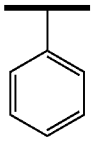 | 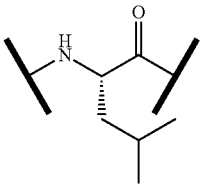 |
| 592 | Me | F |  | 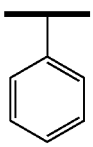 | —(CH$_2$)$_5$—NH— |
| 593 | Me | F | 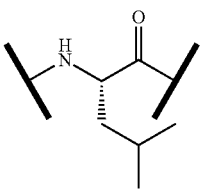 | 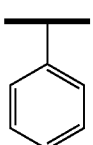 | —(CH$_2$)$_6$—NH— |
| 594 | Me | F | 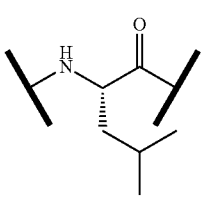 | 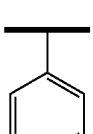 | —(CH$_2$)$_7$—NH— |

TABLE 3-continued
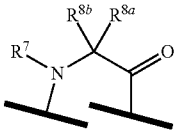
| Example# | R2a | R2b | R6 | | —W—M— |
|---|---|---|---|---|---|
| 595 | Me | F | | | —(CH₂)₅—C(O)NH— |
| 596 | Me | F | | | —(CH₂)₆—C(O)NH— |
| 597 | Me | F | | | —(CH₂)₇—C(O)NH— |
| 598 | Me | F | | | |
| 599 | Me | F | | | |
| 600 | Me | F | | | —(CH₂)₆—OC(O)NH— | and;

(d) compounds of Formula X,

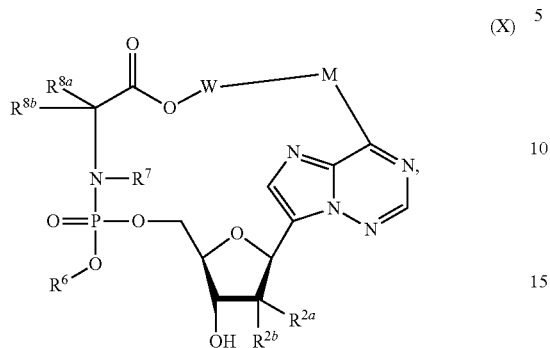

wherein, $R^{2a}$, $R^{2b}$, $R^6$, $R^7$, $R^{8a}$, $R^{8b}$ and —W-M- are delineated for each compound Table 4, or a pharmaceutically acceptable salt, ester or solvate thereof,

TABLE 4

| Example # | $R^{2a}$ | $R^{2b}$ | $R^6$ | $R^{8b}R^{8a}$ / $R^7$-N | —W—M— |
|---|---|---|---|---|---|
| 601 | Me | OH | phenyl-CH2- | L-Ala | —(CH$_2$)$_4$—O— |
| 602 | Me | OH | phenyl-CH2- | L-Ala | —(CH$_2$)$_5$—O— |
| 603 | Me | OH | phenyl-CH2- | L-Ala | —(CH$_2$)$_6$—O— |
| 604 | Me | OH | phenyl-CH2- | L-Ala | —(CH$_2$)$_7$—O— |
| 605 | Me | OH | phenyl-CH2- | L-Ala | —(CH$_2$)$_8$—O— |

TABLE 4-continued

| Example # | R$^{2a}$ | R$^{2b}$ | R$^6$ | (R$^7$, R$^{8a}$, R$^{8b}$ group) | —W—M— |
|---|---|---|---|---|---|
| 606 | Me | OH | phenyl | -NH-CH(CH$_3$)-C(O)- | gem-dimethyl alkyl-O- chain |
| 607 | Me | OH | phenyl | -NH-CH(CH$_3$)-C(O)- | -CF$_2$- containing alkyl-O- chain |
| 608 | Me | OH | phenyl | -NH-CH(CH$_3$)-C(O)- | —(CH$_2$)$_3$—O—(CH$_2$)$_5$—O— |
| 609 | Me | OH | phenyl | -NH-CH(CH$_3$)-C(O)- | alkenyl-O- chain |
| 610 | Me | OH | phenyl | -NH-CH(CH$_3$)-C(O)- | gem-dimethyl alkenyl-O- chain |
| 611 | Me | OH | phenyl | -NH-CH(CH$_3$)-C(O)- | cyclopropyl-containing alkyl-O- chain |
| 612 | Me | OH | phenyl | -NH-CH(CH$_3$)-C(O)- | —(CH$_2$)$_5$—NH— |
| 613 | Me | OH | phenyl | -NH-CH(CH$_3$)-C(O)- | —(CH$_2$)$_6$—NH— |
| 614 | Me | OH | phenyl | -NH-CH(CH$_3$)-C(O)- | —(CH$_2$)$_7$—NH— |

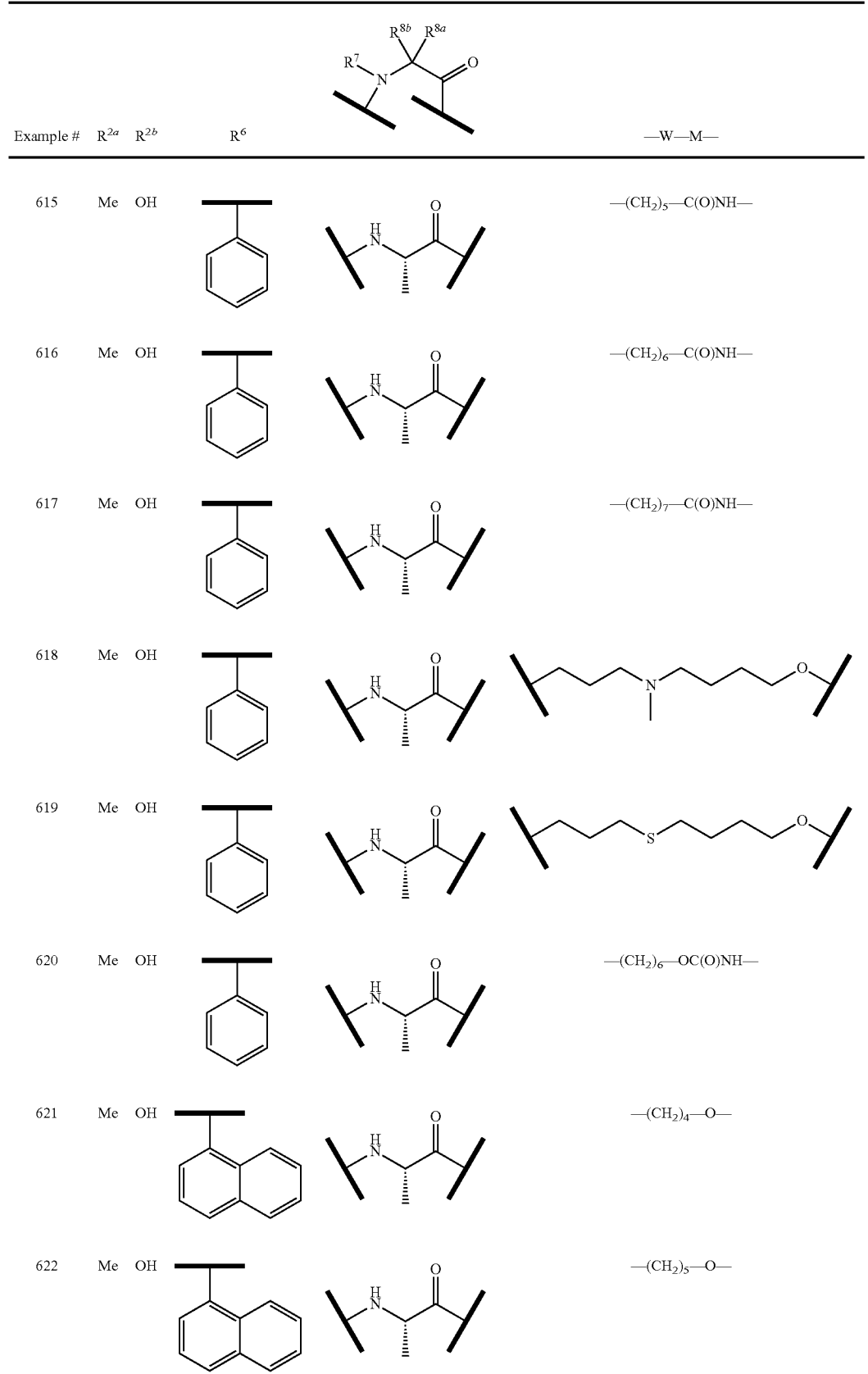

TABLE 4-continued

| Example # | R$^{2a}$ | R$^{2b}$ | R$^6$ | $\begin{array}{c}R^{8b}\ R^{8a}\\R^7\diagdown\!\!\!\!\diagup\!\!\!\!\diagdown\!\!\!\!\diagup O\\N\end{array}$ | —W—M— |
|---|---|---|---|---|---|
| 623 | Me | OH | 1-naphthyl | N-H, CH(Me), C=O (L-Ala) | —(CH$_2$)$_6$—O— |
| 624 | Me | OH | 1-naphthyl | N-H, CH(Me), C=O (L-Ala) | —(CH$_2$)$_7$—O— |
| 625 | Me | OH | 1-naphthyl | N-H, CH(Me), C=O (L-Ala) | —(CH$_2$)$_8$—O— |
| 626 | Me | OH | 1-naphthyl | N-H, CH(Me), C=O (L-Ala) | —C(Me)$_2$(CH$_2$)$_4$CH$_2$—O— |
| 627 | Me | OH | 1-naphthyl | N-H, CH(Me), C=O (L-Ala) | —(CH$_2$)$_5$CF$_2$CH$_2$—O— |
| 628 | Me | OH | 1-naphthyl | N-H, CH(Me), C=O (L-Ala) | —(CH$_2$)$_3$—O—(CH$_2$)$_5$—O— |
| 629 | Me | OH | 1-naphthyl | N-H, CH(Me), C=O (L-Ala) | —(CH$_2$)$_3$CH=CHCH$_2$CH$_2$—O— (trans) |
| 630 | Me | OH | 1-naphthyl | N-H, CH(Me), C=O (L-Ala) | —C(Me)$_2$CH$_2$CH=CHCH$_2$CH$_2$—O— (trans) |
| 631 | Me | OH | 1-naphthyl | N-H, CH(Me), C=O (L-Ala) | —(CH$_2$)$_3$-(cyclopropyl)-CH$_2$CH$_2$—O— |

TABLE 4-continued
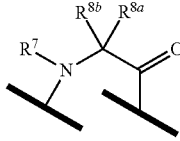
| Example # | R²ᵃ | R²ᵇ | R⁶ | | —W—M— |
|---|---|---|---|---|---|
| 632 | Me | OH | 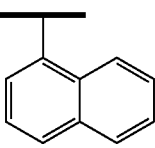 | 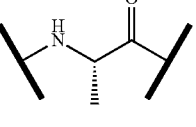 | —(CH₂)₅—NH— |
| 633 | Me | OH | 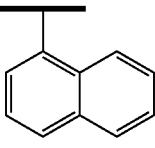 | 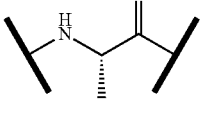 | —(CH₂)₆—NH— |
| 634 | Me | OH | 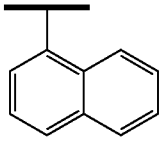 | 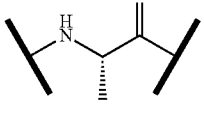 | —(CH₂)₇—NH— |
| 635 | Me | OH | 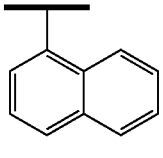 | 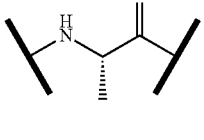 | —(CH₂)₅—C(O)NH— |
| 636 | Me | OH | 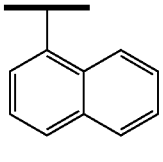 | 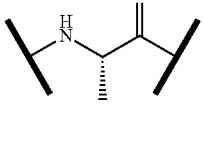 | —(CH₂)₆—C(O)NH— |
| 637 | Me | OH | 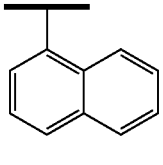 | 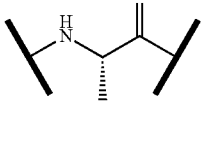 | —(CH₂)₇—C(O)NH— |
| 638 | Me | OH | 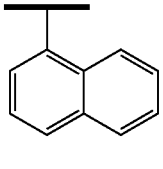 | 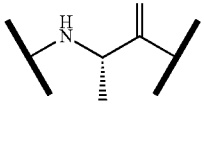 | 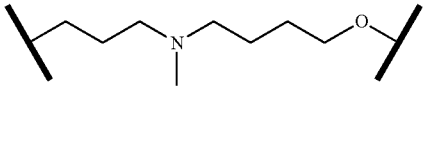 |
| 639 | Me | OH | 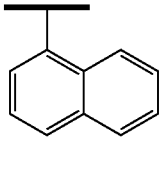 | 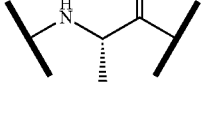 | 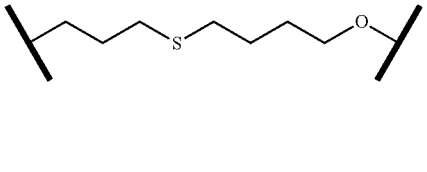 |

TABLE 4-continued
| Example # | R²ᵃ | R²ᵇ | R⁶ | | —W—M— |
|---|---|---|---|---|---|
| 640 | Me | OH |  |  | —(CH₂)₆—OC(O)NH— |
| 641 | Me | F |  | 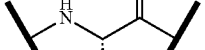 | —(CH₂)₄—O— |
| 642 | Me | F |  |  | —(CH₂)₅—O— |
| 643 | Me | F |  |  | —(CH₂)₆—O— |
| 644 | Me | F |  |  | —(CH₂)₇—O— |
| 645 | Me | F |  |  | —(CH₂)₈—O— |
| 646 | Me | F |  |  |  |
| 647 | Me | F |  |  | 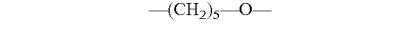 |
| 648 | Me | F |  |  | —(CH₂)₃—O—(CH₂)₅—O— |

TABLE 4-continued
| Example # | R²ᵃ | R²ᵇ | R⁶ | | —W—M— |
|---|---|---|---|---|---|
| 649 | Me | F | 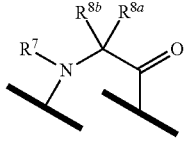 | 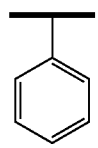 | 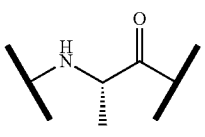 |
| 650 | Me | F | 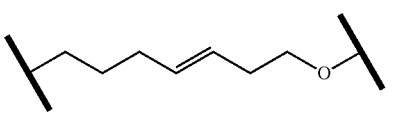 | 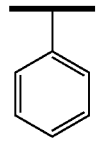 | 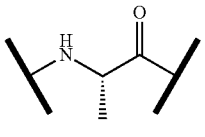 |
| 651 | Me | F | 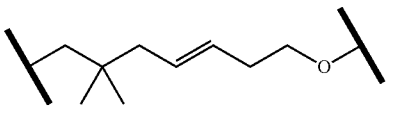 | 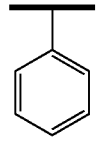 | 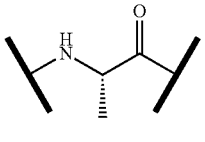 |
| 652 | Me | F | 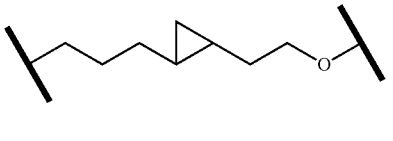 | 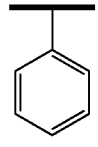 | —(CH$_2$)$_5$—NH— |
| 653 | Me | F | 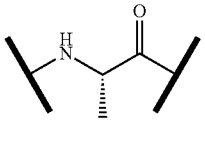 | 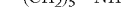 | —(CH$_2$)$_6$—NH— |
| 654 | Me | F | 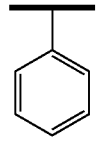 | 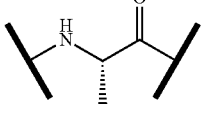 | —(CH$_2$)$_7$—NH— |
| 655 | Me | F | 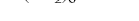 | 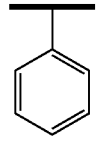 | —(CH$_2$)$_5$—C(O)NH— |
| 656 | Me | F | 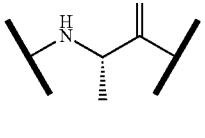 |  | —(CH$_2$)$_6$—C(O)NH— |

TABLE 4-continued

| Example # | R²ᵃ | R²ᵇ | R⁶ | | —W—M— |
|---|---|---|---|---|---|
| 657 | Me | F | phenyl | alanine | —(CH₂)₇—C(O)NH— |
| 658 | Me | F | phenyl | alanine | —(CH₂)₃—N(CH₃)—(CH₂)₄—O— |
| 659 | Me | F | phenyl | alanine | —(CH₂)₃—S—(CH₂)₄—O— |
| 660 | Me | F | phenyl | alanine | —(CH₂)₆—OC(O)NH— |
| 661 | Me | F | naphth-1-yl | alanine | —(CH₂)₄—O— |
| 662 | Me | F | naphth-1-yl | alanine | —(CH₂)₅—O— |
| 663 | Me | F | naphth-1-yl | alanine | —(CH₂)₆—O— |
| 664 | Me | F | naphth-1-yl | alanine | —(CH₂)₇—O— |
| 665 | Me | F | naphth-1-yl | alanine | —(CH₂)₈—O— |

TABLE 4-continued
| Example # | R2a | R2b | R6 | 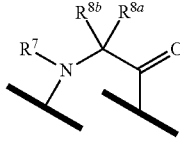 | —W—M— |
|---|---|---|---|---|---|
| 666 | Me | F | 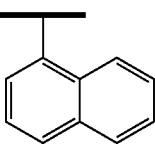 | 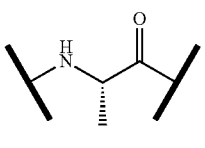 | 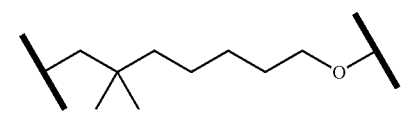 |
| 667 | Me | F | 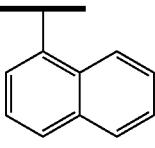 | 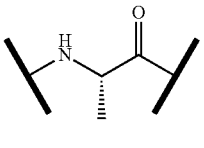 | 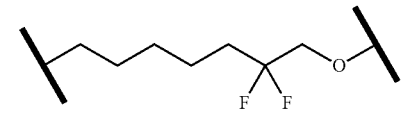 |
| 668 | Me | F | 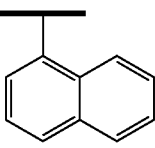 | 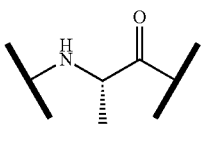 | —(CH$_2$)$_3$—O—(CH$_2$)$_5$—O— |
| 669 | Me | F | 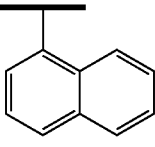 | 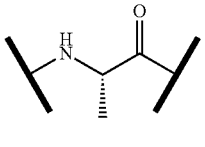 | 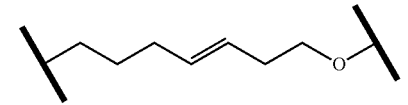 |
| 670 | Me | F | 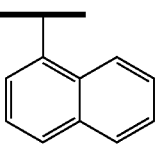 | 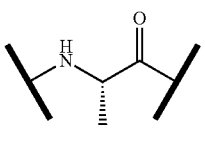 | 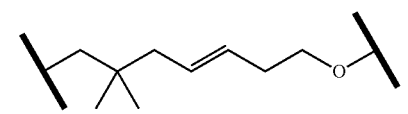 |
| 671 | Me | F | 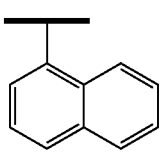 | 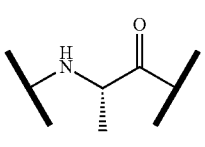 | 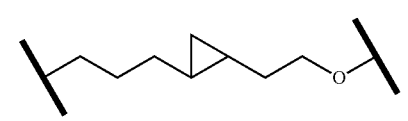 |
| 672 | Me | F | 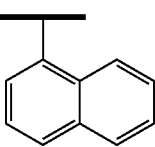 | 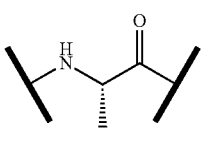 | —(CH$_2$)$_5$—NH— |
| 673 | Me | F | 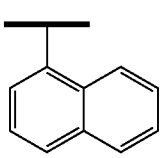 | 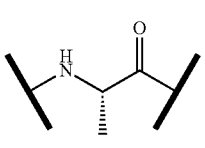 | —(CH$_2$)$_6$—NH— |

TABLE 4-continued

| Example # | R2a | R2b | R6 | | —W—M— |
|---|---|---|---|---|---|
| 674 | Me | F | 1-naphthyl | NH-CH(CH3)-C(O) | —(CH2)7—NH— |
| 675 | Me | F | 1-naphthyl | NH-CH(CH3)-C(O) | —(CH2)5—C(O)NH— |
| 676 | Me | F | 1-naphthyl | NH-CH(CH3)-C(O) | —(CH2)6—C(O)NH— |
| 677 | Me | F | 1-naphthyl | NH-CH(CH3)-C(O) | —(CH2)7—C(O)NH— |
| 678 | Me | F | 1-naphthyl | NH-CH(CH3)-C(O) | —(CH2)3—N(CH3)—(CH2)4—O— |
| 679 | Me | F | 1-naphthyl | NH-CH(CH3)-C(O) | —(CH2)3—S—(CH2)4—O— |
| 680 | Me | F | 1-naphthyl | NH-CH(CH3)-C(O) | —(CH2)6—OC(O)NH— |
| 681 | CHF2 | OH | phenyl | NH-CH(CH3)-C(O) | —(CH2)4—O— |
| 682 | CHF2 | OH | phenyl | NH-CH(CH3)-C(O) | —(CH2)5—O— |

TABLE 4-continued

| Example # | $R^{2a}$ | $R^{2b}$ | $R^6$ | | —W—M— |
|---|---|---|---|---|---|
| 683 | $CHF_2$ | OH | phenyl | NH-CH(CH₃)-C(=O) | $-(CH_2)_6-O-$ |
| 684 | $CHF_2$ | OH | phenyl | NH-CH(CH₃)-C(=O) | $-(CH_2)_7-O-$ |
| 685 | $CHF_2$ | OH | phenyl | NH-CH(CH₃)-C(=O) | $-(CH_2)_8-O-$ |
| 686 | $CHF_2$ | OH | phenyl | NH-CH(CH₃)-C(=O) | gem-dimethyl alkyl ether |
| 687 | $CHF_2$ | OH | phenyl | NH-CH(CH₃)-C(=O) | gem-difluoro alkyl ether |
| 688 | $CHF_2$ | OH | phenyl | NH-CH(CH₃)-C(=O) | $-(CH_2)_3-O-(CH_2)_5-O-$ |
| 689 | $CHF_2$ | OH | phenyl | NH-CH(CH₃)-C(=O) | alkenyl ether |
| 690 | $CHF_2$ | OH | phenyl | NH-CH(CH₃)-C(=O) | gem-dimethyl alkenyl ether |

TABLE 4-continued

| Example # | $R^{2a}$ | $R^{2b}$ | $R^6$ | | —W—M— |
|---|---|---|---|---|---|
| 691 | $CHF_2$ | OH | phenyl | NH-CH(CH3)-C(O) | cyclopropyl-CH2CH2-O linker |
| 692 | $CHF_2$ | OH | phenyl | NH-CH(CH3)-C(O) | —(CH$_2$)$_5$—NH— |
| 693 | $CHF_2$ | OH | phenyl | NH-CH(CH3)-C(O) | —(CH$_2$)$_6$—NH— |
| 694 | $CHF_2$ | OH | phenyl | NH-CH(CH3)-C(O) | —(CH$_2$)$_7$—NH— |
| 695 | $CHF_2$ | OH | phenyl | NH-CH(CH3)-C(O) | —(CH$_2$)$_5$—C(O)NH— |
| 696 | $CHF_2$ | OH | phenyl | NH-CH(CH3)-C(O) | —(CH$_2$)$_6$—C(O)NH— |
| 697 | $CHF_2$ | OH | phenyl | NH-CH(CH3)-C(O) | —(CH$_2$)$_7$—C(O)NH— |
| 698 | $CHF_2$ | OH | phenyl | NH-CH(CH3)-C(O) | —(CH$_2$)$_3$—N(CH$_3$)—(CH$_2$)$_4$—O— |
| 699 | $CHF_2$ | OH | phenyl | NH-CH(CH3)-C(O) | —(CH$_2$)$_3$—S—(CH$_2$)$_3$—O— |

TABLE 4-continued

| Example # | R2a | R2b | R6 | | —W—M— |
|---|---|---|---|---|---|
| 700 | CHF2 | OH | phenyl | N-CH(CH3)-C(O) | —(CH2)6—OC(O)NH— |
| 701 | CHF2 | OH | 1-naphthyl | N-CH(CH3)-C(O) | —(CH2)4—O— |
| 702 | CHF2 | OH | 1-naphthyl | N-CH(CH3)-C(O) | —(CH2)5—O— |
| 703 | CHF2 | OH | 1-naphthyl | N-CH(CH3)-C(O) | —(CH2)6—O— |
| 704 | CHF2 | OH | 1-naphthyl | N-CH(CH3)-C(O) | —(CH2)7—O— |
| 705 | CHF2 | OH | 1-naphthyl | N-CH(CH3)-C(O) | —(CH2)8—O— |
| 706 | CHF2 | OH | 1-naphthyl | N-CH(CH3)-C(O) | —C(CH3)2(CH2)4CH2O— |
| 707 | CHF2 | OH | 1-naphthyl | N-CH(CH3)-C(O) | —CH2(CH2)4CF2CH2O— |

TABLE 4-continued

| Example # | $R^{2a}$ | $R^{2b}$ | $R^6$ | (R7, R8a, R8b group) | —W—M— |
|---|---|---|---|---|---|
| 708 | $CHF_2$ | OH | 1-naphthyl | NH-Ala | $-(CH_2)_3-O-(CH_2)_5-O-$ |
| 709 | $CHF_2$ | OH | 1-naphthyl | NH-Ala | (alkenyl ether) |
| 710 | $CHF_2$ | OH | 1-naphthyl | NH-Ala | (gem-dimethyl alkenyl ether) |
| 711 | $CHF_2$ | OH | 1-naphthyl | NH-Ala | (cyclopropyl alkyl ether) |
| 712 | $CHF_2$ | OH | 1-naphthyl | NH-Ala | $-(CH_2)_5-NH-$ |
| 713 | $CHF_2$ | OH | 1-naphthyl | NH-Ala | $-(CH_2)_6-NH-$ |
| 714 | $CHF_2$ | OH | 1-naphthyl | NH-Ala | $-(CH_2)_7-NH-$ |
| 715 | $CHF_2$ | OH | 1-naphthyl | NH-Ala | $-(CH_2)_5-C(O)NH-$ |
| 716 | $CHF_2$ | OH | 1-naphthyl | NH-Ala | $-(CH_2)_6-C(O)NH-$ |

TABLE 4-continued
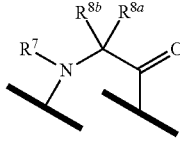
| Example # | R²ᵃ | R²ᵇ | R⁶ | | —W—M— |
|---|---|---|---|---|---|
| 717 | CHF₂ | OH | 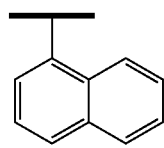 | 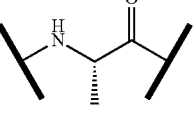 | —(CH₂)₇—C(O)NH— |
| 718 | CHF₂ | OH | 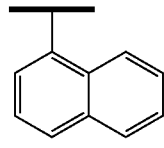 | 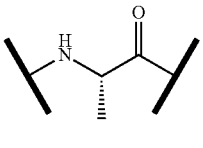 | 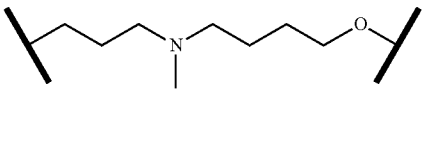 |
| 719 | CHF₂ | OH | 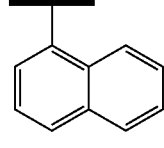 | 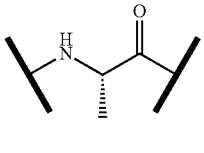 | 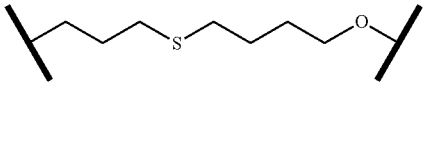 |
| 720 | CHF₂ | OH | 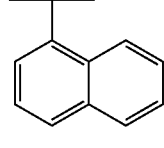 | 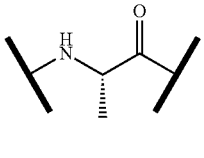 | —(CH₂)₆—OC(O)NH— |
| 721 | CHF₂ | F | 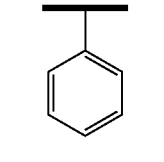 | 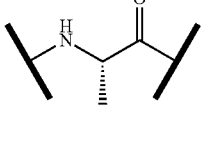 | —(CH₂)₄—O— |
| 722 | CHF₂ | F | 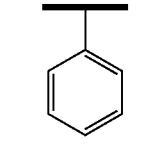 | 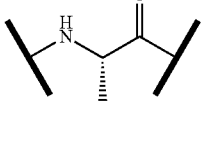 | —(CH₂)₅—O— |
| 723 | CHF₂ | F | 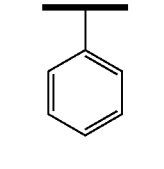 | 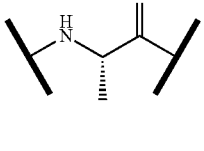 | —(CH₂)₆—O— |
| 724 | CHF₂ | F | 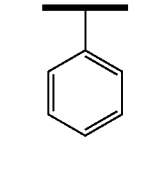 | 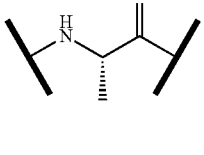 | —(CH₂)₇—O— |

TABLE 4-continued
| Example # | R²ᵃ | R²ᵇ | R⁶ | 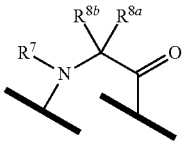 | —W—M— |
|---|---|---|---|---|---|
| 725 | CHF₂ | F | 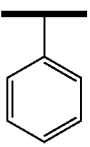 | 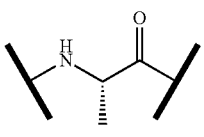 | —(CH₂)₈—O— |
| 726 | CHF₂ | F | 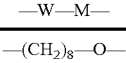 | 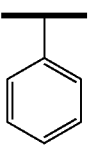 | 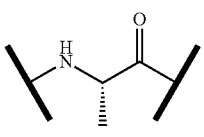 |
| 727 | CHF₂ | F | 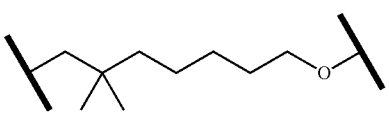 | 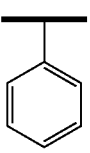 | 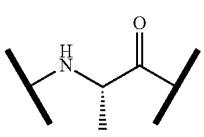 |
| 728 | CHF₂ | F | 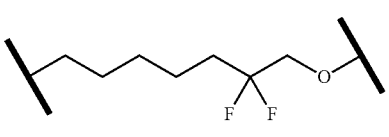 | 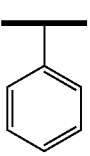 | —(CH₂)₃—O—(CH₂)₅—O— |
| 729 | CHF₂ | F | 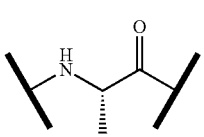 | 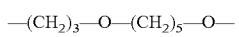 | 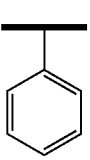 |
| 730 | CHF₂ | F | 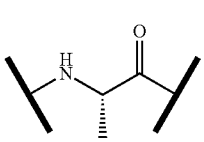 | 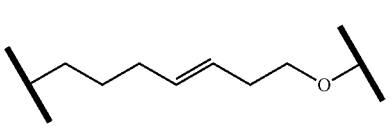 | 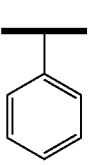 |
| 731 | CHF₂ | F | 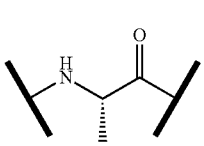 | 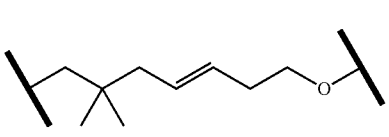 | 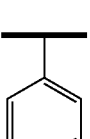 |
| 732 | CHF₂ | F | 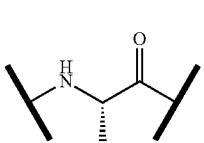 | 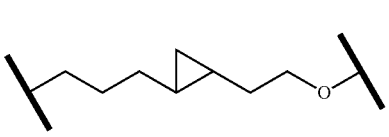 | —(CH₂)₅—NH— |
| 733 | CHF₂ | F | 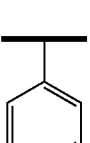 | 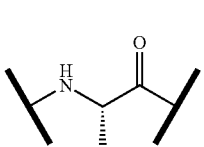 | —(CH₂)₆—NH— |

TABLE 4-continued

| Example # | R²ᵃ | R²ᵇ | R⁶ | | —W—M— |
|---|---|---|---|---|---|
| 734 | CHF₂ | F | phenyl | NH-CH(CH₃)-C(O) | —(CH₂)₇—NH— |
| 735 | CHF₂ | F | phenyl | NH-CH(CH₃)-C(O) | —(CH₂)₅—C(O)NH— |
| 736 | CHF₂ | F | phenyl | NH-CH(CH₃)-C(O) | —(CH₂)₆—C(O)NH— |
| 737 | CHF₂ | F | phenyl | NH-CH(CH₃)-C(O) | —(CH₂)₇—C(O)NH— |
| 738 | CHF₂ | F | phenyl | NH-CH(CH₃)-C(O) | —(CH₂)₃—N(CH₃)—(CH₂)₄—O— |
| 739 | CHF₂ | F | phenyl | NH-CH(CH₃)-C(O) | —(CH₂)₃—S—(CH₂)₄—O— |
| 740 | CHF₂ | F | phenyl | NH-CH(CH₃)-C(O) | —(CH₂)₆—OC(O)NH— |
| 741 | CHF₂ | F | naphthyl | NH-CH(CH₃)-C(O) | —(CH₂)₄—O— |

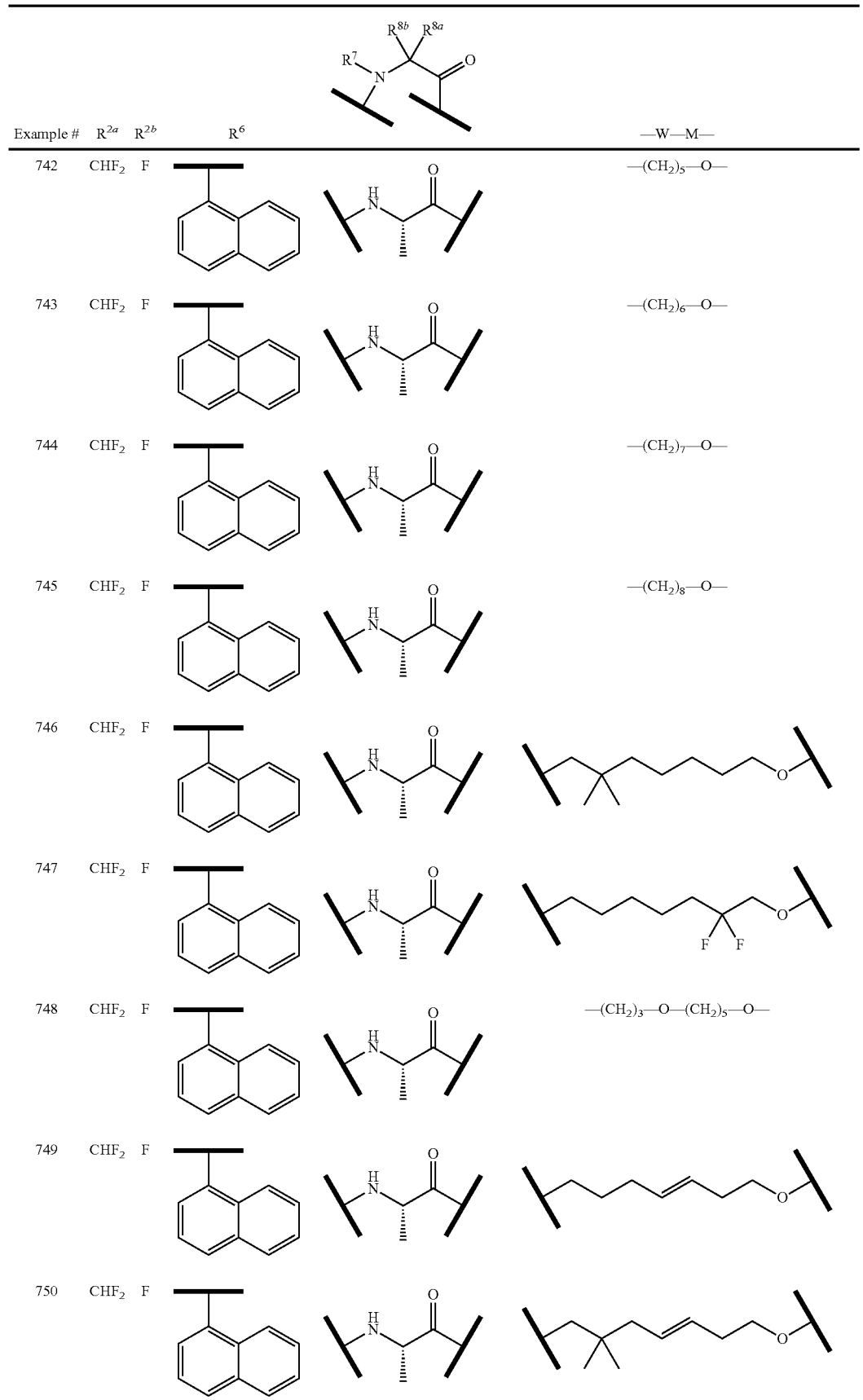

TABLE 4-continued
| Example # | R²ᵃ | R²ᵇ | R⁶ | 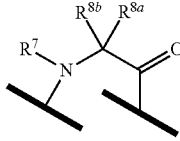 | —W—M— |
|---|---|---|---|---|---|
| 751 | CHF₂ | F | 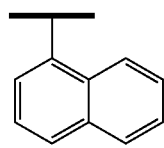 | 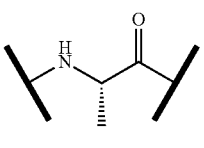 | 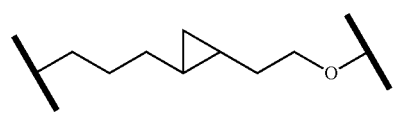 |
| 752 | CHF₂ | F | 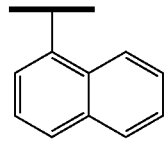 | 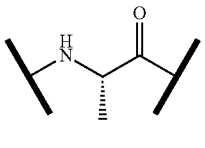 | —(CH₂)₅—NH— |
| 753 | CHF₂ | F | 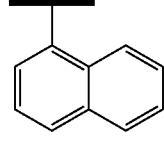 | 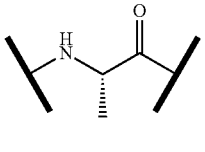 | —(CH₂)₆—NH— |
| 754 | CHF₂ | F | 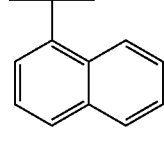 | 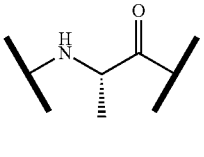 | —(CH₂)₇—NH— |
| 755 | CHF₂ | F | 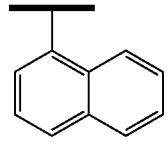 | 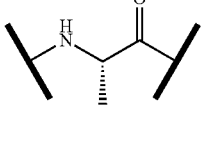 | —(CH₂)₅—C(O)NH— |
| 756 | CHF₂ | F | 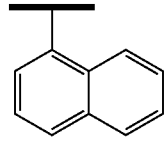 | 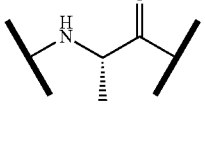 | —(CH₂)₆—C(O)NH— |
| 757 | CHF₂ | F | 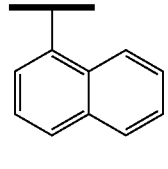 | 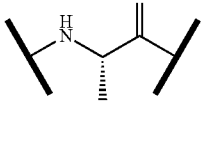 | —(CH₂)₇—C(O)NH— |
| 758 | CHF₂ | F | 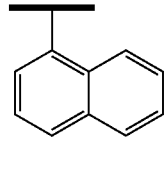 | 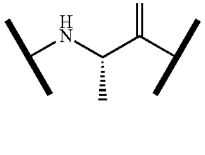 | 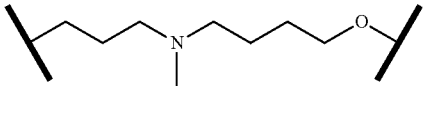 |

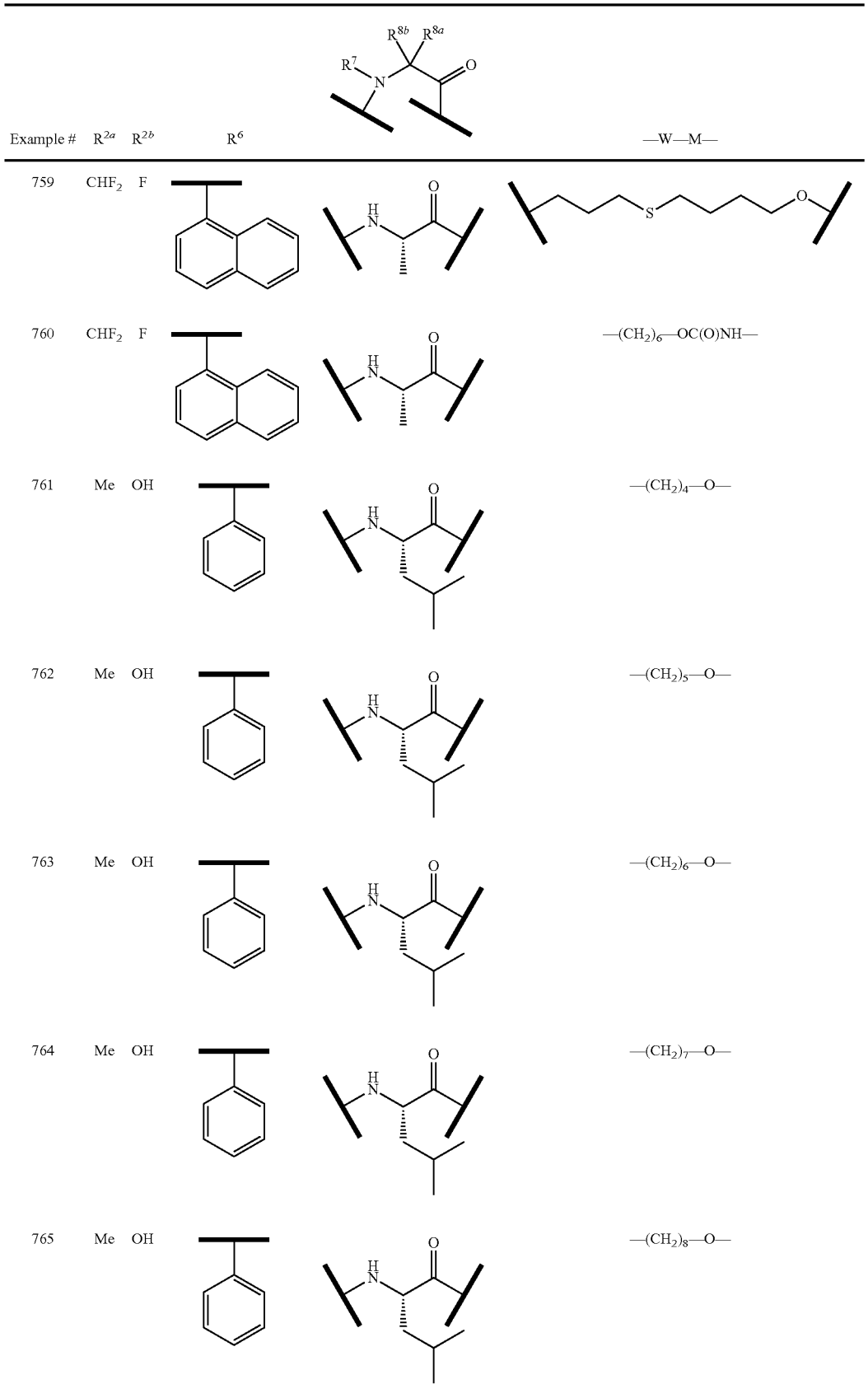

TABLE 4-continued
| Example # | $R^{2a}$ | $R^{2b}$ | $R^6$ | 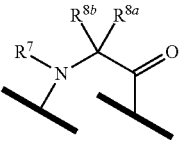 | —W—M— |
|---|---|---|---|---|---|
| 766 | Me | OH | 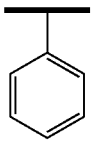 | 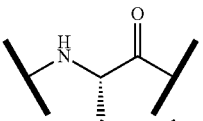 | 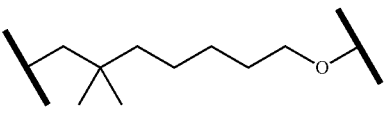 |
| 767 | Me | OH | 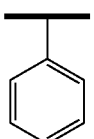 | 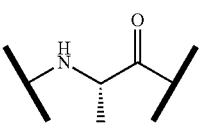 | 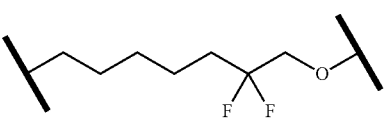 |
| 768 | Me | OH | 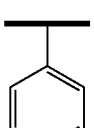 | 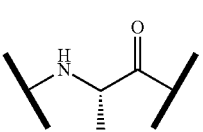 | —(CH$_2$)$_3$—O—(CH$_2$)$_5$—O— |
| 769 | Me | OH | 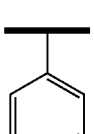 | 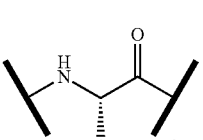 | 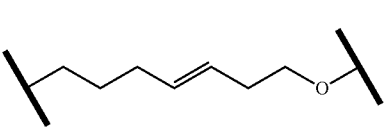 |
| 770 | Me | OH |  | 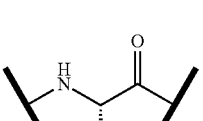 | 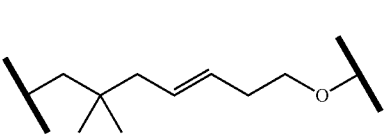 |
| 771 | Me | OH | 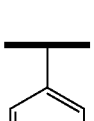 | 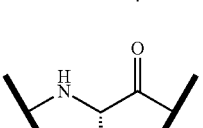 | 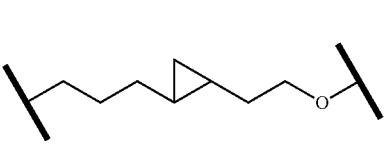 |
| 772 | Me | OH | 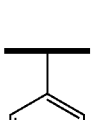 | 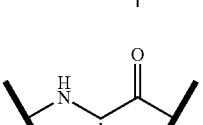 | —(CH$_2$)$_5$—NH— |

TABLE 4-continued
| Example # | R2a | R2b | R6 | | —W—M— |
|---|---|---|---|---|---|
| 773 | Me | OH | 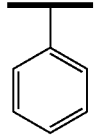 | 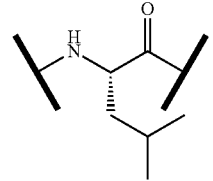 | —(CH$_2$)$_6$—NH— |
| 774 | Me | OH | 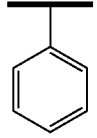 | 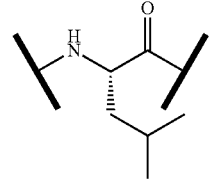 | —(CH$_2$)$_7$—NH— |
| 775 | Me | OH | 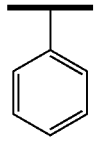 | 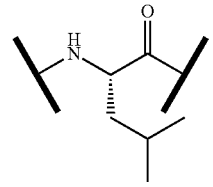 | —(CH$_2$)$_5$—C(O)NH— |
| 776 | Me | OH | 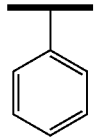 | 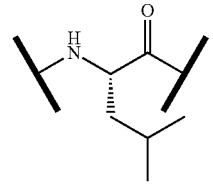 | —(CH$_2$)$_6$—C(O)NH— |
| 777 | Me | OH | 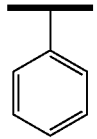 | 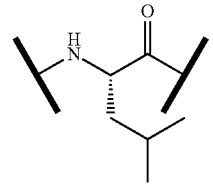 | —(CH$_2$)$_7$—C(O)NH— |
| 778 | Me | OH | 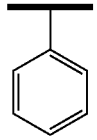 | 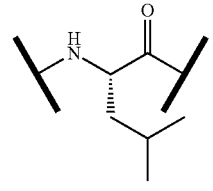 | 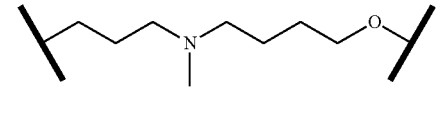 |
| 779 | Me | OH | 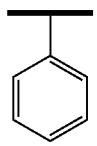 | 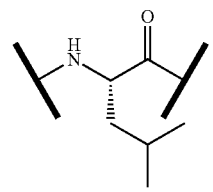 | 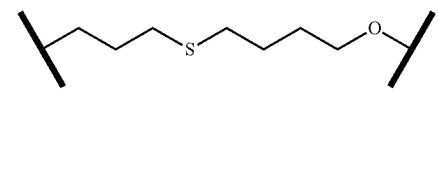 |

TABLE 4-continued

| Example # | $R^{2a}$ | $R^{2b}$ | $R^6$ | | —W—M— |
|---|---|---|---|---|---|
| 780 | Me | OH | (phenyl) | (Leu) | —(CH$_2$)$_6$—OC(O)NH— |
| 781 | Me | F | (phenyl) | (Leu) | —(CH$_2$)$_4$—O— |
| 782 | Me | F | (phenyl) | (Leu) | —(CH$_2$)$_5$—O— |
| 783 | Me | F | (phenyl) | (Leu) | —(CH$_2$)$_6$—O— |
| 784 | Me | F | (phenyl) | (Leu) | —(CH$_2$)$_7$—O— |
| 785 | Me | F | (phenyl) | (Leu) | —(CH$_2$)$_8$—O— |
| 786 | Me | F | (phenyl) | (Leu) | (gem-dimethyl-(CH$_2$)$_5$—O—) |

TABLE 4-continued
| Example # | $R^{2a}$ | $R^{2b}$ | $R^6$ | 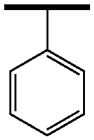 | —W—M— |
|---|---|---|---|---|---|
| 787 | Me | F | 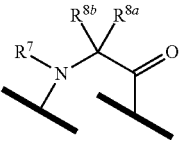 | 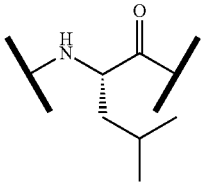 |  |
| 788 | Me | F | 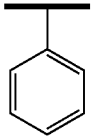 | 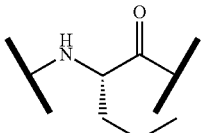 | —(CH$_2$)$_3$—O—(CH$_2$)$_5$—O— |
| 789 | Me | F | 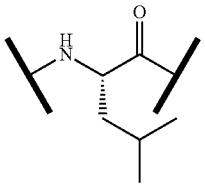 | 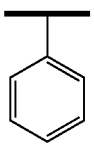 | 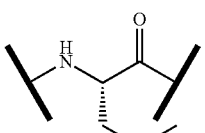 |
| 790 | Me | F | 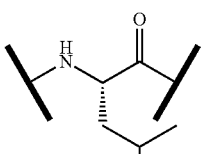 |  | 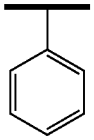 |
| 791 | Me | F | 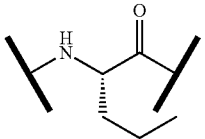 | 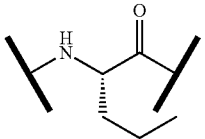 |  |
| 792 | Me | F | 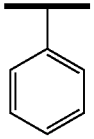 | 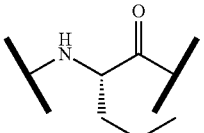 | —(CH$_2$)$_5$—NH— |
| 793 | Me | F | 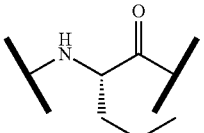 |  | —(CH$_2$)$_6$—NH— |

TABLE 4-continued

| Example # | R$^{2a}$ | R$^{2b}$ | R$^6$ | | —W—M— |
|---|---|---|---|---|---|
| 794 | Me | F | | | —(CH$_2$)$_7$—NH— |
| 795 | Me | F | | | —(CH$_2$)$_5$—C(O)NH— |
| 796 | Me | F | | | —(CH$_2$)$_6$—C(O)NH— |
| 797 | Me | F | | | —(CH$_2$)$_7$—C(O)NH— |
| 798 | Me | F | | | |
| 799 | Me | F | | | |
| 800 | Me | F | | | —(CH$_2$)$_6$—OC(O)NH—. |

9. A pharmaceutical composition comprising a compound according to claim 1 and a pharmaceutically acceptable carrier or excipient.

10. A method of treating a viral infection in a subject, comprising administering to the subject an effective amount of a pharmaceutical composition according to claim 9.

11. The method according to claim 10, wherein the viral infection is hepatitis C virus.

12. A method of inhibiting the replication of hepatitis C virus, the method comprising contacting the virus with a hepatitis C viral NS3 protease inhibitory amount of the pharmaceutical composition of claim 9.

13. The method of claim 11, further comprising administering concurrently an additional anti-hepatitis C virus agent.

14. The method of claim 13, wherein said additional anti-hepatitis C virus agent is selected from the group consisting of α-interferon, β-interferon, ribavarin, and adamantine.

15. The method of claim 13, wherein said additional anti-hepatitis C virus agent is an inhibitor of hepatitis C virus helicase, polymerase, metalloprotease, or IRES.

16. The pharmaceutical composition of claim 9, further comprising another anti-HCV agent.

17. The pharmaceutical composition of claim 9, further comprising an agent selected from interferon, ribavirin, amantadine, another HCV protease inhibitor, an HCV polymerase inhibitor, an HCV helicase inhibitor, or an internal ribosome entry site inhibitor.

18. The pharmaceutical composition of claim 9, further comprising pegylated interferon.

19. The pharmaceutical composition of claim 9, further comprising another anti-viral, anti-bacterial, anti-fungal or anti-cancer agent, or an immune modulator.

20. The pharmaceutical composition of claim 9, further comprising a cytochrome P450 monooxygenase inhibitor or a pharmaceutically acceptable salt thereof.

21. The pharmaceutical composition of claim 20, wherein the cytochrome P450 monooxygenase inhibitor is ritonavir.

22. A method of treating a hepatitis C viral infection in a subject in need thereof comprising administering to the subject a cytochrome P450 monooxygenase inhibitor or a pharmaceutically acceptable salt thereof and a compound as set forth in claim 1.

* * * * *